(12) United States Patent
Fuh et al.

(10) Patent No.: US 7,985,840 B2
(45) Date of Patent: Jul. 26, 2011

(54) SYNTHETIC ANTIBODY PHAGE LIBRARIES

(75) Inventors: Germaine Fuh, Pacifica, CA (US); Sachdev S. Sidhu, San Francisco, CA (US)

(73) Assignee: Genentech, Inc, South San Francisco, CA (US)

( * ) Notice: Subject to any disclaimer, the term of this patent is extended or adjusted under 35 U.S.C. 154(b) by 631 days.

(21) Appl. No.: 10/939,309

(22) Filed: Sep. 9, 2004

(65) Prior Publication Data

US 2005/0119455 A1 Jun. 2, 2005

Related U.S. Application Data

(63) Continuation of application No. PCT/US03/17545, filed on Jun. 3, 2003.

(60) Provisional application No. 60/436,656, filed on Apr. 16, 2003, provisional application No. 60/385,338, filed on Jun. 3, 2002.

(51) Int. Cl.
*C07K 16/00* (2006.01)
*G01N 33/53* (2006.01)

(52) U.S. Cl. ...................... 530/387.1; 435/7.1
(58) Field of Classification Search ............... 530/387.1; 435/7.1
See application file for complete search history.

(56) References Cited

U.S. PATENT DOCUMENTS

| | | | |
|---|---|---|---|
| 4,816,567 A | 3/1989 | Cabilly et al. | |
| 5,223,409 A | 6/1993 | Ladner et al. | |
| 5,403,484 A | 4/1995 | Ladner et al. | |
| 5,427,908 A | 6/1995 | Dower et al. | |
| 5,432,018 A | 7/1995 | Dower et al. | |
| 5,498,530 A | 3/1996 | Schatz et al. | |
| 5,534,615 A | 7/1996 | Baker et al. | |
| 5,565,332 A | 10/1996 | Hoogenboom et al. | |
| 5,580,717 A | 12/1996 | Dower et al. | |
| 5,580,723 A | 12/1996 | Wells et al. | |
| 5,591,828 A | 1/1997 | Bosslet et al. | |
| 5,658,727 A * | 8/1997 | Barbas et al. | 506/9 |
| 5,667,780 A | 9/1997 | Ho et al. | |
| 5,667,988 A | 9/1997 | Barbas et al. | |
| 5,702,892 A | 12/1997 | Mulligan-Kehoe | |
| 5,723,286 A | 3/1998 | Dower et al. | |
| 5,723,323 A | 3/1998 | Kauffman et al. | |
| 5,733,743 A | 3/1998 | Johnson et al. | |
| 5,750,373 A | 5/1998 | Garrard et al. | |
| 5,759,817 A | 6/1998 | Barbas | |
| 5,763,192 A | 6/1998 | Kauffman et al. | |
| 5,770,434 A | 6/1998 | Huse | |
| 5,780,279 A | 7/1998 | Matthews et al. | |
| 5,821,337 A | 10/1998 | Carter et al. | |
| 5,834,250 A | 11/1998 | Wells et al. | |
| 5,837,242 A | 11/1998 | Holliger et al. | |
| 5,962,255 A | 10/1999 | Griffiths et al. | |
| 5,965,371 A | 10/1999 | Marasco et al. | |
| 5,969,108 A | 10/1999 | McCafferty et al. | |
| 6,037,454 A | 3/2000 | Jardieu et al. | |
| 6,040,136 A | 3/2000 | Garrard et al. | |
| 6,054,297 A | 4/2000 | Carter et al. | |
| 6,057,098 A | 5/2000 | Buechler et al. | |
| 6,096,551 A | 8/2000 | Barbas et al. | |
| 6,140,471 A | 10/2000 | Johnson et al. | |
| 6,172,197 B1 | 1/2001 | McCafferty et al. | |
| 6,627,196 B1 | 9/2003 | Baughman et al. | |
| 6,696,245 B2 | 2/2004 | Winter et al. | |
| 6,699,974 B2 | 3/2004 | Ono et al. | |
| 6,846,634 B1 | 1/2005 | Tomlinson et al. | |
| 2002/0082396 A1 | 6/2002 | Matsushima et al. | |
| 2002/0086978 A1 | 7/2002 | Verhoeyen | |
| 2003/0028009 A1 | 2/2003 | Huse | |
| 2004/0123343 A1 | 6/2004 | La Rosa et al. | |
| 2005/0119455 A1 | 6/2005 | Fuh et al. | |
| 2005/0202512 A1 * | 9/2005 | Tomlinson et al. | 435/7.1 |
| 2005/0266000 A1 | 12/2005 | Bond et al. | |

FOREIGN PATENT DOCUMENTS

| | | |
|---|---|---|
| EP | 266032 | 4/1988 |
| EP | 368684 | 5/1990 |
| EP | 0 628 639 | 6/1999 |
| WO | WO 92/01047 | 1/1992 |
| WO | WO 92/03461 | 3/1992 |
| WO | WO 92/20791 | 11/1992 |
| WO | WO 93/06213 | 4/1993 |
| WO | WO 93/11161 | 6/1993 |
| WO | WO 93/11236 | 6/1993 |
| WO | WO 93/19172 | 9/1993 |
| WO | WO 97/35196 | 9/1997 |
| WO | WO 98/15833 | 4/1998 |
| WO | WO 99/06587 | 2/1999 |
| WO | WO 99/46284 | 9/1999 |

(Continued)

OTHER PUBLICATIONS

Barbas, C.F., Bain, J.D., Hoekstra, D.M., and Lerner, R.A. Semisynthetic combinatorial antibody libraries: a chemical solution to the diversity problem. Proceedings of the National Academy of Sciences, 1992. vol. 89, pp. 4457-4461.*

Barbas, C.F., Kang, A.S., Lerner, R.A., and Benkovic, S.J. Assembly of combinatorial antibody libraries on phage surfaces: The gene III site. Proceedings of the National Academy of Sciences, 1991. vol. 88, pp. 7978-7982.*

Rudikoff, S., Giusti, A.M., Cook, W.D., and Scharff, M.D. Single amino acid substitution altering antigen-binding specificity. Proceedings of the National Academy of Sciences, 1982. vol. 79, pp. 1979-1983.*

MacCallum, R.M., Martin, A.C.R., and Thornton, J.M. Antibody-antigen interactions: contact analysis and binding site topography. Journal of Molecular Biology, 1996. vol. 262, pp. 732-745.*

(Continued)

*Primary Examiner* — Hong Sang
(74) *Attorney, Agent, or Firm* — Merchant & Gould P.C.

(57) ABSTRACT

The invention provides comprising variant amino acids in CDRs of antibody variable domains. These polypeptides provide a source of great sequence diversity that can be used as a source for identifying novel antigen binding polypeptides. The invention also provides these polypeptides as fusion polypeptides to heterologous polypeptides such as at least a portion of phage or viral coat proteins, tags, and linkers. Libraries comprising a plurality of these polypeptides are also provided. In addition, methods of and compositions for generating and using these polypeptides and libraries are provided.

49 Claims, 64 Drawing Sheets

FOREIGN PATENT DOCUMENTS

| | | |
|---|---|---|
| WO | WO 00/24884 | 5/2000 |
| WO | WO 00/77194 A1 | 12/2000 |
| WO | WO 01/44463 | 6/2001 |
| WO | WO 01/70266 | 9/2001 |
| WO | WO 01/90190 A2 | 11/2001 |
| WO | WO 03/102157 | 6/2003 |

OTHER PUBLICATIONS

Chen, Y., Wiesmann, C., Fuh, G., Li, B., Christinger, H.W., McKay, P., De Vos, A.M. and Lowman, H.B. Selection and analysis of an optimized anti-VEGF antibody: crystal structure of an affinity-matured Fab in complex with antigen. Journal of Molecular Biology, 1999. vol. 293, pp. 865-881.*

Wu, H., Nie, Y., Huse, W.D., and Watkins, J.D. Humanization of a murine monoclonal antibody by simultaneous optimization of framework and CDR residues. Journal of Molecular Biology, 1999. vol. 294, pp. 151-162.*

Holm, P., Jafari, R., and Sundstrom, B.E. Functional mapping and single chain construction of the anti-cytokeratin 8 monoclonal antibody TS1. Molecular Immunology, 2007. vol. 44, pp. 1075-1084.*

Vajdos, F.F., Adams, C.W., Breece, T., Presta, L.G., De Vos, A.M., and Sidhu, S.S. Comprehensive functional maps of the antigen-binding site of an anti-ErbB2 antibody obtained with shotgun scanning mutagenesis. Journal of Molecular Biology, 2002. vol. 320, pp. 415-428.*

Casset, F., Roux, F., Mouchet, P., Bes, C., Chardes, T., Granier, C., Mani, J.C., Pugniere, M., Laune, D., Pau, B., Kaczorek, M., Lahana, R., and Rees, A. A peptide mimetic of an anti-CD4 monoclonal antibody by rational design. Biochemical and Biophysical Research Communications, 2003. vol. 307, pp. 198-205.*

De Pascalis, Iwahashi, Tamura, Padlan, Gonzales, Santos, Giuliano, Schuck, Schlom, and Kashmiri. Grafting of 'abbreviated' complementarity-determining regions containing specificity-determining residues essential for ligand contact to engineer a less immunogenic humanized monoclonal antibody. Journal of Immunology, 2002. vol. 169, p. 3076-3084.*

Willuda et al., Cancer Res., 1999, 59:5758-5767.*

Iba et al., Gene, 1997, 194: 35-46.*

Supplementary Partial European Search Report dated Jul. 4, 2005.

Wu et al., "Stepwise in vitro affinity maturation of Vitaxin, an $\alpha_v\beta_3$-specific humanized mAb", *Proc. Natl. Acad. Sci. USA*, 95:6037-6042 (1998).

Fuh, "Synthetic Antibodies as therapeutics", *Expert Opinion on Biological Therapy*, 7(1):73-87 (2007).

Pini et al., "Design and use of a phage display library. Human antibodies with subnanomolar affinity against a marker of angiogenesis eluted from a two-dimensional gel", *Journal of Biological Chemistry*, 273(34):21769-21776 (1998).

Supplementary European Search Report dated Apr. 23, 2008.

Amit, A. et al., *Science*, 233:747-753 (1986) "Three-Dimensional Structure of an Antigen-Antibody Complex at 2.8 Å Resolution".

Baca et al., *The Journal of Biological Chemistry*, 272(16):10678-10684 (1997) "Antibody Humanization Using Monovalent Phage Display".

Bassing et al., *Cell*, 109:S45-S55 (2002) "The Mechanism and Regulation of Chromosomal V(D)J Recombination".

Bendig, *Methods: A Companion to Methods in Enzymology*, 8:83-93 (1995) "Humanization of Rodent Monoclonal Antibodies by CDR Grafting".

Bond et al., *J. Mol. Biol.*, 348:699-709 (2005) "A Structure-Based Database of Antibody Variable Domain Diversity".

Bullock et al., *BioTechniques*, 5:376-379 (1987) "XL1-Blue: A High Efficiency Plasmid Transforming recA *Escherichia coli* Strain With Beta-Galactosidase Selection".

Chang, C. et al., *Gene*, 55:189-196 (1987) "High-Level Secretion of Human Growth Hormone by *Escherichia coli*".

Chothia et al, *J. Mol. Biol.*, 227:799-817 (1992) "Structural Repertoire of the Human $V_H$ Segments".

Chothia and Lesk, *J. Mol. Biol.*, 196:901-917 (1987) "Canonical Structures for the Hypervariable Regions of Immunoglobulins".

Crea et al., *Proc. Natl. Sci. USA*, 75(12):5765-4769 (1978) "Chemical synthesis of genes for human insulin".

Davies et al., *Proc. Natl. Sci. USA*, 93:7-12 (1996) "Interactions of Protein antigens with Antibodies".

Enshell-Seijffers et al., *Nucleic Acids Research*, 29(10):1-13 (2001) "The rational design of a 'type 88' genetically stable peptide display vector in the filamentous bacteriophage fd".

Glockshuber et al., *Biochemistry*, 30(12):3049-3054 (1991) "Mapping and Modification of an Antibody Hapten Binding Site: A Site-Directed Mutagenesis Study of McPC603".

Graille et al., *PNAS*, 97(10):5399-5404 (2000) "Crystal structure of a *Staphylococcus aureus* protein A domain complexed with the Fab fragment of a human IgM antibody: Structural basis for recognition of B-cell receptors and superantigen activity".

Harris, *Biochem. Soc. Transactions*, 23:1035-1038 (1995) "Therapeutic Monoclonals".

Hufton et al., *Journal of Immunological Methods*, 231:39-51 (1999) "Phage display of cDNA repertoires: the pVI display system and its applications for the selection of immunogenic ligands".

Hurle and Gross, *Current Opinion in Biotechnology*, 5:428-433 (1994) "Protein engineering techniques for antibody humanization".

Jones et al., *Nature*, 321:522-525 (1986) "Replacing the complementarity-determining regions in a human antibody with those from a mouse".

Kabat et al., *The Journal of Biological Chemistry*, 252(19):6609-6616 (1977) "Unusual Distributions of Amino Acids in Complementarity-determining (Hypervariable) Segments of Heavy and Light Chains of Immunoglobulins and Their Possible Roles in Specificity of Antibody-combining Sites".

Kabat, *Pharmacological Reviews*, 34(1):23-38 (1982) "Antibody Diversity Versus Antibody Complementarity".

Kabat. et al., *Annals New York Acad. Sci.*, 190:382-393 (1971) "Attempts to Locate Complementarity Determining Residues in the Variable Positions of Light and Heavy Chain".

Kelley et al., *Biochemistry*, 31(24):5434-5441 (1992) "Antigen Binding Thermodynamics and Antiproliferative Effects of Chimeric and Humanized anti-p185$^{HER2}$ Antibody Fab Fragments".

Kyte et al., *J. Mol. Biol.*, 157:105-132 (1982) "A Simple Method for Displaying the Hydropathic Character of a Protein".

Marks et al., *J. Mol. Biol.*, 222:581-597 (1991) "By-passing Immunization—Human Antibodies from V-gene Libraries Displayed on Phage".

Mian et al., J. Mol. Biol., 217:133-151 (1991) "Structure, Function and Properties of Antibody Binding Sites".

Morea et al., *J. Mol. Biol.*, 275:269-294 (1998) "Conformations of the Third Hypervariable Region in the VH Domain of Immunoglobulins".

Morrison et al., *PNAS*, 81:6851-6855 (1984) "Chimeric human antibody molecules: Mouse antigen-binding domains with human constant region domains".

Muyldermans et al., *Reviews of Molecular Microbiology*, 74:277-302 (2003) "Single domain camel antibodies: current status".

Muyldermans et al., *TIBS*, 26:230-235 (2001) "Recognition of antigens by single-domain antibody fragments: the superfluous luxury of paired domains".

Padlan et al., *The FASEB Journal*, 9:133-139 (1995) "Identification of specificity-determining residues in antibodies".

Padlan, *Molecular Immunology*, 31(3):169-217 (1994) "Review—Anatomy of the Antibody Molecule".

Padlan, *Molecular Immunology*, 34(11):765-770 (1997) "Does Base Composition Help Predispose the Complementarity—Determining Regions of Antibodies to Hypermutation?"

Paul, W. E., ed., *Fundamental Immunology*, 3$^{rd}$ ed., Raven Press:New York, Ch. 9, pp. 292-295 (1993) "Structure and Function of Immunoglobulins".

Pereboev et al., *Journal of Virology*, 75(15):7107-7113 (2001) "Phage Display of Adenovirus Type 5 Fiber Knob as a Tool for Specific Ligand Selection and Validation".

Presta, L., 1992, *Current Opinion in Structural Biology*, 2:593-596 "Antibody engineering".

Radley et al. *J. Mol. Biol.*, 332(3)529-758 (2003) "Allosteric Switching by Mutually Exclusive Folding of Protein Domains".

Randen et al., *Eur. J. Immunol.*, 23:2682-2686 (1993) "Complementarity-determining region 2 is implicated in the binding of staphylococcal protein A to human immunoglobulin $V_H$III variable regions".

Riechmann et al., *Nature*, 332:323-327 (1988) "Reshaping human antibodies for therapy".

Rondot et al., *Nature Biotechnology*, 19:75-78 (2001) "A helper phage to improve single-chain antibody presentation in phage display".

Saerens et al., *J. Molecular Biology*, 23:597-607 (2005).

Spinelli et al., *Biochemistry*, 39:1217-1222 (2000) "Camelid heavy-chain variable domains provide efficient combining sites to haptens".

Stewart et al., *Molecular Immunology*, 34(15):1067-1082 (1997) "A Shannon Entropy Analysis of Immunoglobulin and T Cell Receptor".

Thompson et al., *Nucleic Acids Res.*, 22(22):4673-4680 (1994) "Clustal W: improving the sensitivity of progressive multiple sequence alignment through sequence weighting, position-specific gap penalties and weight matrix choice".

Tonegawa, *Nature*, 302:575-581 (1983) "Somatic generation of antibody diversity".

Vaswani and Hamilton, *Annals of Allergy, Asthma, & Immunology*, 81:105-119 (1998) "Humanized antibodies as potential therapeutic drugs".

Verhoeyen et al., *Science*, 239:1534-1536 (1988) "Reshaping Human Antibodies: Grafting an Antilysozyme Activity".

Viera et al., *Meth. Enzymol.*, 153:3-11 (1987) "Production of Single-Stranded Plasmic DNA".

Weiss et al., *Protein Science*, 9:647-654 (2000) "Mutational analysis of the major coat protein of M13 identifies residues that control protein display".

Wilson et al., *J. Exp. Med.*, 191(11):1881-1894 (2000) "Receptor Revision of Immunoglobulin Heavy Chain Variable Region Genes in Normal Human B Lymphocytes".

Wong et al., *Gene*, 68:193-203 (1988) "Expression of secreted insulin-like growth factor-1 in *Escherichia coli*".

Wu et al., *J. Exp. Med.*, 132:211-250 (1970) "An Analysis of the Sequences of the Variable Regions of Bence Jones Proteins and Myeloma Light Chains and Their Implications for Antibody Complementarity".

Zemlin et al, *J. Mol. Biol.* 334:733(2003) "Expressed Murine and Human CDR-H3 Intervals of Equal Length Exhibit distinct repertoires that differ in amino acid composition and predicted structures".

Zoller et al., *Nucleic Acids Res.*, 10(20):6487-6504 (1987) "Oligonucleotide-directed mutagenesis using M13-derived vectors: an efficient and general procedure for the production of point mutations in any fragment of DNA".

Supplementary European Search Report dated May 13, 2008.

Nissim et al., *EMBO Journal*, 13: 692-698 (1994) "Antibody fragments from a 'single pot' phage display library as immunochemical reagents".

Arbabi Ghahroudi, M. et al., "Selection and identification of single domain antibody fragments from camel heavy-chain antibodies", *FEBS Letter*, 414:521-526 (1997).

Arndt, K. et al., "Factors Influencing the Dimer to Monomer Transition of an Antibody Single-Chain Fv Fragment", *Biochemistry*, 37:12918-12926 (1998).

Barbas, C. et al., "In Vitro evolution of a neutralizing human antibody to human immunodeficiency virus type 1 to enhance affinity and broaden strain cross-reactivity", *Proc. Natl. Acad. Sci. USA*, 91:3809-3813 (1994).

Barbas, C. et al., "Selection and evolution of high-affinity human anti-viral antibodies", *Trends Biotech*, 14:230-234 (1996).

Bass, S. et al., "Hormone Phage: An Enrichment Method for Variant Proteins with Altered Binding Properties", *Proteins*, 8:309-314 (1990).

Bond, C. et al., "Contributions of CDR3 to $V_HH$ Domain Stability and the Design of Monobody Scaffolds for Naïve Antibody Libraries", *J. Mol. Bio.*, 332:649-655 (2003).

Braunagel, M. et al., "Construction of a semisynthetic antibody library using trinucleotide oligos", *Nucleic Acids Research*, 25(22):4690-4691 (1997).

Carter et al., "Humanization of an anti-p185$^{HER2}$ antibody for human cancer therapy", *Proc. Natl. Acad. Sci. USA*, 89:4285-4289 (1992).

Chen, Y. et al., "Selection and Analysis of an Optimized Anti-VEGF Antibody: Crystal Structure of an Affinity-matured Fab in Complex with Antigen", *J. Mol. Biol.*, 293:865-881 (1999).

Clackson, T. et al., "Making antibody fragments using phage display libraries", *Nature*, 352:624-628 (1991).

Connolly, J., "Analytical Molecular Surface Calculation", *J. Appl. Cryst.*, 16:548-558 (1983).

Cunningham, B. et al., "High-Resolution Epitope Mapping of hGH-Receptor Interactions by Alanine-Scanning Mutagenesis", *Science*, 244(4908):1081-1085 (1989).

Dall'Acqua, W. et al., "Antibody Engineering", *Current Opinion in Structural Biology*, 8:443-450 (1998).

Davis, B. et al., *Microbiology Including Immunology and Molecular Genetics*, pp. 237, 245-247, 374 (1980).

de Kruif, J. et al., "Selection and application of human single chain Fv antibody fragments from a semi-synthetic phage antibody display library with designed CDR3 regions", *J. Mol. Biol.*, 248:97-105 (1995).

de Kruif, J. et al., "Leucine Zipper Dimerized Bivalent and Bispecific scFv Antibodies from a Semi-synthetic Antibody Phage Display Library", *The Journal of Biological Chemistry*, 271(13):7630-7634 (1996).

de Wildt, R. et al., "Antibody arrays for high-throughput screening of antibody-antigen interactions", *Nature Biotechnology*, 18:989-994 (2000).

Decanniere, K. et al., "A single-domain antibody fragment in complex with RNase A: non-canonical loop structures and nanomolar affinity using two CDR loops", *Structure*, 7:361-370 (1999).

Decanniere, K. et al., "Canonical antigen-binding loop structures in immunoglobulins: More structures, more canonical classes?", *J. Mol. Bio.*, 300:83-91 (2000).

Decanniere, K. et al., "Degenerate interfaces in antigen-antibody complexes", *J. Mol. Bio.*, 313:473-478 (2001).

Deng, S. et al., "Selection of Antibody Single-chain Variable Fragments with Improved Carbohydrate Binding by Phage Display", *J. Biol. Chem.*, 269:9533-9538 (1994).

Desmyter, A. et al., "Antigen specificity and high affinity binding provided by one single loop of a camel single-domain antibody", *J. Biol. Chem.*, 276:26285-26290 (2001).

Desmyter, A. et al., "Crystal structure of a camel single-domain $V_H$ antibody fragment in complex with lysozyme", *Nat. Struct. Biol.*, 3:803-811 (1996).

Desmyter, A. et al., "Three camelid VHH domains in complex with porcine pancreatic α-amylase: Inhibition and versatility of binding topology" *The Journal of Biological Chemistry*, 277:23645-23650 (2002).

Distenfano, M. et al., "Quantifying β-Sheet Stability by Phage Display", *J. Mol. Biol.*, 322:179-188 (2002).

Dubaquié, Y. et al., "Total Alanine-Scanning Mutagenesis of Insulin-like Growth Factor I (IGF-I) Identifies Differential Binding Epitopes for IGFBP-1 and IGFBP-3", *Biochemistry*, 38:6386-6396 (1999).

Dumoulin, M. et al., "A camelid antibody fragment inhibits the formation of amyloid fibrils by human lysozyme", *Nature*, 424:783-788 (2003).

Dumoulin, M. et al., "Single-domain antibody fragments with high conformational stability", *Nat. Struct. Biol.*, 11:500-515 (2002).

Eigenbrot et al., "X-ray Structures of the Antigen-binding Domains from Three Variants of Humanized anti-p185$^{HER2}$ Antibody 4D5 and Comparison with Molecular Modeling," *J. Mol. Biol.*, 229:969-995 (1993).

Els Conrath, K. et al., "Camel single-domain antibodies as modular building units in bispecific and bivalent antibody constructs", *J. Biol. Chem.*, 276:7346-7350 (2001).

Engels et al., "Gene Synthesis", *Agnew. Chem. Int. Ed. Engl.*, 28:716-734 (1989).

Ewert, S. et al., "Biophysical properties of camelid $V_{HH}$ domains compared to those of human $V_H3$ domains", *Biochemistry*, 41:3628-3636 (2002).

Ewert, S. et al., "Biophysical properties of human antibody variable domains", *J. Mol. Bio.*, 325:531-553 (2003).

Ferrat, G. et al., "A peptide mimic of an antigenic loop of α-human chorionic gonadotropin hormone: solution structure and interaction with a llama $V_{HH}$ domain", *Biochem. J.*, 366:415-422 (2002).

Forsberg, G. et al., "Identification of Framework Residues in a Secreted Recombinant Antibody Fragment that Control Production Level and Localization in *Escherichia coli*", *J. Biol. Chem.*, 272:12430-12436 (1997).

Froehler, B. et al., "Synthesis of DNA via deoxynucleoside H-phosphonate intermediates", *Nucl. Acids Res.*, 14(13):5399-5407 (1986).

Fuh, G. et al., "Requirements for Binding and Signaling of the Kinase Domain Receptor for Vascular Endothelial Growth Factor", *J. Biol. Chem.*, 273:11197-11204 (1998).

Garrard, L. et al., "Selection of an anti-IGF-1 Fab from a Fab phage library created by mutagenesis of multiple CDR loops", *Gene*, 128:103-109 (1993).

Glockshuber, R. et al., "A Comparison of Strategies to Stabilize Immunoglobulin $F_v$-Fragments", *Biochemistry*, 29:1362-1367 (1990).

Gregoret, L. et al., "Additivity of mutant effects assessed by binomial mutagenesis", *Proc. Natl. Acad. Sci. USA*, 90:4246-4250 (1993).

Griffiths et al., "Isolation of high affinity human antibodies directly from large synthetic repertoires", *The EMBO Journal*, 13(14):3245-3260 (1994).

Hamers-Casterman, C. et al., "Naturally occurring antibodies devoid of light chains", *Nature*, 363:446-448 (1993).

Harmsen, M. et al., "Llama heavy-chain V regions consist of at least four distinct subfamilies revealing novel sequence features", *Molecular Immunology*, 37:579-590 (2000).

Hawkins, R. et al., "Selection of Phage Antibodies by Binding Affinity: Mimicking Affinity Maturation", *J. Mol. Biol.*, 226:889-896 (1992).

Hollinger, P. et al., "Diabodies: Small bivalent and bispecific antibody fragments", *Proc. Nail. Acad. Sci. USA*, 90:6444-6448 (1993).

Honegger, A. et al., "Yet Another Numbering Scheme for Immunoglobulin Variable Domains: An Automatic Modeling and Analysis Tool", *J. Mol. Biol.*, 309:657-670 (2001).

Hoogenboom, "Antibody phage display technology and its applications", *Immunotechnology*, 4:1-20 (1988).

Hoogenboom, H., "Designing and optimizing library selection strategies for generating high-affinity antibodies", *Trends in Biotechnology*, 15:62-70, 1997.

Hoogenboom, H., "Overview of antibody phage-display technology and its applications", *Methods Mol. Biol.*, 178: 1-37 (2002).

Hoogenboom, H. et al., "By-passing Immunisation: Human Antibodies from Synthetic Repertoires of Germline $V_H$ Gene Segments Rearranged in Vitro", *J. Mol. Biol.*, 227:381-388 (1992).

Jackson, J. et al., "In Vitro Antibody Mutation: Improvement of a High Affinity, Neutralizing Antibody Against IL-1β", *The Journal of Immunology*, 154:3310-3319 (1995).

Jung, S. et al., "Selection for Improved Protein Stability by Phage Display", *J. Mol. Biol.*, 294:163-180 (1999).

Knappik, A. et al., "Fully Synthetic Human Combinatorial Antibody Libraries (HuCAL) Based on Modular Consensus Frameworks and CDRs Randomized with Trinucleotides", *J. Mol. Biol.*, 296:57-86 (2000).

Kostelny, S. et al., "Formation of a Bispecific Antibody by the Use of Leucine Zippers", *The Journal of Immunology*, 148(5):1547-1553 (1992).

Kunkel, T. et al., "Rapid and Efficient Site-Specific Mutagenesis without Phenotypic Selection", *Methods in Enzymology*, 154:367-382 (1987).

Ladner, R. et al., "Novel frameworks as a source of high-affinity ligands", *Curr. Opin. Biotechnol.*, 12:406-410 (2001).

Lee et al., "The Interpretation of Protein Structures: Estimation of Static Accessibility", *J. Mol. Biol.*, 55:379-400 (1971).

Lowman, H. et al., "Monovalent Phage Display: A Method for Selecting Variant Proteins from Random Libraries", *Methods: A Companion to Methods in Enzymology*, 3:205-216 (1991).

Lowman, H. et al., "Selecting High-Affinity Binding Proteins by Monovalent Phage Display", *Biochemistry*, 30:10832-10838 (1991).

Morrison, K. et al., "Combinatorial alanine-scanning", *Current Opinion in Chemical Biology*, 5:302-307 (2001).

Muyldermans, S. et al., "Sequence and structure of $V_H$ domain from naturally occurring camel heavy chain immunoglobulins lacking light chains", *Protein Eng.*, 7:1129-35 (1994).

Muyldermans, S., "Single domain camel antibodies: current status", *Journal of Biotechnology*, 74(4):277-302 (2001).

Nieba, L. et al., "Disrupting the hydrophobic patches at the antibody variable/constant domain interface: improved in vivo folding and physical characterization of an engineered scFv fragment", *Protein Engineering*, 10(4):435-444 (1997).

O'Neil, K. et al., "Phage display: protein engineering by directed evolution", *Current Opinion in Structural Biology*, 5:443-449 (1995).

Pacios, L. et al., "ARVOMOL/CONTOUR: molecular surface areas and volumes on personal computers," *Computers Chem.*, 18(4):377-386 (1994).

Pacios, L., "Variations of Surface Areas and Volumes in Distinct Molecular Surfaces of Biomolecules", *Journal of Molecular Modeling*, 1:46-53 (1995).

Pack, P. et al., "Miniantibodies: Use of Amphipathic Helices to Produce Functional, Flexibly Linked Dimeric $F_v$ Fragments with High Avidity in *Escherichia coli*", *Biochemistry*, 31(6):1579-1584 (1992).

Plückthun, A., "Antibodies from *Escherichia coli*", *The Pharmacology of Monoclonal Antibodies*, vol. 113, Rosenburg and Moore eds. Springer-Verlag, New York, pp. 269-315 (1994).

Presta, L. et al., "Humanization of an Anti-Vascular Endothelial Growth Factor Monoclonal Antibody for the Therapy of Solid Tumors and Other Disorders," *Cancer Research*, vol. 57, pp. 4593-4599 (Oct. 15, 1997).

Rader, C. et al., "Phage display of combinatorial antibody libraries", *Curr. Opin. Biotechnol.*, 8:503-508 (1997).

Renislo, J. et al., "Solution Structure and Backbone Dynamics of an Antigen-Free Heavy Chain Variable Domain (VHH) from *Llama*", *Proteins*, 47(4)546-555 (2002).

Sheriff, S. et al., "Redefining the minimal antigen-binding fragment", *Nat. Struct. Biol.*, 3:733-736 (1996).

Sidhu, S. et al., "Phage-displayed Antibody Libraries of Synthetic Heavy Chain Complementarity Determining Regions," *J. Mol. Biol.*, vol. 338, pp. 299-310 (2004).

Sidhu, S. et al., "High Copy Display of Large Proteins on Phage for Functional Selections", *J. Mol. Biol.*, 296:487-495 (2000).

Sidhu, S. et al., "Phage Display for Selection of Novel Binding Peptides", *Methods in Enzymology*, 328:333-363 (2000).

Sidhu, S., Phage Display in Pharmaceutical Biotechnology, *Curr. Opin. Biotechnol.*, 11:610-616 (2000).

Skerra, A. et al., "Assembly of a Functional Immunoglobulin $F_v$ Fragment in *Escherichia coli*", *Science*, 240:1038-1041 (1988).

Skerra, A., "Engineered protein scaffolds for molecular recognition", *Journal of Molecular Recognition*, 13:167-187 (2000).

Smith, G. et al., "Filamentous Fusion Phage: Novel Expression Vectors that Display Cloned Antigens on the Virion Surface", *Science*, 228:1315-1317 (1985).

Spinelli, S. et al., "Lateral recognition of a dye hapten by a llama VHH domain", *J. Mol. Bio.*, 311:123-129 (2001).

Spinelli, S. et al., "The crystal structure of a llama heavy chain variable domain", *Nature Structural Biology*, 3(9):752-757 (1996).

Tanha, J. et al., "Optimal Design Features of Camelized Human Single-domain Antibody Libraries," *The Journal of Biological Chemistry*, vol. 276, No. 27, Issue of Jul. 6, pp. 24774-24780 (2001).

Tanha, J. et al., "Selection by phage display of llama conventional V(H) fragments with heavy chain antibody V(H)H properties", *J. Imm. Meth.*, 263:97-109 (2002).

Ulrich, H. et al., "Expression studies of catalytic antibodies", *Proc. Nat'l Acad. Sci. USA* 92:11907-11911 (1995).

Vajdos, F. et al., "Comprehensive functional maps of the antigen-binding site of an anti-ErbB2 antibody obtained with shotgun scanning mutagenesis", *J. Mol. Bio.*, 320:415-428 (2002).

van der Linden, R. et al., "Induction of immune responses and molecular cloning of the heavy chain antibody repertoire of Lama glama", *J. Imm. Meth.*, 240:185-195 (2000).

Vaughan et al., "Human Antibodies with Sub-nanomolar Affinities Isolated from a Large Non-immunized Phage Display Library", *Nat. Biotech*, 14:309-314 (1996).

Vranken, W. et al., "Solution structure of a llama single-domain antibody with hydrophobic residues typical of the VH/VL interface", *Biochemistry*, 41:8570-8579 (2002).

Weiss, G. et al., "Rapid mapping of protein functional epitopes by combinatorial alanine scanning", *Proc. Natl. Acad. Sci. USA*, 97(16):8950-8954 (2000).

Wells et al., "Rapid evolution of peptide and protein binding properties in vitro", *Curr. Opin. Struct. Biol.*, 3:355-362 (1992).

Wiesmann, C. et al., "Crystal Structure at 1.7 Å Resolution of VEGF in Complex with Domain 2 of the Flt-1 Receptor", *Cell*, 91:695-704 (1997).

Wu, T. et al., "Length distribution of CDRH3 in antibodies", *Proteins*, 16, 1-7 (1993).

Yelton, D. et al., "Affinity Maturation of the BR96 Anti-Carcinoma Antibody by Codon-Based Mutagenesis", *J. Immunol.*, 155:1994-2004 (1995).

Zapata, G. et al., "Engineering linear F(ab')$_2$ fragments for efficient production in *Escherichia coli* and enhanced antiproliferative activity", *Protein Eng.*, 8(10):1057-1062 (1995).

Zhu, Z. et al., "Remodeling domain interfaces to enhance heterodimer formation", *Protein Science*, 6:781-788 (1997).

International Search Report dated Nov. 18, 2004.

\* cited by examiner

FIG. 1

LC frequency

| Pos | AA/Count stacks (bottom → top) |
|---|---|
| 28 | S 511; N 262; V 258; D 186; G 178; I 44; T 39; L 16; X 35 |
| 29 | I —; S 272; V 254; G 192; N 147; X 70 |
| 30 | S 612; N 176; K 169; G 86; R 81; Y 63; T 29; D 28; A 17; X 53 |
| 31 | S 849; N —; T 170; R 47; — 29; D 28; K 25; G 18; X 69 |
| 32 | Y 1055; N 128; W 97; F 77; S 61; — 40 |
| 50 | G 386; A 341; D 294; W 151; K 116; L 91; E 39; X 82 |
| 53 | S 545; N 438; T 407; K 41; I —; R 23 |
| 91 | Y 849; S 196; R 169; A 118; G 61; H 41; X 148; — 38; X 91 |
| 92 | Y 362; G 356; N 248; S 193; D 114; L 94; T 64; H 43; X 112; — 24 |
| 93 | S 738; N 346; Q 117; T 101; H 66; G 51; D 47; R 35; V 33; N 18 |
| 94 | S 386; T 365; W 288; W —; Y 172; L 114; F 79; A 46; P 43; X 40 |
| 96 | L 264; Y 205; W 176; F 140; — 117; R 115; P 46; X 121 |

*Note: "—" indicates a dash/blank mark in the source; "X" denotes other/miscellaneous.*

FIG. 2

| Residue | Natural Diversity | Diversity<DNA codon> | % good | %covering |
|---|---|---|---|---|
| L1-28 | SNVDGI | SNVDGI<RDT> | 100% | 94% |
| L1-29 | ISVGN | ISVG<RKT> | 100% | 86% |
| L1-29 | | IV<RTT> | 100% | 56% |
| L1-30 | SNKGRYTDA | SNKGGRTTDAAE<RVW> | 92% | 93% |
| L1-31 | SNTRIDKG | SNTTRDKGGAAE<RVW> | 75% | 95% |
| L1-31 | | SNTTRIIK<ANW> | 100% | 94% |
| L1-32 | YNWFSDR | YNFSDATIV<DHT> | 55% | 88% |
| L1-32 | | YFS<THT> | 100% | 77% |
| L2-50 | GADWKLES | GAWLSV<KBG> | 83% | 67% |
| L2-53 | SNTKIR | SNT<AVC> | 100% | 90% |
| L3-91 | YSRAGH | YSAD<KMT> | 75% | 74% |
| | | YS<TMT> | 100% | 66% |
| L3-92 | YGNSDLTHI | YNSDTIFAV<DHT> | 67% | 64% |
| | | YNSDTA<DMC> | 83% | 62% |
| L3-93 | SNQTHGDR | SNTGDA<RVT> | 83% | 80% |
| | | SNTDYAFIV<DHT> | 44% | 76% |
| L3-94 | STWYLFAPVI | STYLFAPVINDH<NHT> | 75% | 78% |
| | | STYFIN<WHT> | 83% | 43% |
| L3-96 | LYWFIRP | LYFPHS<YHT> | 67% | 52% |
| | | LYFIHN<HWT> | 67% | 58% |
| | | LFI<HTT> | 100% | 42% |
| | | LLWR<YKG> | 100% | 47% |
| | | YF<TWT> | 100% | 29% |
| H1-28 | TS | TSN<AVT> | 67% | 92% |
| | | TS<WCC> | 100% | 90% |
| | | T | 100% | 54% |
| H1-30 | STNRDG | STTNRDGGAAE<RVM> | 73% | 96% |
| | | STN<AVT> | 100% | 90% |
| H1-31 | SNGDTRA | SNGGDTTRAAE<RVM> | 91% | 95% |
| | | SNGDTA<RVT> | 100% | 83% |
| | | SNGD<RRT> | 100% | 82% |
| H1-32 | YSNGFA | YSNT<WMY> | 75% | 81% |
| H1-33 | AYWGSDTNV | AAYWGGSSDCE*<KVK> | 75% | 87% |
| | | AGSDTNVI<RNT> | 87% | 58% |
| | | AYSDTN<DMT> | 100% | 62% |
| | | AYSD <KMT> | 100% | 56% |
| | | WG <KGG> | 100% | 30% |
| H2-50 | RYWVGIEASNL | YWVVGGELCDF* <KDK> | 67% | 49% |
| | | RWVGASLMT<DBG> | 78% | 59% |
| | | RWG<DGG> | 100% | 35% |
| | | YVIASNDFT<DHT> | 67% | 45% |
| H2-52 | SYNKIRDT | SYNIDTAFV<DHT> | 67% | 79% |
| | | SYNDTA<DMT> | 83% | 77% |
| H2-53 | SDYGHNITW | SDYHNTAP<NMT> | 75% | 75% |
| | | SDYNTA<DMT> | 83% | 66% |
| H2-54 | GSDNKFT | SSDKTTAEY*<DMK> | 60% | 47% |
| | | SDTNAY<DMT> | 67% | 47% |
| | | GSDN<RRC> | 100% | 81% |
| H2-56 | STNDYEGA | SSTTNDYEA*<DMK> | 90% | 90% |
| | | STNDYA<DMT> | 100% | 86% |
| H2-58 | YNDRSITH | YNDSTA<DMT> | 83% | 77% |
| | | YND<DAC> | 100% | 69% |

| Oligo | 93 S | 94 R | 95 W | 96 G | 97 G | 98 D | 99 G | 100 F | - | 100b Y | 100c A | M | 101 D | 102 Y | leng | Diversity |
|---|---|---|---|---|---|---|---|---|---|---|---|---|---|---|---|---|
| F59 | S | R | W | G | DVK | DVK | DVK | DVK | – | DVK | A | M | D | Y | 11 | 1.90E+06 |
| F63 | S | R | W | DVK | DVK | DVK | DVK | DVK | – | DVK | A | M | D | Y | 11 | 6.00E+08 |
| F64 | S | R | DVK | DVK | DVK | DVK | DVK | DVK | – | Y | A | M | D | Y | 11 | 6.00E+07 |
| F65 | S | R | DVK | DVK | DVK | DVK | DVK | NNK | NNK | Y | A | M | D | Y | 12 | 1.10E+09 |
| | | | | | | | | | | | | | | | | |
| F59 | S | R | W | G | DVK | DVK | DVK | DVK | – | DVK | A | M | D | Y | 11 | 1.90E+06 |
| F63 | S | R | W | DVK | DVK | DVK | DVK | DVK | – | DVK | A | M | D | Y | 11 | 6.00E+08 |
| F64 | S | R | DVK | DVK | DVK | DVK | DVK | DVK | – | Y | A | M | D | Y | 11 | 6.00E+07 |
| F65 | S | R | DVK | DVK | DVK | DVK | DVK | NNK | NNK | Y | A | M | D | Y | 12 | 1.10E+09 |
| F66 | S | R | NNK | NNK | NNK | NNK | NNK | NNK | NNK | Y | – | L | D | Y | 11 | 1.90E+06 |
| F78 | S | R | DVK | DVK | DVK | DVK | DVK | – | – | – | – | – | – | – | 8 | 1.90E+06 |
| | | | | | | | | | | | | | | | | |
| F165 | A | R/K | DVK | DVK | DVK | DVK | DVK | NNK | – | Y | A | M | D | Y | 11 | 1.20E+08 |
| F166 | A | R/K | W | NVT | NVT | NVT | NVT | DVK | – | DSG | A | M | D | Y | 11 | 7.50E+06 |
| F134 | A | R/K/Π | NVT | NVT | NVT | NVT | NVT | NVT | NVT | Y | A | M | D | Y | 12 | 2.90E+06 |
| F136 | A | R/K/Π | W | NVT | NVT | NVT | NVT | NVT | NVT | Y | A | M | D | Y | 12 | 2.90E+06 |
| F137 | A | R/K/Π | NVT | NVT | NVT | NVT | NVT | NVT | NVT | Y | A | M | D | Y | 12 | 2.90E+06 |
| F138 | A | R/K/Π | NVT | NVT | NVT | NVT | NVT | NVT | W | Y | A | M | D | Y | 12 | 2.90E+06 |
| F142 | A | R/K | W | W | NVT | NVT | NVT | NVT | W | Y | A | M | D | Y | 12 | 2.30E+07 |
| F155 | A | R/K | NVT | NVT | NVT | NVT | NVT | NVT | NVT | G/S/A/W | A | M | D | Y | 12 | 2.30E+07 |
| F156 | A | R/K | NVT | NVT | NVT | NVT | NVT | NVT | NVT | G/S/A/W | A | M | D | Y | 12 | 2.30E+07 |
| F157 | A | R/K | NVT | NVT | NVT | NVT | NVT | NVT | NVT | G/S/A/W | A | M | D | Y | 12 | 2.30E+07 |
| F158 | A | R/K | NVT | NVT | NVT | NVT | NVT | NVT | NVT | G/S/A/W | A | M | D | Y | 12 | 2.30E+07 |
| F160 | A | R/K | NVT | NVT | NVT | NVT | NVT | NVT | W | G/S/A/W | A | M | D | Y | 12 | 2.30E+07 |
| F160g | A | R/K | NVT | NVT | NVT | NVT | NVT | NVT | W | G/S/A/W | A | M | D | Y | 12 | 2.30E+07 |
| | | | | | | | | | | | | | | | | |
| F165 | A | R/K | DVK | DVK | DVK | DVK | DVK | NNK | – | Y | A | M | D | Y | 11 | 1.20E+08 |
| F166 | A | R/K | W | NVT | NVT | NVT | NVT | DVK | – | DSG | A | M | D | Y | 11 | 7.50E+06 |
| F163a | A | R/K | DVK | DVK | DVK | DVK | DVK | DVK | DVK | KSG | A | M | D | Y | 11 | 2.70E+08 |
| F164a | A | R | DVK | DVK | DVK | DVK | DVK | DVK | DVK | Y | A | M | D | Y | 12 | 6.10E+08 |
| F164b | A | R | DVK | DVK | DVK | DVK | DVK | DVK | DVK | DSG | A | M | D | Y | 12 | 3.60E+09 |
| F165a | A | R | DVK | DVK | DVK | DVK | DVK | DVK | DVK | DVK | Y | A | M | Y | 13 | 1.10E+10 |
| F165b | A | R | DVK | DVK | DVK | DVK | DVK | DVK | DVK | DVK | DSG | A | D | Y | 13 | 6.60E+10 |
| F155 | A | R/K | NVT | NVT | NVT | NVT | NVT | NVT | NVT | G/S/A/W | A | M | D | Y | 12 | 2.30E+07 |

FIG. 4B

| | | | | | | | | | | | | | | | |
|---|---|---|---|---|---|---|---|---|---|---|---|---|---|---|---|
| F156  | A | R/K   | NVT | W   | NVT | NVT | NVT | NVT | G/S/A/W | A | M | D | Y |    | 12 | 2.30E+07 |
| F157  | A | R/K   | NVT | NVT | W   | NVT | NVT | NVT | G/S/A/W | A | M | D | Y |    | 12 | 2.30E+07 |
| F160  | A | R/K   | NVT | NVT | NVT | NVT | W   | NVT | G/S/A/W | A | M | D | Y |    | 12 | 2.30E+07 |
| F160g | A | R/K   | NVT | NVT | NVT | NVT | NVT | W   | G/S/A/W | A | M | D | Y |    | 12 | 2.30E+07 |
| F167  | A | R/K   | W   | NVT | NVT | NVT | NVT | —   | DSG     | A | M | D | Y |    | 11 | 1.90E+06 |
| F134  | A | R/K/I | NVT | NVT | NVT | NVT | NVT | —   | Y       | A | M | D | Y |    | 11 | 2.90E+06 |
| F135  | S | R/K/I | W   | NVT | NVT | NVT | NVT | NVT | NVT     | Y | A | M | D |    | 11 | 2.90E+06 |
| F103  | A | R     | NVT | NVT | NVT | NVT | NVT | —   | Y       | A | M | D | Y | Y  | 13 | 4.20E+08 |
| F66a  | A | R     | NNS | NNS | NNS | NNS | NNS | —   | DSG     | A | M | D | Y |    | 11 | 1.10E+09 |
| F66b  | A | R     | NNS | NNS | NNS | NNS | NNS | —   | DSG     | A | M | D | Y |    | 11 | 6.40E+09 |

FIG. 4C

| Oligo | 93 | 94 | 95 | 96 | 97 | 98 | 99 | 100 | 100a | 100b | 100c | 101 | 102 | length | Diversity |
|---|---|---|---|---|---|---|---|---|---|---|---|---|---|---|---|
| F66c | S | A | W | G | G | D | G | F | Y | A | M | D | Y | 10 | 1.00E+08 |
| F66d | A | R | NNS | NNS | NNS | NNS | NNS | | Y | A/G/V | M | D | Y | 10 | 4.00E+08 |
| F66e | A | R | NNS | NNS | NNS | NNS | NNS | | KSG | A/G/V | M | D | Y | 10 | 3.10E+06 |
| F66f | A | R | NNS | NNS | NNS | NNS | NNS | | Y | A/G/V | M | D | Y | 9 | 1.20E+07 |
| F66f | A | R | NNS | NNS | NNS | NNS | NNS | | KSG | A/G/V | M | D | Y | 9 | 3.20E+09 |
| F66a1 | A | R | NNS | NNS | NNS | NNS | NNS | NNS | Y | A/G/V | M | D | Y | 11 | 1.28E+10 |
| F66b1 | A | R | NNS | NNS | NNS | NNS | NNS | NNS | KSG | A/G/V | M | D | Y | 11 | 1.23E+10 |
| F66g | A | R | NNS | NNS | NNS | NNS | NNS | NNS | KSG | A/G/V | M | D | Y | 12 | 3.28E+12 |
| F66h | A | R | NNS | NNS | NNS | NNS | NNS | NNS | Y | A/G/V | M | D | Y | 12 | 1.31E+13 |
| F66i | A | R | NNS | NNS | NNS | NNS | NNS | NNS | NNS | Y | A/G/V | M | D | Y | 13 | 1.26E+13 |
| F66j | A | R | NNS | NNS | NNS | NNS | NNS | NNS | NNS | KSG | A/G/V | M | D | Y | 13 | 3.20E+07 |
| F171c | A | R/K | NNK | NNK | NNK | NNK | NNK | – | – | – | F | D | Y | 8 | 1.02E+09 |
| F171d | A | R/K | NNK | NNK | NNK | NNK | NNK | – | – | – | F | D | Y | 9 | 3.28E+10 |
| F171e | A | R/K | NNK | NNK | NNK | NNK | NNK | NNK | – | – | F | D | Y | 10 | 1.00E+06 |
| F171 | A | R/K | NNK | NNK | NNK | NNK | NNK | – | – | – | F | D/A | Y | 7 | |
| F185 | A | R/K | XYZ | XYZ | XYZ | XYZ | XYZ | – | – | – | F | D | Y | 7 | |
| F186 | A | R/K | XYZ | XYZ | XYZ | XYZ | XYZ | XYZ | – | – | F | D | Y | 10 | |
| F187 | A | R/K | XYZ | XYZ | XYZ | XYZ | XYZ | XYZ | XYZ | – | F | D | Y | 11 | |
| F190 | A | R/K | XYZ | XYZ | XYZ | XYZ | XYZ | XYZ | XYZ | XYZ | Y | A | M | 14 | D Y |
| F190a | A | R/K | XYZ | XYZ | XYZ | XYZ | XYZ | XYZ | XYZ | XYZ | Y | A/V/G | M | 13 | D Y |
| F190b | A | R/K | XYZ | XYZ | XYZ | XYZ | XYZ | XYZ | XYZ | KSG | KSG | A/V/G | M | 13 | D Y |
| F190c | A | R/K | XYZ | XYZ | XYZ | XYZ | XYZ | XYZ | XYZ | XYZ | KSG | A/V/G | M | 14 | D Y |
| F190d | A | R/K | XYZ | XYZ | XYZ | XYZ | XYZ | XYZ | XYZ | XYZ | XYZ | Y | A/V/G | 15 | M D Y |
| F190e | A | R/K | XYZ | XYZ | XYZ | XYZ | XYZ | XYZ | XYZ | XYZ | XYZ | KSG | A/V/G | 15 | M D Y |

MRT RHSN  KSG WSAG
GBT AVG   GNT AVGD

Light Chain Designed Diversity
Diversity: ~ $2.9 \times 10^9$

CDR-L1: diversity ~ $7 \times 10^3$

| 28 | 29 | 30 | 31 | 32 |
|----|----|----|----|----|
| RDT | RTT | RVW | RVW | DHT |
| D | I | D | D | A |
| G | V | E | E | D |
| I |   | G | G | F |
| N |   | K | K | I |
| S |   | N | N | N |
| V |   | S | S | S |
|   |   | T | T | T |
|   |   | R | R | V |
|   |   |   |   | Y |

CDR-L2: diversity = 18

| 50 | 53 |
|----|----|
| KBG | AVC |
| A | N |
| G | S |
| L | T |
| S |   |
| V |   |
| W |   |

CDR-L3: diversity ~ $2.3 \times 10^4$

| 91 | 92 | 93 | 94 | 96 |
|----|----|----|----|----|
| KMT | DHT | DHT | NHT | YHT |
| A | A | A | A | F |
| D | D | D | D | H |
| S | F | F | F | L |
| Y | I | I | H | P |
|   | N | N | I | S |
|   | S | S | L | Y |
|   | T | T | N |   |
|   | V | V | P |   |
|   | Y | Y | S |   |
|   |   |   | T |   |
|   |   |   | V |   |
|   |   |   | Y |   |

FIG. 5

Light Chain Designed Diversity
Diversity: ~ 6.1 x $10^8$

CDR-L1: diversity ~ 3.4 x $10^3$

| 28 | 29 | 30 | 31 | 32 |
|----|----|----|----|----|
| RDT | RTT | RVW | ANW | THT |
| D | I | D | I | F |
| G | V | E | K | S |
| I |   | G | N | Y |
| N |   | K | R |   |
| S |   | N | S |   |
| V |   | S | T |   |
|   |   | T |   |   |
|   |   | V |   |   |

CDR-L2: diversity = 18

| 50 | 53 |
|----|----|
| KBG | AVC |
| A | N |
| G | S |
| L | T |
| S |   |
| V |   |
| W |   |

CDR-L3: diversity ~ 1.0 x $10^4$

| 91 | 92 | 93 | 94 | 96 |
|----|----|----|----|----|
| KMT | DMC | RVT | NHT | YHT |
| A | A | A | A | F |
| D | D | D | D | H |
| S | N | G | F | L |
| Y | S | N | H | P |
|   | T | S | I | S |
|   | Y | T | L | Y |
|   |   |   | N |   |
|   |   |   | P |   |
|   |   |   | S |   |
|   |   |   | T |   |
|   |   |   | V |   |
|   |   |   | Y |   |

FIG. 6

Light Chain Designed Diversity

CDR-L3: diversity ~ $1.3 \times 10^3$

| 91 | 92 | 93 | 94 | 96 |
|----|----|----|----|----|
| TMT | DMC | RVT | WHT | HTT |
| S | A | A | F | F |
| Y | D | D | I | I |
|   | N | G | N | L |
|   | S | N | S |   |
|   | T | S | T |   |
|   | Y | T | Y |   |

FIG. 7

CDR-L1

| 28 | 29 | 30 | 31 | 32 |
|---|---|---|---|---|
| RDT | RTT | RVW | RVW | DHT |
| D | I | D | D | A |
| G | V | E | E | D |
| I |   | G | G | F |
| N |   | K | K | I |
| S |   | N | N | N |
| V |   | S | S | S |
|   |   | T | T | T |
|   |   | V | V | V |
|   |   |   |   | Y |

CDR-L2

| 50 | 53 |
|---|---|
| DVK | AVM |
| A | N |
| G | K |
| L | R |
| S | S |
| V | T2 |
| W |   |

CDR-L3

| 91 | 92 | 93 | 94 | 96 |
|---|---|---|---|---|
| NRT | NRT | RVM | NNK | TDK |
| C | C | A2 | A | C |
| D | D | D | C | F |
| G | G | E | D | L |
| H | H | G2 | E | W |
| N | N | K | F | Y |
| R | R | N | G | * |
| S | S | R | H |   |
| Y | Y | S | I |   |
|   |   | T2 | L |   |
|   |   |   | M |   |
|   |   |   | N |   |
|   |   |   | P |   |
|   |   |   | Q |   |
|   |   |   | R |   |
|   |   |   | etc |   |
|   |   |   | * |   |

*Amber stop codon is encoded by the degenerate codon

FIG. 8

CDR-H1

| 28 | 30 | 31 | 32 | 33 |
|---|---|---|---|---|
| WCC | RVM | RVM | WMY | RNT |
| S | A | A | N | A |
| T | D | D | S | D |
|   | E | E | T | G |
|   | G | G | Y | I |
|   | K | K |   | N |
|   | N | N |   | S |
|   | R | R |   | T |
|   | S | S |   | V |
|   | T | T |   |   |

CDR-H2

| 50 | 52 | 54 | 55 | 57 | 59 |
|---|---|---|---|---|---|
| DBG | DHT | NMY | DMT | DMT | DMT |
| A | A | A | A | A | A |
| G | D | D | D | D | D |
| L | F | H | N | N | N |
| M | I | N | S | S | S |
| R | N | P | T | T | T |
| S | S | S | Y | Y | Y |
| T | T | T |   |   |   |
| V | V | Y |   |   |   |
| W | Y |   |   |   |   |

CDR-H3
6-8 "DVK" codons encoding
11 amino acids (ACDEGKNRSYW)

FIG. 9

CDR-H1

| 28 | 30 | 31 | 32 | 33 |
|----|----|----|----|----|
| WCC | RVM | RVM | WMY | DMT |
| S | A | A | N | A |
| T | D | D | S | D |
|   | E | E | T | N |
|   | G | G | Y | S |
|   | K | K |   | T |
|   | N | N |   | Y |
|   | R | R |   |   |
|   | S | S |   |   |
|   | T | T |   |   |

CDR-H2

| 50 | 52 | 54 | 55 | 57 | 59 |
|----|----|----|----|----|----|
| DBG | DMT | DMT | RRC | DMT | DMT |
| A | A | A | D | A | A |
| G | D | D | G | D | D |
| L | N | N | N | N | N |
| M | S | S | S | S | S |
| R | T | T |   | T | T |
| S | Y | Y |   | Y | Y |
| T |   |   |   |   |   |
| V |   |   |   |   |   |
| W |   |   |   |   |   |

CDR-H3:
6-8 "DVK" codons encoding
11 amino acids (ACDEGKNRSYW) with 18 codons or 5-8 "NVT" coding 12 amino acids with 12 codons
(SYCPHRTNSADG)

FIG. 10

CDR-H1

| 28 | 30 | 31 | 32 | 33 |
|----|----|----|----|----|
| ACC | AVT | RVT | WMY | DMT |
| T | N | A | N | A |
|  | S | D | S | D |
|  | T | G | T | N |
|  |  | N | Y | S |
|  |  | S |  | T |
|  |  | T |  | Y |

CDR-H2

| 50 | 52 | 54 | 55 | 57 | 59 |
|----|----|----|----|----|----|
| DBG | DMT | DMT | RRC | DMT | DAC |
| A | A | A | D | A | D |
| G | D | D | G | D | N |
| L | N | N | N | N | Y |
| M | S | S | S | S |  |
| R | T | T |  | T |  |
| S | Y | Y |  | Y |  |
| T |  |  |  |  |  |
| V |  |  |  |  |  |
| W |  |  |  |  |  |

CDR-H3
6-8 "DVK" codons encoding
11 amino acids (ACDEGKNRSYW) with 18 codons
or 5-8 "NVT" coding 12 amino acids with 12 codons
(SYCPHRTNSADG)

CDR-L3

| 91 | 92 | 93 | 94 | 96 |
|----|----|----|----|----|
| TMT | DMC | RVT | WHT | HTT |
| S | A | A | F | F |
| Y | D | D | I | I |
|  | N | G | N | L |
|  | S | N | S |  |
|  | T | S | T |  |
|  | Y | T | Y |  |

FIG. 11

CDR-H1

| 28 | 30 | 31 | 32 | 33 |
|----|----|----|----|----|
| ACC | AVT | RRT | WMY | DMT |
| T | N | D | N | A |
|  | S | G | S | D |
|  | T | N | T | N |
|  |  | S | Y | S |
|  |  |  |  | T |
|  |  |  |  | Y |

CDR-H2

| 50 | 52 | 54 | 55 | 57 | 59 |
|----|----|----|----|----|----|
| DBG | DMT | DMT | RRC | DMT | DAC |
| A | A | A | D | A | D |
| G | D | D | G | D | N |
| L | N | N | N | N | Y |
| M | S | S | S | S |  |
| R | T | T |  | T |  |
| S | Y | Y |  | Y |  |
| T |  |  |  |  |  |
| V |  |  |  |  |  |
| W |  |  |  |  |  |

CDR-H3
6-8 "NVT" coding 11 amino acids with 12 codons
(SYCPHRTNADG) ($12^6$=2.9e6 - $12^8$=4.2e8)

CDR-L3

| 91 | 92 | 93 | 94 | 96 |
|----|----|----|----|----|
| TMT | DMC | RVT | NHT | HTT |
| S | A | A | A | F |
| Y | D | D | D | I |
|  | N | G | F | L |
|  | S | N | H |  |
|  | T | S | I |  |
|  | Y | T | L |  |
|  |  |  | N |  |
|  |  |  | P |  |
|  |  |  | S |  |
|  |  |  | T |  |
|  |  |  | V |  |
|  |  |  | Y |  |

FIG. 12

CDR-H1

| 28 | 30 | 31 | 32 | 33 |
|---|---|---|---|---|
| ACC | AVT | RRT | WMY | KGG/KMT |
| T | N | D | N | W/A |
|  | S | G | S | G/D |
|  | T | N | T | S |
|  |  | S | Y | Y |

CDR-H2

| 50 | 52 | 54 | 55 | 57 | 59 |
|---|---|---|---|---|---|
| DGG/DHT | DMT | DMT | RRC | DMT | DAC |
| R / A | A | A | D | A | D |
| W /D | D | D | G | D | N |
| G /F | N | N | N | N | Y |
| I | S | S | S | S |  |
| N | T | T |  | T |  |
| S | Y | Y |  | Y |  |
| T |  |  |  |  |  |
| Y |  |  |  |  |  |

CDR-H3
6 "NVT" coding 11 amino acids with 12 codons
(SYCPHRTNADG) with one W walking through,
or "DVK" (SSYCWTTNKSRAADEGG*), * is stop codon

CDR-L3

| 91 | 92 | 93 | 94 | 96 |
|---|---|---|---|---|
| TMT | DMC | RVT | NHT | YKG/TWT |
| S | A | A | A | L2/F |
| Y | D | D | D | W/Y |
|  | N | G | F | R/ |
|  | S | N | H |  |
|  | T | S | I |  |
|  | Y | T | L |  |
|  |  |  | N |  |
|  |  |  | P |  |
|  |  |  | S |  |
|  |  |  | T |  |
|  |  |  | V |  |
|  |  |  | Y |  |

```
  1 GAAATGAGCT GTTGACAATT AATCATCGGC TCGTATAATG TGTGGAATTG TGAGCGGATA ACAATTTCAC ACAGGAAACA GCCAGTCCGT TTAGTGTTT
    CTTTACTCGA CAACTGTTAA TTAGTAGCCG AGCATATTAC ACACCTTAAC ACTCGCCTAT TGTTAAGTG TGTCCTTTGT CGGTCAGGCA AATCACAAA
    ^Ptac promoter 101 TCACGAGCAC TTCACCAACA AGGACCATAG ATTATGAAAA TAAAAACAGG TGCACGCATC CTCGCATTAT CCGCATTAAC GACGATGATG TTTTCCGCCT
    AGTGCTCGTG AAGTGGTTGT TCCTGGTATC TAATACTTTT ATTTTTGTCC ACGTGCGTAG GAGCGTAATA GGGCGTAATTG CTGCTACTAC AAAAGGCGGA
                                    ^Start malE secretion signal 201 CGGCTTATGC ATCCGATATC CAGATGACCC AGTCCCTGTCC CTCCCTGTCC GCCTCTGTGG GCGATAGGGT CACCATCACC TGCCGTGCA GTCAGGATGT
    GCCGAATACG TAGGCTATAG GTCTACTGGG TCAGGGACTC GAGGGACAGG CGGAGACACC CGCTATCCCA GTGTAGTGG ACGGCACGT CAGTCCTACA
    ^light chain start                                                                       ^CDR-L1

301 GAATACTGCT GTAGCCTGGT ATCAACAGAA ACCAGGAAAA GCTCCGAAGC TTCTGATTTA CTCGGCATCC TTCCTCTACT CTGGAGTCCC TTCTCGCTTC
    CTTATGACGA CATCGGACCA TAGTTGTCTT TGGTCCTTTT CGAGGCTTCG AAGACTAAAT GAGCCGTAGG AAGGAGATGA GACCTCAGG AAGAGCGAAG
                                                                     ^CDR-L2

401 TCTGGTAGCC GTTCCGGGAC GGATTTCACT CTGACCATCA GCAGTCTGCA GCCGGAAGAC TTCGCAACTT ATTACTGTCA GCAACATTAT ACTACTCTC
    AGACCATCGG CAAGGCCCTG CCTAAAGTGA GACTGGTAGT CGTCAGACGT CGGCCTTCTG AAGCGTTGAA TAATGACAGT CGTTGTAATA TGATGAGGAG
                                                                                 ^CDR-L3

501 CCACGTTCGG ACAGGGTACC AAGGTGGAGA TCAAATCGGA TATGCCGATG GCTGATCCGA ACCGTTCCG CGGTAAGAAC CTGGTTTTTC ATTCTGAGAT
    GGTGCAAGCC TGTCCCATGG TTCCACCTCT AGTTTAGCCT ATACGGCTAC CGACTAGGCT TGGCAAAGGC GCCATTCTTG GACCAAAAAG TAAGACTCTA
                                                ^linker        ^gD-tag              ^heavy chain start 601 CTCCGAGGTT CAGCTGGTGG AGTCTGGGCG TGGCCTGGTG CAGCCAGGGG GTCGGTCCCC GCTCACTCCG TTTGTCCTGT GCAGCTTCTG GCTTCAACAT TAAAGACACC
    GAGGCTCCAA GTCGACCACC TCAGACCCGC ACCGGACCAC GTCGGTCCCC CGAGTGAGGC AAACAGACA CGTCGAAGAC CGAAGTCGTA ATTTCTGTGG
                                                                                                    ^CDR-H1

701 TATATACACT GGGTGCGTCA GGCCACGCAGT CCCGGGCCCA AAGGGCCTGG AATGGGTTGC AATGGGTTGC TTACCCAACG TTCCCGGACC TTCCTAAATA GGATGCTTAC CAATATGAT TATACGGCTA TCGCAGTTCC
    ATATATGTGA CCCACGCAGT GGGGCCGCGA TTCCCGGACC AAGGGCCTGG TTCCCGGACC TTCCCGGACC AAGGATTTAT CCTACGAATG GTTATACTAG CAATATGATC TATACGGCTA TCGCAGTTCC
                                                                                                    ^CDR-H2

801 GCCGTTTCAC TATAAGCGCA GACACATCCA AAACACAGCA CTACTACAAA ATGAACAGCT TAAGAGCTGA GGACACTGCC TCTGTAGCGCTG GTAGCCGCTG
    CGGCAAAGTG ATATTCGCGT CTGTGTAGGT TTTTGTGTCG GATGATGTT TACTTGTCGA ATTCTCGACT CCTGTGACGG CAGATAATAA CATCGGCGAC
                                                                                                    ^CDR-H3

901 GGGAGGGGAC GGCTTCTATG CTATGGACTA CTGGGGTCAA GGAACACTAG TCACCGTCTC CAGCAGTGGC GGTGGCTCTG GTTCCGGTGA TTTTGATTAT
    CCCTCCCCTG CCGAAGATAC GATATCCTGAT GACCCCAGTT CCTTGTGATC AGTGGCAGAG GTCGTCACCG CCACCGAGAC CAAGGCCACT AAAACTAATA
                                                                   ^start p3 C-terminal domain
```

FIG. 14B

```
1001 GAAAGATGG CAAACGCTAA TAAGGGGGCT ATGACCGAAA ATGCCGATGA AAACGCGCTA CAGTCTGACG CTAAAGGCAA ACTTGATTCT GTCGCTACTG
     CTTTCTACC GTTTGCGATT ATTCCCCCGA TACTGGCTTT TACGGCTACT TTTGCGCGAT GTCAGACTGC GATTTCCGTT TGAACTAAGA CAGCGATGAC

1101 ATTACGGTGC TGCTATCGAT GGTTTCATTG CGTTTCATTC CGGCCTTGCT GTGACGTTTC AATGGTAATG GTGCTACTGG TGATTTTGCT GGCTCTAATT CCCAAATGGC
     TAATGCCACG ACGATAGCTA CCAAAGTAAC GCCGGAACGA TTACCATTAC CACGATGACC ACTAAAACGA CCGAGATTAA GGGTTTACCG

1201 TCAAGTCGGT GACGGTGATA ATTCACCTTT AATGAATAAT TTCCGTCAAT ATTTACCTTC CCTCCCTCAA TCGGTTGAAT GTCGCCCTTT TGTCTTTAGC
     AGTTCAGCCA CTGCCACTAT TAAGTGGAAA TTACTTATTA AAGGCAGTTA TAAATGGAAG GGAGGGAGTT AGCCAACTTA CAGCGGGAAA ACAGAAATCG

1301 GCTGGTAAAC CATATGAATT TTCTATTGAT TGTGACAAAA TAAACTTATT CCGTGGTGTC TTTGCGTTTC TTTTATATGT TGCCACCTTT ATGTATGTAT
     CGACCATTTG GTATACTTAA AAGATAACTA ACACTGTTTT ATTTGAATAA GGCACCACAG AAACGCAAAG ACGGTGGAAA TACATACATA

1401 TTTCTACGTT TGCTAACATA CTGCGTAATA AGGAGTCTTA A
     AAAGATGCAA ACGATTGTAT GACGCATTAT TCCTCAGAAT T
                                    ^p3 end
```

FIG. 15A

```
  1 GAAATGAGCT GTGACAATT AATCATCGGC TCGTATAATG TGTGGAATTG TGAGCGGATA ACAATTTCAC ACAGGAAACA GCCAGTCCGT TTAGGTGTTT
    CTTTACTCGA CAACTGTTAA TTAGTAGCCG AGCATATTAC ACACCTTAAC ACTCGCCTAT TGTTAAAGTG TGTCCTTTGT CGGTCAGGCA AATCCACAAA
                      ^Ptac promoter 101 TCACGAGCAC TTTCACCAACA AGAACATAG ATTATGAAAA TAAAACAGG TGCACGCATC CTCGCATTAT CCGCATTAAC GACGATGATG TTTTCCGCCT
    AGTGCTCGTG AAGTGGTTGT TCCTGGTATC TAATACTTTT ATTTTGTCC ACGTGCGTAG GAGCGTAATA GGCGTAATTG CTGCTACTAC AAAAGGCGGA
                                                          ^Start malE secretion signal 201 CGGCTTATGC ATCCGATATC CAGATGACCC AGTCCCCGAG CTCCCTGTCC GCCCTTGTGG GCGATAGGGT CACCATCACC TGCCGTGCCA GTCAGGATGT
    GCCGAATACG TAGGCTATAG GTCTACTGGG TCAGGGGCTC GAGGGACAGG CGGAGACACC CGCTATCCCA GTGTAGTGG ACGGCACGGT CAGTCCTACA
              ^light chain start                                                                    ^CDR-L1

301 GAATACTGCT GTAGCCTGGT ATCAACAGAA ACCAGAAGAA GCTCCGAAGC TTCTGATTTA CTCGGCATCC TTCCTCTACT CTGGAGTCCC TTCTCGCTTC
    CTTATGACGA CATCGGACCA TAGTTGTCTT TGGTCCTTTT CGAGGCTTCG AAGACTAAAT GAGCCGTAGG AAGGAGATGA GACCTCAGGG AAGAGCGAAG
                                                                       ^CDR-L2

401 TCTGGTAGCC GTTCCGGGAC GGAATTCACT CTGACCATCA GCAGTCTGCA GCCGGAAGAC TTCGCAACTT ATTACTGTCA GCAACATTAT ACTACTCCTC
    AGACCATCGG CAAGGCCCTG CCTTAAGTGA GACTGGTAGT CGTCAGACGT CGGCCTTCTG AAGCGTTGAA TAATGACAGT CGTTGTAATA TGATGAGGAG
                                                                                                  ^CDR-L3

501 CCACGTTCGG ACAGGGTACC AAGGTGGAGA TCAAATCGGA TATGCCGATG GCTGATCCGA ACCGTTTCCG CGTAAGAAC CTGGTTTTTC ATTCTGAGAT
    GGTGCAAGCC TGTCCCATGG TTCCACCTCT AGTTTAGCCT ATACGGCTAC CGACTAGGCT TGGCAAAGGC GCATTCTTG GACCAAAAAG TAAGACTCTA
              ^linker              ^gD-tag                                                         heavy chain start^

601 CTTCGGAGTT CAGCTGGTGG AGTCTGGCGG TGGCCTTGTG CAGCCAGGGG GTCGGTCCCC CGAGTGAGGC GCTCACTCCG TTTGTCCTGT GCTTCAACAT TAAAGACACC
    GAAGCCTCAA GTCGACCACC TCAGACCGCC ACCGGAACAC GTCGGTCCCC CAGCCAGGGG GCTCACTCCG CGAGTGAGGC AAACAGGACA CGTCGAAGAC CGAAGTTGTA ATTTCTGTGG
                                                                                                   ^CDR-H1

701 TATATACACT GGGTGCGTCA GGCCCCGGGT AAGGGCCTGG AATGGGTTGC AAGGATTTAT CCTTACGAATG GTTATACTAG ATATGCCGAT AGCGTCAAGG
    ATATATGTGA CCCACGCAGT CCGGGGCCCA TTCCCGGACC TTACCCAACG TTCCTAAATA GGATGCTTAC CAATATGATC TATACGGCTA TCGCAGTTCC
                                                                          ^CDR-H2

801 GCCGTTTCAC TATAAGCGCA GACACATCCA AAAACAGCT CTACCTACAA ATGAACAGCT TAAGAGCTGA GGACACTGCC GTCTATTATT GTAGCCGCTG
    CGGCAAAGTG ATATTCGCGT CTGTGTAGGT TTTTGTGTCG GATGGATGTT TACTTGTCGA ATTCTCGACT CCTGTGACGG CAGATAATAA CATCGGCGAC
                                                                                                                ^CDR-H3

901 GGGAGGGGAC GGCTTCTATG CTATGGACTA CTGGGGTCAA GGAACACTAG TCCTTGTGATC CAGCACCAGA CCGCCCTGCC CAGCCACATGC CCGCCCTGCC CAGCCACCGGA ACTGTGGGC
    CCCTCCCCTG CCGAAGATAC GATACCTGAT GACCCCAGTT CCTTGTGATC AGTGGCAGAG GTCGTGTACG GGCGGACGG GTCGTGGTCT TGACGACCCG
                                                                                              ^start zipper
```

FIG. 15B

```
1001 GGCCGCATGA AACAGCTAGA GGACAAGGTC GAAGAGCTAC TCTCCAAGAA CTACCACCTA GAGAATGAAG TGGCAAGACT CAAAAAACTT GTCGGGGAGC
     CCGGCGTACT TTGTCGATCT CCTGTTCCAG CTTCTCGATG AGAGGTTCTT GATGGTGGAT CTCTTACTTC ACCGTTCTGA GTTTTTTGAA CAGCCCCTCG

1101 GCGGAAAGCT TAGTGGCGGT GGCTCTGGTT CCGGTGATTT TGATTATGAA AAGATGGCAA ACGCTAATAA GGGGGCTATG ACCGAAAATG CCGATGAAAA
     CGCCTTTCGA ATCACCGCCA CCGAGACCAA GGCCACTAAA ACTAATACTT TTCTACCGTT TGCGATTATT CCCCGATAC TGGCTTTTAC GGCTACTTTT
      ^start p3 C-terminal domain 1201 CGGCGCTACAG TCTGACGCTA AAGGCAAACT TGATTCTGTC GCTACTGATT ACGGTGCTGC TATCGATGGT TTCATTGGTG ACGTTTCCGG CCTTGCTAAT
     GCGCGATGTC AGACTGCGAT TTCCGTTTGA ACTAAGACAG CGATGACTAA TGCCACGACG ATAGCTACCA AAGTAACCAC TGCAAAGGCC GGAACGATTA 1301 GGTAATGGTG CTACTGGTGA TTTTGCTGGC TCTAATTCCC AAATGGCTCA AGTCGGTGAC GGTGATAATT CACCTTTAAT GAATAATTTC CGTCAATATT
     CCATTACCAC GATGACCACT AAAACGACCG AGATTAAGGG TTTACCGAGT TCAGCCACTG CCACTATTAA GTGGAAATTA CTTATTAAAG GCAGTTATAA 1401 TACCTTCCCT CCCTCAATCG GTTGAATGTC GCCCTTTTGT CTTTAGCGCT GGTAAACCAT ATGAATTTTC TATTGATTGT GACAAAATAA ACTTATTCCG
     ATGGAAGGGA GGGAGTTAGC CAACTTACAG CGGGAAAACA GAAATCGCGA CCATTTGGTA TACTTAAAAG ATAACTAACA CTGTTTTATT TGAATAAGGC 1501 TGGTGTCTTT GCGTTTCTTT TATATGTTGC CACCTTTATG CTACGTTTGC TATGTATTTT TAACATACTG CGTAATAAGG AGTCTTAA
     ACCACAGAAA CGCAAAGAAA ATATACAACG GTGGAAATAC GATGCAAACG ATACATAAAA ATTGTATGAC GCATTATTCC TCAGAATT
                                                                                          ^p3 end
```

FIG. 16A

```
   1 GAAATGAGCT GTTGACAATT AATCATCGGC TCGTATAATG TGTGGAATTG TGAGCGGATA ACAATTTCAC ACAGGAAACA GCCAGTCCGT TTAGGTGTTT
     CTTACTCGA CAACTGTTAA TTAGTAGCCG AGCATATTAC ACACCTTAAC ACTCGCCTAT TGTTAAAGTG TGTCCTTTGT CGGTCAGGCA AATCCACAAA
                        ^Ptac promoter 101 TCACGAGCAC TTCACCAACA AGGACCATAG ATTATGAAAA TAAAAACAGG TGCACGCATC CTTCCATTAT CCGCATTAAC GACGATGATG TTTTCCGCCT
     AGTGCTCGTG AAGTGGTTGT TCCTGGTATC TAATACTTTT ATTTTTGTCC ACGTGCGTAG GGAGCTAATA GGCGTAATTG CTGCTACTAC AAAAGGCGGA
                                              ^start malE secretion signal 201 CGGCTTATGC ATCCGATATC CAGATGACCC AGTCCCCGAG CTCCCTGTCC GCCTCTGTGG GCGATAGGGT CACCATCACC TGCCGTGCA GTCAGGATGT
     GCCGAATACG TAGGCTATAG GTCTACTGGG TCAGGGGCTC GAGGGACAGG CGGAGACACC CGCTATCCCA GTGTAGTGG ACGGCACGGT CAGTCCTACA
     ^light chain start                                                                              ^CDR-L1

301 GAATACTGCT GTAGCCTGGT ATCAACAGAA ACCAGAGAA TTGGTCCTTTT CGAGGCTTCG AAGACTAAAT GAGGCGTAGG AAGGAGATGA GACCTCAGGG AAGAGGCGAAG
     CTTATGACGA CATCGGACCA TAGTTGTCTT TGGTCCTTTT CGAGGCTTCG AAGACTAAAT GAGGCGTAGG AAGGAGATGA GACCTCAGGG AAGAGGCGAAG
            ^CDR-L2                                                       ^CDR-L3

401 TCTGGTAGCC GTTCCGGGAC GGATTTCACT CTGACCATCA GCAGTCTGCA GCCGGAAGAC TTCGCAACTT ATTACTGTCA GCAACATTAT ACTACTCTC
     AGACCATCGG CAAGGCCCTG CCTAAAGTGA GACTGGTAGT CGTCAGACGT CGGCCTTCTG AAGCGTTGAA TAATGACAGT CGTTGTAATA TGATGAGAG

501 CCACGTTCGG ACAGGGTACC AAGGTGGAGA TCAAACGAAC TGTGGCTGCA CCATCTGTCT TCATCTTCCC GCCATCTGAT GAGCAGTTGA AATCTGGAAC
     GGTGCAAGCC TGTCCCATGG TTCCACCTCT AGTTTGCTG ACACCGACGT GGTAGACAGA AGTAGAAGGG CGGTAGACTA CTCGTCAACT TTAGACTTG

601 TGCCTCTGTT GTGTGCCTGC TGAATAACTT CTATCCCAGA GAGGCCAAAG TACAGTGGAA GGTGATAAC GCCCTCCAAT CGGGTAACTC CCAGGAGAGT
     ACGGAGACAA CACACGGACG ACTTATTGAA GATAGGGTCT CTCCGGTTTC ATGTCACCTT CCACCTATTG CGGGAGGTTA GCCCATTGAG GGTCCTCTCA

701 GTCACAGAGC AGGACAGCAA GGACACGCAC TACGCGCTCA GCAGCACCCT GACGCTGAGC AAAGCAGACT ACGAGAAACA CAAAGTCTAC GCCTGCGAAG
     CAGTGTCTCG TCCTGTCGTT CCTGTCGTGG ATGTCGGAGT CGTCGTGGGA CTGCGACTCG TTTCGTCTGA TGCTCTTTGT GTTTCAGATG CGGACGCTTC

801 TCACCCATCA GGGCCTGAGC TCGCCCGTCA CAAAGAGCTT CAACAGGGGA GAGTGTGGTG CCAGTCCGG TATGGCTGAT ATACCGACTA CCGAACCGTT TCCGGGTAA
     AGTGGGTAGT CCCGGACTCG AGCGGGCAGT GTTTCTCGAA GTTGTCCCCT CTCACACCAC GGTCAGGCC ATACCGACTA GGCTTGGCAA AGGCGCCATT

901 GGACCTGGCA TAACTCGAGG CTGACCGAGG CCTGGCCGCT ACGCCGGACG TGCGGCCTGC GTAGCACCGG AGTTCACGTA AAAAGGGTAA CTAGAGGTTG AGTTGATTTT
     CCTGGACCGT ATTGAGCTCC GACTGGCTCC GGACCGGCGA TGCGGCCTGA ACGCCGGACG GTCAGCAT TTTTCCCATT GATCTCCAAC TCCACTAAAA
     ^light chain stop 1001 ATGAAAAAGA ATATCGCATT TCTTCTTGCA TCTATGTTCG TCTATGTTCG TGCTACAAAC GCGTACGCTG AGATCTCCGA GGTTCAGCTG GTGAGTCTG
     TACTTTTTCT TATAGCGTAA AGAAGAACGT AGATACAAGC AAAAAAGATA ACGATGTTTG CGCATGCGAC TCTAGAGGCT CCAAGTCGAC CACCTCGAC
     ^start stII secretion signal                                                                   ^heavy chain start
```

FIG. 16B

```
1101 GCGGTGGCCT GGTGCAGCCA GGGGGCTCAC TCCGTTGTC CTGTGCAGCT TCTGGCTTCA ACATTAAAGA CACCTATATA CACTGGGTGC GTCAGGCCCC
     CGCCACCGGA CCACGTCGGT CCCCCGAGTG AGGCAAACAG GACACGTCGA AGACCGAAGT TGTAATTTCT GTGGATATAT GTGACCCACG CAGTCCGGGG
                                                               ^CDR-H1
1201 GGGTAAGGGC CTGAATGGG TTGCAAGGAT TTATCCTACG AATGGTTATA CTAGATATGC CGATAGCGTC AAGGGCCGTT TCACTATAAG CGCAGACACA
     CCCATTCCCG GACTTACCC AACGTTCCTA AATAGGATGC TTACCAATAT GATCTATACG GCTATCGCAG TTCCCGGCAA AGTGATATTC GCGTCTGTGT
                            ^CDR-H2
1301 TCCAAAAACA CAGCCTACCT ACAAATGAAC AGCTTAAGAG CTGAGACACA TGCCGTCTAT TATTGTAGCC GCTGGGGAGG GGACGGCTTC TATGCTATGG
     AGGTTTTTGT GTCGGATGGA TGTTTACTTG TCGAATTCTC GACTCTGTG ACGGCAGATA ATAACATCGG CGACCCCTCC CCTGCCGAAG ATACGATACC
                                                                                                  ^CDR-H3
1401 ACTACTGGGG TCAAGGAACC CTGGTCACCG TCTCCTCCGC CTCCACCAAG GGCCCATCGG TCTTCCCCCT GGCACCCTCC TCCAAGAGCA CCTCTGGGGG
     TGATGACCCC AGTTCCTTGG GACCAGTGGC GAGGAGTGGC CCGGGTAGCC AGAAGGGGGA TGTAATTTCT GTGGATATAT GGAGACCCCC
1501 CACAGCGGCC CTGGGCTGCC TGGTCAAGGA CTACTTCCCC GAACCGGTGA CGGTGTCGTG GAACTCAGGC GCCCTGACCA GCGGCGTGCA CACCTTCCCG
     GTGTCGCCGG GACCCGACGG ACCAGTTCCT GATGAAGGGG CTTGGCCACT GCCACAGCAC CTTGAGTCCG CGGGACTGGT CGCCGCACGT GTGGAAGGGC
1601 GCTGTCCTAC AGTCCTCAGG ACTCTACTCC CTCAGCAGCG TGGTGACCGT GCCCTCCAGC AGCTTGGGCA CCCAGACCTA CATCTGCAAC GTGAATCACA
     CGACAGGATG TCAGGAGTCC TGAGATGAGG GAGTCGTCGC ACCACTGGCA CGGGAGGTCG TCGAACCCGT GGGTCTGGAT GTAGACGTTG CACTTAGTGT
1701 AGCCAGCAA CACCAAGGTC GACAAGAAAG TTGAGCCCAA ATCTTGTGAC AAAACTCACC TCAGTGGCGG TGGCTCTGGT TCCGGTGATT TTGATTATGA
     TCGGGTCGTT GTGGTTCCAG CTGTTCTTTC AACTCGGGTT TAGAACACTG TTTTGAGTGG AGTCACCGCC ACCGAGACCA AGGCCACTAA AACTAATACT
                                                                                 ^start p3 C-terminal domain
1801 AAAGATGGCA AACGCTAATA AGGGGGCTAT GACCGAAAAT GCCGATGAAA ACGGCGCTACA GTCTGACGCT AAAGGCAAAC TTGATTCTGT CGCTACTGAT
     TTTCTACCGT TTGCGATTAT TCCCCCGATA CTGGCTTTTA CGGCTACTTT TGCGCGATGT CAGACTGCGA TTTCCGTTTG AACTAAGACA GCGATGACTA
1901 TACGGTGCTG CTATCGATGG TTTCATTGGT GACGTTTCCG GCCTTGCTAA TGGTAATGGT GCTACTGGTG CTACTGGTG CGATGACCAC TGAAAACGACC CAAATGCTC
     ATGCCACGAC GATAGCTACC AAAGTAACCA CTGCAAAGGC CGGAACGATT ACCATTACCA CGATGACCAC CGATGACCAC GCTACTGGTG GTTACCGAG
2001 AAGTCGGTGA CGGTGATAAT TCACCTTTAA TGAATAATTT ACTTATTAAA CCGTCAATAT TTACCTTCCC GGTTGAATGT CGCCCTTTG TCTTTAGCGC
     TTCAGCCACT GCCACTATTA AGTGGAAATT ACTTATTAAA TGAATAATTT TGCCAGTTATA AATGGAAGGG CCAACTTACA GCGGGAAAAC AGAAATCGCG
2101 TGGTAAACCA TATGAATTTT CTATTGATTG TGACAAAATA ACTGTTTTAT TGCGTTTCTT GTGGTGTCTT TGCGTTTCTT TTATATGTTG CCACCTTTAT GTATGTATTT
     ACCATTGGT ATACTTAAAA GATAACTAAC ACTGTTTTAT TGACAAAATA AGCAAAGAA ACGCAAAGAA AATATACAAC GGTGGAAATA CATACATAAA
2201 TCTACGTTTG CTAACATACT GGGTAATAAG GAGTCTTAA
     AGATGCAAAC GATTGTATGA CGCATTATTC CTCAGAATT
                                  ^end p3
```

FIG. 17A

```
   1 GAAATGAGCT GTTGACAATT AATCATCGGC TCGTATAATG TGTGGAATTG TGAGCGGATA ACAATTTCAC ACAGGAAACA GCCAGTCCGT TTAGGTGTTT
     CTTTACTCGA CAACTGTTAA TTAGTAGCCG AGCATATTAC ACACCTTAAC ACTCGCCTAT TGTTAAAGTG TGTCCTTTGT CGGTCAGGCA AATCCACAAA
                   ^Ptac promoter 101 TCACGAGGAC TTCCACAACA AGGACCATAG ATTATGAAAA TAAAAACAGG TGCACGCATC CTCGCATTAT CCGCATTAAC GACGATGATG TTTTCCGCCT
     AGTGCTCGTG AAGTGGTTGT TCCTGGTATC TAATACTTTT ATTTTTGTCC ACGTGCGTAG GAGCGTAATA GGCGTAATTG CTGCTACTAC AAAAGGCGGA
                                                              ^Start malE secretion signal 201 CGGCTTATGC ATCCGATATC CAGATGACCC AGTCCCGTCC CTCCCTGTGC GCCCTCTGTG GCGATAGGGT CACCATCACC TGCCGTGCCA GTCAGGATGT
     GCCGAATACG TAGGCTATAG GTCTACTGGG TCAGGGCAGG GAGGGACAGG CGGAGACACC CGCTATCCCA GTGGTAGTGG ACGGCACGGT CAGTCCTACA
              ^light chain start                                                                  ^CDR-L1

301 GAATACTGCT GTAGCCTGGT ATCAACAGAA ACCAGGGAAA GCTCCGAAGC TTCTGATTTA CTCGGCATCC TTCCTCTACT CTGGAGTCCC TTCTCGCTTC
     CTTATGACGA CATCGGACCA TAGTTGTCTT TGGTCCCTTT CGAGGCTTCG AAGACTAAAT GAGCCGTAGG AAGGAGATGA GACCTCAGGG AAGAGCGAAG
                                                                        ^CDR-L2

401 TCTGGTAGCC GTTCCGGGAC GGATTTCACT CTAAAGATCA GCAGTCTGCA GCCGGAAGAC TTCGCAACTT ATTACTGTCA GCAACATATT ACTACTCCTC
     AGACCATCGG CAAGGCCCTG CCTAAAGTGA GATTTCTAGT CGTCAGACGT CGGCCTTCTG AAGCGTTGAA TAATGACAGT CGTTGTAATA TGATGAGGAG
                                                                                            ^CDR-L3

501 CCACGTTCGG ACAGGGTACC AAGGTGGAGA TCAAACGAAC TGTGGCTGCA CCATCTGTCT TCATCTTCCC GCCATCTGAT GAGCAGTTGA AATCTGGAAC
     GGTGCAAGCC TGTCCCATGG TTCCACCTCT AGTTTGCTTG ACACCGACGT GGTAGACAGA AGTAGAAGGG CGGTAGACTA CTCGTCAACT TTAGACCTTG

601 TGCCTCTGTT GTGTGCCTGC TGAATAACTT CTATCCCAGA GAGGCCAAAG TACAGTGGAA GGTGATAACG CCCTCCAAT GCCCTCCAAT CGGGTAACTC CCAGAGAGT
     ACGAGACAA CACACGGACG ACTTATTGAA GATAGGGTCT CTCCCGGTTTC ATGTCACCTT ATCACCTT CGGAGGTTA GCCCATTGAG GGTCCTCTCA

701 GTCACAGAGC AGGACAGCAA GGACAGCACC TACAGCCTCA GCAGCACCCT GACGCTGAGC AAAGCAGACT ACGAGAAACA CAAAGTCTAC GCCTGCGAAG
     CAGTGTCTCG TCCTGTCGTT CCTGTCGTGG ATGTCGGAGT CGTCGTGGGA CTGCGACTCG TTTCGTCTGA TGCTCTTTGT GTTTCAGATG CGGACGCTTC

801 TCACCCATCA GGGCCTGAGC TCGCCCGTCA CAAAGAGCTT CAACAGGGGA GAGTGTGGTG CCAGGTCCGG TATGGCTGAT CCGAACCGTT TCCGCGGTAA
     AGTGGGTAGT CCCGGACTCG AGCGGGCAGT GTTTCTCGAA GTTGTCCCCT CTCACACCAC GGTCCAGGCC ATACCGACTA GGCTTGGCAA AGGCGCCATT

901 GGACCTGGCA TAACTCGAGG CTGATCCTCT ACGCCGGACG CATCGTGGCC AGTTCACGTA AAAAGGGTAA CTAGAGGTTG AGTTGATTTT
     CCTGGACCGT ATTGAGCTCC GACTAGGAGA TGCGGCCTGC GTAGCACCGG GTAGCACCGG TCAAGTGCAT TCAAGTGCAT TTTTCCCATT GATCTCCAAC TCAACTAAAA
              ^light chain stop 1001 ATGAAAAAGA ATATCGCAATT TCTTCTTGCA TCTATGTTCG TTTTTTCTAT TGCTACAAAC GCGTACGCTG AGATCTCCGA GGTTCAGCTG GTGGAGTCTG
     TACTTTTCT TATAGCGTTA AGAAGAACGT AGATACAAGC AAAAAAGATA ACGATGTTTG CGCATGCGAC TCTAGAGGCT CCAAGTCGAC CACCTCAGAC
            ^start stII secretion signal                                                         ^heavy chain start
```

FIG. 17B

```
1101  GCGGTGGCCT GGTGCAGCCA GGGGGCTCAC TCCGTTTGTC CTGTGCAGCT TCTGGCTTCA ACATTAAAGA CACCTATATA CACTGGGTGC GTCAGGCCCC
      CGCCACCGGA CCACGTCGGT CCCCCGAGTG AGGACAAACAG GACACGTCGA AGACCGAAGT TGTAATTTCT GTGGATATAT GTGACCCACG CAGTCCGGGG
                                                       ^CDR-H1

1201  GGGTAAGGGC CTGGAATGGG TTGCAAGGAT TTATCCTACG AATGGTTATA CTAGATATGC CGATAGGGTC AAGGGCCGTT TCACTATAAG CGCAGACACA
      CCCATTCCCG GACCTTACCC AACGTTCCTA AATAGGATGC TTACCAATAT GATCTATACG GCTATCCCAG TTCCCGGCAA AGTGATATTC GCGTCTGTGT
                                      ^CDR-H2

1301  TCCAAAAACA CAGCCTACCT ACAAATGAAC AGCTTAAGAG CTGAGGACAC TGCCGTCTAT TATTGTAGCC GCTGGGGAGG GGACGGCTTC TATGCTATGG
      AGGTTTTTGT GTCGGATGGA TGTTTACTTG TCGAATTCTC GACTCCTGTG ACGGCAGATA ATAACATGG CGACCCCTCC CCTGCCGAAG ATACGATACC
                                                                                                ^CDR-H3

1401  ACTACTGGGG TCAAGGAACC CTGGTCACCG TCTCCTCGGC CTCCACCAAG GGCCCATCGG TCTTCCCCCT GGCACCCTCC TCCAAGAGCA CCTCTGGGG
      TGATGACCCC AGTTCCTTGG GACCAGTGGC AGAGGAGCCG GAGGTGGTTC CCGGGTAGCC AGAAGGGGGA CCGTGGGAGG AGGTTCTCGT GGAGACCCCC

1501  CACAGCGGCC CTGGGCTGCC TGGTCAAGGA CTACTTCCCC GAACCGGTGA CGGTGTCGTG GAACTCAGGC GCCCTGACCA GCGGCGTGCA CACCTTCCCG
      GTGTCGCCGG GACCCGACGG ACCAGTTCCT GATGAAGGGG CTTGGCCACT GCCACAGCAC CTTGAGTCCG CGGGACTGGT CGCCGCACGT GTGGAAGGGC

1601  GCTGTCCTAC AGTCCTCAGG ACTCTACTCC CTCAGCAGCG TGGTGACCGT GCCCTCCAGC AGCTTGGGCA CCCAGACCTA CATCTGCAAC GTGAATCACA
      CGACAGGATG TCAGGAGTCC TGAGATGAGG GAGTCGTCGC ACCACTGGCA CGGGAGGTCG TCGAACCCGT GGGTCTGGAT GTAGACGTTG CACTTAGTGT

1701  AGCCCAGCAA CACCAAGGTC GACAAGAAAG TTGAGCCCAA ATCTTGTGAC AAAACTCACA CATGCCCGCC GTGCCCAGCA CCTGAACTGC TGGGGGGACCG
      TCGGGTCGTT GTGGTTCCAG CTGTTCTTTC AACTCGGGTT TAGAACACTG TTTTGAGTGT GTACGGGCGG CACGGGTCGT GGTCTTGACG ACCCGCCGGC
                                                                                  ^start zipper 1801  CATGAAACAG CTAGAGGACA AGTCGAAGA GCTACTCTCC AAGAACTACC ACCTAGAGAA TGAAGTGGCA AGACTCAAAA AACTTGTCGG GGAGCGCGGA
      GTACTTTGTC GATCCCTGT TCCAGCTTCT CGATGAGAGG TTCTTGATGG TGGATCTCTT ACTTCACCGT TCTGAGTTTT TTGAACAGCC CCTCGCGCCT 1901  AAGCTTAGTG GCGGTGGCTC TGGTTCCGGT GATTTTGATT ATGAAAAGAT GGCAAACGCT AATAAGGGGG CTATGACCGA AATGCCGAT GAAAACGCGC
      TTCGAATCAC CGCCACCGAG ACCAAGGCCA CTAAAACTAA TACTTTTCTA CCGTTTGCGA TTATTCCCCC GATACTGGCT TTTACGGCTA CTTTTGCCG
                 ^start p3 C-terminal domain 2001  TACAGTCTGA CGCTAAAGGC AAACTTGATT CTGTCGCTAC TGATTACGGT GCTGCTATCG ATGGTTTCAT TGGTGACGTT TCCGGCCTTG CTAATGGTAA
      ATGTCAGACT GCGATTTCCG TTTGAACTAA GACAGCGATG ACTAATGCCA CGACGATAGC CACCGAAAGTA ACCACTGCAA AGGCCGGAAC GATTACCATT 2101  TGGTGCTACT GGTGATTTTG CTGGCTCTAA TTCCCAAATG GCTCAAGTCG GTGACGGTGA TAATTCACCT ATTAAGTGGA AATTACTTAT TAAAGGCAGT
      ACCACGATGA CCACTAAAAC GACCGAGATT AAGGGTTTAC CGAGTTCAGC CACTGCCACT ATTTAAGGA AATTACTTTAT TTAAAGGCAGT 2201  TCCCTCCCTC AATCGGTTGA ATCGGTTTTA GGCGCTGGTAA TTTGTCTTTA GGCTGGTAA ACCATATGGA TTTTCTATTG ATTGTGACAA AATAAACTTA TTCCGTGGTG
      AGGGAGGGAG TTAGCCAACT TACAGCCAACT CCGCAACCATT TGGTATACTT AAAAGATAAC TAACACTGTT TTATTGAAT AAGGCACCAC 2301  TCTTTGCGTT TCTTTATAT GTTGCCACCT TTATGTATGT ATTTTCTACG TTTGCTAACA TACTGCCTAA TAAGGAGTCT TAA
      AGAAACGCAA AGAAATATA CAACGGTGGA AATACATACA TAAAGATGC AACGATTGT ATTCCTCAGA ATT
                                                                                 ^end p3
```

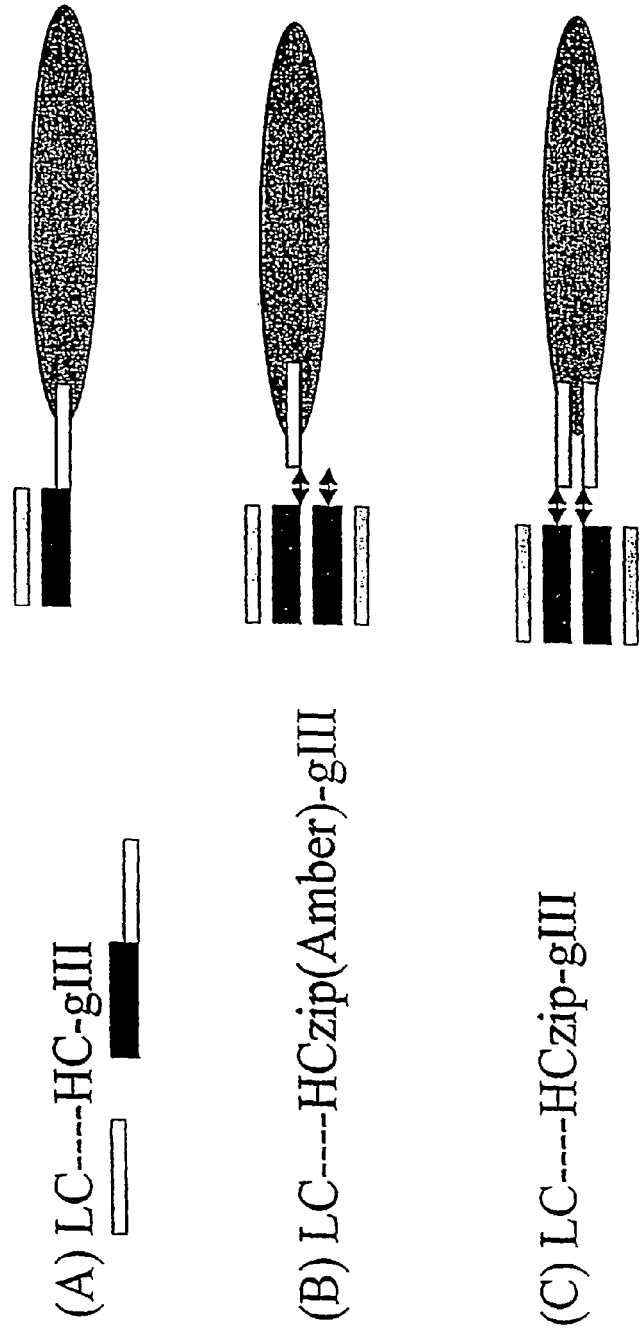

CDR-H1:

| 28 | 30 | 31 | 32 | 33 |
|----|----|----|----|----|
| AVT | RVM | RVM | WMY | KVK |
| N | A2 | A2 | N | A2 |
| S | D | D | S | C |
| T | E | E | T | D |
|   | G2 | G2 | Y | E |
|   | K | K |   | G2 |
|   | N | N |   | S2 |
|   | R | R |   | Y |
|   | S | S |   | W |
|   | T2 | T2 |   | * |

CDR-H2:

| 50 | 52 | 53 | 54 | 56 | 58 |
|----|----|----|----|----|----|
| KDK | DMT | NMY | DMK | DMK | DMT |
| C | A | A | A2 | A2 | A |
| D | D | D | D | D | D |
| E | N | H | E | E | N |
| F | S | N | K | K | S |
| G2 | T | P | N | N | T |
| L | Y | S | S2 | S2 | Y |
| V2 |   | T | T2 | T2 |   |
| W |   | Y | Y | Y |   |
| Y |   |   | * | * |   |
| * |   |   |   |   |   |

*Amber (TAG) stop codon is encoded by the degenerate codon

CDR-H3:
6-8 "DVK" codons (18) encoding
12 amino acids (ACDEGKNRSTYW) and stop (*)

FIG. 24

ScFv Library Sorting Results

| Library | Binders | | |
|---|---|---|---|
| | Her2 | IGF | VEGF |
| scFv-1 (H1/H2/H3)Zip | 100% | 100% | 63% |
| ScFv-2 (L3/H1/H2/H3)Zip | 50% | 63% | 25% |
| scFv-3 (L3/H3)Zip | 88% | 88% | 88% |
| scFv-4 (H1/H2/H3) | 38% | 50% | 63% |
| scFv-5 (L3/H1/H2/H3) | 25% | 13% | 25% |

FIG. 25

Detailed Analysis of scFv Zipper Libraries

Binding clones

| Library | IGF | | VEGF | |
|---|---|---|---|---|
| | Total | Specific | Total | Specific |
| scFv-1 | 91% | 67% | 79% | 70% |
| scFv-2 | 84% | 54% | 52% | 22% |
| scFv-3 | 88% | 8% | 91% | 4% |

FIG. 26

Summary of Sequencing Results

| Library | Round | Sequences | |
|---|---|---|---|
| | | Total | Unique |
| anti-IGF | | | |
| scFv-1 | 2 | 72 | 65 |
| scFv-1 | 3 | 95 | 79 |
| scFv-4 | 3 | 88 | 48 |
| Sum | | 255 | 192 |
| anti-VEGF | | | |
| scFv-1 | 2 | 24 | 22 |
| scFv-1 | 3 | 87 | 45 |
| scFv-4 | 3 | 91 | 19 |
| Sum | | 202 | 86 |

FIG. 27

CDR-H3 Usage in Binding Clones

|     | 95 | 96 | 97 | 98 | 99 | 100 |   | 100a |
|-----|----|----|----|----|----|----|----|------|
| 4D5 | W  | G  | G  | D  | G  | F  |    | Y    |
| F59 | W  | G  | X  | X  | X  | X  |    | X    |
| F63 | X  | X  | X  | X  | X  | X  |    | X    |
| F64 | X  | X  | X  | X  | X  | X  |    | Y    |
| F65 | X  | X  | X  | X  | X  | X  | X  | Y    |

Binders from L3/H3 library, sort 2 (1-4% hit rate)

| H3 Sequences of IGF1 binders (3/8) | | | |
|---|---|---|---|
| Sequences | # clones | Source Oligo | IC50 (uM) |
| I1 | SR WKYATR YAM | 1 | (DVK)5(NNK)1 | 40 |
| I2 | SR SRGWWTA AM | 1 | (DVK)7 | 0.3 |
| I3 | SR ASRDWYG AM | 1 | (DVK)7 | 15 |
| H3 sequences of mVEGF binders (10/25) | | | |
| V1 | SR NAWA F | 6 | (DVK)5 | 5.0 |
| V2 | SR NLSENS YAM | 1 | (NNK)6 | 0.2 |
| V5 | SR AGWAGW YAM | 1 | (DVK)5(NNK)1 | 0.6 |
| V8 | SR AAKAGW YAM | 1 | (DVK)5(NNK)1 | 4.7 |
| V10 | SR SDGRDSA YAM | 1 | (DVK)6(NNK)1 | 6.0 |

FIG. 29

Further Characterization of the mVEGF binders

| | H3 seq | IC50 (uM) | Blocking reagent | | | Fab Protein |
|---|---|---|---|---|---|---|
| | | | Flt-D2 | KDR | Y317 | |
| V1 | SR NAWA F | 5.0 | - | + | + | - |
| V2 | SR NLSENS YAM | 0.2 | + | + | + | + |
| V5 | SR AGWAW YAM | 0.6 | - | +/- | +/- | + |
| V8 | SR AAKAGW YAM | 4.7 | - | +/- | +/- | + |

| | 28 | 30 | 31 | 32 | 33 | | 49 | 50 | 52 | 53 | 54 | 56 | 58 | 71 | | 93 | 94 | 95 | 96 | 97 | 98 | 99 | 100 | 100a | Affinity |
|---|---|---|---|---|---|---|---|---|---|---|---|---|---|---|---|---|---|---|---|---|---|---|---|---|---|
| mVEGF-201 | T | T | S | N | G | | A | Y | S | S | N | Y | Y | R | | A | R | W | S | R | A | S | F | Y | >5uM |
| mVEGF-202 | T | T | G | T | D | | A | I | T | Y | D | S | Y | R | | A | K | A | G | D | R | E | G | Y | 200nM |
| mVEGF-203 | T | T | D | S | G | | G | R | S | Y | S | S | N | R | | A | K | W | P | W | Y | N | A | W | 700nM |
| | 28 | 30 | 31 | 32 | 33 | | 49 | 50 | 52 | 53 | 54 | 56 | 58 | 71 | | 93 | 94 | 95 | 96 | 97 | 98 | 99 | 100 | 100a | Affinity |
| hFc-10 | T | T | G | Y | W | | G | Y | S | Y | Y | G | T | R | | A | K | A | X | K | G | S | L | Y | 2uM |
| hFc-11 | T | T | G | N | A | | G | Y | S | | Y | G | T | R | | A | K | A | X | K | G | S | L | Y | >1uM |
| hFc-12 | T | T | D | N | Y | | | | | | | | | | | | | | | | | | | | |
| hFc-13 | T | T | S | S | G | | A | S | S | | Y | S | Y | R | | A | K | Y | X | A | R | E | G | X | |
| hFc-14 | T | T | S | T | W | | G | Y | N | | S | G | S | R | | A | K | W | R | T | S | W | K | Y | |
| hFc-15 | T | T | N | S | Y | | A | W | S | | N | G | Y | R | | A | X | T | A | G | W | A | R | Y | |
| hFc-16 | T | T | N | N | Y | | G | D | Y | | D | G | Y | R | | A | X | W | R | W | G | G | G | Y | |
| hFc-17 | T | T | N | T | W | | G | W | S | | N | G | Y | R | | A | R | Y | S | G | S | G | G | Y | |
| hFc-18 | T | T | G | N | Y | | G | R | S | | Y | N | Y | R | | A | X | G | X | T | W | S | R | A | |
| hFc-19 | T | T | S | N | D | | A | W | S | | Y | Z | Y | R | | A | R | R | S | R | W | S | R | | 40nM |
| hFc-20 | | | | | | (sequence not determined) | | | | | | | | | | | | | | | | | | | |
| hFc2 | | | | | | | | | | | | | | | | | | | | | | | | | ~2μM |

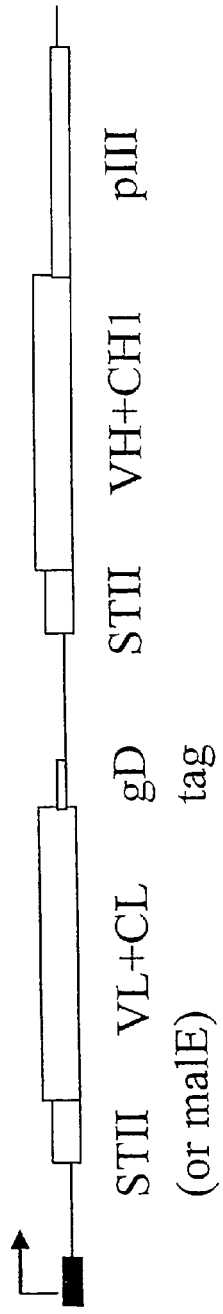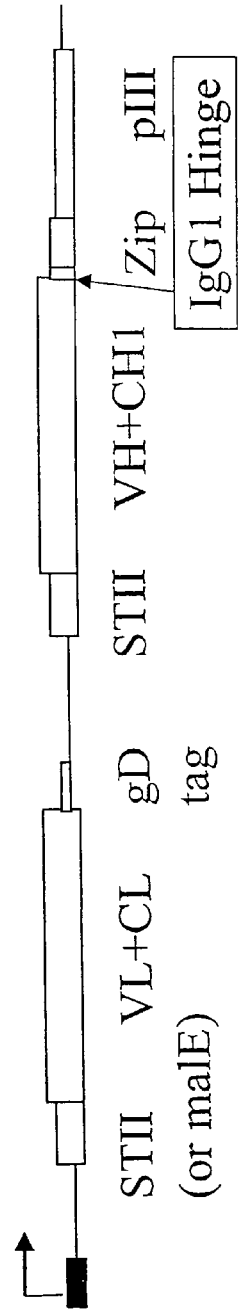
FIG. 34A-B

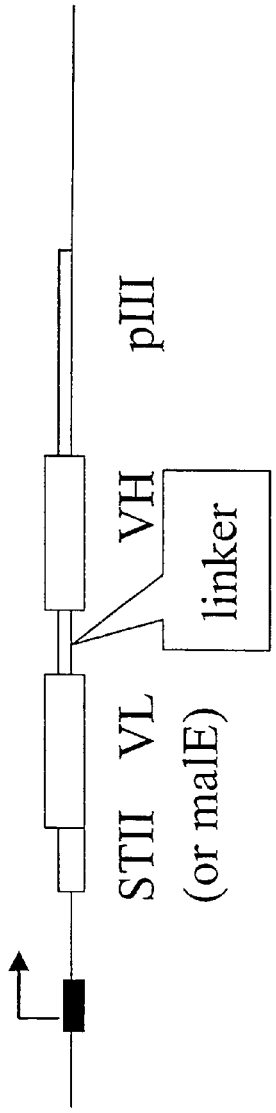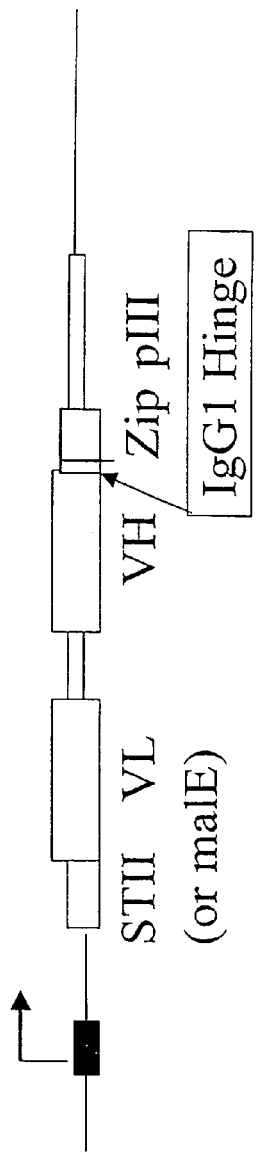
FIG. 34C-D

| | 28 | 30 | 31 | 32 | 33 | 50 | 52 | 53 | 54 | 56 | 58 | 95 | 96 | 97 | 98 | 99 | 100 | 100a | Affinity uM |
|---|---|---|---|---|---|---|---|---|---|---|---|---|---|---|---|---|---|---|---|
| mVEGF-109 | T | G | N | S | W | V | A | T | Y | Y | N | W | G | A | K | G | T | W | 0.13 |
| mVEGF-126 | N | A | D | S | A | Y | A | Y | D | Y | Y | W | G | W | T | T | N | G | 0.58 |
| mVEGF-127 | N | D | N | T | A | V | S | H | D | T | Y | W | G | W | E | T | D | G | 0.83 |
| mVEGF-130 | N | A | D | S | A | L | D | S | S | Y | D | S | R | A | G | Y | T | Y | 0.2 |
| mVEGF-136 | N | G | K | S | S | W | S | Y | E | A | A | T | S | W | S | K | P | Y | 0.45 |
| mVEGF-169 | N | T | A | Y | G | V | T | Y | D | D | T | W | G | W | E | A | N | W | 0.15 |
| mVEGF-173 | T | G | G | S | W | V | Y | T | Y | Y | D | W | G | A | G | G | T | W | 0.27 |
| mVEGF-174 | T | G | G | S | W | V | S | D | Y | Y | D | W | G | S | G | Y | T | W | 0.13 |
| mVEGF-176 | S | A | G | Y | D | L | A | Y | A | Y | N | A | A | A | W | A | S | Y | 0.7 |
| mVEGF-179 | T | T | E | S | G | V | Y | H | D | K | Y | W | W | Y | S | W | N | W | 0.13 |

```
3001 TTCCGGATCT GCATGCAGG ATGCTGCTGG CTACCCTGTG GAACACCTAC ATCTGTATTA ACGAAGCGCT GGCATTGACC CTGAGTGATT TTTCTCTGGT
     AAGGCCTAGA CGTAGCGTCC TACGACGACC GATGGGACAC CTTGTGGATG TAGACATAAT TGCTTCGCGA CCGTAACTGG GACTCACTAA AAAGAGACCA

3101 CCGGCGCAT CCATACCGCC AGTTGTTAC CCTCACAACG TTCCAGTAAC CGGGCATGTT AACCCGTATC AACCCGTATC GTGAGCATCC TCTCTCGTTT
     GGGCGGCGTA GGTATGGCGG TCAACAAATG GGAGTGTTGC AAGTCATTG GCCCGTACAA GTAGTAGTCA TTGGGCATAG CACTCGTAGG AGAGCAAA

3201 CATCGGTATC ATTACCCCCA TGAACAGAAA TTCCCCCTTA CACGGAGGCA TCAAGTGACC AAACAGGAAA AAACGGCCCT TAACATGGCC CGCTTTATCA
     GTAGCCATAG TAATGGGGGT ACTTGTCTTT AAGGGGGAAT GTGCCTCCGT AGTTCACTGG TTTGTCCTTT TTTGCCGGGA ATTGTACCGG GCGAATAGT

3301 GAAGCCAGAC ATTAACGGCT CTGGAGAAAC TCAACGAGCT GGACGCGGAT GAACAGGCAG ACATCGTGA ATCGCTTCAC GACCAGCTG ATGAGCTTA
     CTTCGGTCTG TAATTGCCGA GACCTCTTTG AGTTGCTCGA CCTGCGCCTA CTTGTCCGTC TGTAGACACT TAGCGAAGTG CTGGTGCGAC TACTCGAAAT

3401 CCGAGGATC AAACGTAAT ATTTTGTTAA AATCGCGTT AAATTTTGT TAAATCAGCT CATTTTTAA CCAATAGGCC GAAATCGGCA
     GGCGTCCTAG GCCTTAACA TTTGCAATTA TAAACAATT TTAAGCGCAA TTTAAAAACA ATTTAGTCGA GTAAAAAATT GGTTATCCGG CTTTAGCCGT

3501 AAATCCCTTA TAAATCAAA GAATAGACCG AGATAGGGT GAGTGTGTT CCAGTTTGGA ACAAGAGTCC ACTATTAAAG AACGTGACT CCAACGTCAA
     TTTAGGGAAT ATTTAGTTTT CTTATCTGGC TCTATCCCAA CTCACAACAA GGTCAAACCT TGTTCTCAGG TGATAATTC TTGCACCTGA GGTTGCAGTT

3601 AGGGCGAAAA ACCGTCTATC AGGGGCTATGG CCCACTACGT GAACCATCAC CGGAGAACGT TTTTTGGG TCGAGGTGCC GTAAAGCACT AAATCGGAAC
     TCCCGCTTTT TGGCAGATAG TCCCGATACC GGGTGATGCA CTTGGTAGTG GCCGCTTGCA CCGGCTTTC AAAAAACCCC AGCTCCACGG CATTTCGTGA TTTAGCCTTG

3701 CCTAAAGGGA GCCCCGATT TAGAGCTTGA CGGGAAAGC CGGAGAACGT GGGAGAAGA AAGCGAAAGG AGCGGGCGCT AGGGCGCTGG
     GGATTTCCCT CGGGGGCTAA ATCTCGAACT GCCCTTTCG CGGCTCTTCT CCCGCTCT TTCGCTTTCC TCGCCCCGGA TCCCGGACC

3801 CAAGTGTAGC GGTCACGCTG CGGCTAACCA CCACACCCGC CGCGCTTAAT AGGGCGGTC CGGATCCTGC CTCGGCCGTT TCGGTGATGA
     GTTCACATCG CCAGTGCGAC GCCGATTGGT GGTGTGGGCG GCGCGAATTA CGCGCCGATG TCCCGCCAG GCCTAGGACG GAGCCGCAA AGCCACTACT

3901 CGGTGAAAAC CTCTGACACA TGCAGCTCCC GGAGACGGTC ACAGCTTGTC TGTAAGGGA TGCCGGGAGC AGACAAGCCC GTCAGCGAGC GTCAGCGGGT
     GCCACTTTG GAGACTGTGT AGCTCGAGGG CCCTGCCAG TGTCGAACAG ACATTCGCCT ACGGCCCCTCG TCTGTTCGG CAGTCCCGCG CAGTCGCCCA

4001 GTTGGCGGGT GTCGGGGGCC AGCCATGACC CAGTCACGTA GCGATAGCGG AGTGTATACT GGCTTAACTA TGCGGATCA GAGCAGATTG TACTGAGAGT
     CAACCGCCCA CAGCCCCCGG TCGGTACTGG GTCAGTGCAT CGCTATCGCC TCACATATGA CCGAATTGAT ACGCCGTAGT CTTGTCTAAC ATGACTCTCA

4101 GCACCATATG CGGTGTGAAA TACCGCACAG ATGCGTAAGG AGAAAATACC GCATCAGGCG CTCTTCCGCT TCCTCGCTCA CTGACTCGCT GCGCTCGGTC
     CGTGGTATAC GCCACACTTT ATGGCGTGTC TACGCATTCC TCTTTTATGG CGTAGTCCGC GAGAAGGCGA AGGAGCGAGT GACTGAGCGA CGCAGCCAG

4201 GTTCGGCTGC GGCGAGCGGT ATCAGCTCAC TCAAAGCGGT AATACGGTT ATCCACAGAA TCAGGGGATA AGGCTCCGCC CCCCTGACGA GCATCACAAA GAACATGTGA GCAAAAGGCC
     CAAGCCGACG CCGCTCGCCA TAGTCGAGTG AGTTTCGCCA ATTATGCCAA TAGGTGTCTT AGTCCCCTAT TCCGAGGCGG GGGGACTGCT CGTAGTGTTT CTTGTACACT CGTTTTCCGG

4301 AGCAAAAGGC CAGGAACCGT AAAAAGGCCG CGTTGCTGGC CGTTTTCCAT AGGCTCCGCC CCCCTGACGA GCATCACAAA AATCGACGCT CAAGTCAGAG
     TCGTTTTCCG GTCCTTGGCA TTTTTCCGGC GCAACGACCG GCAAAAGGTA TCCGAGGCGG GGGGACTGCT CGTAGTGTTT TTAGCTGCGA GTTCAGTCTC

4401 GTGGCGAAAC CCGACAGGAC TATAAAGATA CCAGGCGTTT CCCCCTGGAA GCTCCCTCGT GCGCTCTCCT GTTCCGACCC CGGATACCTG CAAGTCAGAG
     CACCGCTTTG GGCTGTCCTG ATATTTCTAT GGTCCGCAAA GGGGGACCTT CGAGGGAGCA CGCGAGAGGA CAAGGCTGGG ACGGCGAATG GCCTATGGAC
```

FIG. 37D

```
4501  TCCGCCTTTC  TCCCTTCGGG  AAGCGTGGCG  CTTTCTCATA  GCTCACGCTG  TAGGTATCTC  AGTTCGGTGT  AGGTCGTTCG  CTCCAAGCTG  GGCTGTGTGC
      AGGCGGAAAG  AGGGAAGCCC  TTCCGCACCGC GAAAGAGTAT  CGAGTGCGAC  ATCCATAGAG  TCAAGCCACA  TCCAGCAAGC  GAGGTTCGAC  CCGACACACG

4601  ACGAACCCCC  CGTTCAGCGC  GACCGCTGCG  CCTTATCCGG  TTGAGTCCA   CTTGAGTCCA  ACCCGGTAAG  ACACGACTTA  TCGCCACTGG  CAGCAGCCAC
      TGCTTGGGGG  GCAAGTCGGG  CTGGCGACCGC GGAATAGGCC  ATTGATAGCA  GAACTCAGGT  TGGGCCATTC  TGTGCTGAAT  AGCGGTGACC  GTCGTCGGTG

4701  TGGTAACAGG  ATTAGCAGAG  CGAGGTATGT  AGGCGGTGCT  ACAGAGTTCT  TGAAGTGGTG  GCCTAACTAC  GGCTACACTA  GAAGGACAGT  ATTTGGTATC
      ACCATTGTCC  TAATCGTCTC  GCTCCATACA  TCCGCCACGA  TGTCTCAAGA  ACTTCACCAC  CGGATTGATG  CCGATGTGAT  CTTCCTGTCA  TAAACCATAG

4801  TGGCTCTGC   TGAAGCCAGT  TACCTTCGGA  AAAAGAGTTG  GTAGCTCTTG  ATCCGGCAAA  CAAACCACCG  CTGGAGCGG   TGGTTTTTT   GTTTGCAAGC
      ACGGAGACG   ACTTCGGTCA  ATGGAAGCCT  TTTTCTCACC  CATCGAGAAC  TAGGCCGTTT  GTTTGGTGGC  GACCATCGCC  ACCAAAAAAA  CAAACGTTCG

4901  AGCAGATTAC  GCGCAGAAAA  AAAGGATTCC  AAGAGATCC   TTTGATCTTT  TCTACGGGGT  CTGACGCTCA  GTGGAACGAA  AACTCACGTT  AAGGATTTT
      TCGTCTAATG  CGCGTCTTT   TTTCCTAAGG  TTCTTCTAGG  AAACTAGAAA  AGATGCCCCA  GACTGCGAGT  CACCTTGCTT  TTGACTGCAA  TTCCCTAAAA

5001  GGTCATGAGA  TTATCAAAAA  GGATCTTCAC  CTAGATCCTT  TTAAATTAAA  AATGAAGTTT  TAAATCAATC  TAAAGTATAT  ATGAGTAAAC  TTGGTCTGAC
      CCAGTACTCT  AATAGTTTTT  CCTAGAAGTG  GATCTAGGAA  AATTTAATTT  TTACTTCAAA  ATTTAGTTAG  ATTTCATATA  TACTCATTTG  AACCAGACTG

5101  AGTTACCAAT  GCTTAATCAG  TGAGGCACCT  ATCTCAGCGA  TCTGTCTATT  TCGTTCATCC  ATAGTTGCCT  GACTCCCCGT  CGTGTAGATA  ACTACGATAC
      TCAATGGTTA  CGAATTAGTC  ACTCCGTGGA  TAGAGTCGCT  AGACAGATAA  AGCAAGTAGG  TATCAACGGA  CTGAGGGGCA  GCACATCTAT  TGATGCTATG

5201  GGGAGGGCTT  ACCAGTGCTG  CCCAGTAGCC  CAATGATACC  GCGAGACCCA  CGCTCACCGG  CTCCAGATTT  ATCAGCAATA  AACCAGCCAG  CCGGAAGGGC
      CCCTCCCGAA  TGGTCACGAC  GGGTCAGCGA  GTTACTATGG  CGCTCTGGGT  GCGAGTGGCC  GAGGTCTAAA  TAGTCGTTAT  TTGGTCGGTC  GGCCTTCCCG

5301  CGAGCGCAGA  AGTGGTCCTG  CAACTTTATC  CGCCTCCATC  CAGTCTATTA  ATTGTTGCCG  GGAAGCTAGA  GTAAGTAGTT  CGCCAGTTAA  TAGTTTGCGC
      GCTCGGCGTCT TCACCAGGAC  GTTGAAATAG  GCGGAGGTAG  GTCAGATAAT  TAACAACGGC  CCTTCGATCT  CATTCATCAA  GCGGTCAATT  ATCAAAGCG

5401  AACGTTGTTG  CCATTGCTGC  AGGCATCGTG  GTGTCACGCT  CGTCGTTTGG  TATGCTTCA   TTCAGCTCCG  GTTCCCAACG  ATCAAGGCGA  GTTACATGAT
      TTGCAACAAC  GGTAACGACG  TCCGTAGCAC  CACAGTGCGA  GCAGCAAACC  ATACCGAAGT  AAGTCGAGGC  CAAGGGTTGC  TAGTTCCGCT  CAATGTACTA

5501  CCCCCATGTT  GTGCAAAAAA  GCGGTTAGCT  CCTTCGGTCC  TCCGATCGTT  GTCAGAAGTA  AGTTGGCCGC  AGTGTTATCA  CTCATGGTTA  TGGCAGCACT
      GGGGGTACAA  CACGTTTTTT  CGCCAATCGA  GGAAGCCAGG  AGGCTAGCAA  CAGTCTTCAT  TCAACCGGCG  TCACATAGT   GAGTACCAAT  ACCGTCGTGA

5601  GCATAATTCT  CTTACTGTCA  TGCCATCCGT  AAGATGCTTT  TCTGTGACTG  GTGAGTACTC  AACCAAGTCA  TTCTTGAGAAT AGTGTATGCG GCGACCGAGT
      CGTATTAAGA  GAATGACAGT  ACGGTAGGCA  TTCTACGAAA  AGACACTGAC  CACTCATGAG  TTGGTTCAGT  AAGACTCTTA  TCACATACGC  CGCTGGCTCA

5701  TGCCCTTGCC  CGGCGTCAAC  ACGGAGTAAT  ACCGCGCCAC  ATAGCAGAAC  TTTAAAAGTG  CTCATCATTG  GAAAACGTTC  TTCGGGGCGA  AAACTCTCAA
      ACGAGAACGG  GCCGCAGTTG  TGCCCTATTA  TGGCGCGGTG  TATCGTCTTG  AAATTTTCAC  GAGTAGTAAC  CTTTTGCAAG  AAGCCCCGCT  TTTGAGAGTT

5801  GGATCTTACC  GCTGTTGAGA  TCCAGTTCGA  TGTAACCCAC  TCGTGCACCC  AACTGATCTT  CAGCATCTTT  TACTTTCACC  AGCGTTTCTG  GGTGAGCAAA
      CCTAGAATGG  CGACAACTCT  AGGTCAAGCT  ACATTGGGTG  AGCACGTGGG  TTGACTAGAA  GTCGTAGAAA  ATGAAAGTGG  TCGCAAAGAC  CCACTCGTTT

5901  AACAGGAAGG  CAAAATGCCG  CAAAAAAGGG  AATAAGGGCG  ACACGGAAAT  GTTGAATACT  CATACTCTTC  CTTTTTCAAT  ATATTGAAG   CATTATCAG
      TTGTCCTTCC  GTTTTACGGC  GTTTTTCCC   TTATTCCCGC  TGTGCCTTTA  CAACTTATGA  GTATGAGAAG  GAAAAGTTA   TAATAACTTC  GTAAATAGTC
```

FIG. 37E

```
6001 GGTTATGTGTC TCATGAGCGG ATACATATTT GAATGTATTT AGAAAAATAA ACAAATAGGG GTTCCGCGCA CATTTCCCCG AAAAGTGCCA CCTGACGTCT
     CCAATAACAG AGTACTCGCC TATGTATAAA CTTACATAAA TCTTTTATTT TGTTTATCCC CAAGGCGCGT GTAAAGGGGC TTTTCACGGT GGACTGCAGA

6101 AAGAAACCAT TATTATCATG ACATTAACCT ATAAAAATAG GCGTATCACG AGGCCCTTTC GTCTTCAATA CAGGTAGACC TTTCGTAGAG ATGTACAGTG
     TTCTTTGGTA ATAATAGTAC TGTAATTGGA TATTTTTATC CGCATAGTGC TCCGGGAAAG CAGAAGTTAT GTCCATCTGG AAAGCATCTC TACATGTCAC

6201 AAATCCCGA AATTATACAC ATGACTGAAG GAAGGGAGCT CGTCATTCCC TGCCGGGTTA CGTCACCTAA CATCACTGTT ACTTTAAAAA AGTTCCACT
     TTTAGGGGCT TTAATATGTG TACTGACTTC CTTCCCTCGA GCAGTAAGGG ACGGCCCAAT GCAGTGGATT GTAGTGACAA TGAAATTTTT TCAAAGGTGA

6301 TGACACTTTG ATCCCTGATG GAAAACGCAT AATCTGGGAC AGTAGAAAGG GCTTCATCAT ATCAAATGCA AGTACAAAG AAATAGGGCT TCTGACCTGT
     ACTGTGAAAC TAGGGACTAC CTTTTGCGTA TTAGACCCTG TCATCTTTCC CGAAGTAGTA TAGTTTACGT TGCATGTTTC TTTATCCCGA AGACTGGACA

6401 GAAGCAACAG TCAATGGGCA TTTGTATAAG ACAAACTATC TCACACATCG ACAAACCAAT ACAATACAGG TAGACCTTTC GTAGAGATGT ACAGTGAAAT
     CTTCGTTGTC AGTACCCGT AAACATATTC TGTTTGATAG AGTGTGTAGC TGTTTGGTTA TGTTATGTCC ATCTGGAAAG CATCTCTACA TGTCACTTTA

6501 CCCCGAAATT ATACACATGA CTGAAGGAAG GGAGCTCGTC ATTCCCTGCC GGGTTACGTC ACCTAACATC ACTGTTACTT TAAAAAGTT TCCACTTGAC
     GGGGCTTTAA TATGTGTACT GACTTCCTCC CCTCGAGCAG TAAGGGACGG CCCAATGCAG TGGATTGTAG TGACAATGAA ATTTTTCAA AGGTGACTTG

6601 ACTTTGATCC CTGATGGAAA ACGCATAATC TGGGACAGTA GAAAGGGCTT CATCATATCA AATGCAAGT TACGTTGCA ACAAAGAAAT AGGGCTTCTG
     TGAAACTAGG GACTACCTTT TGCGTATTAG ACCCTGTCAT CTTTCCCGAA GTAGTATAGT TTACGTTCA ATGCAACGT TGTTTCTTTA TCCCGAAGAC

6701 ACCTGTGAAG CACTTGACAC TCACTTGACA CTGAACTGTG
     TGGACACTTC AGGTGAACTG TGAACTGTGAC

6701 CAACAGTCAA TGGGCATTTG TATAAGACAA ACTATCTCAC ACATCGACAA ACACAA TCTACAGGTA ACCAATACAA CATGTTACT GACCTTTGCT AGATGTAGTAC AGTGAAATCC
     GTTGTCAGTT ACCCGTAAAC ATATTCTGTT TGATAGAGTG TGTAGCTGTT AGATGTCCAT TGTTATGTCC CTGGAAAGCA TCTCTACATG TCACTTTAGG

6801 CCGAAATTAT ACACATGACT GAAGGAAGGG AGCTCGTCAT TCCCTGCCGG AAGGACGGCC CAATGCAGTG GATTGTAGT ACAATGAA TTT
     GGCTTTAATA TGTGTACTGA CTTCCTTCCC TCGAGCAGTA TCCGGCCGG GTTACGTCAC CTAACATC ACTGTTACT

6801 CCGAAATTAT ACACATGACT GAAGGAAGGG AGCTCGTCAT TCCCTGCCGG GTTACGTCAC CTAACATCAC TGTTACTTTA AAAAGTTTC CACTTGACAC
     GGCTTTAATA TGTGTACTGA CTTCCTTCCC TCGAGCAGTA AGGGACGGCC CAATGCAGTG GATTGTAGTG ACAATGAAAT TTTTCAAAG GTGAACTGTG

6901 TTTGATCCCT GATGGAAAAC GCATAATCTG GGACAGTAGA AAGGCTTCA TCATATCAAA TGCAACGTAC AGTTGCATG AAAGAAATAG GGCTTCTGAC CTGTGAAGCA
     AAACTAGGGA CTACCTTTTG CGTATTAGAC CCTGTCATCT TTCCCGAAGT AGTATAGTTT ACGTTGCATG TCAACGTAC TTTCTTTATC CCGAAGACTG GTGAACTGTG CACTTGACAC

7001 ACAGTCAATG GGCATTTGTA TAAGACAAAC ATCGACAAAC CAATACAAT
     TGTCAGTTAC CCGTAAACAT ATTCTGTTTG TAGCTGTTTG GTTATGTTAG
```

```
1901 CTCAGGACTC TACTCCCTCA GGAGGTGTGT GACCGTGCCC TCCAGCAGCT TGGGCACCCA GACTTACATC TGCAACGTGA ATCACAAGCC CAGCAACACC
     GAGTCCTGAG ATGAGGGAGT CGTCCACCA CTGGCACGGG AGGTCGTCGA ACCCGTGGGT CTGAATGTAG ACGTTGCACT TAGTGTTCGG GTCGTTGTGG
 180  S   G   L   Y   S   L   S   S   V   V   T   V   P   S   S   S   L   G   T   Q   T   Y   I   C   N   V   N   H   K   P   S   N   T

2001 AAGGTCGACA AGAAAGTTGA GCCCAAATCT TGTGACAAAA CTCACGCCCG CATGAAACAG CTAGAGGACA AGTCCGAAGA GCTACTCTCC AAGAACTACC
     TTCCAGCTGT TCTTTCAACT CGGGTTTAGA ACACTGTTTT GAGTGCGGGC GTACTTTGTC GATCTCCTGT TCAGCTTCT CGATGAGAGG TTCTTGATGG
 213  K   V   D   K   K   V   E   P   K   S   C   D   K   T   H   G   R   M   K   Q   L   E   D   K   V   E   E   L   L   S   K   N   Y   H
                                                  "end of heavy chain, start of leucine zipper 2101 ACCTAGAGA TGAAGTGGCA AGACTCAAAA CTCGAGTTTT TTGAACAGCC GGAGCGCGGA AAGCTTAGTG GCGGTGGCTC TGGTGGCGGT GATTTGATT ATGAAAGAT
     TGGATCTCTT ACTTCACCGT TCTGAGTTTT AGACTCAAAA AACTTGTCGG CCTCGCGCCT TTCGAATCGA CCGCCACCGAG ACCAAGGCCA CTAAAACTAA TACTTTCTA
 247  L   E   N   E   V   A   R   L   K   K   L   V   G   E   R   G   K   L   S   G   G   G   S   G   G   G   S   G   D   F   P   D   Y   E   K   M
     end of leucine zipper, start of gene III coat protein (267-end)^

2201 GGCAAACGCT AATAAGGGGG CTATGACCGA AAATGCCGAT GAAAACGGC TACAGTCTGA CGTAAAGGC CGCATTGATT CTGTCGCTAC TGATTACGGT
     CCGTTTGCGA TTATTCCCCC GATACTGGCT TTTACGGCTA CTTTTGCCCG ATGTCAGACT GCATTTCCG TTGAACTAA GACAGCGATG ACTAATGCCA
 280  A   N   K   G   A   M   T   E   N   A   D   E   N   A   L   Q   S   D   A   K   G   K   L   D   S   V   A   T   D   Y   G

2301 GCTGCTATCG ATGGTTTCAT TGGTGACGTT TCCGGCCTTG CTAATGGTAA GGTGATTTG CTGGCTCTAA TTCCCAAATG GCTCAAGTCG
     CGACGATAGC TACCAAAGTA ACCACTGCAA AGGCCGGAAC GATTACCATT CCACTAAAC GACCGAGATT AAGGGTTTAC CGAGTTCAGC
 313  A   A   I   D   G   F   I   G   D   V   S   G   L   A   N   G   N   G   A   T   G   D   F   A   G   S   N   S   Q   M   A   Q   V   G

2401 GTGACGGTGA TAATTACCT TTAATGAATA ATTTCGTCA ATATTTACCT TCCCTCCCTC AATGGTTGA ATGTCGCCCT TTTGTCTTTA GCGCTGTAA
     CACTGCCACT ATTAATGGA AATTACTTAT TAAAGCAGT TATAAATGGA AGGGACGGAG TTACCAACT TACAGCGGGA AAACAGAAAT CGCGACCATT
 347  D   G   D   N   S   P   L   M   N   N   F   R   Q   Y   L   P   S   L   P   Q   S   V   E   C   R   P   F   V   F   S   A   G   K

2501 ACCATATGAA TTTTCTATTG ATTGTGACAA AATAAACTTA TTCCGTGGTG TCTTTTGCGT AGAAAATATA CAACGGTGGA AATACATACA TAAAGATGC
     TGGTATACTT AAAAGATAAC TAACACTGTT TTATTTGAAT AAGGCACCAC AGAAAACGCA AGCTTTTATAT GTTGCCACCT TTATGTATGT ATTTCTACG
 380  P   Y   E   F   S   I   D   C   D   K   I   N   L   F   R   G   V   F   A   F   L   L   Y   V   A   T   F   M   Y   V   F   S   T

2601 TTTGCTAACA TACTGCGTAA TAAGGAGTCT TAAATCATGC AGTTCTTTG GCTAGCGCCG CCCTATACCT TGTCTGCTCC CCCGCGTTGC GTCGCGGTGC
     AAACGATTGT ATGACGCATT ATTCCTCAGA ATTTAGTACG TCAAGAAAAC CGATCGCGGC GGGATATGGA ACAGACGAGG GGGCGCAACG CAGCGCCACG
 413  F   A   N   I   L   R   N   K   E   S

2701 ATGAGGCCGG GCCACCTCGA CCTGAATGGA AGCCGGCGGC TCGCGGCCCG GCCGATTACC GGACTTACCT TGGAGCGATT GCCTAAGTGG TGAGGTTCTT AACTTCGGTT CGGAGAACTG
     TACTCCGGCC CGGTGGAGCT GGACTTACCT CGGCCGCCG AGCGCCGGGC CGGCTAATGG ACCTCGCTAA CGGATTCACC ACTCCAAGAA TTGAAGCCAA AGTTAAGAAC GCCTCTTGAC

2801 TGAATGCGCA AACCAACCCT TGGTTGGA TATCCATCGC GTCCAGCAGC TCCAGCAGCC AGGTCGTCGG GCACGGGCG CATTCGGGCG AGCGTTGGT CCTGGCCACG
     ACTTACGCGT TTGGTTGGGA ACCGGTCTTGT ATAGGTAGCG CAGGCGGTAG AGTTCGTCGG CGTGCGCCGC TCCAACCCA GTAGAGCCCG TCGACCGTGC GGACCGGTGC

2901 GGTGGCGCATG ATCGTGCTCC TGTCGTTGAG GACCCGGCTA GCTGGGGGGG GTTGCCTTAC TGGTTAGCAG AATGAATCAC CGATACGCGA GCGAACGTGA
     CCACCGCGTAC TAGCACGAGG ACAGCAACTC CTGGGCCGAT CGACCCCCCC CAACCGGAATG ACCAATCGTC TTACTTAGTG GCTATGCGCT CGCTTGCACT

3001 AGCGACTGCT GCTCAAAAC GTCTGCGACC TGAGCAACAA CATGAATGGT CGTGTTTCGT GAAGCCAAAG GCACAAAGCA TTTCAGACCT AAAGTCTGGA AACGGCGAAG TCAGCGCCCT
     TCGCTGACGA CGACGTTTG CAGACGCTGG ACTCGTTGTT GTACTTACCA GCACAAAGCA CTTCGGTTGT GCAGCCACCA GCAGGTCGCT GCAGCCACGA
```

FIG. 38C

```
3101 GCACCATTAT GTTCCGGATC TGCATCGCAG GATGCTGCTG GTACCCTGT  GGAACACCTA CATTCTATT  AACGAAGCGC TGGCATTGAC CCTGAGTGAT
     CGTGGTAATA CAAGGCCTAG ACGTAGGGTC CTACGACGAC CGATGGGACA CCTTGTGGAT GTAAGATAA  TTGCTTCGCG ACCGTAACTG GGACTCACTA

3201 TTTTCTCTGG TCCCGCCGCA TCCATACCGC CAGTGTTTA  CCCTCACAAC GTCCAGTGA  CCGGGCAATG TCATCATCAG TAACCGTAT  CGTGAGCATC
     AAAGAGACC  AGGGCGGCGT AGGTATGGCG GTCAACAAAT GGGAGTGTTG CAGGTCATT  GGCCCGTACA AGTAGTAGTC ATTGGGCATA GCACTCGTAG

3301 CTCTCTCGT  TCATCGGTAT CATTACCCCC ATGAACAGAA ATTCCCCCTT ACACGGAGGC ATCAAGTGAC CAAACAGGAA AAAACCGCCC TTAACATGGC
     GAGAGAGCAA AGTAGCCATA GTAATGGGGG TACTTGTCTT TAAGGGGGAA TGTGCCTCCG TAGTTCACTG GTTTGTCCTT TTTTGGCGGG AATTGTACCG

3401 CCGCTTTATC AGAAGGCAGA CATTAAGGCT TCTGAGAAA  CTCAACGAGC TGAACAGGCA GACATTGTG  AATCGCTTCA CGACCACGCT
     GGCGAAATAG TCTTCCGTCT GTAATTCGGA AGACCCTTT  GAGTTGCTCG ACTTGTCCGT CTGTACACAC TTAGCGAAGT GCTGGTGCGA

3501 GATGAGCTTT ACCGCAGGAT CCGGAAATTG TAAACGTTAA TATTTGTTA  AAATTGCGT  TAAATTTTG  TTAAATCAGC TCATTTTTTA ACCAATAGGC
     CTACTCGAAA TGGCCGTCCTA GGCCTTTAAC ATTTGCAATT ATAAACAAT  TTTAAGCGCA ATTTAAAAC  AATTTAGTCG AGTAAAAAAT TGGTTATCCG

3601 CGAAATCGCG AAAATCCCTT ATAAATCAAA AGATAGACC  GAGATAGGGT TGAGTGTTGT TCCAGTTTGG AACAAGAGTC CACTATTAAA GAACGTGAC
     GCTTTAGCCG TTTTAGGGAA TATTTAGTTT TCTTATCTGG CTCTATCCCA ACTCACACA  AGGTCAAACC TTGTTCTCAG GTGATAATTT CTTGCACCTG

3701 TCCAACGTCA AAGGGCGAAA AACCGTCTAT CAGGGCTATG TGAACCATCA CCCTAATCAA GTTTTTTGGG GTCGAGGTGC CGTAAGCAC
     AGGTTGCAGT TTCCCGCTTT TTGGCAGATA GTCCCGATAC ACTTGGTAGT GGGATTAGTT CAAAAAACCC CAGCTCCACG GCATTTCGTG

3801 TAAATCGGAA CCCTAAGGG  AGCCCCGAT  TTAGAGCTTG ACGGGAAAG  CCGGCAACG  TGGCGAAACG CCGGCGTTGC ACCGCTCTTT GGAAGGGAAG GGAAGGGCGC
     ATTTAGCCTT GGGATTCCC  TCGGGCCTA  AATCTCGAAC TGCCCCTTTC GGCCGTTGCG ACCGCTTGC  ACCGCTCTTT CCTTCCCTTC CCTTCCCGCG

3901 TAGGGCGTG  GCAAGTTAG  CGGTCACGCT GGCGTAACC  ACCACACCCG CGGCGCTTAA TGGCCGCGTA TGGGGCGCGT CAGGGCGCGT CCTCGGCGCT
     ATCCCGCGAC CGTTCACATC GCCAGTCGA  CGCCATTGG  TGGTGTGGGC GCCGCGAATT ACGCGGCGAT GTCCCGCGCA GTCCGCGCCA GGAGCGCGCA

4001 TTCGGTGATG ACGGTCAAA  CCCTGACAC  ATGCAGCTCC CGGACACGGT GCTCTGCCA  CACAGTTCGT CTGTAAGGCG ATGCGGGAG  CGTCAGGGCG
     AAGCCACTAC TGCCACTTTT GGAGACTGTG TACGTCGAGG GCCTCTGCCA GTGTCGAACA GACATTCCGC GACATTCGG  TACGCCCTC  GCAGTCCCGC

4101 CGTCAGCGGG TGTTGCGGCG TGTCGGGGCG CAGCCATGAC CCAGTCACGT AGCGATAGCG GAGTGTATAC TGGCTTAACT ATGCGGCATC AGAGCAGATT
     GCAGTCGCCC ACAACCGCCC ACAGCCCGC  GTCAGTAGCC GGTCAGTGA  TCGCTATCGC CTCACATATG ACCGAATTGA TACGCCGTAG TCTCGTCTAA

4201 GTACTGAGAG TGCACCATAT GGGGTGTGAA ATACCGCACA GATGCGTAAG GAGAAAATAC CGGCATCAGC GTCCTCCGC  TTCCTCGTC  ACTGACCGCC
     CATGACTCTC ACGTGGTATA CCCCACACTT TATGGCGTGT CTACGCATTC CTCTTTATG  GCCGTAGTCG CAGGAGGCG  AAGGAGCGAG TGACTGAGCG

4301 TGGCTCCGT  CGTTGCGGCTG CGGCGAGCGG TATCAGCTCA CTCAAAGGCG GTAATACGGT TATCCACAGA ATCAGGGGAT AACGCAGGAA AGAACATGTG
     ACGCGAGCCA GCAAGCGCA  GCCGCTCGCC ATAGTCGAGT GAGTTTCCGC CATTATGCCA ATAGGTGTCT TAGTCCCCTA TTGCGTCCTT TCTTGTACAC

4401 AGCAAAAGGC CAGCAAAAGG CCAGGAACCG TAAAAAGGCC GCGTTGCTG  CGTTTTTTCA TAGGCTCCG  CCCCCCTGACG AGCATCACAA AAATCGACGC
     TCGTTTTCCG GTCGTTTTCC GGTCCTTGGC ATTTTTCCGG CGCAACGACC GCAAAAAGT  ATCCGAGGC  GGGGGACTGC TCGTAGTGTT TTTAGCTGCG

4501 TCAAGTCAGA GGTGGCGAAA CCCGACAGGA CTATAAAGAT CCACAGGCGT TTCCCCCTGGA AGCTCCCTCG TGCGCTCTCC TGTTCCGACC CTGCCCGCTTA
     AGTTCAGTCT CCACCGCTTT GGGCTGTCCT GATATTTCTA GGTGTCCGCA AAGGGGACCT TCGAGGGAGC ACGCGAGAGG ACAAGGCTGG GACGGCGAAT
```

FIG. 38D

```
4601 CCGGATACCT GTCCGCCTTT CTCCCTTCGG GAAGCGTGGC GCTTTCTCAT AGCTCACGCT GTAGGTATCT CAGTTCGGTG TAGTCGTTC GCTCCAAGCT
     GGCCTATGGA CAGGCGGAAA GAGGGAAGCC CTTCGCACCG CGAAAGAGTA TCGAGTGCGA CATCCATAGA GTCAGCCCAC ATCCAGCAAG CGAGGTTCGA

4701 GGGTGTGTG CACGAACCCC CCGTTCAGCC CGACCGCTGC GCCTATTCCG GCCTTGAGTCC GTAACTAATCG TCTTGAGTCC AACCCGGTAA GACACGACTT ATCGCCACTG
     CCCGACACAC GTGCTTGGGG GGCAAGTCGG GCTGGCGACG CGGAATAGGC CGGATAGGC CATTGATAGC AGAACTCAGG TTGGGCCATT CTGTGCTGAA TAGCGGTGAC

4801 GCAGCAGCCA CTGGTAACAG GATTAGCAGA GCGAGGTATG TAGGCGGTGC AAATCGCCACG TACAGAGTTC TTTGAAGTGT GGCCTAACTA CCGGATTGAT GCCGATGTGA TCTTCCTGTC
     CGTCGTCCGT GACCATTGTC CTAATCGTCT CGCTCCATAC ATCCGCCACG ATGTCTCAAG AACTTCACCA CCGGATTGAT GCCGATGTGA TCTTCCTGTC

4901 TATTTGGTAT CTGCCTCTG CTGAAGCCAG TRACCTTCGG AAAAAGAGT GGTAGCTCTT GATCCGGCAA ACAAACCACC GCTGGTAGCG GTGGTTTTT
     ATAACCATA GACGCGAGAC GACTTCGGTC AATGGAAGCC TTTTTCTAA CCATCGAGAA CTAGGCCGTT TGTTTGGTGG CGACCATCGC CACCAAAAA

5001 TGTTTGCAAG CAGCAGATTA CGGGCAGAAA AAAAGGATCT CAAGAAGATC CTTTGATCTT TTCTACGGGG TCTGACGCTC AGTGGAACGA AAACTCACGT
     ACAAACGTTC GTCGTCTAAT GCCCGTCTTT TTTTTCCTAGA GTTCTTCTAG GAAACTAGAA AAGATGCCCC AGACTGCGAG TCACCTTGCT TTTGAGTGCA

5101 TAAGGGATTT TGGTCATGAG ATTATCAAAA AGGATCTTCA CCTAGATCCT TTTAAATTAA AAATGAAGTT TTAAATCAAT CTAAAGTATA TATGAGTAA
     ATTCCCTAAA ACCAGTACTC TAATAGTTTT TCCTAGAAGT GGATCTAGGA GAAACTAGAA AAATTTAATT TTTACTTCAA GATTCATAT ATACTCATT

5201 CTTGGTCTGA CAGTTACCAA TGCTTAATCA GTGAGGCACC TATCTCAGCG ATCGTGTCTAT TCCGTTCATC CATAGTTGCC TGACTCCCCG TCGTGTAGAT
     GAACCAGACT GTCAATGGTT ACGATTAGT CACTCCGTGG ATAGAGTCGC TAGACAGATA AAGCAGTAG GTATCAACGG ACTGAGGGGC AGCACATCTA

5301 AACTACGATA CGGGAGGGCT TACCATCTGG CCCCAGTGCT GCAATGATAC CGCGAGACCC AGCCTCACCG GCTCCAGATT TATCAGCAAT AAACCAGCCA
     TTGATGCTAT GCCCTCCCGA ATGGTAGACC CGTTACTATG CGTTACTATG GGCTCTGG TGCGAGTGG CGAGTCAA ATAGTCGTTA TTTGGTCGT

5401 GCCGAAGGG CCGAGCGGAG AAGTGGTCCT GCAACTTAT CGGGCCTCAT CCAGTCTATT AATTGTTGCC GGGAAGCTAG AGTAAGTAGT TCGCCAGTTA
     CGGCCTTCCC GGCTCGCGTC TTCACCAGGA CGTTGAAATA GGGCGAGTA TTAACACGG CCCTTCGATC TCATTCATCA AGCGGTCAT

5501 ATAGTTTGCG CAACGTTGTT GCCATTGCTA CAGGCATCGT GGTGTCACGC TCGTCGTTTG GTATCGTTTC ATTCAGCTCC GGTTCCAAC GATCAAGCCG
     TATCAAACGC GTTGCAACGA CGGTAACGAC GTCCGTAGCA AGCAGCAAAC CATACCGAAG TAAGTCGAGG CCAAGGGTTG CTAGTTCCGC

5601 AGTTACATGA TCCCCCATGT TGTGCAAAAA AGCGGTTAGC TCCTTCGGTC CTCCGATCGT TGTCAGAAGT AAGTTGGCCG CAGTGTATC ACTCATGGTT
     TCAATGTACT AGGGGGGTACA ACACGTTTT TCGCCAATCG AGGAAGCCAG ACAGTCTTCA TTCAACCGGC GTCACAATAG TGAGTACCAA

5701 ATGGCAGCAC TGCATAAATC TCTTACTGTC ATGCCATCCG TAAGATGCTT TTCTGTGACT CATAGCCAGAA CTTTAAAAGT GTCATCATT ATTCTGAGAA TAGTCTGATGC
     TACCGTCGTG ACGTATTAAG AGAATGACAG TACGGTAGGC ATTCTACGAA AAGACACTGA CCACCTATGA CTTTAAAAGT CTTTTGCAA CCTTTCAA TCGCAACGGC

5801 GGCGACCGAG TTGCTCTTGC CCGGCGTCAA CACGGAGTT ATCCGGCTGT GCCGCCAGT GTGCCTATT ATGGCGGGGT GTATCGTCTT GAAATTTTCA CCTTTGCAA GAAGCCCGC
     CGGCTTGGCTC AACGAGAACG GGCCGCAGTT GTGCCTCGAA CACGGCGTCA GCCCCTATT ATGGCGGGGT GTATCGTCTT GAAATTTTCA CCTTTGCAA GAAGCCCGC

5901 AAAACTCTCA AGGATCTTAC CGCTGTTGAG ATCCAGTTCG ATGTAACCCA CTCGTGCACC CAACTGATCT TCAGCATCTT TTACTTTCAC CAGCGTTTCT
     TTTTGAGAGT TCCTAGAATG GCGACAACTC TAGGTCAAGC TACATTGGGT GAGCACGTGG GTTGACTAGA AGTCGTAGAA AATGAAAGTG GTCGCAAGA

6001 GGGTGAGCAA AAACAGGAAG GCAAAATGCC GCAAAAAAGG GAATAAGGGC GACACGGAAA TGTTGAATAC ACACTTATG AGTATGAGA CCTTTTCAA TATTATTGAA
     CCCACTCGTT TTTGTCCTTC CGTTTTACGG CGTTTTTTCC CTTATTCCCG CTGTGCCTTT ACAACTTATG TCATACTCTT AGTATGAGA GGAAAAGTT ATAATAACTT
```

FIG. 38E

```
6101 GCATTATCA GGGTTATGT CTCATGAGCG GATACATATT TGAATGTATT TAGAAAATA AACAAATAGG GGTTCCGCGC ACATTTCCCC GAAAAGTGCC
     CGTAAATAGT CCCAATACA GAGTACTCGC CTATGTATAA ACTTACATAA ATCTTTTAT TTGTTTATCC CCAAGGCGCG TGTAAAGGGG CTTTTCACGG

6201 ACCTGACGTC TAAGAACCA TATAAAATA GACATTACAT TATAAAAATA GGGCCCTTT GAGGCCCTTT CGTCTTCAAT ACAGGTAGAC CTTTCGTAGA
     TGGACTGCAG ATTCTTGGT AATAATAGTA CTGTAATGTA ATATTTTTAT CCGACATAGTG CTCCGGGAAA GCAGAAGTTA TGTCCATCTG GAAAGCATCT

6301 GATGTACAGT GAAATCCCCG AAATATACA CATGACTGAA GGAAGGGAGC CCTTCCATCG TGTCATTCC CTGCCGGGT ACGTCACCTA ACATCACTGT TACTTAAAA
     CTACNTGTCA CTTTAGGGGC TTTAATATGT GTACTGACTT CCTTCCCTCG AGCAGTAAGG GACGGCCAA TGCAGTGGAT TGTAGTGACA ATGAAATTT

6401 AAGTTCCAC TTGACACTTT GATCCCTGAT GGAAACGCA TAATCTGGAA CAGTAGAAAG GGCTTCATCA TATCAAATGC AACGTACAAA GAAATAGGGC
     TTCAAAGGTG AACTGTGAAA CTAGGGACTA CCTTTGCGT ATTAGACCCT GTCATCTTC CCGAAGTAGT ATAGTTTACG TTGCATGTTT CTTTATCCCG

6501 TTCTGACCTG TGAAGCAACA GTCAATGGGC ATTTGTATAA GACAAACTAC CTCACACATC GACAAACCAA TACAATACAG GTAGACCTTT CGTAGAGATG
     AAGACTGGAC ACTTCGTTGT CAGTTACCCG TAAACATATT CTGTTTGATA GAGTGTGTAG CTGTTTGGTT ATGTTATGTC CATCTGAAA GCATCTCTAC

6601 TACAGTGAAA TCCCCGAAAT TATACACATG ACTGAAGGAA GGGAGCTCGT CATTCCCTGC CGGTTACGT CACCTAACAT CACTGTTACT TTAAAAAGT
     ATGTCACTTT AGGGGCTTTA ATATGTGTAC TGACTTCCTT CCCTCGAGCA GTAAGGGACG GCCAATGCA GTGGATTGTA GTGACAATGA AATTTTTCA

6701 TTCCACTGA CACTTTGATC CCTGATGGAA AACGCATAAT CTGGGACAGT GACCCTGTCA TCTTTCCCGA AGTAGTAGT TTTACGTTGC ATGTTTCTTT ATCCCGAAGA
     AAGGTGACT GTGAAACTAG GGACTACCTT TTGCGTATTA GACCCTGTCA TCTTTCCCGA AGTAGTAGT TTTACGTTGC ATGTTTCTTT ATCCCGAAGA

6801 GACCTGTGAA GCAACAGTCA ATGGGCATTT GTATAAGACA AACTACTCA CACATCACAC ACATCACCAG GATCACAGGT AGACCTTTCG TAGAGATGTA
     CTGGACACTT CGTTGTCAGT TACCCGTAAA CATATTCTGT TTGATAGAGT GTGTAGCTGT TAGATGTCA TCTGAAAGC TCTGAAAGC ATCTCTACAT

6901 CAGTGAAATC CCCGAAATTA TACACATGAC TGAAGGAAGG GAGCTCGTCA TTCCCTGCCG GTTACGTCA CCTAACATCA CTGTTACTTT AAAAAGTTT
     GTCACTTTAG GGGCTTTAAT ATGTGTACTG ACTTCCTTCC CCTCGAGCAG TAAGGGACGG CCAATGCAGT GGATTGTAGT GACAATGAAA TTTTTCAAA

7001 CCACTTGACA CTTTGATCCC TGATGGAAAA CGCATAATCT GGGACAGTAG CCCTGTCATC TTTCCCGAAG ATCATATCAA TGCAACGTA CAAGAAATA GGGCTTCTGA
     GGTGAACTGT GAAACTAGGG ACTACCTTTT GCGTATTAGA CCCTGTCATC TTTCCCGAAG TAGTAGTT TACGTTGCAT GTTTCTTTAT CCCGAAGACT

7101 CCTGAAGC AACAGTCAAT GGGCATTTGT ATAAGACAAA CTATCCACA CATCGACAAA CCAATACAAT C
     GGACACTTCG TTGTCAGTTA CCCGTAAACA TATTCTGTTT GATAGAGTGT GTAGTGTTT GGTATGTTA G
```

FIG. 38F

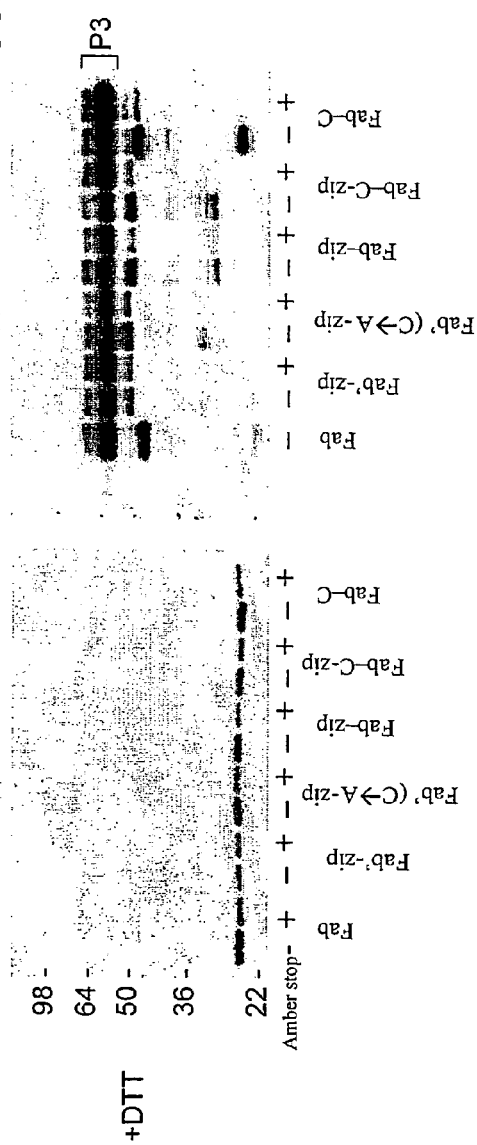
FIG. 41A  FIG. 41B  FIG. 41C  FIG. 41D

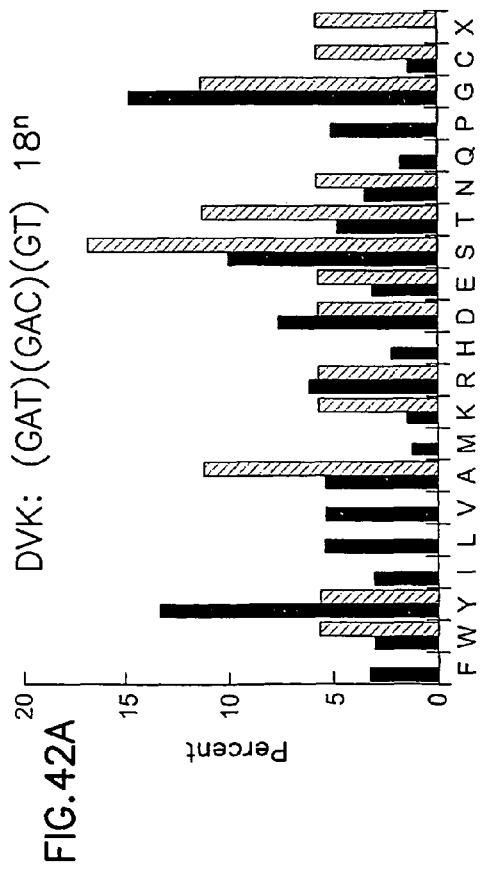
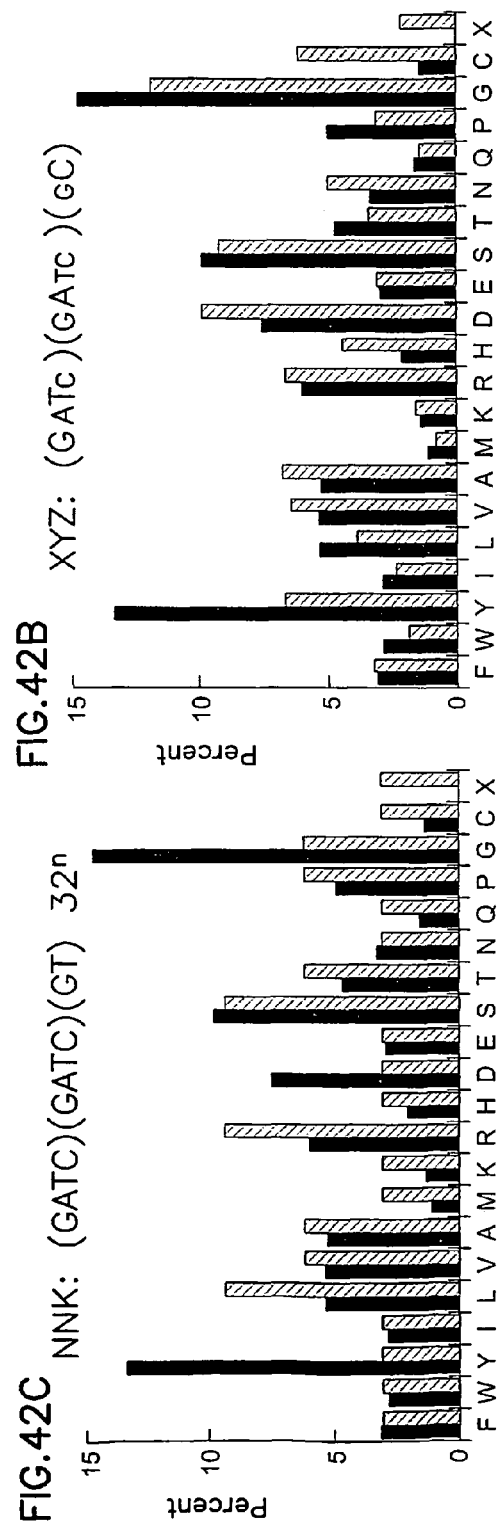
FIG.42A DVK: (GAT)(GAC)(GT) $18^n$
FIG.42B XYZ: (GATc)(GATc)(GC)
FIG.42C NNK: (GATC)(GATC)(GT) $32^n$

FIG. 43

Phage IC50: reliable as affinity estimates

Single-spot competition

SYNTHETIC ANTIBODY PHAGE LIBRARIES

CROSS REFERENCE TO RELATED APPLICATION

This is application is a continuation application of PCT/US03/17545, filed Jun. 3, 2003, pending, which claims benefit of application Ser. No. 60/436,656, filed on Apr. 16, 2003 and application Ser. No. 60/385,338, filed on Jun. 3, 2002, which applications are hereby incorporated by reference.

FIELD OF THE INVENTION

The invention generally relates to libraries of antibodies or antibody variable domains. The libraries include a plurality of different antibody variable domains generated by creating diversity in the CDR regions. In particular, diversity in CDR regions is designed to maximize the diversity while minimizing the structural perturbations of the antibody variable domain. The invention also relates to fusion polypeptides of one or more antibody variable domain and a heterologous protein such as a coat protein of a virus. The invention also relates to replicable expression vectors which include a gene encoding the fusion polypeptide, host cells containing the expression vectors, a virus which displays the fusion polypeptide on the surface of the virus, libraries of the virus displaying a plurality of different fusion polypeptides on the surface of the virus and methods of using those compositions. The methods and compositions of the invention are useful for identifying novel antibodies that can be used therapeutically or as reagents.

BACKGROUND

Phage display technology has provided a powerful tool for generating and selecting novel proteins that bind to a ligand, such as an antigen. Using the techniques of phage display allows the generation of large libraries of protein variants that can be rapidly sorted for those sequences that bind to a target antigen with high affinity. Nucleic acids encoding variant polypeptides are fused to a nucleic acid sequence encoding a viral coat protein, such as the gene III protein or the gene VIII protein. Monovalent phage display systems where the nucleic acid sequence encoding the protein or polypeptide is fused to a nucleic acid sequence encoding a portion of the gene III protein have been developed. (Bass, S., *Proteins*, 8:309 (1990); Lowman and Wells, *Methods: A Companion to Methods in Enzymology*, 3:205 (1991)). In a monovalent phage display system, the gene fusion is expressed at low levels and wild type gene III proteins are also expressed so that infectivity of the particles is retained. Methods of generating peptide libraries and screening those libraries have been disclosed in many patents (e.g. U.S. Pat. No. 5,723,286, U.S. Pat. No. 5,432,018, U.S. Pat. No. 5,580,717, U.S. Pat. No. 5,427,908 and U.S. Pat. No. 5,498,530).

The demonstration of expression of peptides on the surface of filamentous phage and the expression of functional antibody fragments in the periplasm of *E. coli* was important in the development of antibody phage display libraries. (Smith et al., Science (1985), 228:1315; Skerra and Pluckthun, Science (1988), 240:1038). Libraries of antibodies or antigen binding polypeptides have been prepared in a number of ways including by altering a single gene by inserting random DNA sequences or by cloning a family of related genes. Methods for displaying antibodies or antigen binding fragments using phage display have been described in U.S. Pat. Nos. 5,750,373, 5,733,743, 5,837,242, 5,969,108, 6,172,197, 5,580,717, and 5,658,727. The library is then screened for expression of antibodies or antigen binding proteins with desired characteristics.

Phage display technology has several advantages over conventional hybridoma and recombinant methods for preparing antibodies with the desired characteristics. This technology allows the development of large libraries of antibodies with diverse sequences in less time and without the use of animals. Preparation of hybridomas or preparation of humanized antibodies can easily require several months of preparation. In addition, since no immunization is required, phage antibody libraries can be generated for antigens which are toxic or have low antigenicity (Hogenboom, Immunotechniques (1988), 4:1-20). Phage antibody libraries can also be used to generate and identify novel human antibodies.

Human antibodies have become very useful as therapeutic agents for a wide variety of conditions. For example, humanized antibodies to HER-2, a tumor antigen, are useful in the diagnosis and treatment of cancer. Other antibodies, such as anti-INF-γ antibody, are useful in treating inflammatory conditions such as Crohn's disease. Phage display libraries have been used to generate human antibodies from immunized, non-immunized humans, germ line sequences, or naïve B cell Ig repertoires (Barbas & Burton, Trends Biotech (1996), 14:230; Griffiths et al., EMBO J. (1994), 13:3245; Vaughan et al., Nat. Biotech. (1996), 14:309; Winter EP 0368 684 B1). Naïve, or nonimmune, antigen binding libraries have been generated using a variety of lymphoidal tissues. Some of these libraries are commercially available, such as those developed by Cambridge Antibody Technology and Morphosys (Vaughan et al., Nature Biotech 14:309 (1996); Knappik et al., J. Mol. Biol. 296:57 (1999)). However, many of these libraries have limited diversity.

The ability to identify and isolate high affinity antibodies from a phage display library is important in isolating novel human antibodies for therapeutic use. Isolation of high affinity antibodies from a library is dependent on the size of the library, the efficiency of production in bacterial cells and the diversity of the library. See, for e.g., Knappik et al., J. Mol. Biol. (1999), 296:57. The size of the library is decreased by inefficiency of production due to improper folding of the antibody or antigen binding protein and the presence of stop codons. Expression in bacterial cells can be inhibited if the antibody or antigen binding domain is not properly folded. Expression can be improved by mutating residues in turns at the surface of the variable/constant interface, or at selected CDR residues. (Deng et al., J. Biol. Chem. (1994), 269:9533, Ulrich et al., PNAS (1995), 92:11907-11911; Forsberg et al., J. Biol. Chem. (1997), 272:12430). The sequence of the framework region is a factor in providing for proper folding when antibody phage libraries are produced in bacterial cells.

Generating a diverse library of antibodies or antigen binding proteins is also important to isolation of high affinity antibodies. Libraries with diversification in limited CDRs have been generated using a variety of approaches. See, for e.g., Tomlinson, Nature Biotech. (2000), 18:989-994. CDR3 regions are of interest in part because they often are found to participate in antigen binding. CDR3 regions on the heavy chain vary greatly in size, sequence and structural conformation.

Others have also generated diversity by randomizing CDR regions of the variable heavy and light chains using all 20 amino acids at each position. It was thought that using all 20 amino acids would result in a large diversity of sequences of variant antibodies and increase the chance of identifying novel antibodies. (Barbas, *PNAS* 91:3809 (1994); Yelton, D E, *J. Immunology*, 155:1994 (1995); Jackson, J. R., *J. Immunology*, 154:3310 (1995) and Hawkins, R E, *J. Mol. Biology*, 226:889 (1992)).

There have also been attempts to create diversity by restricting the group of amino acid substitutions in some CDRs to reflect the amino acid distribution in naturally occurring antibodies. See, Garrard & Henner, *Gene* (1993), 128: 103; Knappik et al., *J. Mol. Biol.* (1999), 296:57. However, these attempts have had varying success and have not been applied in a systematic and quantitative manner. Creating diversity in the CDR regions while minimizing the number of amino acid changes has been a challenge.

There is a need to isolate novel high affinity antibodies for clinical uses, for example therapeutic and diagnostic uses. To meet this need, there remains a need to generate a highly diverse library of antibody variable domains that can be expressed in high yield in cells. The invention described herein meets this need and provides other benefits.

SUMMARY OF INVENTION

The present invention provides methods of systematically and efficiently generating polypeptides comprising diversified CDRs. In one embodiment, the invention provides rapid identification of high affinity binders to target antigens that can also be readily produced in high yield in cell culture. Unlike conventional methods that propose that adequate diversity of target binders can be generated only if a particular CDR(s), or all CDRs should be diversified, and unlike conventional notions that adequate diversity is dependent upon the broadest range of amino acid substitutions (generally by substitution using all or most of the 20 amino acids), the invention provides methods capable of generating high quality target binders that are not necessarily dependent upon diversifying a particular CDR(s) or a particular number of CDRs of a reference polypeptide or source antibody. The invention is based, at least in part, on the surprising and unexpected finding that highly diverse libraries of high quality can be generated by systematic and selective substitution of a minimal number of amino acid positions with a minimal number of amino acid residues. Methods of the invention are convenient, based on objective and systematic criteria, and rapid. Candidate binder polypeptides generated by the invention possess high-quality target binding characteristics and have structural characteristics that provide for high yield of production in cell culture. The invention also provides unique dimerization/multimerization techniques that further enhance library characteristics, and the binding characteristics of candidate fusion polypeptide binders therein.

In particular, fusion polypeptides comprising diversified CDR(s) and a heterologous polypeptide sequence (preferably that of at least a portion of a viral polypeptide) are generated, individually and as a plurality of unique individual polypeptides that are candidate binders to targets of interest. Compositions (such as libraries) comprising such polypeptides find use in a variety of applications, in particular as large and diverse pools of candidate immunoglobulin polypeptides (in particular, antibodies and antibody fragments) that bind to targets of interest. The invention encompasses various aspects, including polypeptides generated according to methods of the invention, and systems, kits and articles of manufacture for practicing methods of the invention, and/or using polypeptides and/or compositions of the invention.

In another aspect, the invention provides methods of generating a polypeptide and polypeptides comprising at least one, two, three, four or all variant CDRs (i.e., selected from the group consisting of CDRs L1, L2, L3, H1 and H2 wherein said polypeptide is capable of binding a target antigen of interest, and wherein said CDR is not CDRH3, said method comprising: (a) identifying at least one (or any number up to all) solvent accessible and highly diverse amino acid position in a CDR; and (b) replacing the amino acid at the solvent accessible and high diverse position with a target amino acid (as defined herein) by generating variant copies of the CDR using a non-random codon set, wherein at least about 50%, 60%, 70%, 80%, 90% or all of the amino acids encoded by the non-random codon set are target amino acids (as defined herein) for that position in known antibody and/or naturally occurring variable domains.

In another aspect, the invention provides a method of generating a polypeptide comprising at least one, two, three, four, five or all of variant CDRs selected from the group consisting of H1, H2, H3, L1, L2 and L3, wherein said polypeptide is capable of binding a target antigen of interest, said method comprising: (a) with respect to L1, L2, L3, H1 and H2, (i) identifying at least one (or any number up to all) solvent accessible and highly diverse amino acid position in a reference CDR corresponding to the variant CDR; and (ii) replacing the amino acid at the solvent accessible and high diverse position with a target amino acid by generating variant copies of the CDR using a non-random codon set, wherein at least about 50%, 60%, 70%, 80%, 90% or all of the amino acids encoded by the non-random codon set are target amino acids for that position in known antibodies or antigen binding fragments (e.g. antibody variable domains)); and (b) with respect to H3, replacing at least one (or any number up to all) position with a variant amino acid.

In another aspect, the invention provides a method of generating a polypeptide comprising at least one, two, three, four, five or all of variant CDRs selected from the group consisting of L1, L2, L3, H1, H2 and H3, said method comprising: (a) substituting at least one (or any number up to all) solvent accessible and highly diverse amino acid position in L1, L2, L3, H1 and/or H2 with a variant amino acid which is encoded by a nonrandom codon set, wherein at least 50%, 60%, 70%, 80%, 90% or all of amino acids encoded by the nonrandom codon set are target amino acids for said amino acid position in known antibodies or antigen binding fragments; and (b) substituting at least one (or any number up to all) amino acid position in H3 with a variant amino acid.

Various aspects and embodiments of methods of the invention are useful for generating and/or using a pool comprising a plurality of polypeptides of the invention, in particular for selecting and identifying candidate binders to target antigens of interest. For example, the invention provides a method of generating a composition comprising a plurality of polypeptides, each polypeptide comprising at least one, two, three, four, five or all of variant CDRs selected from the group consisting of L1, L2, L3, H1, H2 and H3, said method comprising: (a) substituting at least one (or any number up to all) solvent accessible and highly diverse amino acid position in L1, L2, L3, H1 and/or H2 with a variant amino acid which is encoded by a nonrandom codon set, wherein at least 50%, 60%, 70%, 80%, 90% or all of amino acids encoded by the nonrandom codon set are target amino acids for said amino acid position in known antibodies or antigen binding fragments; and/or (b) substituting at least one (or any number up to all) amino acid position in H3 with a variant amino acid; wherein a plurality of polypeptides are generated by amplifying a template polynucleotide with a set of oligonucleotides comprising degeneracy in the sequence encoding a variant amino acid, wherein said degeneracy reflects the multiple codon sequences of the nonrandom codon set.

In another example, the invention provides a method comprising: constructing an expression vector comprising a polynucleotide sequence which encodes a light chain, a heavy chain, or both, the light chain and the heavy chain variable domains of a source antibody comprising at least one, two, three, four, five or all CDRs selected from the group consisting of CDR L1, L2, L3, H1, H2 and H3; and mutating at least one, two, three, four, five or all CDRs of the source antibody at at least one (or any number up to all) solvent accessible and highly diverse amino acid position using a nonrandom codon set, wherein at least about 50%, 60%, 70%, 80%, 90% or all of the amino acids encoded by the non-random codon set are target amino acids for that position in known and/or naturally occurring antibodies or antigen binding fragments (for e.g. antibody variable domains).

In another example, the invention provides a method comprising: constructing a library of phage or phagemid particles displaying a plurality of polypeptides of the invention; contacting the library of particles with a target antigen under conditions suitable for binding of the particles to the target antigen; and separating the particles that bind from those that do not bind to the target antigen.

In any of the methods of the invention described herein, a solvent accessible and/or highly diverse amino acid position can be any that meet the criteria as described herein, in particular any combination of the positions as described herein, for example any combination of the positions described for the polypeptides of the invention (as described in greater detail below). Suitable variant amino acids can be any that meet the criteria as described herein, for example variant amino acids in polypeptides of the invention as described in greater detail below.

Designing diversity in CDRH3 regions involves designing diversity in the length (preferably 7 to 19 amino acids) and/or in the sequence of CDRH3. In some embodiments, a portion of CDRH3 has a length ranging from 4 to 14 amino acids and has a variant amino acid at one or more positions encoded by codon sets that encode amino acids found in CDRH3 regions in known and/or naturally occurring antibody variable domains such as NNK, NNS, DVK, NVT, XYZ or mixtures thereof and another portion of the CDR, preferably at the C terminal end (e.g amino acid positions $X_2$, $X_3$, $X_4$, $X_5$ and $X_6$ shown below), has much more limited diversity. In some embodiments, the C terminal end has an amino acid sequence YAMDY or FDY.

One aspect of the invention provides a polypeptide, such as an antibody variable domain, comprising a variant CDRH3 that comprises an amino acid sequence:

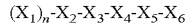

wherein $X_1$ is any naturally occurring amino acid encoded by a codon set of NNK, NNS, DVK, NVT, XYZ or is tryptophan or glycine or mixtures thereof, and n=4 to 14;

$X_2$ is any naturally occurring amino acid encoded by a codon set of KSG, DVK, DSG, NVT, KSG, NNS, XYZ, NNK or is tyrosine, phenylalanine, serine, alanine, glycine, leucine, or tryptophan;

$X_3$ is missing when $X_2$ is phenylalanine or leucine, or if present, is alanine, valine, aspartic acid or glycine;

$X_4$ is missing when $X_2$ is phenylalanine or leucine, or if present, is methionine;

$X_5$ is aspartic acid, alanine, valine, or glycine; and $X_6$ is tyrosine or valine.

A polypeptide or library of polypeptides with variant CDRH3 of the formula as shown above may be generated using any one or combination of the oligonucleotides illustrated in FIG. 4 and FIG. 43.

In one embodiment, CDRH3 comprises an amino acid sequence $(X_1)_n$-$X_2$-$X_3$-$X_4$-$X_5$-$X_6$, wherein $X_1$ is any naturally occurring amino acid encoded by a codon set of NNK, NNS, DVK, NVT, XYZ or tryptophan or glycine or mixtures thereof, and n=4 to 14; $X_2$ is any naturally occurring amino acid encoded by a codon set of KSG, DVK, DSG, NVT, KSG, NNS, XYZ, NNK or is tyrosine, phenylalanine, serine, glycine, alanine, leucine, or tryptophan; $X_3$ is alanine, valine, aspartic acid or glycine; $X_4$ is methionine; $X_5$ is aspartic acid, alanine, valine, or glycine; and $X_6$ is tyrosine or valine.

In some embodiments, n is preferably 4 and $X_1$ is any naturally occurring amino acid encoded by codon sets NNK, NNS or XYZ, $X_2$ is any naturally occurring amino acid encoded by KSG, NNK, XYZ or is tyrosine, $X_3$ is alanine, glycine or valine, $X_4$ is methionine, $X_5$ is aspartic acid and $X_6$ is tyrosine. A polypeptide or plurality of polypeptides comprising variant CDRH3 region in these embodiments can be generated using at least one or more than one of oligonucleotides F66e and F66f.

In some embodiments, n is preferably 6, and $X_1$ is any naturally occurring amino acid encoded by codon sets DVK, NVT, NNK, NNS or XYZ or tryptophan or glycine or mixtures thereof, $X_2$ is any naturally occurring amino acid encoded by DSG, DVK, KSG, NNK, XYZ or is tyrosine, glycine, serine, alanine or tryptophan, $X_3$ is alanine, $X_4$ is methionine, $X_5$ is aspartic acid and $X_6$ is tyrosine. In some embodiments, $X_1$ corresponds to amino acid position 95, $X_2$ corresponds to amino acid position 100a, A is in position 100b, M is in position 100c, D is in position 101 and Y is in position 102 of CDRH3 of antibody 4D5. A polypeptide or plurality of polypeptides comprising a variant CDRH3 region in these embodiments can be generated using at least one or more than one of oligonucleotides F63, F64, F65, F66, F165, F134, F135, F163a, F166, F167, F66a, F66b, F66a1, F66b1, F190f, and F190n.

In another embodiment, CDRH3 comprises an amino acid sequence $(X_1)_n$-$X_2$-$X_3$-$X_4$-$X_5$-$X_6$; wherein $X_1$ is any naturally occurring amino acid encoded by a codon set of NNK, NNS, DVK, NVT, XYZ or is tryptophan or glycine or mixtures thereof, and n=4 to 14; $X_2$ is leucine or phenylalanine; $X_3$ is missing; $X_4$ is missing; $X_5$ is aspartic acid, alanine, valine, or glycine; and $X_6$ is tyrosine or valine. In some embodiments, the variant CDRH3 comprises an amino acid sequence $(X_1)_n$-$X_2$-D-Y; wherein $X_1$ is any naturally occurring amino acid encoded by a codon set of NNK, NNS, DVK, NVT, XYZ or tryptophan or glycine or mixtures thereof, and n=4 to 14; $X_2$ is leucine or phenylalanine; D is aspartic acid and Y is tyrosine. In other embodiments, n is preferably 6 and $X_1$ corresponds to amino acid position 95, $X_2$ corresponds to amino acid position 100a, $X_5$ is in position 101 and $X_6$ is in position 102 of CDRH3 of antibody 4D5. A polypeptide or plurality of polypeptides comprising a variant CDRH3 region in these embodiments can be generated using at least one or more than one of oligonucleotides F171c, F171d, F171e, F171, F185, F186, F187, F185a, F185b, F185b1, F187a, F186a, F187b, and F187c.

In another aspect of the invention, methods and polypeptides, such as antibody variable domains, are provided comprising one, two or all variant CDRs selected from the group consisting of CDRH1, CDRH2 and CDRH3, wherein said variant CDRH3 comprises an amino acid sequence

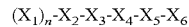

wherein $X_1$ is any naturally occurring amino acid encoded by a codon set of NNK, NNS, DVK, NVT, XYZ or is tryptophan or glycine or mixtures thereof, and n=4 to 14;

$X_2$ is any naturally occurring amino acid encoded by a codon set of KSG, DVK, DSG, NVT, KSG, NNS, XYZ, NNK or is tyrosine, phenylalanine, glycine, serine, alanine, leucine, or tryptophan;

$X_3$ is missing when $X_2$ is phenylalanine or leucine, or if present, is alanine, valine, aspartic acid or glycine;

$X_4$ is missing when $X_2$ is phenyalanine or leucine, or if present, is methionine;

$X_5$ is aspartic acid, alanine, valine, or glycine; and $X_6$ is tyrosine or valine;

and wherein the variant CDRH1 or CDRH2 or both comprise at least one variant amino acid in a solvent accessible and highly diverse amino acid position, wherein the variant amino acid is encoded by a nonrandom codon set, wherein at least about 50%, 60%, 70%, 80%, 90%, or all of the amino acids encoded by the nonrandom codon set are target amino for that position in known antibodies or antigen binding fragments (for e.g. antibody variable domains).

In some embodiments of any of the methods and polypeptides described herein, the position in H3 is any of positions 95 to 102 of antibody according to Kabat numbering system (e.g. antibody 4D5). For example, position 95 can have a variant amino acid encoded by codon set DVK, NVT, NNS, XYZ, NNK or is tryptophan; position 96 can be encoded by DVK, NVT, NNS, XYZ, or is glycine or tryptophan; position 97 can be encoded by DVK, NVT, NNS, XYZ, or is tryptophan; position 98 can be encoded by DVK, NVT, NNS, XYZ, or is tryptophan; position 99 can be encoded by DVK, NVT, NNS, XYZ; position 100 can be encoded by DVK, NVT, NNS, XYZ, or is tryptophan; position 100a can be encoded by DVK, DSG, KSG, NVT, NNS, XYZ, or can be tyrosine, glycine, serine, alanine, tryptophan, aspartic acid, methionine, phenylalanine, leucine, valine; position 100b can be encoded by DSG, KSG, XYZ or is alanine, tyrosine, glycine, valine, aspartic acid, methionine, or phenylalanine; Position 100c can be encoded by KSG, XYZ, or is methionine, phenylalanine, leucine, alanine, glycine, valine, tyrosine, aspartic acid; position 101 can be encoded by KSG, XYZ or is aspartic acid, methionine, alanine, valine, glycine, tyrosine, phenylalanine, leucine; and position 102 can be encoded by KSG or XYZ or is tyrosine, aspartic acid, methionine, alanine, valine, glycine. A polypeptide or plurality of polypeptides comprising a variant CDRH3 region in these embodiments can be generated using at least one or more than one of oligonucleotides illustrated in FIG. 4 and FIG. 43.

In another embodiment, methods and polypeptides, such as antibody variable domains, are provided that comprise at least one or all variant CDRL1, CDRL2 or CDRL3, wherein the variant CDRL1, CDRL2 or CDRL3 or mixtures thereof comprise at least one variant amino acid in a solvent accessible and highly diverse amino acid position, wherein the variant amino acid is encoded by a nonrandom codon set, wherein at least about 50%, 60%, 70%, 80%, 90% or all of the amino acids encoded by the nonrandom codon are target amino acids for that position in known antibodies or antigen binding fragments (for e.g. antibody variable domains).

Polypeptides of the invention can be in a variety of forms as long as the target binding function of the polypeptides is retained. In some embodiments, a polypeptide of the invention is a fusion polypeptide (ie. a fusion of two or more sequences from heterologous polypeptides). Polypeptides with diversified CDRs according to the invention can be prepared as fusion polypeptides to at least a portion of a viral coat protein for use in phage display. Viral coat proteins that can be used for display of the polypeptides of the invention comprise protein pIII, major coat protein pVIII, Soc (T4 phage), Hoc (T4 phage), gpD (lambda phage), pVI or variants thereof.

In some embodiments, in which the polypeptide with diversified CDRs is one or more antibody variable domains, the antibody variable domains can be displayed on the surface of the virus in a variety of formats including ScFv, Fab, $ScFv_2$, $F(ab')_2$ and $F(ab)_2$. For display of the polypeptides in bivalent manner, the fusion protein preferably includes a dimerization domain. The dimerization domain can comprise at least one of a dimerization sequence, and/or sequence comprising one or more cysteine residues. The dimerization domain is preferably linked to the C-terminal end of a heavy chain variable or constant domain. The structure of the dimerization domain can be varied depending on whether the antibody variable domain is produced as a fusion protein component with the viral coat protein component (without an amber stop codon after dimerization domain) or whether the antibody variable domain is produced predominantly without viral coat protein component (eg. with an amber stop codon after dimerization domain). When the antibody variable domain is produced predominantly as a fusion protein with viral coat protein component, one or more disulfide bonds and/or a single dimerization sequence provides for bivalent display. For antibody variable domains predominantly produced without being fused to a viral coat protein component (eg. with amber stop), it is preferable to have a dimerization domain comprising both a cysteine residue and a dimerization sequence.

In addition, optionally, a fusion polypeptide can comprise a tag that may be useful in purification, detection and screening such as FLAG, poly-his, gD tag, c-myc, fluorescence protein or B-galactosidase. In one embodiment, a fusion polypeptide comprises a light chain variable or constant domain fused to a polypeptide tag.

In another aspect of the invention, a polypeptide such as an antibody variable domain is obtained from a single source or template molecule. The source or template molecule is preferably selected or designed for characteristics such as good yield and stability when produced in prokaryotic or eukaryotic cell culture, and/or to accommodate CDRH3 regions of varying lengths. The sequence of the template molecule can be altered to improve folding and/or display of the variable domain when presented as a fusion protein with a phage coat protein component. For example, a source antibody may comprise the amino acid sequence of the variable domains of humanized antibody 4D5 (light chain variable domain, SEQ ID NO: 1; heavy chain variable domain, SEQ ID NO: 2). For example, in an antibody variable domain of a heavy or light chain, framework region residues can be modified or altered from the source or template molecule to improve folding, yield, display or affinity of the antibody variable domain. In some embodiments, framework residues are selected to be modified from the source or template molecule when the amino acid in the framework position of the source molecule is different from the amino acid or amino acids commonly found at that position in naturally occurring antibodies or in a subgroup consensus sequence. The amino acids at those positions can be changed to the amino acids most commonly found in the naturally occurring antibodies or in a subgroup consensus sequence at that position. In one embodiment, framework residue 71 of the heavy chain may be R, V or A. In another example, framework residue 93 of the heavy chain may be S or A. In yet another example, framework residue 94 may be R, K or T. In yet another example, framework residue 49 in the heavy chain may be alanine or glycine. In the light chain, the amino acid at position 66 may be arginine or glycine.

Methods of the invention are capable of generating a large variety of polypeptides comprising a diverse set of CDR sequences. For example, in one embodiment, the invention provides a polypeptide comprising at least one, two, three, four, five or all of variant CDRs selected from the group consisting of CDR L1, CDR L2, CDR L3, CDR H1, CDR H2 and CDR H3; wherein (i) each of CDRs L1, L2, L3, H1 and H2 has a variant amino acid in at least one (or any number up to all) solvent accessible and highly diverse amino acid position, wherein the variant amino acid is encoded by a non-random codon set, and wherein at least about 50%, 60%, 70%, 80%, 90% or all of the amino acids encoded by the non-random codon set are target amino acids for that position in known antibodies or antigen binding fragments; and (ii) variant CDR H3 has a variant amino acid in at least one (or any number up to all) amino acid position.

In another embodiment, the invention provides a polypeptide comprising: (a) at least one, two, three, four or all of variant CDRs selected from the group consisting of CDR L1, CDR L2, CDR L3, CDR H1 and CDR H2; wherein each of CDRs L1, L2, L3, H1 and H2 has a variant amino acid in at least one (or any number up to all) solvent accessible and highly diverse amino acid position, wherein the variant amino acid is encoded by a non-random codon set, and wherein at least about 50%, 60%, 70%, 80%, 90% or all of the amino acids encoded by the non-random codon set are target amino acids for that position in known antibodies or antigen binding fragments; and (b) a variant CDR H3 comprising a variant amino acid in at least one (or any number up to all) amino acid position.

In one embodiment, the invention provides a polypeptide comprising at least one, two, three, four or all of CDRs selected from the group consisting of CDRL1, CDRL2, CDRL3, CDRH1, CDRH2 and CDRH3, wherein: (a) CDRL1 comprises a variant amino acid in at least one, two, three, four or all of amino acid positions 28, 29, 30, 31 and 32; (b) CDRL2 comprises a variant amino acid in at least one or both of amino acid positions 50 and 53; (c) CDRL3 comprises a variant amino acid in at least one, two, three, four or all of amino acid positions 91, 92, 93, 94 and 96; (d) CDRH1 comprises a variant amino acid in at least one, two, three, four or all of amino acid positions 28, 30, 31, 32 and 33; (e) CDRH2 comprises a variant amino acid in at least one, two, three, four, five or all of amino acid positions 50, 52, 53, 54, 56 and 58; and (f) CDRH3 comprises a variant amino acid in at least one, two, three, four, five, six or all of amino acid positions corresponding to amino acid positions 95, 96, 97, 98, 99, 100, and 100a in antibody 4D5; wherein the amino acid positions correspond to the Kabat numbering system; and wherein each variant amino acid of (a) to (e) is encoded by a non-random codon set, and wherein at least about 50%, 60%, 70%, 80%, 90% or all of the amino acids encoded by the non-random codon set are target amino acids for that amino acid position in known antibodies or antibody fragments. In some embodiments of these polypeptides, at least one variant amino acid of (f) is encoded by codon set NNK, NNS, DVK, XYZ or NVT. In some embodiments, the polypeptide comprises an antibody heavy and/or light chain variable domain. In some embodiments, CDRH3 amino acid positions 100b, 100c, 101 and 102 are also varied.

In some embodiments, the invention provides a polypeptide comprising antibody light chain and heavy chain variable domains, wherein: (a) CDR L1 comprises a variant amino acid in at least one, two, three, four or all of amino acid positions 28, 29, 30, 31 and 32; (b) CDR L2 comprises a variant amino acid in at least one or both of amino acid positions 50 and 53; (c) CDR L3 comprises a variant amino acid in at least one, two, three, four or all of amino acid positions 91, 92, 93, 94 and 96; (d) CDR H1 comprises a variant amino acid in at least one, two, three, four or all of amino acid positions 28, 30, 31, 32 and 33; (e) CDR H2 comprises a variant amino acid in at least one, two, three, four, five or all of amino acid positions 50, 52, 53, 54, 56 and 58; and (f) CDR H3 comprises a variant amino acid in at least one, two, three, four, five, six or all of amino acid positions corresponding to amino acid positions 95, 96, 97, 98, 99, 100 and 100a in antibody 4D5; wherein the amino acid positions correspond to the Kabat numbering system; and wherein each variant amino acid of (a) to (e) is encoded by a non-random codon set, and wherein at least about 50%, 60%, 70%, 80%, 90% or all of the amino acids encoded by the non-random codon set are target amino acids for that amino acid position in known antibodies or antibody fragments. In some embodiments, the variant amino acid of (f) is encoded by codon set NNK, NNS, DVK, XYZ or NVT or is tryptophan or glycine or mixtures thereof.

In some embodiments, the invention provides a polypeptide comprising at least one, two, three, four, five or all of CDRs selected from the group consisting of CDR L1, CDR L2, CDR L3, CDR H1, CDR H2 and CDR H3, wherein: (a) CDR L1 comprises a variant amino acid in amino acid positions 28, 29, 30, 31 and 32; (b) CDR L2 comprises a variant amino acid in amino acid positions 50 and 53; (c) CDR L3 comprises a variant amino acid in amino acid positions 91, 92, 93, 94 and 96; (d) CDR H1 comprises a variant amino acid in amino acid positions 28, 30, 31, 32 and 33; (e) CDR H2 comprises a variant amino acid in amino acid positions 50, 52, 53, 54, 56 and 58; and (f) CDR H3 comprises a variant amino acid in amino acid positions corresponding to amino acid positions 95, 96, 97, 98, 99, 100 and 100a in antibody 4D5; wherein the amino acid positions correspond to the Kabat numbering system; and wherein each variant amino acid of (a) to (e) is encoded by a non-random codon set, and wherein at least about 50%, 60%, 70%, 80%, 90% or all of the amino acids encoded by the non-random codon set are target amino acids for that amino acid position in known antibodies or antibody fragments. In some embodiments, the variant amino acid of (e) is encoded by codon set NNK, NNS, DVK, XYZ or NVT or tryptophan or glycine or mixtures thereof.

In another embodiment, the invention provides a polypeptide comprising at least one, two, three, four, five or all of CDRs selected from the group consisting of CDRL1, CDRL2, CDRL3, CDRH1, CDRH2 and CDRH3, wherein: (a) CDRL1 comprises a variant amino acid in amino acid positions 28, 29, 30, 31 and 32, wherein: (i) the variant amino acid at position 28 is encoded by codon set RDT; (ii) the variant amino acid at position 29 is encoded by codon set RKT or RTT; (iii) the variant amino acid at position 30 is encoded by codon set RVW; (iv) the variant amino acid at position 31 is encoded by codon set RVW or ANW; (v) the variant amino acid at position 32 is encoded by codon set DHT or THT; (b) CDRL2 comprises a variant amino acid in amino acid positions 50 and 53, wherein: (i) the variant amino acid at position 50 is encoded by codon set KBG; (ii) the variant amino acid at position 53 is encoded by codon set AVC; (c) CDRL3 comprises a variant amino acid in amino acid positions 91, 92, 93, 94 and 96, wherein: (i) the variant amino acid at position 91 is encoded by codon set KMT or TMT or the combination of codon sets TMT and SRT; (ii) the variant amino acid at position 92 is encoded by codon set DHT or DMC; (iii) the variant amino acid at position 93 is encoded by codon set RVT or DHT; (iv) the variant amino acid at position 94 is encoded by codon set NHT or WHT; (v) the variant amino acid at position 96 is encoded by codon set YHT, HWT, HTT or TDK or the combination of codon sets YKG and TWT; (d) CDRH1 comprises a variant amino acid in amino acid positions 28, 30, 31, 32 and 33, wherein: (i) the variant amino acid at position 28 is encoded by codon set AVT or WCC or is threonine; (ii) the variant amino acid at position 30 is encoded by codon set RVM or AVT; (iii) the variant amino acid at position 31 is encoded by codon set RVM, RVT or RRT; (iv) the variant amino acid at position 32 is encoded by codon set WMY; (v) the variant amino acid at position 33 is encoded by codon set KVK, RNT, DMT, KMT, KGG or the combination of codon sets KMT and KGG; (e) CDRH2 comprises a variant amino acid in amino acid positions 50, 52, 53, 54, 56 and 58, wherein: (i) the variant amino acid at position 50 is encoded by codon set KDK or DBG or the combination of codon sets DGG and DHT; (ii) the variant amino acid at position 52 is encoded by codon set DHT or DMT; (iii) the variant amino acid at position 53 is encoded by codon set NMT or DMT; (iv) the variant amino acid at position 54 is encoded by codon set DMK, DMT or RRC; (v) the variant amino acid at position 56 is encoded by codon set DMK or DMT; (vi) the variant amino acid at position 58 is encoded by codon set DMT or DAC; and (f) CDRH3 comprises a valiant amino acid in amino acid positions 95, 96, 97, 98, 99, 100 and 100a, wherein: the variant amino acid at each of positions 95, 96, 97, 98, 99, 100 and 100a is encoded by codon set NNK, NNS, XYZ, DVK or NVT or tryptophan or glycine or mixtures thereof; wherein the amino acid positions correspond to the Kabat numbering system. In some embodiments, the polypeptide comprises an antibody heavy and/or light chain variable domain.

In some embodiments of polypeptides comprise a variant CDRH3, the variant CDRH3 has a variant amino acid in at least one, two, three, four, five, six or all of amino acid positions corresponding to amino acid position 95 to 100a of antibody 4D5 wherein amino acid positions correspond to the Kabat numbering system. In some embodiments, the variant amino acid of variant CDRH3 is an amino acid encoded by codon set NNK, XYZ, NNS, DVK or NVT or tryptophan or glycine or mixtures thereof. In some embodiments of polypeptides of the invention, the variant amino acid at position 100a of CDRH3 is encoded by NNS, NVT, DVK, XYZ, or is tyrosine, phenylalanine, glycine, serine, alanine, tryptophan, aspartic acid, methionine, or valine. In some embodiments, CDRH3 has a variant amino acid in amino acid positions corresponding to 100b, 100c, 101 and 102 of antibody 4D5.

In various embodiments of polypeptides of the invention, amino acids encoded by a non-random codon set preferably include (generally are) amino acids found at the corresponding position in preferably at least about 50%, 60% or 70% of known antibodies or antigen binding fragments. In some embodiments, said known antibodies or antigen binding fragments are as in "Sequences of Proteins of Immunological Interest" (5th edition) published by the U.S. National Institutes of Health. In some embodiments, said known antibodies or antigen binding fragments are as in the database of Kabat at http:immuno/bme/nwu/edu.

In some embodiments of polypeptides of the invention, a nonrandom codon set does not encode cysteine. In some embodiments, a non-random codon set does not include a stop codon.

As described herein, a variant CDR refers to a CDR with a sequence variance as compared to the corresponding CDR of a single reference polypeptide/source antibody. Accordingly, the CDRs of a single polypeptide of the invention preferably correspond to the set of CDRs of a single reference polypeptide or source antibody.

Polypeptides of the invention can be in a variety of forms as long as the target binding function of the polypeptides are retained. In some embodiments, a polypeptide of the invention is a fusion polypeptide (i.e., a fusion of two or more sequences from heterologous polypeptides). In some embodiments, the fusion polypeptide is fused to at least a portion of a viral coat protein, such as a viral coat protein selected from the group consisting of pIII, pVIII, Soc, Hoc, gpD, pVI, and variants thereof.

In some embodiments, a polypeptide of the invention comprises a light chain and a heavy chain antibody variable domain, wherein the light chain variable domain comprises at least 1, 2 or 3 variant CDRs selected from the group consisting of CDR L1, L2 and L3, and the heavy chain variable domain comprises at least 1, 2 or 3 variant CDRs selected from the group consisting of CDR H1, H2 and H3.

In some embodiments, a polypeptide of the invention is an ScFv. In some embodiments, it is a Fab fragment. In some embodiments, it is a $F(ab)_2$ or $F(ab')_2$. Accordingly, in some embodiments, a polypeptide of the invention further comprises a dimerization domain. In some embodiments, the dimerization domain is located between an antibody heavy chain or light chain variable domain and at least a portion of a viral coat protein. The dimerization domain can comprise at least one of a dimerization sequence, and/or sequence comprising one or more cysteine residues. The dimerization domain is preferably linked to the C-terminal end of a heavy chain variable or constant domain. The structure of the dimerization domain can be varied depending on whether the antibody variable domain is produced as a fusion protein component with the viral coat protein component (without an amber stop codon after dimerization domain) or whether the antibody variable domain is produced predominantly without viral coat protein component (eg. with an amber stop codon after dimerization domain). When the antibody variable domain is produced predominantly as a fusion protein with viral coat protein component, one or more disulfide bond and/or a single dimerization sequence provides for bivalent display. For antibody variable domains predominantly produced without being fused to a viral coat protein component (eg. with amber stop), it is preferable to have a dimerization domain comprising both a cysteine residue and a dimerization sequence. In some embodiments, heavy chains of the $F(ab)_2$ dimerize at a dimerization domain not including a hinge region. The dimerization domain may comprise a leucine zipper sequence (for example, a GCN4 sequence as depicted in SEQ ID NO: 3).

In some embodiments, a polypeptide of the invention further comprises a light chain constant domain fused to a light chain variable domain, which in some embodiments comprises at least one, two or three variant CDRs. In some embodiments of polypeptides of the invention, the polypeptide comprises a heavy chain constant domain fused to a heavy chain variable domain, which in some embodiments comprises at least one, two or three variant CDRs.

In some embodiments, a polypeptide of the invention comprises an antibody light chain variable domain, wherein the variant CDR is CDR L1 and the amino acid positions that are diversified are those positions that correspond to amino acid positions 28, 29, 30, 31 and 32. In some embodiments, the variant amino acid at position 28 is encoded by codon set RDT, the variant amino acid at position 29 is encoded by codon set RKT or RTT, the variant amino acid at position 30 is encoded by codon set RVW, the variant amino acid at position 31 is encoded by codon set RVW or ANW, and the variant amino acid at position 32 is encoded by codon set DHT or THT. In one embodiment, the amino acid at position 30 is asparagine or serine.

In another embodiment, a polypeptide of the invention comprises an antibody light chain variable domain, wherein the variant CDR is CDR L2, and the amino acid positions that are diversified are those that correspond to amino acid positions 50 and 53. In some embodiments, the variant amino acid at position 50 is encoded by KBG codon set, and the variant amino acid at position 53 is encoded by codon set AVC.

In another embodiment, a polypeptide of the invention comprises an antibody light chain variable domain, wherein the variant CDR is CDR L3, and the amino acid positions that are diversified are selected from those that correspond to amino acid positions 91, 92, 93, 94, or 96. In some embodiments, the variant amino acid at position 91 is encoded by codon set KMT, TMT or the combination of codon sets TMT and SRT, the variant amino acid at position 92 is encoded by codon set DHT or DMC, the variant amino acid at position 93 is encoded by codon set RVT or DHT, the variant amino acid at position 94 is encoded by codon set NHT or WHT, and the variant amino acid at position 96 is encoded by codon set YHT, HWT, HTT or the combination of codon sets YKG and TWT. In one embodiment, amino acid position 91 is histidine or serine.

In another embodiment, a polypeptide of the invention comprises a heavy chain variable domain, the variant CDR is CDR H1, and the amino acid positions that are diversified are those selected from amino acids positions corresponding to amino acids 28, 30, 31, 32 or 33. In some embodiments, the variant amino acid at position 28 is encoded by codon set AVT, WCC or is threonine, the variant amino acid at position 30 is encoded by codon set RVM or AVT, the variant amino acid at position 31 is encoded by codon set RVM, RVT or RRT, the variant amino acid at position 32 is encoded by codon set WMY, and the variant amino acid at position 33 is encoded by codon set KVK, RNT, DMT, KMT or the combination of codon sets KMT and KGG.

In another embodiment, a polypeptide of the invention comprises a heavy chain variable domain, the variant CDR is CDR H2, and the amino acid positions that are diversified are those selected from amino acid positions corresponding to amino acids 50, 52, 53, 54, 56 or 58. In some embodiments, the variant amino acid at position 50 is encoded by codon set KDK, DBG or the combination of codon sets DGG and DHT, the variant amino acid at position 52 is encoded by codon set DHT or DMT, the variant amino acid at position 53 is encoded by codon set NMT or DMT, the variant amino acid at position 54 is encoded by codon set DMK, DMT or RRC, the variant amino acid at position 56 is encoded by codon set DMK or DMT, and the variant amino acid at position 58 is encoded by codon set DMT or DAC.

In another embodiment, a polypeptide of the invention comprises a heavy chain variable domain, and the variant CDR is CDR H3 comprising a variant amino acid in at least one, two, three, four, five, six or all of amino acid positions 95 to 100a, wherein the variant amino acids is encoded by codon set NNK, NNS, XYZ, DVK or NVT or tryptophan or glycine or mixtures thereof.

In some instances, it may be preferable to mutate a framework residue such that it is variant with respect to a reference polypeptide or source antibody. For example, framework residue 71 of the heavy chain may be amino acid R, V or A. In another example, framework residue 93 of the heavy chain may be amino acid S or A. In yet another example, framework residue 94 of the heavy chain may be amino acid R, K or T or encoded by MRT. In yet another example, framework residue 49 of the heavy chain may be amino acid A or G. Framework residues in the light chain may also be mutated. For example, framework residue 66 in the light chain may be amino acid R or G.

As described herein, a variant CDR refers to a CDR with a sequence variance as compared to the corresponding CDR of a single reference polypeptide/source antibody. Accordingly, the CDRs of a single polypeptide of the invention preferably correspond to the set of CDRs of a single reference polypeptide or source antibody. Polypeptides of the invention may comprise any one or combinations of variant CDRs. For example, a polypeptide of the invention may comprise a variant CDRH1 and CDRH2. A polypeptide of the invention may comprise a variant CDRH1, variant CDRH2 and a variant CDRH3. In another example, a polypeptide of the invention may comprise a variant CDRH1, H2, H3 and L3. In another example, a polypeptide of the invention comprises a variant CDRL1, L2 and L3. Any polypeptide of the invention may further comprise a variant CDRL3. Any polypeptide of the invention may further comprise a variant CDRH3.

Polypeptides of the invention may be in a complex with one another. For example, the invention provides a polypeptide complex comprising two polypeptides, wherein each polypeptide is a polypeptide of the invention, and wherein one of said polypeptides comprises at least one, two or all of variant CDRs H1, H2 and H3, and the other polypeptide comprises a variant CDR L3. A polypeptide complex may comprise a first and a second polypeptide (wherein the first and second polypeptides are polypeptides of the invention), wherein the first polypeptide comprises at least one, two or three variant light chain CDRs, and the second polypeptide comprises at least one, two or three variant heavy chain CDRs. The invention also provides complexes of polypeptides that comprise the same variant CDR sequences. Complexing can be mediated by any suitable technique, including by dimerization/multimerization at a dimerization/multimerization domain such as those described herein or covalent interactions (such as through a disulfide linkage) (which in some contexts is part of a dimerization domain, for e.g. a dimerization domain may contain a leucine zipper sequence and a cysteine).

In another aspect, the invention provides compositions comprising polypeptides and/or polynucleotides of the invention. For example, the invention provides a composition comprising a plurality of any of the polypeptides of the invention described herein. Said plurality may comprise polypeptides encoded by a plurality of polynucleotides generated using a set of oligonucleotides comprising degeneracy in the sequence encoding a variant amino acid, wherein said degeneracy is that of the multiple codon sequences of the nonrandom codon set encoding the variant amino acid.

In one aspect, the invention provides a polynucleotide encoding a polypeptide of the invention as described herein. A polynucleotide of the invention may be a replicable expression vector comprising a sequence encoding a polypeptide of the invention.

In another aspect, the invention provides a library comprising a plurality of vectors of the invention, wherein the plurality of vectors encode a plurality of polypeptides.

The invention also provides a host cell comprising any of the polynucleotides and/or vectors of the invention described herein.

In another aspect, the invention provides a virus or viral particle (such as phage or phagemid particles) displaying a polypeptide of the invention on its surface. The invention also provides a library comprising a plurality of the viruses or viral particles of the invention, each virus or virus particle displaying a polypeptide of the invention. A library of the invention may comprise any number of distinct polypeptides (sequences), preferably at least about $1\times10^8$, preferably at least about $1\times10^9$, preferably at least about $1\times10^{10}$ distinct sequences.

The invention also provides libraries containing a plurality of polypeptides, wherein each type of polypeptide is a polypeptide of the invention as described herein.

In another aspect of the invention provides methods for selecting for high affinity binders to specific target antigens such as growth hormone, bovine growth hormone, insulin like growth factors, human growth hormone including n-methionyl human growth hormone, parathyroid hormone, thyroxine, insulin, proinsulin, amylin, relaxin, prorelaxin, glycoprotein hormones such as follicle stimulating hormone (FSH), leutinizing hormone (LH), hemapoietic growth factor, fibroblast growth factor, prolactin, placental lactogen, tumor necrosis factors, mullerian inhibiting substance, mouse gonadotropin-associated polypeptide, inhibin, activin, vascular endothelial growth factors, integrin, nerve growth factors such as NGF-beta, insulin-like growth factor-I and II, erythropoietin, osteoinductive factors, interferons, colony stimulating factors, interleukins, bone morphogenetic proteins, LIF, SCF, FLT-3 ligand and kit-ligand.

The methods of the invention provide for libraries of polypeptides (eg. antibody variable domains) with one or more diversified CDR regions. These libraries are sorted (selected) and/or screened to identify high affinity binders to a target antigen. In one aspect, polypeptide binders from the library are selected for binding to target antigens, and for affinity. The polypeptide binders selected using one or more of these selection strategies, then, may be screened for affinity and/or for specificity (binding only to target antigen and not to non-target antigens).

A method comprises generating a plurality of polypeptides with one or more diversified CDR regions, sorting the plurality of polypeptides for binders to a target antigen by contacting the plurality of polypeptides with a target antigen under conditions suitable for binding; separating the binders to the target antigen from those that do not bind; isolating the binders; and identifying the high affinity binders. The affinity of the binders that bind to the target antigen can be determined using competition ELISA such as described herein. Optionally, the polypeptides can be fused to a polypeptide tag such as gD, poly his or FLAG which can be used to sort binders in combination with sorting for the target antigen.

Another embodiment provides a method of selecting for an antibody variable domain that binds to a target antigen from a library of antibody variable domain comprising: a) generating a library of replicable expression vectors comprising a plurality of polypeptides of any of claims 1 to 9 and 17 to 44; b) isolating polypeptide binders to a target antigen from the library by contacting the library with an immobilized target antigen under conditions suitable for binding; c) separating the polypeptide binders in the library from the nonbinders and eluting the binders from the target antigen; d) amplifying the replicable expression vectors having the polypeptide binders; and e) optionally, repeating steps a-d at least twice.

The method may further comprise: f) incubating the amplified replicable expression vectors comprising polypeptide binders with a concentration of labelled target antigen in the range of 0.1 nM to 1000 nM under conditions suitable for binding to form a mixture; g) contacting the mixture with an immobilized agent that binds to the label on the target antigen; h) separating the polypeptide binders bound to labelled target antigen and eluting the polypeptide binders from the labelled target antigen; i) amplifying replicable expression vectors comprising the polypeptide binders; and j) optionally, repeating steps f) to i) at least twice, using a lower concentration of labelled target antigen each time. Optionally, the method may comprise adding an excess of unlabelled target antigen to the mixture and incubating for a period of time sufficient to elute low affinity binders from the labelled target antigen.

Another embodiment provides a method of isolating or selecting for high affinity binders to a target antigen from a library of replicable expression vectors comprising: a) generating a library of replicable expression vectors comprising a plurality of polypeptides of any of claims 1-9 and 17-44; b) contacting the library with a target antigen in a concentration of at least about 0.1 nM to 1000 nM to isolate polypeptide binders to the target antigen; c) separating the polypeptide binders from the target antigen and amplifying the replicable expression vector comprising the polypeptide binders; d) optionally, repeating steps a-c at least twice, each time with a lower concentration of target antigen to isolate polypeptide binders that bind to lowest concentration of target antigen; e) selecting the polypeptide binder that binds to the lowest concentration of the target antigen for high affinity by incubating the polypeptide binders with several different dilutions of the target antigen and determining the IC50 of the polypeptide binder; and f) identifying a polypeptide binder that has an affinity for the target antigen of about 0.1 nM to 200 nM.

Another embodiment provides an assay for selecting polypeptide binders from a library of replicable expression vectors comprising a plurality of polypeptides of any of claims 1 to 9 and 17 to 44 comprising: a) contacting the library with a concentration of labelled target antigen in a concentration range of 0.1 nM to 1000 nM, under conditions suitable for binding to form a complex of a polypeptide binders and the labelled target antigen; b) isolating the complexes and separating the polypeptide binders from the labelled target antigen; c) amplifying the replicable expression vector comprising the polypeptide binders; d) optionally, repeating steps a-c at least twice, each time using a lower concentration of target antigen. Optionally, the method may further comprise adding an excess of unlabelled target antigen to the complex of the polypeptide binder and target antigen. In a preferred embodiment, the steps of the method are repeated twice and the concentrations of target in the first round of selection is about 100 nM to 250 nM, and in the second round of selection is about 25 nM to 100 nM, and in the third round of selection is about 0.1 nM to 25 nM.

The invention also includes a method of screening a library of replicable expression vectors comprising a plurality of polypeptides of any of claims 1 to 9 and 17-44 comprising: a) incubating first a sample of the library with a concentration of a target antigen under conditions suitable for binding of the polypeptides to the target antigen; b) incubating a second sample of the library without a target antigen; c) contacting each of the first and second sample with immobilized target antigen under conditions suitable for binding of the polypeptide to the immobilized target antigen; d) detecting the amount of the bound polypeptides to immobilized target antigen for each sample; e) determining the affinity of the polypeptide for the target antigen by calculating the ratio of the amounts of bound polypeptide from the first sample over the amount of bound polypeptide from the second sample.

The libraries generated as described herein may also be screened for binding to a specific target and for lack of binding to nontarget antigens. In one aspect, another embodiment provides a method of screening for an antibody variable domain that binds to a specific target antigen from a library of antibody variable domain comprising: a) generating a library of replicable expression vectors comprising a plurality of polypeptides of any of claims 1 to 9 and 17 to 44; b) contacting the library with a target antigen and at least one nontarget antigen under conditions suitable for binding; c) separating the polypeptide binders in the library from the nonbinders; d) identifying the binders that bind to the target antigen and do not bind to the nontarget antigen; e) eluting the binders from the target antigen; and f) amplifying the replicable expression vectors comprising the polypeptide binder that bind to a specific antigen.

Combinations of any of the sorting/selection methods described above may be combined with the screening methods. For example, in one embodiment, polypeptide binders are first selected for binding to immobilized target antigen. Polypeptide binders that bind to the immobilized target antigen can then be amplified and screened for binding to the target antigen and for lack of binding to nontarget antigens. Polypeptide binders that bind specifically to the target antigen are amplified. These polypeptide binders can then selected for higher affinity by contact with a concentration of a labelled target antigen to form a complex, wherein the concentration range of labelled target antigen is from about 0.1 nM to about 1000 nM, the complexes are isolated by contact with an agent that binds to the label on the target antigen. The polypeptide binders are then eluted from the labeled target antigen and optionally, the rounds of selection are repeated, each time a lower concentration of labelled target antigen is used. The high affinity polypeptide binders isolated using this selection method can then be screened for high affinity using for example, the solution phase ELISA assay as described in Example 8 or the spot competition ELISA assay as described in Example 9.

BRIEF DESCRIPTION OF THE FIGURES

FIG. 1 shows the frequency of amino acids (identified by single letter code) in human antibody light chain CDR sequences from the Kabat database. The frequency of each amino acid at a particular amino acid position is shown starting with the most frequent amino acid at that position at the left and continuing on to the right to the least frequent amino acid. The number below the amino acid represents the number of naturally occurring sequences in the Kabat database that have that amino acid in that position.

FIG. 2 shows the frequency of amino acids (identified by single letter code) in human antibody heavy chain CDR sequences from the Kabat database. The frequency of each amino acid at a particular amino acid position is shown starting with the most frequent amino acid at that position at the left and continuing on to the right to the least frequent amino acid. The number below the amino acid represents the number of naturally occurring sequences in the Kabat database that have that amino acid in that position. Framework amino acid positions 71, 93 and 94 are also shown.

FIG. 3 shows illustrative embodiments of suitable codon set design for amino acid positions in CDRL1, CDRL2, CDRL3, CDRH1 and CDRH2. The codon sets are identified by three capital letters in italics and are bracketed by < and >, e.g. <RDT>. The amino acids encoded by that codon set are indicated by single letter code under the column labelled Diversity<DNA codon>. The column labelled Natural Diversity shows the most commonly occurring amino acids at those positions in the naturally occurring antibody variable domains in the Kabat database. The % good is the % of amino acids that are encoded by the codon set that are target amino acids for that position. The % covering is the % of natural occurring antibodies in the Kabat database that have the amino acids encoded by the codon set at that position.

FIGS. 4A & B & C show illustrative embodiments of designed diversity in CDRH3. The different oligonucleotides encode for diversity at amino acid positions in CDRH3 as well as diversity in sequence length. The oligonucleotides are identified as F59, F63, and F64 etc in the left hand column. The amino acid sequence at each amino acid position for CDRH3 for each oligonucleotide is shown. The CDRH3 sequence in the source antibody 4D5 is shown across the top: $S_{93}$, $R_{94}$, $W_{95}$, $G_{96}$, $G_{97}$, $D_{98}$, $G_{99}$, $F_{100}$, $Y_{100a}$, $A_{100c}$, $M_{100c}$, $D_{101}$, and $Y_{102}$. Amino acid positions 93 and 94 are considered framework positions. In some embodiments, certain positions may have a fixed amino acid shown in single letter code, e.g. position 93 is S (serine); amino acid position 94 may be R/K/T (arginine/lysine/threonine); amino acid position 100a may be G/S/A/W (glycine/serine/alanine/tryptophan). Other amino acid positions are diversified using codon sets identified by three capital letters in italics, e.g. DVK, NVT, DSG, KSG. The length of the CDRH3 is indicated at the right column. The lengths of the CDRH3 regions varied from 7 to 15. The diversity of the library generated with the strategy shown for each oligonucleotide is also shown on the right. A single oligonucleotide may be used or oligonucleotides may be pooled to generate a library. (SEQ ID NOs:10-13, SEQ ID NOs:31-76 and SEQ ID NO:162)

FIG. 5 shows an illustrative embodiment of designed diversity for CDR's L1 and L2 and L3. The codon sets for each position is shown. The amino acids (in single letter code) encoded by the codon set at each position are shown below in a column. The diversity generated with this design results in a library with $2.9 \times 10^9$ sequences.

FIG. 6 shows an illustrative embodiment of designed diversity using nonrandom codon sets for amino acid positions in CDRL1, L2 and L3. The amino acids (in single letter code) encoded by the codon set at each position are shown below in a column. The diversity generated with this design results in $6.1 \times 10^8$ sequences.

FIG. 7 shows an illustrative embodiment of designed diversity using nonrandom codon sets at amino acid positions in CDRL3. The amino acids (in single letter code) encoded by the codon set at each position are shown below in a column.

FIG. 8 shows an illustrative embodiment of designed diversity using nonrandom codon sets for CDRs L1, L2 and L3. At some positions, the codon set may encode an increased proportion of one or more amino acids. For example, at position 93 in CDRL3, codon set RVM encodes an increased proportion of alanine (A2), glycine (G2) and threonine (T2). The amino acids (in single letter code) encoded by the codon set at each position are shown below in a column.

FIG. 9 shows an illustrative embodiment of designed diversity using nonrandom codon sets at amino acid positions in CDRH1, H2 and H3. The amino acids (in single letter code) encoded by the codon set at each position are shown below in a column.

FIG. 10 shows an illustrative embodiment of designed diversity using nonrandom codon set at amino acid positions in CDRs H1, H2 and H3. The amino acids (in single letter code) encoded by the codon set at each position are shown below in a column.

FIG. 11 shows an illustrative embodiment of designed diversity using nonrandom codon sets at amino acid positions in CDRs in H1, H2, H3 and L3. The amino acids (in single letter code) encoded by the codon set at each position are shown below in a column.

FIG. 12 shows an illustrative embodiment of designed diversity using nonrandom codon sets at amino acid positions in CDRs in H1, H2, H3 and L3. The amino acids (in single letter code) encoded by the codon set at each position are shown below in a column.

FIG. 13 shows an illustrative embodiment of designed diversity using nonrandom codon sets at amino acid positions in CDRs H1, H2, H3 and L3. The amino acids (in single letter code) encoded by the codon set at each position are shown below in a column.

FIGS. 14 A & B shows nucleotide sequence of Ptac promoter driver cassette for display of ScFv (SEQ ID NO: 23). Sequences encoding malE secretion signal, humanized antibody 4D5 light chain variable domain, linker, gD tag, humanized 4D5 heavy chain variable domain, and C-terminal domain of p3 (cP3) are indicated.

FIGS. 15 A & B shows the DNA sequence of the Ptac promoter driver cassette for display ScFv-zip (SEQ ID NO: 24). Sequences encoding malE secretion signal, humanized 4D5 light chain variable domain, linker, gD tag, humanized 4D5 heavy chain variable domain, zipper sequence, and C-terminal domain p3 (cP3) are indicated.

FIGS. 16 A & B shows DNA sequence of the Ptac promoter driven cassette for display of Fab (SEQ ID NO: 25). Two open reading frames are indicated. The first open reading frame encodes a malE secretion signal, humanized 4D5 light chain variable and constant domain. The second open reading frame encodes stII secretion signal, humanized heavy chain variable domain, humanized 4D5 heavy chain first constant region (CH1) and C-terminal domain of p3.

FIGS. 17 A & B shows the DNA sequence of Ptac promoter driven cassette for display of Fab-zip (SEQ ID NO: 26). Two open reading frames are indicated. The first open reading frame encodes a malE secretion signal, humanized 4D5 light chain variable and constant domain. The second open reading frame encodes a stII secretion signal, humanized 4D5 heavy chain variable domain, humanized 4D5 heavy chain first constant domain (CH1), zipper sequence, and C-terminal of p3 (cP3).

FIG. 18 shows a schematic representation of display of different constructs including F(ab) and F(ab')$_2$. (A) shows a Fab with a light chain, and a heavy chain variable and CH1 domain fused to at least a portion of a viral coat protein; (B) shows a F(ab')$_2$ with two light chains, and one heavy chain with a dimerization domain (zip) fused to at least a portion of the viral coat protein; an amber stop codon is present after the dimerization domain and (C) shows a F(ab')2 with two light chains, and both heavy chain variable and CH1 domains, each with a dimerization domain, and each fused to at least a portion of the viral coat protein

FIG. 24 shows an illustrative embodiment of designed diversity using nonrandom codon sets for amino acid positions in CDRs H1, H2 and H3. The amino acids (in single letter code) encoded by the codon set at that position are shown below in a column.

FIG. 25 shows the results from sorting ScFv libraries for binding to target antigens Her-2, IGF-1 and mVEGF. The ScFv-1 library was generated with a vector having a zipper sequence and with diversity in CDRH1, H2 and H3. The ScFv-2 was generated with a vector having a zipper sequence and with diversity in H1, H2, H3 and L3. The ScFv-3 was generated with a vector with a zipper sequence and with diversity in H3 and L3. The ScFv-4 has no zipper region and the CDR diversity was generated in CDR H1, H2 and H3. The ScFv-5 was generated with no zipper sequence and with CDR diversity in CDR's H1, H2, H3 and L3. The results for each library after three rounds of sorting are shown as a % of clones binding to a target antigen.

FIG. 26 shows the results of specific binders isolated from ScFv-1, ScFv-2 and ScFv-3 libraries. Phage clones from 3 rounds of selection against IGF-1 or mVEGF were analyzed for specific binding by ELISA assays using both IGF1 and mVEGF. Clones that bound to the target for which they were selected and not to the other antigen were identified as specific. The percentage of clones from each selection that bound targets (Total) and the percentage of clones that bound only the target against which they were selected (specific) are shown.

FIG. 27 shows the total number of sequences and of those sequences the number of unique sequences of anti-VEGF or anti-IGF antibody variable domains identified from each library of scFv-1 and scFv-4 after two or three rounds of sorting.

FIG. 29 shows H3 sequences and affinities of some anti-IGF1 and anti-VEGF binders from a F(ab')$_2$ L3/H3 library. Underlined residues represent residues that were fixed in the source library of the clones. (SEQ ID NOs: 77 to 79)

FIG. 32 shows the Fab polypeptide phage CDRH3 amino acid sequences, affinities, epitope specificity and production of Fab in cell culture for clones V1, V2, V3, and V8.

FIG. 33 shows the heavy chain variable domain CDR amino acid sequences and affinities of binders to mVEGF and human Fc receptor from a F(ab) or F(ab')$_2$ library. The amino acid sequence of heavy chain framework positions 49, 71, 93 and 94 are also shown. (SEQ ID NOs: 80 to 115)

FIGS. 34 A-D are a schematic illustration of phagemid constructs. FIG. 34A shows a bicistronic vector allowing expression of separate transcripts for display of Fab. A suitable promoter, such as Ptac or PhoA promoter drives expression of the bicistronic message. The first cistron encodes a malE or heat stable enterotoxin II (stII) secretion signal connected to a sequence encoding a light chain variable and constant domain and a gD tag. The second cistron encodes a secretion signal sequence, a heavy chain variable domain and constant domain 1 (CH1) and at least a portion of a viral coat protein. FIG. 34B shows a bicistronic message for display of F(ab')$_2$. A suitable promoter drives expression of the first and second cistron. The first cistron encodes a secretion signal sequence (malE or stII), a light chain variable and constant domain and a gD tag. The second cistron encodes a secretion signal, a sequence encoding heavy chain variable domain and constant domain 1 (CH1) and dimerization domain and at least a portion of the viral coat protein. FIG. 34C is a monocistronic vector for display of ScFv. A suitable promoter drives expression of $V_L$ and $V_H$ domains linked by a peptide linker. The cistronic sequence is connected at the 5' end to a secretion signal sequence and at 3' end to at least a portion of a viral coat protein (pIII). FIG. 34D shows a vector for display of ScFv$_2$. The vector is similar to FIG. 34C, but comprises a dimerization domain between $V_H$ and the coat protein.

FIG. 35 shows the amino acid sequences for heavy chain variable CDR sequences and affinities of anti-VEGF binders from a ScFv and ScFv$_2$ library. (SEQ ID NOs: 116 to 143)

FIG. 37 A-F shows the DNA (SEQ ID NO: 28) and amino acid sequence of pV3050-2b vector. The sequence shows stII secretion signal sequence, light chain variable and constant domain of 4D5, and a gD tag, another stII secretion signal sequence heavy chain variable domain sequence of 4D5, CH1 heavy chain constant domain, and C-terminal domain of p3.

FIG. 38 A-F shows the DNA (SEQ ID NO: 29) and amino acid sequence of vector pV-0350-4. The pV0350-2b vector was modified by inserting a dimerization domain between heavy chain constant CH1 domain and p3 sequences.

FIG. 41 shows western blot of constructs with different dimerization domains under reducing conditions (Panels C and D) and non-reducing conditions (Panels A and B). Phage samples are labelled at the bottom of each lane and MW markers are labelled at the left. All constructs contained gD-tag fused to the C terminus of the light chain.

Figure 19:
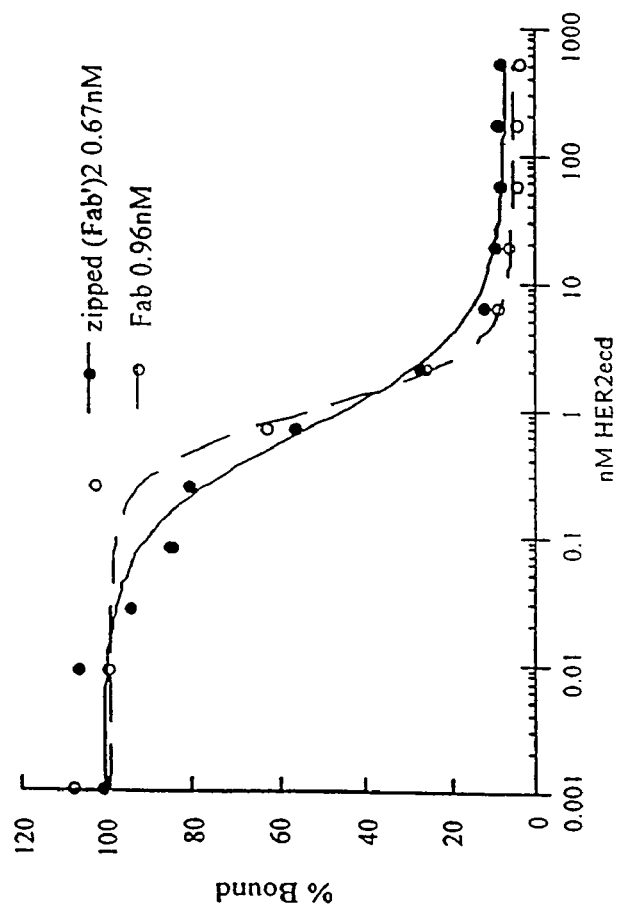
FIG. 19 shows a graph of the % bound of Fab phage constructs in the presence of increasing amounts of HER-2ecd (target antigen). The constructs are Fab phage (-○-) or zipped F(ab')$_2$ phage (-o-). The F(ab) or zipped F(ab')$_2$ phage, each was incubated with increasing concentrations of Her-2ECD (0.001 to 1000 nM) in solution for 5 hours at 37° C. The unbound phage was captured with plates coated with Her-2ECD and measured with HRP-anti-M13 conjugate.

Western blot samples were run under non-reducing (-DTT; Panels A and B) or reducing (+DTT; Panels C and D) conditions, and proteins were detected with an anti-gD-tag antibody (Panels A and C) or anti-P3 antibody (Panels B and D). Phage infected XL-1Blue cells were grown at 30° C. overnight in 2YT medium and phage were purified by precipitation twice with PEG/NaCl and resuspended in 1 mL of 10 mM TRIS, 1.0 mM EDTA, pH 8.0. Phage samples ($3\times10^{11}$, $1OD_{268}=1.3\times10^{13}$) were incubated at 95° C. for 5 min in SDS-PAGE sample buffer (2% SDS, 20 mM Tris pH 6.8, 10% glycerol) with or without 2 mM DTT. The denatured samples were run on a 4-20% Tris-Glycine gel and then electro-transferred to a PVDF filter. The PVDF filter was blocked with 2% milk and 0.1% Tween20 in Tris, pH 7.5, 0.15M NaCl (blocking buffer) for 2 h and then incubated with 2 nM of anti-gD-tag (left) or anti-P3 (right) antibody in blocking buffer for 1 h. The filter was washed with PBS, 0.05% Tween20, incubated with horse radish peroxidase/rabbit anti-mouse Fab conjugate for 30 min and visualized with ECL™ western blotting detection reagent (Amersham Life Sciences).

FIG. 42 shows a comparison of frequency of amino acids in CDRH3 in naturally occurring antibodies (solid bar); amino acids encoded by codon set (A) DVK (cross hatch bar); (B) XYZ (cross hatch bar); and (C) NNK (cross hatch bar). Amino acids are grouped as follows: phenylalanine (F), trytophan (W) and tyrosine (Y) are aromatic amino acids; isoleucine (I), leucine (L), valine (V), alanine (A), and methionine (M) are aliphatic, lysine (K), arginine (R), and histidine (H) are basic; aspartic acid (D) and glutamic acid (E) are acidic; serine (S), threonine (T), asparagine (N), and glutamine (Q) are polar; and proline (P), glycine (G), and cysteine (C) are conformational.

Figure 43:
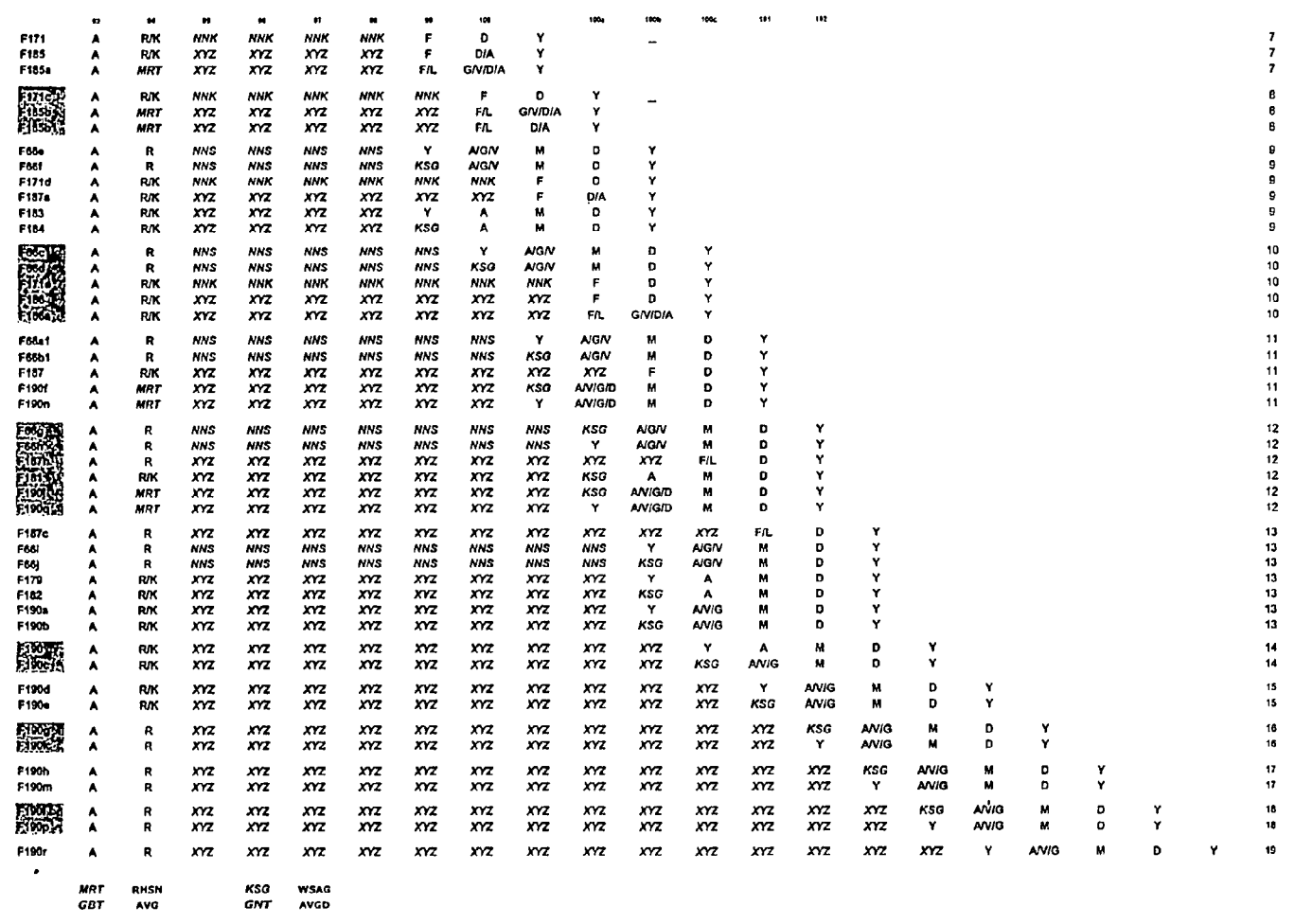

FIG. 43 shows embodiments of oligonucleotides encoding diversity in sequence and in length of CDRH3. The oligonucleotides are identified as F171, F185, F185a etc. in the left hand column. The amino acid sequence at each amino acid position for CDRH3 using each oligonucleotide is shown. The CDRH3 sequence in the source antibody 4D5 is: $S_{93}$, $R_{94}$, $W_{95}$, $G_{96}$, $G_{97}$, $D_{98}$, $G_{99}$, $F_{100}$, $Y_{100a}$, $A_{100b}$, $M_{100c}$, $D_{101}$, and $Y_{102}$. Amino acid positions 93 and 94 are considered framework positions. In some embodiments, certain positions may have a fixed amino acid shown in single letter code, e.g. position 93 is A (alanine); amino acid position 94 may be R/K (arginine/lysine); amino acid position 100a may be A/G/

V/D (alanine/glycine/valine/aspartic acid). Other amino acid positions are diversified using codon sets identified the three capital letters in italics, e.g. NNK, XYZ, NNS, KSG. The length of the CDRH3 is indicated on the right column. (SEQ ID NOs:144 to 161)

Figure 44:
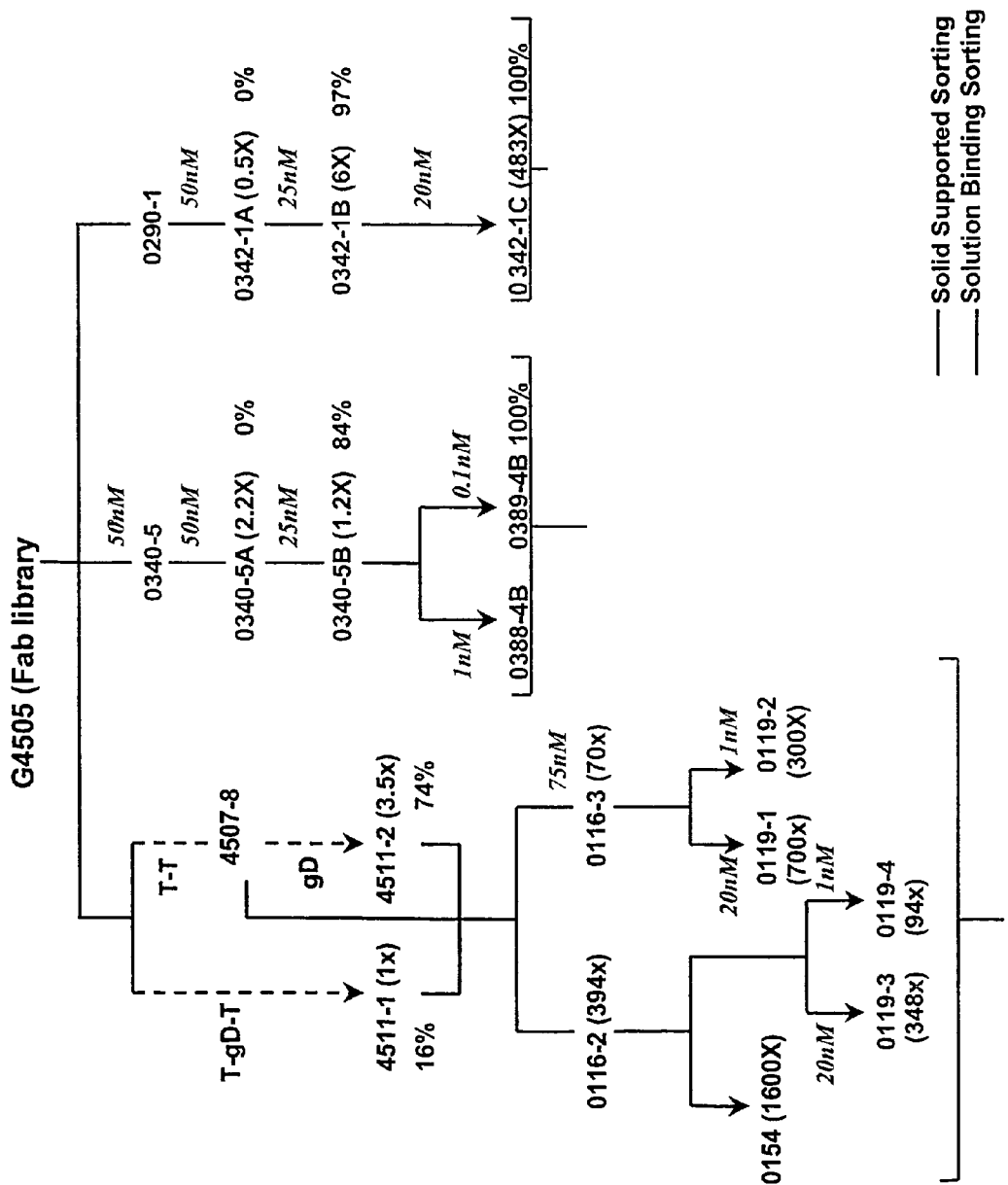

FIG. 44 shows schematic illustration of sorting strategies to select for high affinity anti-VEGF antibody variable domains form libraries using solid support bound target (---) or solution phase target binding as described in Example 9.

Figure 45:
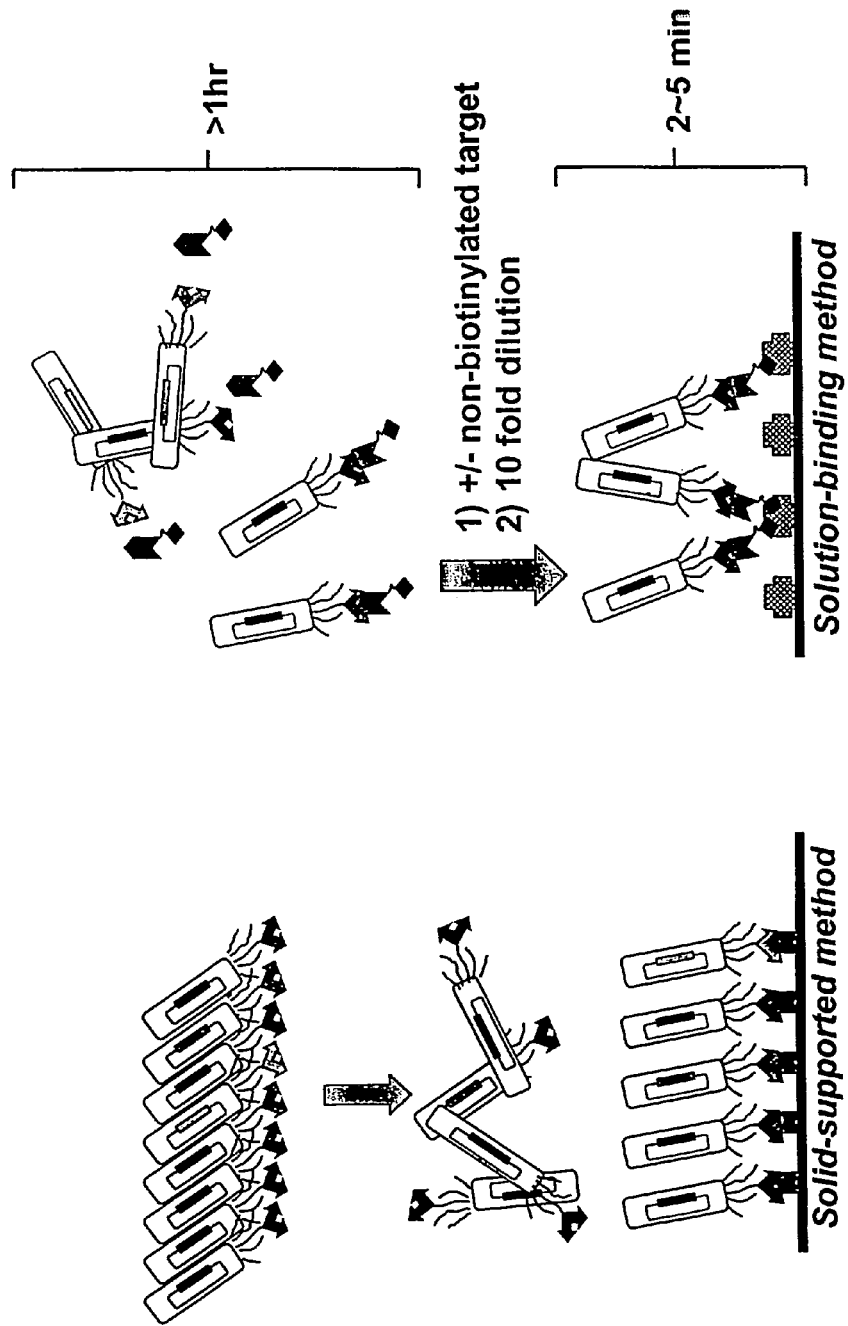

FIG. 45 shows a schematic depiction of two kinds of sorting strategies for selecting high affinity antibody variable domains. The sorting or selection includes sorting against target bound to solid substrate and/or sorting against solution phase target antigens as described in Example 9.

Figure 46:
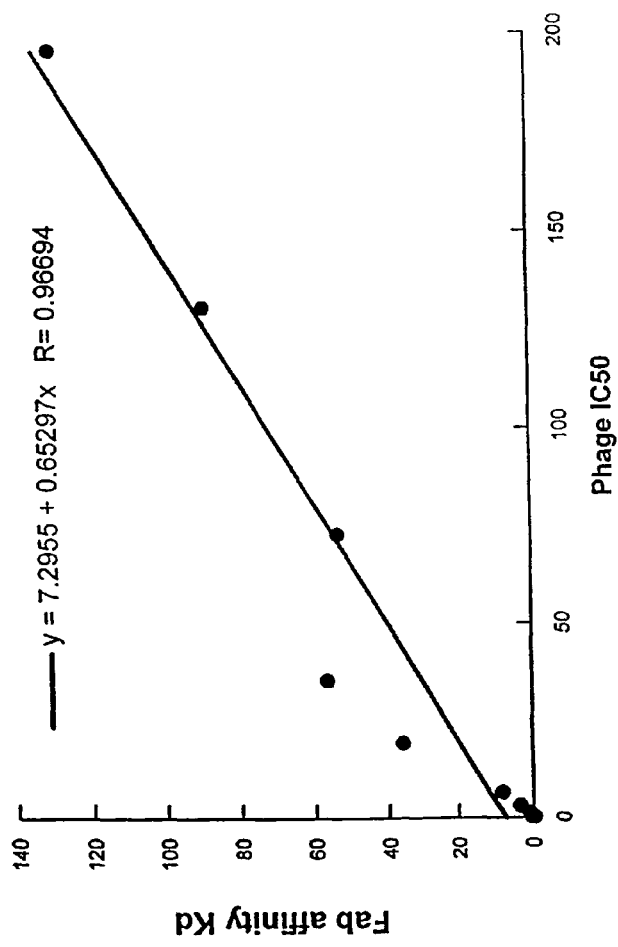

FIG. 46 shows the correlation of affinity determination based on IC50 from a competition ELISA as described in Example 8 with KD of the same clone.

Figure 47:
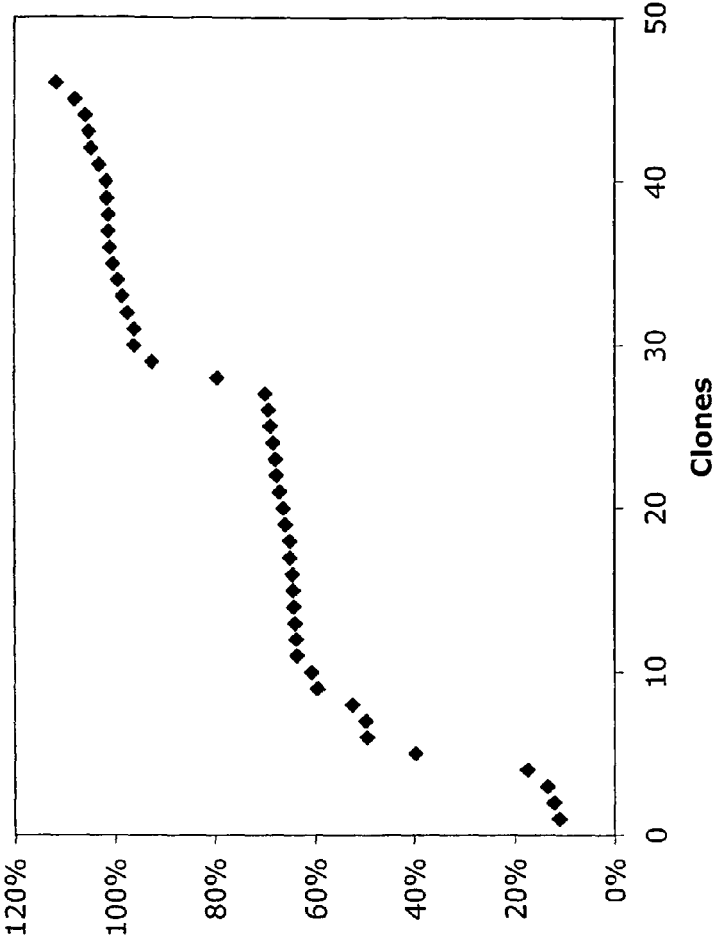

FIG. 47 shows a schematic representation of single spot competition ELISA for binders. The graph shows the data from screening about 40 clones. The % inhibition of binding was calculated by calculating the ratio of OD of samples plus target over samples minus target. The lower the %, the higher the potential affinity. The results show, that of the 40 clones, there was a range of affinities. About 10% of the clones were of very high affinity.

Figure 37A:
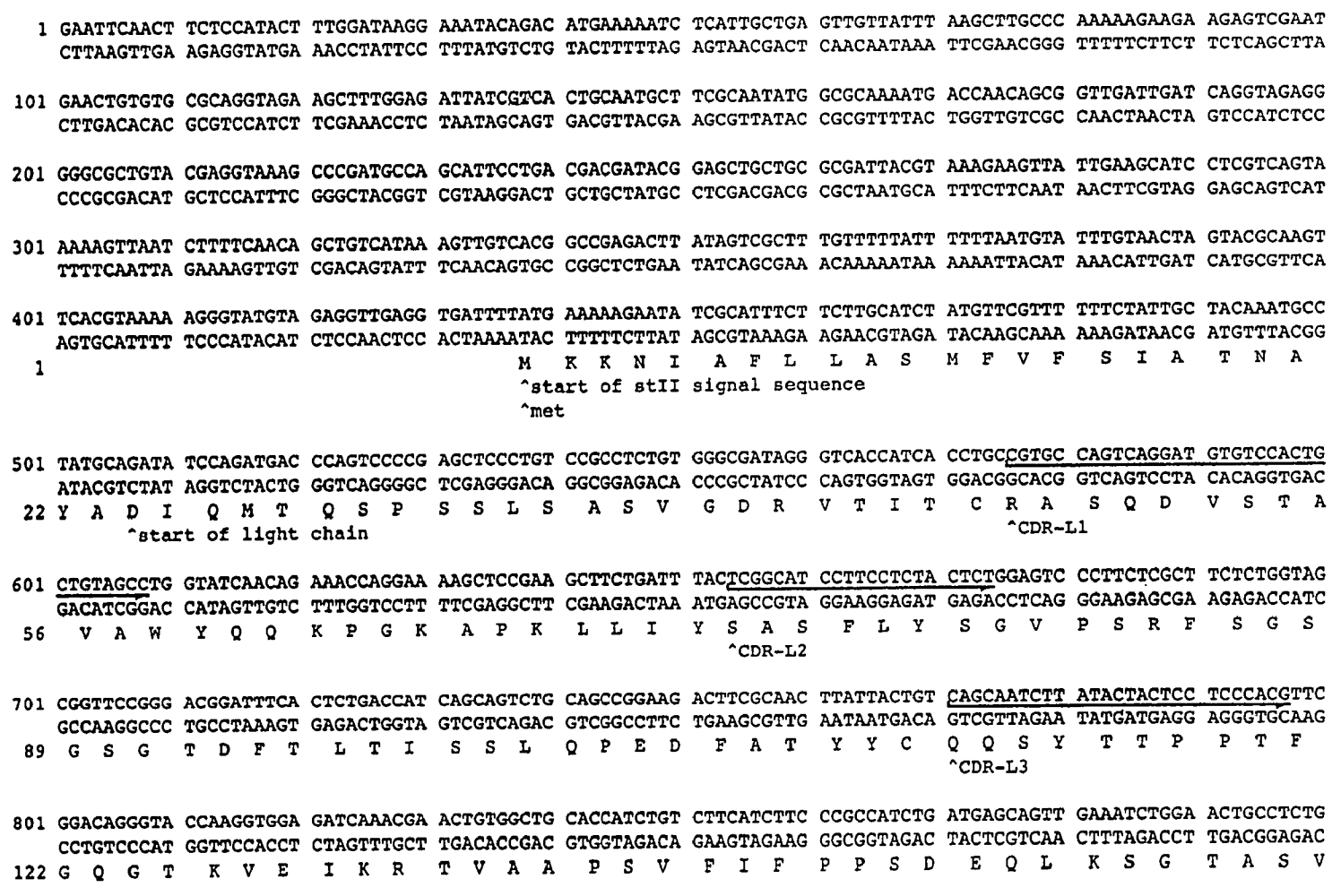
Figure 37B:
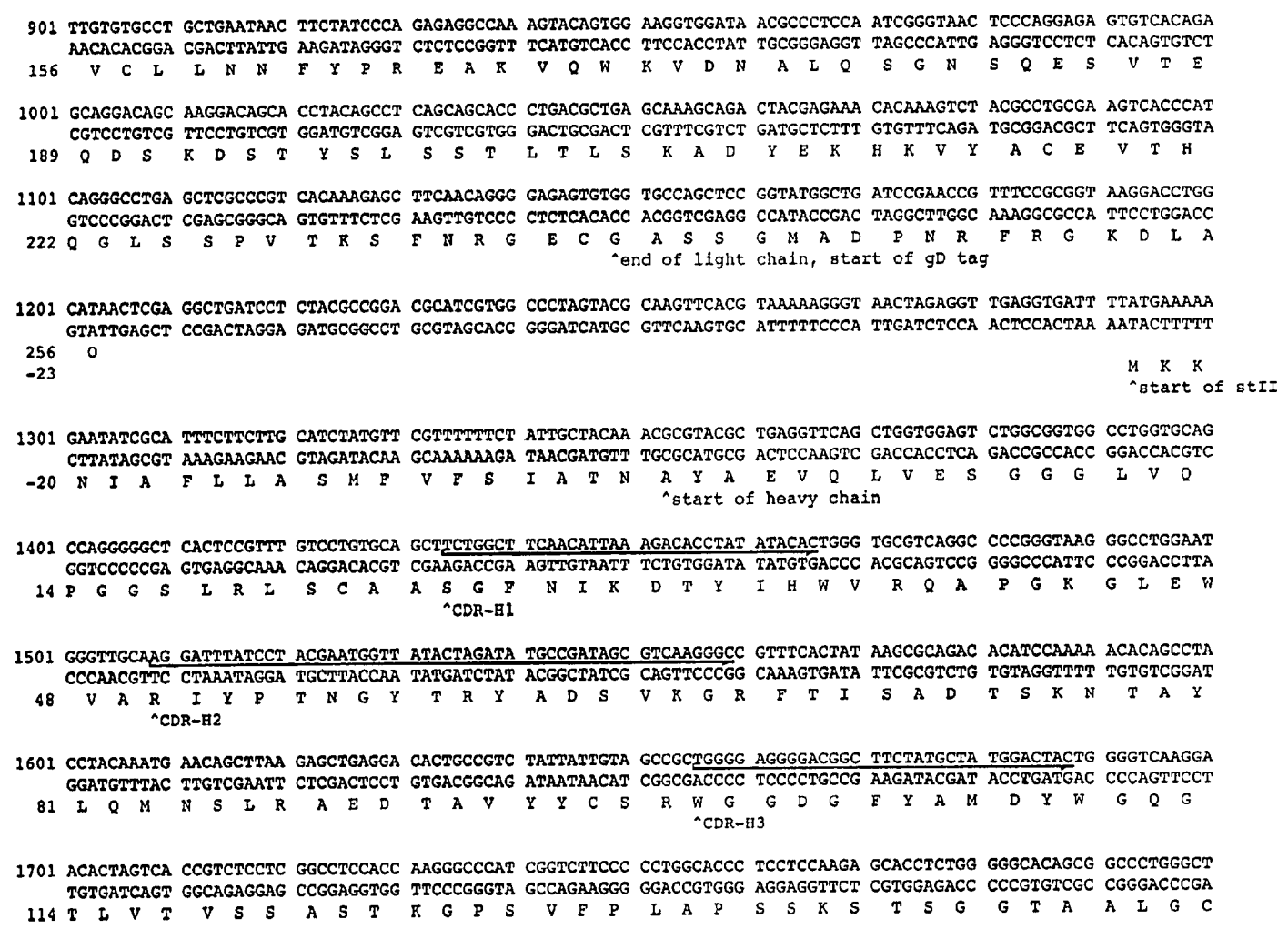
Figure 37C:
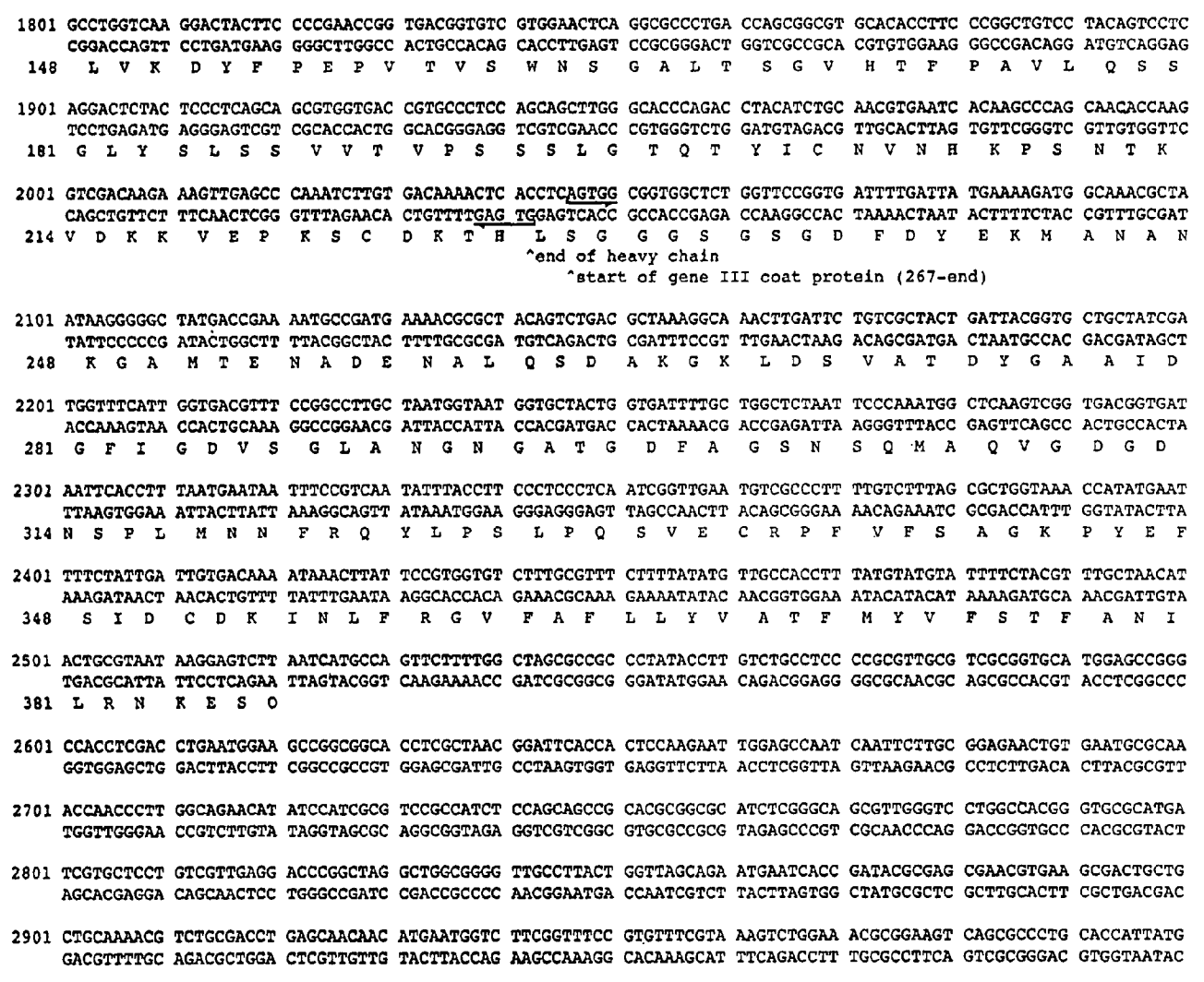
Figure 38A:
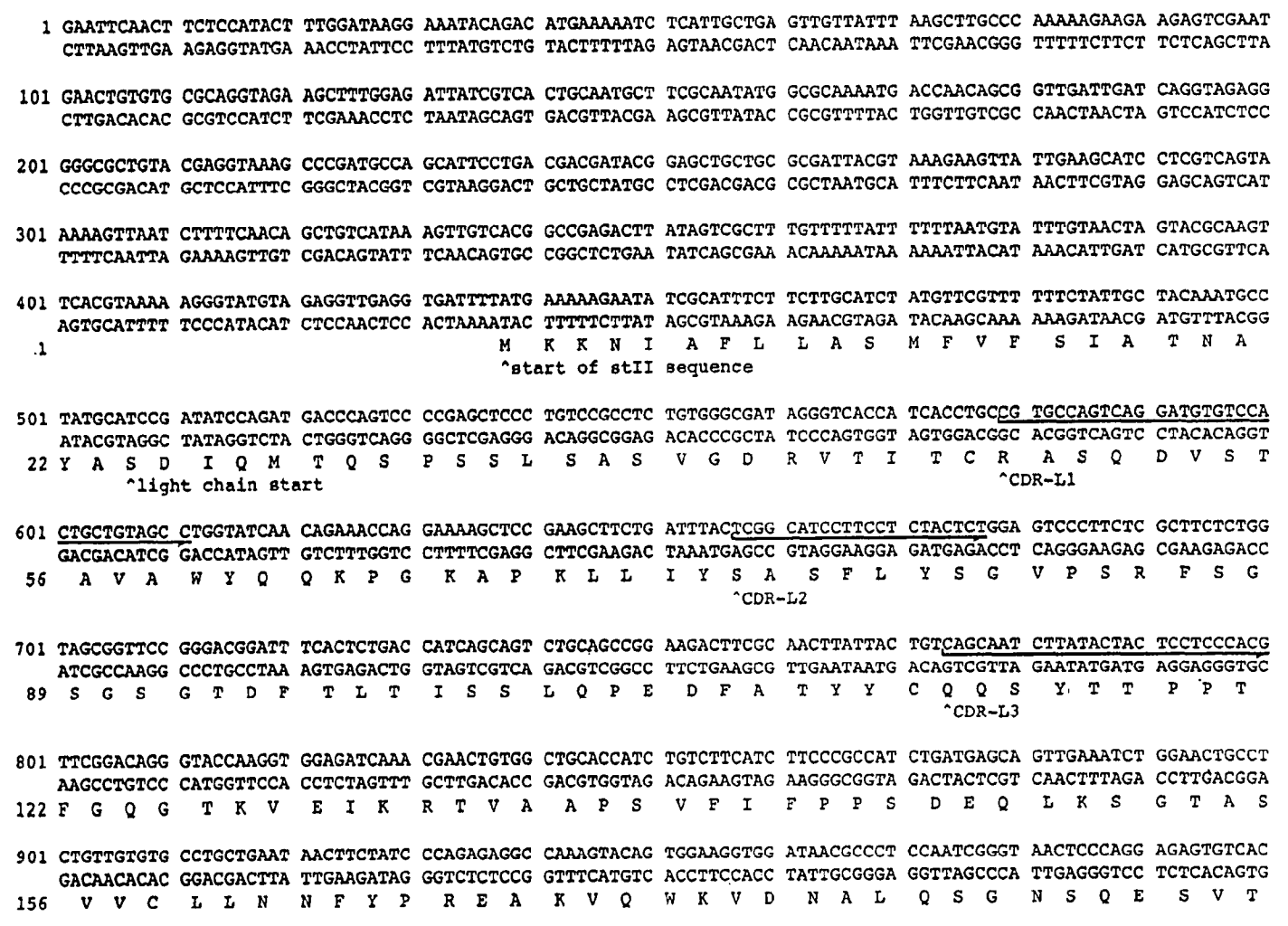
Figure 38B:
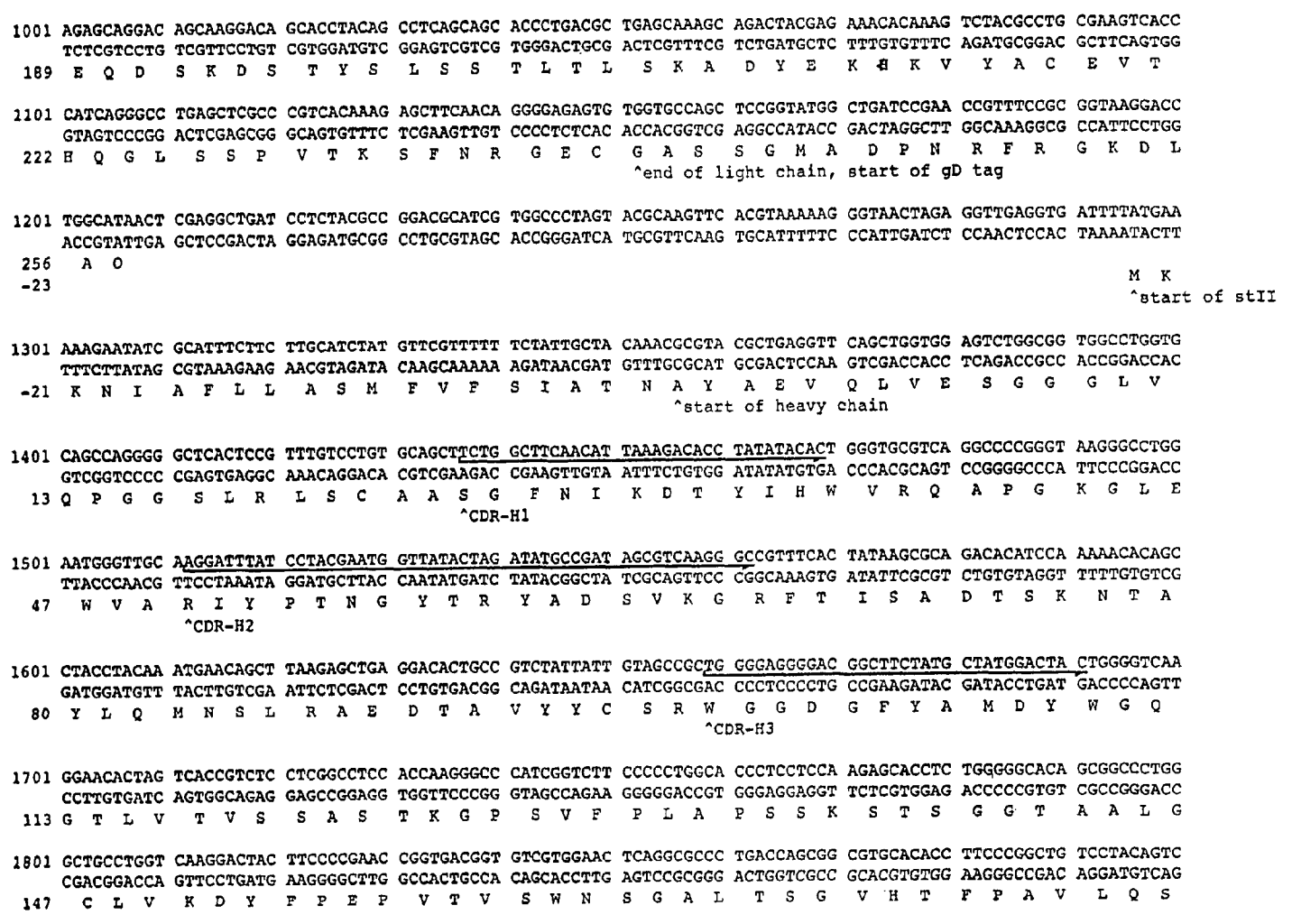

| SEQ ID NO: | Name | Sequence | Page |
|---|---|---|---|
| 1 | 4D5 light chain variable domain | Asp Ile Gln Met Thr Gln Ser Pro Ser Ser Leu Ser Ala Ser Val Gly Asp Arg Val Thr Ile Thr Cys Arg Ala Ser Gln Asp Val Asn Thr Ala Val Ala Trp Tyr Gln Gln Lys Pro Gly Lys Ala Pro Lys Leu Leu Ile Tyr Ser Ala Ser Phe Leu Glu Ser Gly Val Pro Ser Arg Phe Ser Gly Ser Arg Ser Gly Thr Asp - #Phe Thr Leu Thr Ile Ser Ser Leu Gln Pro Glu Asp Phe Ala Thr Tyr Tyr Cys Gln Gln His Tyr Thr Thr Pro Pro Thr Phe Gly Gln Gly Thr Lys Val Glu Ile Lys Arg Thr | 12 |
| 2 | 4D5 heavy chain variable domain | Glu Val Gln Leu Val Glu Ser Gly Gly Gly Leu Val Gln Pro Gly Gly Ser Leu Arg Leu Ser Cys Ala Ala Ser Gly Phe Asn Ile Lys Asp Thr Tyr Ile His Trp Val Arg Gln Ala Pro Gly Lys Gly Leu Glu Trp Val Ala Arg Ile Tyr Pro Thr Asn Gly Tyr Thr Arg Tyr Ala Asp Ser Val Lys Gly Arg Phe Thr Ile Ser Ala Asp Thr Ser Lys Asn Thr Ala Tyr Leu Gln Met Asn Ser Leu Arg Ala Glu Asp Thr Ala Val Tyr Tyr Cys Ser Arg Trp Gly Gly Asp Gly Phe Tyr Ala Met Asp Val Trp Gly Gln Gly Thr Leu Val Thr Val Ser Ser | 12 |
| 3 | GNC4 leucine zipper | GRMKQLEDKVEELLSKNYHLENE VARLKKLVGERG | 18 |
| 4 | C-terminal of CDRH3 | YAMDY | 7 |
| 5 | heavy chain CDR3 | SRNAWAF | 89 |
| 6 | heavy chain CDR3 | SRNLSENSYAM | 89 |
| 7 | heavy chain CDR3 | SRAGWAGWYAM | 89 |
| 8 | heavy chain CDR3 | SRAAKAGWYAM | 89 |
| 9 | heavy chain CDR3 | SRSDGRDSAYAM | 89 |
| 10 | F63 | SRXXXXXXXAMDY | FIG. 4 |
| 11 | F65 | SRXXXXXXXYAMDY | FIG. 4 |
| 12 | F64 | SRXXXXXXYAMDY | FIG. 4 |
| 13 | F66 | SRXXXXXXYAMDY | FIG. 4 |
| 14 | oligonucleotide F151 | gca gct tct ggc ttc acc att ant nnt nnn nnt ata cac tgg gtg cgt cag | 92 |
| 15 | oligonucleotide F152 | gca gct tct ggc ttc acc att ant nnt nnn ngg ata cac tgg gtg cgt cag | 92 |
| 16 | oligonucleotide F175 | gca gct tct ggc ttc acc att ant nnn nnn nnt ata cac tgg gtg cgt cag | 92 |
| 17 | oligonucleotide F176 | gca gct tct ggc ttc acc att ant nnn nnn ngg ata cac tgg gtg cgt cag | 92 |
| 18 | oligonucleotide F153 | aag ggc ctg gaa tgg gtt gnt ngg att nnt cct nnt nnc ggc nnt act nac tat gcc gat agc gtc aag ggc | 92 |
| 19 | oligonucleotide F154 | aag ggc ctg gaa tgg gtt gnt nnt att nnt cct nnt nnc ggc nnt act nac tat gcc gat agc gtc aag ggc | 92 |
| 20 | oligonucleotide F173 | agg gcc ctg gaa tgg gtt gnt ngg att nnt cct nnt nnc ggc nnt act nac tat gcc gat agc gtc aag ggc | 92 |
| 21 | oligonucleotide F174 | aag ggc ctg gaa tgg gtt gnt nnt att nnt cct nnt nnc ggc nnt act nac tat gcc gat agc gtc aag ggc | 92 |
| 22 | oligonucleotide F125 | cgn ttc act ata agc cgt gac aca tcc aaa aac | 92 |
| 23 | single chain Fv | | FIG. 14 |
| 24 | single chain Fv with zipper domain | | FIG. 15 |
| 25 | Fab fragment | | FIG. 16 |
| 26 | Fab fragment with zipper domain | | FIG. 17 |
| 27 | hinge sequence | TCPPCPAPELLG | 97 |
| 28 | Fab phagemid vector pV0350-2b | | FIG. 37 |
| 29 | F(ab)'2 phagemid vector pV0350-4 | | FIG. 38 |
| 30 | olgionucleotide F61 | gca act tat tac tgt cag caa nnt nnt nnn nnn cct tnn acg ttc gga cag ggt acc | 120 |
| 31 | F59 | SRWGGDGFYAMDY | FIG. 4 |
| 32 | F78 | SRXXXXXXFDY | FIG. 4 |

| SEQ ID NO: | Name | Sequence | Page |
|---|---|---|---|
| 33 | F165 | AXXXXXXXYAMDY | FIG. 4 |
| 34 | F166 | AXWXXXXXXAMDY | FIG. 4 |
| 35 | F134 | AXXXXXXXYAMDY | FIG. 4 |
| 36 | F136 | AXWXXXXXYAMDY | FIG. 4 |
| 37 | F137 | AXXWXXXXXYAMDY | FIG. 4 |
| 38 | F138 | AXXXWXXXXYAMDY | FIG. 4 |
| 39 | F142 | AXXXXXXXWYAMDY | FIG. 4 |
| 40 | F155 | AXWXXXXXXXXAMY | FIG. 4 |
| 41 | F156 | AXWXXXXXXXAMDY | FIG. 4 |
| 42 | F157 | AXXWXXXXXXAMDY | FIG. 4 |
| 43 | F158 | AXXXWXXXXXAMDY | FIG. 4 |
| 44 | F160 | AXXXXXXXWXXAMDY | FIG. 4 |
| 45 | F160g | AXXXXXXXXWXAMDY | FIG. 4 |
| 46 | F163a | AXXXXXXXXAMDY | FIG. 4 |
| 47 | F164a | ARXXXXXXXXYAMDY | FIG. 4 |
| 48 | F164b | ARXXXXXXXXAMDY | FIG. 4 |
| 49 | F165a | ARXXXXXXXXYAMDY | FIG. 4 |
| 50 | F165b | ARXXXXXXXXXAMDY | FIG. 4 |
| 51 | F155 | AXWXXXXXXXAMY | FIG. 4 |
| 52 | F167 | AXWXXXXXXAMDY | FIG. 4 |
| 53 | F135 | AXWXXXXXXAMDY | FIG. 4 |
| 54 | F103 | SRXXXXXXXXYAMDY | FIG. 4 |
| 55 | F66a | ARXXXXXXXYAMDY | FIG. 4 |
| 56 | F66b | ARXXXXXXXXAMDY | FIG. 4 |
| 57 | F66c | ARXXXXXXXXYXMDY | FIG. 4 |
| 58 | F66d | ARXXXXXXXXMDY | FIG. 4 |
| 59 | F66e | ARXXXXXYXMDY | FIG. 4 |
| 60 | F66f | ARXXXXXXXMDY | FIG. 4 |
| 61 | F66a1 | ARXXXXXXXYXMDY | FIG. 4 |
| 62 | F66b1 | ARXXXXXXXXMDY | FIG. 4 |
| 63 | F66g | ARXXXXXXXXXMDY | FIG. 4 |
| 64 | F66h | ARXXXXXXXXYXMDY | FIG. 4 |
| 65 | F66i | ARXXXXXXXXXYXMDY | FIG. 4 |
| 66 | F66j | ARXXXXXXXXXXMDY | FIG. 4 |
| 67 | F171c | AXXXXXXXFDY | FIG. 4 |
| 68 | F171d | AXXXXXXXFDY | FIG. 4 |
| 69 | F171e | AXXXXXXXFDY | FIG. 4 |
| 70 | F171 | AXXXXXXFDY | FIG. 4 |
| 71 | F186 | AXXXXXXXXFDY | FIG. 4 |
| 72 | F187 | AXXXXXXXXXFDY | FIG. 4 |
| 73 | F190 | AXXXXXXXXXXYAMD | FIG. 4 |
| 74 | F190a | AXXXXXXXXXXYXMD | FIG. 4 |
| 75 | F190d | AXXXXXXXXXXXXYXMD | FIG. 4 |
| 76 | 4D5 CDRH3 | WGGDGFY | FIG. 4 |
| 77 | CDRH3 | SRWKYATRYAM | FIG. 29 |
| 78 | CDRH3 | SRSRGWWTAAM | FIG. 29 |
| 79 | CDRH3 | SRASRDWYGAM | FIG. 29 |
| 80 | mVEGF-201 CDRH1 | TTSNG | FIG. 33 |
| 81 | mVEGF-201 CDRH2 | AYSSNYYR | FIG. 33 |
| 82 | mVEGF-201 CDRH3 | ARWSRASFY | FIG. 33 |
| 83 | mVEGF-202 CDRH1 | TTGTD | FIG. 33 |
| 84 | mVEGF-202 CDRH2 | AITYDSYR | FIG. 33 |
| 85 | mVEGF-202 CDRH3 | AKAGDREGY | FIG. 33 |
| 86 | mVEGF-203 CDRH1 | TTDSG | FIG. 33 |
| 87 | mVEGF-203 CDRH2 | GRSYSSNR | FIG. 33 |
| 88 | mVEGF-203 CDRH3 | AKWPWYNAW | FIG. 33 |
| 89 | hFc-10 CDRH1 | TNNYW | FIG. 33 |
| 90 | hFc-10 CDRH2 | GYSYGTR | FIG. 33 |
| 91 | hFc-10 CDRH3 | AKAXKGSLY | FIG. 33 |
| 92 | hFc-11 CDRH1 | TTGNA | FIG. 33 |
| 93 | hFc-12 CDRH1 | TNDYY | FIG. 33 |
| 94 | hFc-13 CDRH1 | TSNTG | FIG. 33 |
| 95 | hFc-14 CDRH1 | TTSYG | FIG. 33 |
| 96 | hFc-14 CDRH2 | ASSYSYR | FIG. 33 |
| 97 | hFc-14 CDRH3 | AKYXAREGX | FIG. 33 |
| 98 | hFc-15 CDRH1 | TNNNS | FIG. 33 |
| 99 | hFc-15 CDRH2 | GYNSGSR | FIG. 33 |
| 100 | hFc-15 CDRH3 | AKWRTSWKY | FIG. 33 |
| 101 | hFc-16 CDRH1 | TSSSA | FIG. 33 |
| 102 | hFc-16 CDRH2 | AWSNGSR | FIG. 33 |
| 103 | hFc-16 CDRH3 | AXTAGGAKY | FIG. 33 |

| SEQ ID NO: | Name | Sequence | Page |
|---|---|---|---|
| 104 | hFc-17 CDRH1 | TTNTW | FIG. 33 |
| 105 | hFc-17 CDRH2 | GDYDGYR | FIG. 33 |
| 106 | hFc-17 CDRH3 | AXWRWWGRY | FIG. 33 |
| 107 | hFc-18 CDRH1 | TNGNY | FIG. 33 |
| 108 | hFc-18 CDRH2 | GWSNGYR | FIG. 33 |
| 109 | hFc-18 CDRH3 | ARYSGGRRY | FIG. 33 |
| 110 | hFc-19 CDRH1 | TSNNA | FIG. 33 |
| 111 | hFc-19 CDRH2 | GRSYNYR | FIG. 33 |
| 112 | hFc-19 CDRH3 | AXGXTSGGY | FIG. 33 |
| 113 | hFc-20 CDRH1 | TTSND | FIG. 33 |
| 114 | hFc-20 CDRH2 | AWSYNYR | FIG. 33 |
| 115 | hFc-20 CDRH3 | ARRSRWSRA | FIG. 33 |
| 116 | mVEGF-109 CDRH1 | TGNSW | FIG. 35 |
| 117 | mVEGF-109 CDRH2 | VATYYN | FIG. 35 |
| 118 | mVEGF-109 CDRH3 | WGAKGTW | FIG. 35 |
| 119 | mVEGF-126 CDRH1 | NADSA | FIG. 35 |
| 120 | mVEGF-126 CDRH2 | YAYDYY | FIG. 35 |
| 121 | mVEGF-126 CDRH3 | WGWTTNG | FIG. 35 |
| 122 | mVEGF-127 CDRH1 | NDNTA | FIG. 35 |
| 123 | mVEGF-127 CDRH2 | VSHDTY | FIG. 35 |
| 124 | mVEGF-127 CDRH3 | WGWETDG | FIG. 35 |
| 125 | mVEGF-130 CDRH2 | LDSSYD | FIG. 35 |
| 126 | mVEGF-130 CDRH3 | SRAGYTY | FIG. 35 |
| 127 | mVEGF-136 CDRH1 | NGKSS | FIG. 35 |
| 128 | mVEGF-136 CDRH2 | WSYEAA | FIG. 35 |
| 129 | mVEGF-136 CDRH3 | TSWSKPY | FIG. 35 |
| 130 | mVEGF-169 CDRH1 | NTAYG | FIG. 35 |
| 131 | mVEGF-169 CDRH2 | VTYDDT | FIG. 35 |
| 132 | mVEGF-169 CDRH3 | WGWEANW | FIG. 35 |
| 133 | mVEGF-173 CDRH1 | TGGSW | FIG. 35 |
| 134 | mVEGF-173 CDRH2 | VYTYYD | FIG. 35 |
| 135 | mVEGF-173 CDRH3 | WGAGGTW | FIG. 35 |
| 136 | mVEGF-174 CDRH2 | VSDYYD | FIG. 35 |
| 137 | mVEGF-174 CDRH3 | WGSGYTW | FIG. 35 |
| 138 | mVEGF-176 CDRH1 | SAGYD | FIG. 35 |
| 139 | mVEGF-176 CDRH2 | LAYAYN | FIG. 35 |
| 140 | mVEGF-176 CDRH3 | AAAWASY | FIG. 35 |
| 141 | mVEGF-179 CDRH1 | TTESG | FIG. 35 |
| 142 | mVEGF-179 CDRH2 | VYHDKY | FIG. 35 |
| 143 | mVEGF-179 CDRH3 | WWYSWNW | FIG. 35 |
| 144 | F183 | AXXXXXYAMDY | FIG. 43 |
| 145 | F184 | AXXXXXXAMDY | FIG. 43 |
| 146 | F190f | AXXXXXXXXMDY | FIG. 43 |
| 147 | F190n | AXXXXXXXXYXMDY | FIG. 43 |
| 148 | F187b | ARXXXXXXXXXXDY | FIG. 43 |
| 149 | F181 | AXXXXXXXXXAMDY | FIG. 43 |
| 150 | F190j | AXXXXXXXXXXMDY | FIG. 43 |
| 151 | F190q | AXXXXXXXXXYXMDY | FIG. 43 |
| 152 | F187c | ARXXXXXXXXXXXDY | FIG. 43 |
| 153 | F179 | AXXXXXXXXXXYAMDY | FIG. 43 |
| 154 | F182 | AXXXXXXXXXXAMDY | FIG. 43 |
| 155 | F190g | ARXXXXXXXXXXXXMDY | FIG. 43 |
| 156 | F190k | ARXXXXXXXXXXXXYXMDY | FIG. 43 |
| 157 | F190h | ARXXXXXXXXXXXXXMDY | FIG. 43 |
| 158 | F190m | ARXXXXXXXXXXXXXYXMDY | FIG. 43 |
| 159 | F190i | ARXXXXXXXXXXXXXXMDY | FIG. 43 |
| 160 | F190p | ARXXXXXXXXXXXXXYXMDY | FIG. 43 |
| 161 | F190r | ARXXXXXXXXXXXXXXYXMDY | FIG. 43 |
| 162 | F59 | SRWGXXXXXAMDY | FIG. 4 |
| 163 | C-terminal of CDRH3 | YAMDX | 64 |
| 164 | CDRH3 | $(X)_n$XAMDY where n = 4 to 14 | 72 |

DETAILED DESCRIPTION OF THE INVENTION

The invention provides novel and systematic methods for diversifying antibody variable domain sequences, and libraries comprising a multiplicity, generally a great multiplicity of diversified antibody variable domain sequences. Such libraries provide combinatorial libraries useful for, for example, selecting and/or screening for synthetic antibody clones with desirable activities such as binding affinities and avidities. These libraries are useful for identifying immunoglobulin polypeptide sequences that are capable of interacting with any of a wide variety of target antigens. For example, libraries comprising diversified immunoglobulin polypeptides of the invention expressed as phage displays are particularly useful for, and provide a high throughput, efficient and automatable systems of, selecting and/or screening for antigen binding molecules of interest. The methods of the invention are designed to provide high affinity binders to target antigens with minimal changes to a source or template molecule and provide for good production yields when the antibody or antigens binding fragments are produced in cell culture.

DEFINITIONS

Amino acids are represented herein as either a single letter code or as the three letter code or both.

The term "affinity purification" means the purification of a molecule based on a specific attraction or binding of the molecule to a chemical or binding partner to form a combination or complex which allows the molecule to be separated from impurities while remaining bound or attracted to the partner moiety.

The term "antibody" is used in the broadest sense and specifically covers single monoclonal antibodies (including agonist and antagonist antibodies), antibody compositions with polyepitopic specificity, affinity matured antibodies, humanized antibodies, chimeric antibodies, as well as antigen binding fragments (e.g., Fab, F(ab')$_2$, scFv and Fv), so long as they exhibit the desired biological activity.

As used herein, "antibody variable domain" refers to the portions of the light and heavy chains of antibody molecules that include amino acid sequences of Complementarity Determining Regions (CDRs; ie., CDR1, CDR2, and CDR3), and Framework Regions (FRs). $V_H$ refers to the variable domain of the heavy chain. $V_L$ refers to the variable domain of the light chain. According to the methods used in this invention, the amino acid positions assigned to CDRs and FRs may be defined according to Kabat (Sequences of Proteins of Immunological Interest (National Institutes of Health, Bethesda, Md., 1987 and 1991)). Amino acid numbering of antibodies or antigen binding fragments is also according to that of Kabat.

As used herein, the term "Complementarity Determining Regions (CDRs; ie., CDR1, CDR2, and CDR3) refers to the amino acid residues of an antibody variable domain the presence of which are necessary for antigen binding. Each variable domain typically has three CDR regions identified as CDR1, CDR2 and CDR3. Each complementarity determining region may comprise amino acid residues from a "complementarity determining region" as defined by Kabat (i.e. about residues 24-34 (L1), 50-56 (L2) and 89-97 (L3) in the light chain variable domain and 31-35 (H1), 50-65 (H2) and 95-102 (H3) in the heavy chain variable domain; Kabat et al., Sequences of Proteins of Immunological Interest, 5th Ed. Public Health Service, National Institutes of Health, Bethesda, Md. (1991)) and/or those residues from a "hypervariable loop" (i.e. about residues 26-32 (L1), 50-52 (L2) and 91-96 (L3) in the light chain variable domain and 26-32 (H1), 53-55 (H2) and 96-101 (H3) in the heavy chain variable domain; Chothia and Lesk J. Mol. Biol. 196:901-917 (1987)). In some instances, a complementarity determining region can include amino acids from both a CDR region defined according to Kabat and a hypervariable loop. For example, the CDRH1 of the heavy chain of antibody 4D5 includes amino acids 26 to 35.

"Framework regions" (hereinafter FR) are those variable domain residues other than the CDR residues. Each variable domain typically has four FRs identified as FR1, FR2, FR3 and FR4. If the CDRs are defined according to Kabat, the light chain FR residues are positioned at about residues 1-23 (LCFR1), 35-49 (LCFR2), 57-88 (LCFR3), and 98-107 (LCFR4) and the heavy chain FR residues are positioned about at residues 1-30 (HCFR1), 36-49 (HCFR2), 66-94 (HCFR3), and 103-113 (HCFR4) in the heavy chain residues. If the CDRs comprise amino acid residues from hypervariable loops, the light chain FR residues are positioned about at residues 1-25 (LCFR1), 33-49 (LCFR2), 53-90 (LCFR3), and 97-107 (LCFR4) in the light chain and the heavy chain FR residues are positioned about at residues 1-25 (HCFR1), 33-52 (HCFR2), 56-95 (HCFR3), and 102-113 (HCFR4) in the heavy chain residues. In some instances, when the CDR comprises amino acids from both a CDR as defined by Kabat and those of a hypervariable loop, the FR residues will be adjusted accordingly. For example, when CDRH1 includes amino acids H26-H35, the heavy chain FR1 residues are at positions 1-25 and the FR2 residues are at positions 36-49.

As used herein, "codon set" refers to a set of different nucleotide triplet sequences used to encode desired variant amino acids. A set of oligonucleotides can be synthesized, for example, by solid phase synthesis, including sequences that represent all possible combinations of nucleotide triplets provided by the codon set and that will encode the desired group of amino acids. A standard form of codon designation is that of the IUB code, which is known in the art and described herein. A codon set typically is represented by 3 capital letters in italics, eg. NNK, NNS, XYZ, DVK and the like. A "non-random codon set", as used herein, thus refers to a codon set that encodes select amino acids that fulfill partially, preferably completely, the criteria for amino acid selection as described herein. Synthesis of oligonucleotides with selected nucleotide "degeneracy" at certain positions is well known in that art, for example the TRIM approach (Knappek et al.; J. Mol. Biol. (1999), 296:57-86); Garrard & Henner, Gene (1993), 128:103). Such sets of oligonucleotides having certain codon sets can be synthesized using commercial nucleic acid synthesizers (available from, for example, Applied Biosystems, Foster City, Calif.), or can be obtained commercially (for example, from Life Technologies, Rockville, Md.). Therefore, a set of oligonucleotides synthesized having a particular codon set will typically include a plurality of oligonucleotides with different sequences, the differences established by the codon set within the overall sequence. Oligonucleotides, as used according to the invention, have sequences that allow for hybridization to a variable domain nucleic acid template and also can, but does not necessarily, include restriction enzyme sites useful for, for example, cloning purposes.

An "Fv" fragment is an antibody fragment which contains a complete antigen recognition and binding site. This region consists of a dimer of one heavy and one light chain variable domain in tight association, which can be covalent in nature, for example in scFv. It is in this configuration that the three CDRs of each variable domain interact to define an antigen binding site on the surface of the $V_H$-$V_L$ dimer. Collectively, the six CDRs or a subset thereof confer antigen binding specificity to the antibody. However, even a single variable domain (or half of an Fv comprising only three CDRs specific for an antigen) has the ability to recognize and bind antigen, although usually at a lower affinity than the entire binding site.

The "Fab" fragment contains a variable and constant domain of the light chain and a variable domain and the first constant domain (CH1) of the heavy chain. F(ab')$_2$ antibody fragments comprise a pair of Fab fragments which are generally covalently linked near their carboxy termini by hinge cysteines between them. Other chemical couplings of antibody fragments are also known in the art.

"Single-chain Fv" or "scFv" antibody fragments comprise the $V_H$ and $V_L$ domains of antibody, wherein these domains are present in a single polypeptide chain. Generally the Fv polypeptide further comprises a polypeptide linker between the $V_H$ and $V_L$ domains, which enables the scFv to form the desired structure for antigen binding. For a review of scFv, see Pluckthun in *The Pharmacology of Monoclonal Antibodies*, Vol 113, Rosenburg and Moore eds. Springer-Verlag, New York, pp. 269-315 (1994).

The term "diabodies" refers to small antibody fragments with two antigen-binding sites, which fragments comprise a heavy chain variable domain ($V_H$) connected to a light chain variable domain ($V_L$) in the same polypeptide chain ($V_H$ and $V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90:6444-6448 (1993).

The expression "linear antibodies" refers to the antibodies described in Zapata et al., *Protein Eng.*, 8(10):1057-1062 (1995). Briefly, these antibodies comprise a pair of tandem Fd segments ($V_H$-$C_H$1-$V_H$-$C_H$1) which, together with complementary light chain polypeptides, form a pair of antigen binding regions. Linear antibodies can be bispecific or monospecific.

"Cell", "cell line", and "cell culture" are used interchangeably herein and such designations include all progeny of a cell or cell line. Thus, for example, terms like "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

"Control sequences" when referring to expression means DNA sequences necessary for the expression of an operably linked coding sequence in a particular host organism. The control sequences that are suitable for prokaryotes, for example, include a promoter, optionally an operator sequence, a ribosome binding site, and possibly, other as yet poorly understood sequences. Eukaryotic cells are known to utilize promoters, polyadenylation signals, and enhancers.

The term "coat protein" means a protein, at least a portion of which is present on the surface of the virus particle. From a functional perspective, a coat protein is any protein which associates with a virus particle during the viral assembly process in a host cell, and remains associated with the assembled virus until it infects another host cell. The coat protein may be the major coat protein or may be a minor coat protein. A "major" coat protein is generally a coat protein which is present in the viral coat at preferably at least about 5, more preferably at least about 7, even more preferably at least about 10 copies of the protein or more. A major coat protein may be present in tens, hundreds or even thousands of copies per virion. An example of a major coat protein is the p8 protein of filamentous phage.

The "detection limit" for a chemical entity in a particular assay is the minimum concentration of that entity which can be detected above the background level for that assay. For example, in the phage ELISA, the "detection limit" for a particular phage displaying a particular antigen binding fragment is the phage concentration at which the particular phage produces an ELISA signal above that produced by a control phage not displaying the antigen binding fragment.

A "fusion protein" and a "fusion polypeptide" refers to a polypeptide having two portions covalently linked together, where each of the portions is a polypeptide having a different property. The property may be a biological property, such as activity in vitro or in vivo. The property may also be a simple chemical or physical property, such as binding to a target antigen, catalysis of a reaction, etc. The two portions may be linked directly by a single peptide bond or through a peptide linker containing one or more amino acid residues. Generally, the two portions and the linker will be in reading frame with each other. Preferably, the two portions of the polypeptide are obtained from heterologous or different polypeptides.

"Heterologous DNA" is any DNA that is introduced into a host cell. The DNA may be derived from a variety of sources including genomic DNA, cDNA, synthetic DNA and fusions or combinations of these. The DNA may include DNA from the same cell or cell type as the host or recipient cell or DNA from a different cell type, for example, from a mammal or plant. The DNA may, optionally, include marker or selection genes, for example, antibiotic resistance genes, temperature resistance genes, etc.

As used herein, "highly diverse position" refers to a position of an amino acid located in the variable regions of the light and heavy chains that have a number of different amino acid represented at the position when the amino acid sequences of known and/or naturally occurring antibodies or antigen binding fragments are compared. The highly diverse positions are typically in the CDR regions. In one aspect, the ability to determine highly diverse positions in known and/or naturally occurring antibodies is facilitated by the data provided by Kabat, Sequences of Proteins of Immunological Interest (National Institutes of Health, Bethesda, Md., 1987 and 1991). An internet-based database located at http:/immuno/bme/nwu/edu provides an extensive collection and alignment of human light and heavy chain sequences and facilitates determination of highly diverse positions in these sequences. According to the invention, an amino acid position is highly diverse if it has preferably from about 2 to about 11, preferably from about 4 to about 9, and preferably from about 5 to about 7 different possible amino acid residue variations at that position. In some embodiments, an amino acid position is highly diverse if it has preferably at least about 2, preferably at least about 4, preferably at least about 6, and preferably at least about 8 different possible amino acid residue variations at that position.

As used herein, "library" refers to a plurality of antibody or antibody fragment sequences (for example, polypeptides of the invention), or the nucleic acids that encode these sequences, the sequences being different in the combination of variant amino acids that are introduced into these sequences according to the methods of the invention.

"Ligation" is the process of forming phosphodiester bonds between two nucleic acid fragments. For ligation of the two fragments, the ends of the fragments must be compatible with each other. In some cases, the ends will be directly compatible after endonuclease digestion. However, it may be necessary first to convert the staggered ends commonly produced after endonuclease digestion to blunt ends to make them compatible for ligation. For blunting the ends, the DNA is treated in a suitable buffer for at least 15 minutes at 15° C. with about 10 units of the Klenow fragment of DNA polymerase I or T4 DNA polymerase in the presence of the four deoxyribonucleotide triphosphates. The DNA is then purified by phenol-chloroform extraction and ethanol precipitation or by silica purification. The DNA fragments that are to be ligated together are put in solution in about equimolar amounts. The solution will also contain ATP, ligase buffer, and a ligase such as T4 DNA ligase at about 10 units per 0.5 µg of DNA. If the DNA is to be ligated into a vector, the vector is first linearized by digestion with the appropriate restriction endonuclease(s). The linearized fragment is then treated with bacterial alkaline phosphatase or calf intestinal phosphatase to prevent self-ligation during the ligation step.

A "mutation" is a deletion, insertion, or substitution of a nucleotide(s) relative to a reference nucleotide sequence, such as a wild type sequence.

As used herein, "natural" or "naturally occurring" antibodies, refers to antibodies identified from a nonsynthetic source, for example, from a differentiated antigen-specific B cell obtained ex vivo, or its corresponding hybridoma cell line, or from antibodies obtained from the serum of an animal. These antibodies can include antibodies generated in any type of immune response, either natural or otherwise induced. Natural antibodies include the amino acid sequences, and the nucleotide sequences that constitute or encode these antibodies, for example, as identified in the Kabat database. As used herein, natural antibodies are different than "synthetic antibodies", synthetic antibodies referring to antibody sequences that have been changed from a source or template sequence, for example, by the replacement, deletion, or addition, of an amino acid, or more than one amino acid, at a certain position with a different amino acid, the different amino acid providing an antibody sequence different from the source antibody sequence.

"Operably linked" when referring to nucleic acids means that the nucleic acids are placed in a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contingent and in reading frame. However, enhancers do not have to be contiguous. Linking is accomplished by ligation at convenient restriction sites. If such sites do not exist, the synthetic oligonucleotide adapters or linkers are used in accord with conventional practice.

"Phage display" is a technique by which variant polypeptides are displayed as fusion proteins to at least a portion of coat protein on the surface of phage, e.g., filamentous phage, particles. A utility of phage display lies in the fact that large libraries of randomized protein variants can be rapidly and efficiently soiled for those sequences that bind to a target antigen with high affinity. Display of peptide and protein libraries on phage has been used for screening millions of polypeptides for ones with specific binding properties. Polyvalent phage display methods have been used for displaying small random peptides and small proteins through fusions to either gene m or gene VIII of filamentous phage. Wells and Lowman, Curr. Opin. Struct. Biol., 3:355-362 (1992), and references cited therein. In monovalent phage display, a protein or peptide library is fused to a gene III or a portion thereof, and expressed at low levels in the presence of wild type gene III protein so that phage particles display one copy or none of the fusion proteins. Avidity effects are reduced relative to polyvalent phage so that sorting is on the basis of intrinsic ligand affinity, and phagemid vectors are used, which simplify DNA manipulations. Lowman and Wells, Methods: A companion to Methods in Enzymology, 3:205-0216 (1991).

A "phagemid" is a plasmid vector having a bacterial origin of replication, e.g., Co1E1, and a copy of an intergenic region of a bacteriophage. The phagemid may be used on any known bacteriophage, including filamentous bacteriophage and lambdoid bacteriophage. The plasmid will also generally contain a selectable marker for antibiotic resistance. Segments of DNA cloned into these vectors can be propagated as plasmids. When cells harboring these vectors are provided with all genes necessary for the production of phage particles, the mode of replication of the plasmid changes to rolling circle replication to generate copies of one strand of the plasmid DNA and package phage particles. The phagemid may form infectious or non-infectious phage particles. This term includes phagemids which contain a phage coat protein gene or fragment thereof linked to a heterologous polypeptide gene as a gene fusion such that the heterologous polypeptide is displayed on the surface of the phage particle.

The term "phage vector" means a double stranded replicative form of a bacteriophage containing a heterologous gene and capable of replication. The phage vector has a phage origin of replication allowing phage replication and phage particle formation. The phage is preferably a filamentous bacteriophage, such as an M13, fl, fd, Pf3 phage or a derivative thereof, or a lambdoid phage, such as lambda, 21, phi80, phi81, 82, 424, 434, etc., or a derivative thereof.

"Oligonucleotides" are short-length, single- or double-stranded polydeoxynucleotides that are chemically synthesized by known methods (such as phosphotriester, phosphite, or phosphoramidite chemistry, using solid-phase techniques such as described in EP 266,032 published 4 May 1988, or via deoxynucleoside H-phosphonate intermediates as described by Froeshler et al., Nucl. Acids, Res., 14:5399-5407 (1986)). Further methods include the polymerase chain reaction defined below and other autoprimer methods and oligonucleotide syntheses on solid supports. All of these methods are described in Engels et al., Agnew. Chem. Int. Ed. Engl., 28:716-734 (1989). These methods are used if the entire nucleic acid sequence of the gene is known, or the sequence of the nucleic acid complementary to the coding strand is available. Alternatively, if the target amino acid sequence is known, one may infer potential nucleic acid sequences using known and preferred coding residues for each amino acid residue. The oligonucleotides can be purified on polyacrylamide gels or molecular sizing columns or by precipitation.

DNA is "purified" when the DNA is separated from non-nucleic acid impurities. The impurities may be polar, non-polar, ionic, etc.

A "source antibody", as used herein, refers to an antibody or antigen binding fragment whose antigen binding sequence serves as the template sequence upon which diversification according to the criteria described herein is performed. An antigen binding sequence generally includes an antibody variable region, preferably at least one CDR, preferably including framework regions.

As used herein, "solvent accessible position" refers to a position of an amino acid residue in the variable regions of the heavy and light chains of a source antibody or antigen binding fragment that is determined, based on structure, ensemble of structures and/or modeled structure of the antibody or antigen binding fragment, as potentially available for solvent access and/or contact with a molecule, such as an antibody-specific antigen. These positions are typically found in the CDRs and on the exterior of the protein. The solvent accessible positions of an antibody or antigen binding fragment, as defined herein, can be determined using any of a number of algorithms known in the art. Preferably, solvent accessible positions are determined using coordinates from a 3-dimensional model of an antibody, preferably using a computer program such as the InsightII program (Accelrys, San Diego, Calif.). Solvent accessible positions can also be determined using algorithms known in the art (e.g., Lee and Richards, J. Mol. Biol. 55, 379 (1971) and Connolly, J. Appl. Cryst. 16, 548 (1983)). Determination of solvent accessible positions can be performed using software suitable for protein modeling and 3-dimensional structural information obtained from an antibody. Software that can be utilized for these purposes includes SYBYL Biopolymer Module software (Tripos Associates). Generally and preferably, where an algorithm (program) requires a user input size parameter, the "size" of a probe which is used in the calculation is set at about 1.4 Angstrom or smaller in radius. In addition, determination of solvent accessible regions and area methods using software for personal computers has been described by Pacios ((1994) "ARVOMOL/CONTOUR: molecular surface areas and volumes on Personal Computers." *Comput. Chem.* 18(4): 377-386; and (1995). "Variations of Surface Areas and Volumes in Distinct Molecular Surfaces of Biomolecules." *J. Mol. Model.* 1: 46-53.)

As used herein, "target amino acid" refers to an amino acid that belongs to the group of amino acids that are collectively the most commonly occurring amino acids found at a particular position of known and/or natural occurring antibodies or antigen binding fragments. In some embodiments, the most commonly occurring amino acids" are those amino acids that are found in a particular position in preferably at least about 50%, preferably at least about 70%, preferably at least about 80%, preferably at least about 90%, preferably all of sequences of known and/or natural antibodies or antigen binding fragments. In some embodiments, the most commonly occurring amino acids" are those amino acids that are found in a particular position in preferably from about 50% to about 100%, preferably from about 60% to about 90%, preferably from about 70% to about 85%, preferably from about 80% to about 85% of the sequences of known and/or natural antibodies or antigen binding fragments. Known antibodies or antigen binding fragments are those whose sequences are available in the art, such as those available in publicly-accessible databases, such as the database of Kabat ("Sequence of Proteins of Immunological Interest, National Institutes of Health, Bethesda, Md., 1987 and 1991) and/or as located at http:/immuno/bme/nwu/edu. The amino acid position is preferably a position in the CDR region. A target group of amino acids refers to a group of target amino acids for a particular position. Preferably, a target amino acid is not a cysteine residue. For positions in the light chain CDR1, CDR2, CDR3, and for heavy chain CDR1 and CDR2, typically, a target group of amino acids can include from preferably about 2 to about 11, preferably from about 4 to about 9, preferably from about 5 to about 7, preferably about 6 amino acids at a particular highly diverse and solvent-accessible position of the source sequence.

A "transcription regulatory element" will contain one or more of the following components: an enhancer element, a promoter, an operator sequence, a repressor gene, and a transcription termination sequence. These components are well known in the art. U.S. Pat. No. 5,667,780.

A "transformant" is a cell which has taken up and maintained DNA as evidenced by the expression of a phenotype associated with the DNA (e.g., antibiotic resistance conferred by a protein encoded by the DNA).

"Transformation" means a process whereby a cell takes up DNA and becomes a "transformant". The DNA uptake may be permanent or transient.

A "variant" or "mutant" of a starting or reference polypeptide (for e.g., a source antibody or its variable domain(s)/CDR(s)), such as a fusion protein (polypeptide) or a heterologous polypeptide (heterologous to a phage), is a polypeptide that 1) has an amino acid sequence different from that of the starting or reference polypeptide and 2) was derived from the starting or reference polypeptide through either natural or artificial (manmade) mutagenesis. Such variants include, for example, deletions from, and/or insertions into and/or substitutions of, residues within the amino acid sequence of the polypeptide of interest. For example, a fusion polypeptide of the invention generated using an oligonucleotide comprising a nonrandom codon set that encodes a sequence with a variant amino acid (with respect to the amino acid found at the corresponding position in a source antibody/antigen binding fragment) would be a variant polypeptide with respect to a source antibody or antigen binding fragment. Thus, a variant CDR refers to a CDR comprising a variant sequence with respect to a starting or reference polypeptide sequence (such as that of a source antibody or antigen binding fragment). A variant amino acid, in this context, refers to an amino acid different from the amino acid at the corresponding position in a starting or reference polypeptide sequence (such as that of a source antibody or antigen binding fragment). Any combination of deletion, insertion, and substitution may be made to arrive at the final variant or mutant construct, provided that the final construct possesses the desired functional characteristics. The amino acid changes also may alter post-translational processes of the polypeptide, such as changing the number or position of glycosylation sites. Methods for generating amino acid sequence variants of polypeptides are described in U.S. Pat. No. 5,534,615, expressly incorporated herein by reference.

A "wild type" or "reference" sequence or the sequence of a "wild type" or "reference" protein/polypeptide, such as a coat protein, or a CDR or variable domain of a source antibody, maybe the reference sequence from which variant polypeptides are derived through the introduction of mutations. In general, the "wild type" sequence for a given protein is the sequence that is most common in nature. Similarly, a "wild type" gene sequence is the sequence for that gene which is most commonly found in nature. Mutations may be introduced into a "wild type" gene (and thus the protein it encodes) either through natural processes or through man induced means. The products of such processes are "variant" or "mutant" forms of the original "wild type" protein or gene.

A "plurality" of a substance, such as a polypeptide or polynucleotide of the invention, as used herein, generally refers to a collection of two or more types or kinds of the substance. There are two or more types or kinds of a substance if two or more of the substances differ from each other with respect to a particular characteristic, such as the variant amino acid found at a particular amino acid position. For example, there is a plurality of polypeptides of the invention if there are two or more polypeptides of the invention that are substantially the same, preferably identical, in sequence except for the sequence of a variant CDR or except for the variant amino acid at a particular solvent accessible and highly diverse amino acid position. In another example, there is a plurality of polynucleotides of the invention if there are two or more polynucleotides of the invention that are substantially the same, preferably identical, in sequence except for the sequence that encodes a variant CDR or except for the sequence that encodes a variant amino acid for a particular solvent accessible and highly diverse amino acid position.

The invention provides methods for generating and isolating novel antibodies or antigen binding fragments that preferably have a high affinity for a selected antigen. A plurality of different antibodies or antibody variable domains are prepared by mutating (diversifying) one or more selected amino acid positions in a source antibody light chain variable domain and/or heavy chain variable domain to generate a diverse library of antibody variable domains with variant amino acids at those positions. The amino acid positions are those that are solvent accessible, for example as determined by analyzing the structure of a source antibody, and/or that are highly diverse among known and/or natural occurring immunoglobulin polypeptides.

The amino acid positions that are solvent accessible and highly diverse are preferably those in the CDR regions of the antibody variable domains selected from the group consisting of CDRL1, CDRL2, CDRL3, CDRH1, CDRH2, CDRH3, and mixtures thereof. Amino acid positions are each mutated using a non-random codon set encoding the commonly occurring amino acids at each position. In some embodiments, when a solvent accessible and highly diverse position in a CDR region is to be mutated, a codon set is selected that encodes preferably at least about 50%, preferably at least about 60%, preferably at least about 70%, preferably at least about 80%, preferably at least about 90%, preferably all the target amino acids (as defined above) for that position. In some embodiments, when a solvent accessible and highly diverse position in a CDR region is to be mutated, a codon set is selected that encodes preferably from about 50% to about 100%, preferably from about 60% to about 95%, preferably from at least about 70% to about 90%, preferably from about 75% to about 90% of all the target amino acids (as defined above) for that position. For CDRH3, variant CDRH3 regions are generated that have different lengths and/or are randomized at selected positions using codons set such as NNK, NNS, NVT, DVK, XYZ or tryptophan or glycine or mixtures thereof.

The diversity of the library of the antibody variable domains is designed to maximize diversity while minimizing structural perturbations of the antibody variable domain to provide for increased ability to isolate high affinity antibodies and to provide for antibodies that can be produced in high yield in cell culture. The number of positions mutated in the antibody variable domain is minimized and the variant amino acids at each position are designed to include the commonly occurring amino acids at each position, while preferably (where possible) excluding uncommonly occurring amino acids. Preferably, a single antibody, including at least one CDR, is used as the source antibody. It is surprising that a library of antibody variable domains having diversity in sequences and size can be generated using a single source antibody as a template and targeting diversity to particular positions using particular amino acid substitutions.

Design of Diversity of Antibody Variable Domains

In one aspect of the invention, high quality libraries of antibody variable domains are generated. The libraries have diversity in number of members of the library as well as in the diversity of different sequences of the antibody variable domains. The libraries include high affinity binding antibody variable domains for one or more antigens, including, for example, insulin like growth factor-1 (IGF-1), vascular endothelial growth factor (VEGF), and Her-2. The diversity in the library is designed by selecting amino acid positions that are solvent accessible and highly diverse in a single source antibody and mutating those positions in at least one CDR using nonrandom codon sets. The nonrandom codon set preferably encodes at least a subset of the commonly occurring amino acids at those positions while minimizing nontarget sequences such as cysteine and stop codons.

A preferred source antibody is humanized antibody 4D5, but the methods for diversity design can be applied to other source antibodies whose sequence is known. A source antibody can be a naturally occurring antibody, synthetic antibody, recombinant antibody, humanized antibody, germ line derived antibody, chimeric antibody, affinity matured antibody, or antigen binding fragment thereof. The antibodies can be obtained from a variety of mammalian species including humans, mice and rats. In some embodiments, a source antibody is an antibody that is obtained after one or more initial affinity screening rounds, but prior to an affinity maturation step(s). A source antibody may be selected or modified to provide for high yield and stability when produced in cell culture.

One source antibody is the humanized antibody 4D5. Antibody 4D5 is a humanized antibody specific for a cancer-associated antigen known as Her-2 (erbB2). The antibody includes variable domains having consensus framework regions; a few positions were reverted to mouse sequence during the process of increasing affinity of the humanized antibody. The sequence and crystal structure of humanized antibody 4D5 have been described in U.S. Pat. No. 6,054,297, Carter et al, PNAS 89:4285 (1992), the crystal structure is shown in J. Mol. Biol. 229:969 (1993) and MMDB nos. 990-992 of NCBI's Molecular Modeling Database.

A criterion for generating diversity in antibody variable domains is to mutate residues at positions that are solvent accessible (as defined above). These positions are typically found in the CDRs, and are typically on the exterior of the protein. Preferably, solvent accessible positions are determined using coordinates from a 3-dimensional model of an antibody, using a computer program such as the InsightII program (Accelrys, San Diego, Calif.). Solvent accessible positions can also be determined using algorithms known in the art (e.g., Lee and Richards, J. Mol. Biol. 55, 379 (1971) and Connolly, J. Appl. Cryst. 16, 548 (1983)). Determination of solvent accessible positions can be performed using software suitable for protein modeling and 3-dimensional structural information obtained from an antibody. Software that can be utilized for these purposes includes SYBYL Biopolymer Module software (Tripos Associates). Generally and preferably, where an algorithm (program) requires a user input size parameter, the "size" of a probe which is used in the calculation is set at about 1.4 Angstrom or smaller in radius. In addition, determination of solvent accessible regions and area methods using software for personal computers has been described by Pacios ((1994) "ARVOMOL/CONTOUR: molecular surface areas and volumes on Personal Computers", *Comput. Chem.* 18(4): 377-386; and "Variations of Surface Areas and Volumes in Distinct Molecular Surfaces of Biomolecules." *J. Mol. Model.* (1995), 1: 46-53).

Figure 36:
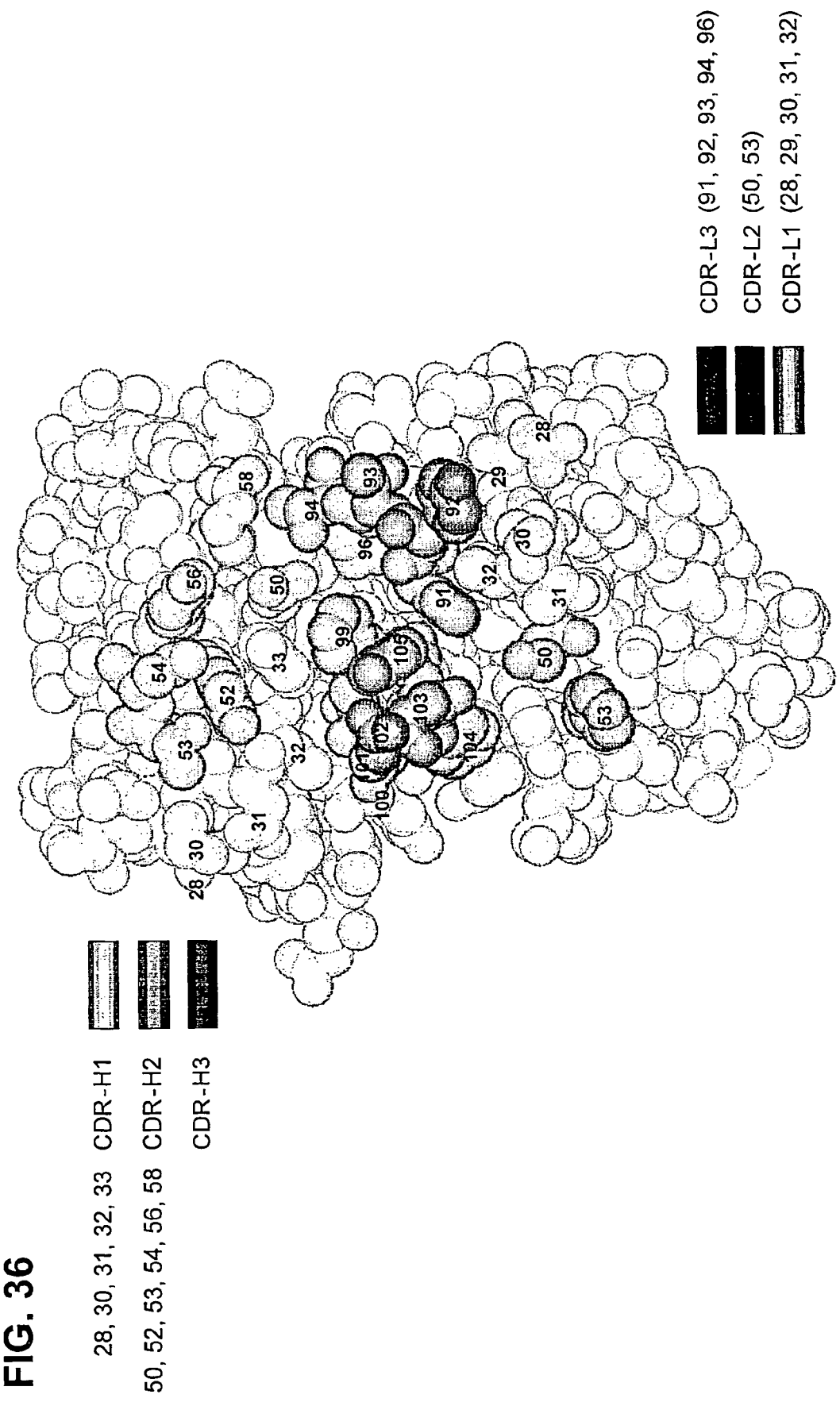
FIG. 36 shows a 3-D modeled structure of humanized 4D5 showing CDR residues that form contiguous patches. Contiguous patches are formed by amino acid residues 28, 29, 30, 31 and 32 in CDRL1; amino acids residues 50 and 53 of CDRL2; amino acid residues 91, 92, 93, 94 and 96 of CDRL3; amino acid residues 28, 30, 31, 32, 33 in CDRH1; and amino acid residues 50, 52, 53, 54, 56, and 58 in CDRH2.

In some instances, selection of solvent accessible residues is further refined by choosing solvent accessible residues that collectively form a minimum contiguous patch, for example when the reference polypeptide or source antibody is in its 3-D folded structure. For example, as shown in FIG. 36, a compact (minimum) contiguous patch is formed by residues selected for CDRH1/H2/H3/L1/L2/L3 of humanized 4D5. A compact (minimum) contiguous patch may comprise only a subset (for example, 2-5 CDRs) of the full range of CDRs, for example, CDRH1/H2/H3/L3. Solvent accessible residues that do not contribute to formation of such a patch may optionally be excluded from diversification. Refinement of selection by this criterion permits the practitioner to minimize, as desired, the number of residues to be diversified. For example, residue 28 in H1 can optionally be excluded in diversification since it is on the edge of the patch. However, this selection criterion can also be used, where desired, to choose residues to be diversified that may not necessarily be deemed solvent accessible. For example, a residue that is not deemed solvent accessible, but forms a contiguous patch in the 3-D folded structure with other residues that are deemed solvent accessible may be selected for diversification. An example of this is CDRL1-29. Selection of such residues would be evident to one skilled in the art, and its appropriateness can also be determined empirically and according to the needs and desires of the skilled practitioner.

The solvent accessible positions identified from the crystal structure of humanized antibody 4D5 for each CDR are as follows (residue position according to Kabat):
CDRL1: 28, 30, 31, 32
CDRL2: 50, 53
CDRL3: 91, 92, 93, 94, 96
CDRH1: 28, 30, 31, 32, 33
CDRH2: 50, 52, 52A, 53, 54, 55, 56, 57, 58.
In addition, residue 29 of CDRL1 was also selected based on its inclusion in a contiguous patch comprising other solvent accessible residues.

Another criterion for selecting positions to be mutated are those positions which show variability in amino acid sequence when the sequences of known and/or natural antibodies are compared. A highly diverse position refers to a position of an amino acid located in the variable regions of the light or heavy chains that have a number of different amino acids represented at the position when the amino acid sequences of known and/or natural antibodies/antigen binding fragments are compared. The highly diverse positions are preferably in the CDR regions. The positions of CDRH3 are all considered highly diverse. According to the invention, amino acid residues are highly diverse if they have preferably from about 2 to about 11 (although the numbers can range as described herein) different possible amino acid residue variations at that position.

Figure 2:
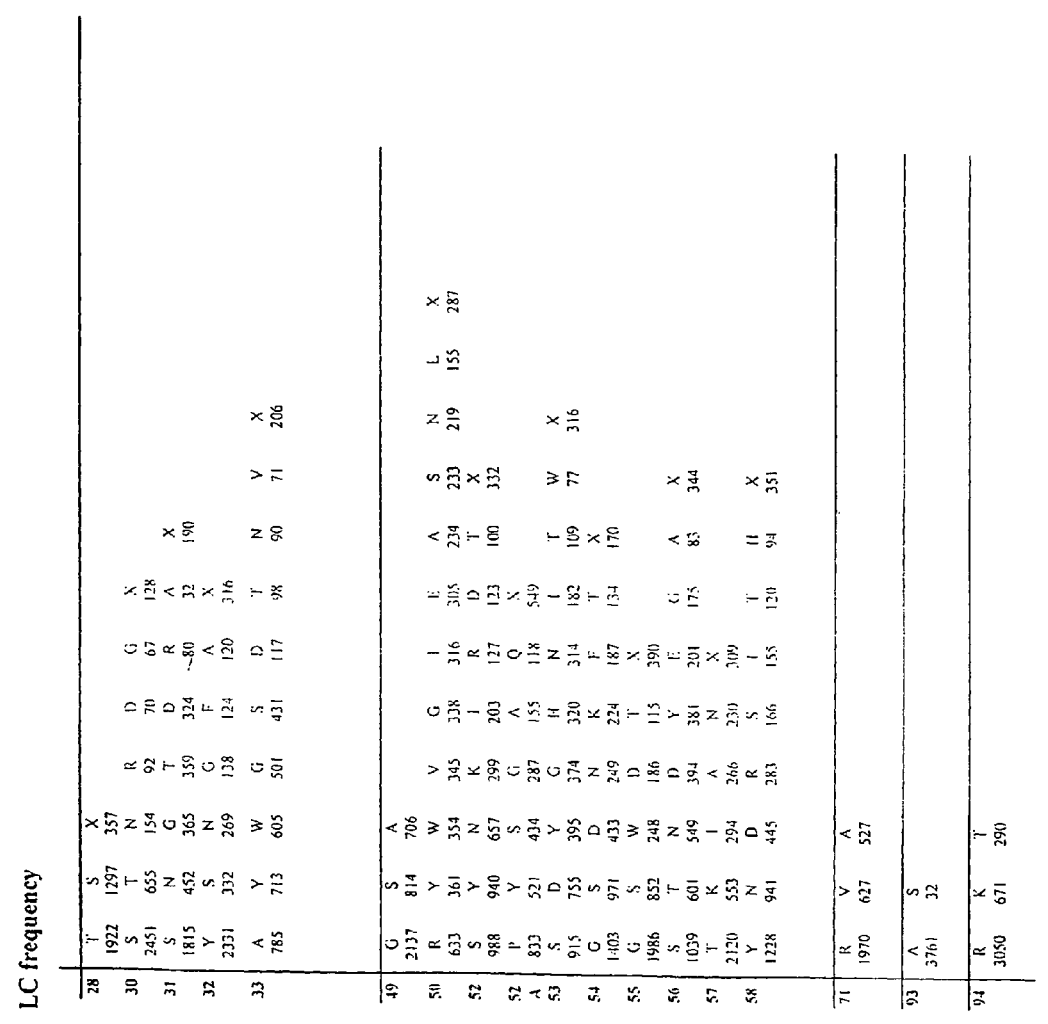

In one aspect, identification of highly diverse positions in known and/or naturally occurring antibodies is facilitated by the data provided by Kabat, Sequences of Proteins of Immunological Interest (National Institutes of Health, Bethesda, Md., 1987 and 1991). An internet-based database located at immuno.bme.nwu.edu provides an extensive collection and alignment of human light and heavy chain sequences and facilitates determination of highly diverse positions in these sequences. The diversity at the solvent accessible positions of humanized antibody 4D5 in known and/or naturally occurring light and heavy chains is shown in FIGS. 1 and 2.

In one aspect of the invention, the highly diverse and solvent accessible residues in at least one CDR selected from the group consisting of CDRL1, CDRL2, CDRL3, CDRH1, CDRH2 and mixtures thereof are mutated (i.e., randomized using codon sets as described herein). In some embodiments, the group also includes CDRH3. For example, the solvent accessible and/or highly diverse residues in CDRL3 and CDRH3 are mutated. Accordingly, the invention provides for a large number of novel antibody sequences formed by replacing the solvent accessible and highly diverse positions of at least one CDR of the source antibody variable domain with variant amino acids.

A target group of amino acids is the group of amino acids found at each solvent accessible and highly diverse position in a CDR in preferably at least about 50%, preferably at least about 70%, preferably at least about 80%, preferably at least about 90% of antibodies when the sequences of known and/or natural antibodies/antigen binding fragments are compared. The variant amino acids are a group of amino acids that include some or all of the target amino acids and are encoded by a nonrandom codon set. Of the amino acids encoded by the nonrandom codon set, preferably at least about 70% of the amino acids are target amino acids and more preferably at least about 80% of the amino acids are target amino acids. The nonrandom codon set for each position preferably encodes at least two amino acids and does not encode cysteine. Nontarget amino acids at each position are minimized and cysteines and stop codons are generally and preferably excluded because they can adversely affect the structure of the antibody variable domain for, in particular, L1, L2, L3, H1 and H2. For positions in the light chain CDR1, CDR2, CDR3, and for heavy chain CDR1 and CDR2, typically, a set of target amino acids can include from about two to eleven amino acids at a particular highly diverse and solvent-accessible position of the source sequence.

As discussed above, the variant amino acids are encoded by nonrandom codon sets. A codon set is a set of different nucleotide triplet sequences which can be used to form a set of oligonucleotides used to encode the desired group of amino acids. A set of oligonucleotides can be synthesized, for example, by solid phase synthesis, containing sequences that represent all possible combinations of nucleotide triplets provided by the codon set and that will encode the desired group of amino acids. Synthesis of oligonucleotides with selected nucleotide "degeneracy" at certain positions is well known in that art. Such sets of nucleotides having certain codon sets can be synthesized using commercial nucleic acid synthesizers (available from, for example, Applied Biosystems, Foster City, Calif.), or can be obtained commercially (for example, from Life Technologies, Rockville, Md.). Therefore, a set of oligonucleotides synthesized having a particular codon set will typically include a plurality of oligonucleotides with different sequences, the differences established by the codon set within the overall sequence. Oligonucleotides, as used according to the invention, have sequences that allow for hybridization to a variable domain nucleic acid template and also can include restriction enzyme sites for cloning purposes.

In one aspect, the target amino acids were identified for each solvent accessible and highly diverse position in CDRs of humanized antibody 4D5. The target amino acids were identified by identifying different amino acids at each of the solvent accessible and highly diverse positions in CDRL1, CDRL2, CDRL3, CDRH1 and CDRH2 using the sequences of known and/or naturally occurring antibodies in the Kabat database. Light chain diversity and heavy chain diversity from the Kabat database are shown in FIGS. 1 and 2, respectively. Based on the diversity as shown in FIGS. 1 and 2, the target amino acids identified at each position are shown in FIG. 3.

Illustrative nonrandom codon sets encoding a group of amino acids comprising preferably at least about 50%, preferably at least about 60%, preferably at least about 70%, preferably at least about 80%, preferably at least about 90%, preferably all of the target amino acids for each position are also shown in FIG. 3. The "% good" in FIG. 3 represents the percentage of amino acids encoded by the nonrandom codon set that are target amino acids for that position. Most preferably, the variant amino acids encoded by the codon set include the amino acids occurring with the highest frequency in known and/or naturally occurring antibodies. The high percentage means very low nontarget amino acids and this is more important than having more of the target amino acids in the design of the nonrandom codon set. The redundancy is included in all calculations.

The "% covering" in FIG. 3, represents the percentage of known and/or natural occurring antibody sequences that are encoded by the designed codons at each position. For example, for L3-91, the amino acids YSA (tyrosine, serine and alanine) are in the group of target amino acids which occur at position 91 in known and/or naturally occurring antibodies. The codon set is designed to encode YSAD (tyrosine, serine, alanine and aspartic acid), which encodes 75% of the target amino acids. These three amino acids are also found in 1190 out of 1580 natural antibody sequences at that site, which is 75% of the known and/or natural antibodies. It is preferable that codon sets are designed for each position in a CDR region to include amino acids found in those positions in at least about 50% of the known and/or naturally occurring antibodies and more preferably in at least about 60% of the known and/or naturally occurring antibodies and most preferably in at least about 70% of the known and/or naturally occurring antibodies.

In one embodiment, a polypeptide having a variant CDR L1, L2, L3, H1, H2 or mixtures thereof is formed, wherein at least one variant CDR comprises a variant amino acid in at least one solvent accessible and highly diverse amino acid position, wherein the variant amino acid is encoded by a nonrandom codon set, and wherein at least 70% of the amino acids encoded by the nonrandom codon set are target amino acids for that position in known antibody variable domain sequences. For example, an antibody variable domain can comprise a variant amino acid in one or more amino acid positions 28, 30, 31, 32 and/or 33 of CDRH1; and/or in one or more amino acid positions 50, 52, 53, 54, 56 and/or 58 of CDRH2; and/or in one or more amino acid positions 28, 29, 30 and/or 31 of CDRL1; and/or in one or more amino acid positions 50 and/or 53 in CDRL2; and/or in one or more amino acid positions 91, 92, 93, 94 and/or 96. The variant amino acids at these positions are preferably encoded by codon sets as exemplified in FIGS. 3, 5-13 and 24.

Heavy chain CDR3s (CDRH3s) in known antibodies have diverse sequences, structural conformations, and lengths. CDRH3s are often found in the middle of the antigen binding pocket and often participate in antigen contact. The design of CDRH3 is thus preferably developed separately from that of the other CDRs because it can be difficult to predict the structural conformation of CDRH3 and the amino acid diversity in this region is especially diverse in known antibodies. In accordance with the present invention, CDRH3 is designed to generate diversity at specific positions within CDRH3 and to exclude amino acids which do not occur frequently in CDRH3 sequences at any position.

To generate diversity in CDRH3, a database of known, generally natural, antibodies can be used as a guideline. In comparison to other CDRs, CDRH3 has the highest diversity in sequences and length, although the sequence diversity is not completely random (i.e., some amino acids occur more often than others). In one embodiment, a library is generated with a degenerate codon set such as NNK, which codes for all 20 amino acids and a stop codon. Clones that display functionally on the phage are analyzed for their sequences. Frequency of amino acids in the synthetically-generated library is then compared with the frequency of amino acids in known antibodies. Good agreement of amino acid frequency can be expected, although in some instances there may be increased frequency of certain classes of amino acids in the synthetic library compared to known antibodies. For example, a library generated with NNK can be expected to contain sequences that utilize more usage of aliphatic/hydrophobic amino acids. This procedure can be performed to obtain useful information on appropriate choice of amino acids, and thus codon sets, to include in generating CDRH3 diversity. In another embodiment, CDRH3 diversity is generated using the codon set NNS. NNS and NNK encode the same amino acid group. However, there can be individual preferences for one codon set or the other, depending on the various factors known in the art, such as efficiency of coupling in oligonucleotide synthesis chemistry.

In some embodiments, the practitioner of methods of the invention may wish to modify the amount/proportions of individual nucleotides (G, A, T, C) for a codon set, such as the N nucleotide in a codon set such as in NNS. This is illustratively represented as XYZ codons indicated in FIG. 4. This can be achieved by, for example, doping different amounts of the nucleotides within a codon set instead of using a straight, equal proportion of the nucleotides for the N in the codon set. For example, a codon set XYZ has the following proportions of nucleotides. X is 38% G, 19% A, 26% T and 17% C; Y is 31% G, 34% A, 17% T and 18% C, and Z is 24% G/76% C. Such modifications can be useful for various purposes depending on the circumstances and desire of the practitioner. For example, such modifications can be made to more closely reflect the amino acid bias as seen in a natural diversity profile, such as the profile of CDRH3.

In some embodiments, a diversified CDRH3 library can be generated with a codon set such as DVK, which encodes 12 amino acids (ACDEGKNRSTYW) and one stop codon. This excludes amino acids that occur infrequently in known antibodies. A CDRH3 library may also be generated using the codon set NVT, which encodes 11 amino acids (ACDGHNPRSTY), but does not encode stop codons or tryptophan (Trp, W). In some embodiments, the design of a codon set, such as NVT, may be doped with Trp.

As discussed previously, there is great diversity in CDRH3 regions in length of the CDRH3 regions. In natural antibodies, lengths of CDRH3 can range from 2 to 24 amino acids with the most common length being 11-13 residues. In one embodiment, diversity in CDRH3 is generated by preparing a number of different libraries, each library having a different length of CDRH3 region ranging from about 7 to 19 amino acids. The libraries with different lengths of CDRH3 regions are then pooled and used to select and/or screen for high affinity binding antibody variable domains. Illustrative embodiments of oligonucleotides that can be utilized to provide for variety in CDRH3 sequence length include those shown in FIG. 4 and FIG. 43.

In some embodiments, the diversity in the N and C-terminal regions of CDRH3 is minimized. At the C-terminus, there may be two types of sequences in known antibodies: $Y_{100a}AMD_{101}(Y/V)_{102}$ or $F_{100a}D_{101}(Y/V)_{102}$. Limited diversity can be targeted at selected residues in the C-terminal region. For example, $Y_{100a}$ position can be varied using codon sets that encode fewer amino acids such as DVK, DSG, KSG, DSG, or may be varied with a codon set that encodes all 20 amino acids such as NNK, NVT, or XYZ.

One aspect of the invention provides a polypeptide, such as an antibody variable domain, comprising a variant CDRH3 that comprises an amino acid sequence:

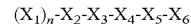

$(X_1)_n$-$X_2$-$X_3$-$X_4$-$X_5$-$X_6$ wherein $X_1$ is any naturally occurring amino acid encoded by a codon set of NNK, NNS, DVK, NVT, XYZ or is tryptophan or glycine or mixtures thereof, and n=4 to 14;

$X_2$ is any naturally occurring amino acid encoded by a codon set of KSG, DVK, DSG, NVT, KSG, NNS, XYZ, NNK or is tyrosine, phenylalanine, serine, alanine, glycine, leucine, or tryptophan;

$X_3$ is missing when $X_2$ is phenylalanine or leucine, or if present, is alanine, valine, aspartic acid or glycine;

$X_4$ is missing when $X_2$ is phenylalanine or leucine, or if present, is methionine;

$X_5$ is aspartic acid, alanine, valine, or glycine; and $X_6$ is tyrosine or valine.

A polypeptide or library of polypeptides with variant CDRH3 of the formula as shown above may be generated using any one or combination of the oligonucleotides illustrated in FIG. 4 and FIG. 43.

In one embodiment, CDRH3 comprises an amino acid sequence $(X_1)_n$-$X_2$-$X_3$-$X_4$-$X_5$-$X_6$, wherein $X_1$ is any naturally occurring amino acid encoded by a codon set of NNK, NNS, DVK, NVT, XYZ or tryptophan or glycine or mixtures thereof, and n=4 to 14; $X_2$ is any naturally occurring amino acid encoded by a codon set of KSG, DVK, DSG, NVT, KSG, NNS, XYZ, NNK or is tyrosine, phenylalanine, serine, glycine, alanine, leucine, or tryptophan; $X_3$ is alanine, valine, aspartic acid or glycine; $X_4$ is methionine; $X_5$ is aspartic acid, alanine, valine, or glycine; and $X_6$ is tyrosine or valine.

In some embodiments, n is preferably 4 and $X_1$ is any naturally occurring amino acid encoded by codon sets NNK, NNS or XYZ, $X_2$ is any naturally occurring amino acid encoded by KSG, NNK, XYZ or is tyrosine, $X_3$ is alanine, glycine or valine, $X_4$ is methionine, $X_5$ is aspartic acid and $X_6$ is tyrosine. A polypeptide or plurality of polypeptides comprising variant CDRH3 region in these embodiments can be generated using at least one or more than one of oligonucleotides F66e and F66f.

In some embodiments, n is preferably 6, and $X_1$ is any naturally occurring amino acid encoded by codon sets DVK, NVT, NNK, NNS or XYZ or tryptophan or glycine or mixtures thereof, $X_2$ is any naturally occurring amino acid encoded by DSG, DVK, KSG, NNK, XYZ or is tyrosine, glycine, serine, alanine or tryptophan, $X_3$ is alanine, $X_4$ is methionine, $X_5$ is aspartic acid and $X_6$ is tyrosine. In some embodiments, $X_1$ corresponds to amino acid position 95, $X_2$ corresponds to amino acid position 100a, A is in position 100b, M is in position 100c, D is in position 101 and Y is in position 102 of CDRH3 of antibody 4D5. A polypeptide or plurality of polypeptides comprising a variant CDRH3 region in these embodiments can be generated using at least one or more than one of oligonucleotides F63, F64, F65, F66, F165, F134, F135, F163a, F166, F167, F66a, F66b, F66a1, F66b1, F190f, and F190n.

In another embodiment, CDRH3 comprises an amino acid sequence $(X_1)_n$-$X_2$-$X_3$-$X_4$-$X_5$-$X_6$; wherein $X_1$ is any naturally occurring amino acid encoded by a codon set of NNK, NNS, DVK, NVT, XYZ or tryptophan or glycine or mixtures thereof, and n=4 to 14; $X_2$ is leucine or phenylalanine; $X_3$ is missing; $X_4$ is missing; $X_5$ is aspartic acid, alanine, valine, or glycine; and $X_6$ is tyrosine or valine. In some embodiments, the variant CDRH3 comprises an amino acid sequence $(X_1)_n X_2$-D-Y; wherein $X_1$ is any naturally occurring amino acid encoded by a codon set of NNK, NNS, DVK, NVT, XYZ or tryptophan or glycine or mixtures thereof, and n=4 to 14; $X_2$ is leucine or phenylalanine; D is aspartic acid and Y is tyrosine. In other embodiments, n is preferably 6 and $X_1$ corresponds to amino acid position 95, $X_2$ corresponds to amino acid position 100a, $X_5$ is in position 101 and $X_6$ is in position 102 of CDRH3 of antibody 4D5. A polypeptide or plurality of polypeptides comprising a variant CDRH3 region in these embodiments can be generated using at least one or more than one of oligonucleotides F171c, F171d, F171e, F171, F185, F186, F187, F185a, F185b, F185b1, F187a, F186a, F187b, and F187c.

In another aspect of the invention, methods and polypeptides, such as antibody variable domains, are provided comprising one, two or all variant CDRs selected from the group consisting of CDRH1, CDRH2 and CDRH3, wherein said variant CDRH3 comprises an amino acid sequence $(X_1)_n$-$X_2$-$X_3$-$X_4$-$X_5$-$X_6$ wherein $X_1$ is any naturally occurring amino acid encoded by a codon set of NNK, NNS, DVK, NVT, XYZ or is tryptophan or glycine or mixtures thereof, and n=4 to 14;

$X_2$ is any naturally occurring amino acid encoded by a codon set of KSG, DVK, DSG, NVT, KSG, NNS, XYZ, NNK or is tyrosine, phenylalanine, glycine, serine, alanine, leucine, or tryptophan;

$X_3$ is missing when $X_2$ is phenylalanine or leucine, or if present, is alanine, valine, aspartic acid or glycine;

$X_4$ is missing when $X_2$ is phenylalanine or leucine, or if present, is methionine;

$X_5$ is aspartic acid, alanine, valine, glycine; and $X_6$ is tyrosine or valine;

and wherein the variant CDRH1 or CDRH2 or both comprise at least one variant amino acid in a solvent accessible and highly diverse amino acid position, wherein the variant amino acid is encoded by a nonrandom codon set, wherein at least about 50%, 60%, 70%, 80%, 90%, or all of the amino acids encoded by the nonrandom codon set are target amino for that position in known antibodies or antigen binding fragments (for e.g. antibody variable domains).

In some embodiments of any of the methods and polypeptides described herein, the position in H3 is any of positions 95 to 102 of antibody according to Kabat numbering system (e.g. antibody 4D5). For example, position 95 can have a variant amino acid encoded by codon set DVK, NVT, NNS, XYZ, NNK or is tryptophan; position 96 can be encoded by DVK, NVT, NNS, XYZ, or is glycine or tryptophan; position 97 can be encoded by DVK, NVT, NNS, XYZ, or is tryptophan; position 98 can be encoded by DVK, NVT, NNS, XYZ, or is tryptophan; position 99 can be encoded by DVK, NVT, NNS, XYZ; position 100 can be encoded by DVK, NVT, NNS, XYZ, or is tryptophan; position 100a can be encoded by DVK, DSG, KSG, NVT, NNS, XYZ, or can be tyrosine, glycine, serine, alanine, tryptophan, aspartic acid, methionine, phenylalanine, leucine, valine; position 100b can be encoded by DSG, KSG, XYZ or is alanine, tyrosine, glycine, valine, aspartic acid, methionine, or phenylalanine; Position 100c can be encoded by KSG, XYZ, or is methionine, phenylalanine, leucine, alanine, glycine, valine, tyrosine, aspartic acid; position 101 can be encoded by KSG, XYZ or is aspartic acid, methionine, alanine, valine, glycine, tyrosine, phenylalanine, leucine; and position 102 can be encoded by KSG or XYZ or is tyrosine, aspartic acid, methionine, alanine, valine, glycine. A polypeptide or plurality of polypeptides comprising a variant CDRH3 region in these embodiments can be generated using at least one or more than one of oligonucleotides illustrated in FIG. 4 and FIG. 43.

It is contemplated that the sequence diversity of libraries created by introduction of variant amino acids in CDRH3 can be increased by combining these CDRH3 variations with variations in other regions of the antibody, specifically in other CDRs of either the light or heavy chain variable sequences. It is contemplated that the nucleic acid sequences that encode members of this set can be further diversified by introduction of other variant amino acids in the CDRs of either the light or heavy chain sequences, via codon sets.

Thus, for example, in one embodiment, CDRH3 sequences from fusion polypeptides that bind a target antigen can be combined with diversified CDRL3, CDRH1, or CDRH2 sequences, or any combination of diversified CDRs.

It should be noted that in some instances framework residues may be varied relative to the sequence of a source antibody or antigen binding fragment, for example, to reflect a consensus sequence or to improve stability or display. For example, framework residues 49, 93, 94 or 71 in the heavy chain may be varied. Heavy chain framework residue 93 may be serine or alanine (which is the human consensus sequence amino acid at that position.) Heavy chain framework residue 94 may be changed to reflect framework consensus sequence from threonine to arginine or lysine. Another example of a framework residue that may be altered is heavy chain framework residue 71, which is R in about 1970 polypeptides, V in about 627 polypeptides and A in about 527 polypeptides, as found in the Kabat database. Heavy chain framework residue 49 may be alanine or glycine. In addition, optionally, the 3 N-terminal amino acids of the heavy chain variable domain can be removed. In the light chain, optionally, the arginine at amino acid position 66 can be changed to glycine.

In one aspect, the invention provides vector constructs for generating fusion polypeptides that bind with significant affinity to potential ligands. These constructs comprise a dimerizable domain that when present in a fusion polypeptide provides for increased tendency for heavy chains to dimerize to form dimers of Fab or Fab'antibody fragments/portions. These dimerization domains may include, eg. a heavy chain hinge sequence that may be present in the fusion polypeptide. Dimerization domains in fusion phage polypeptides bring two sets of fusion polypeptides (LC/HC-phage protein/fragment (such as pIII) together, thus allowing formation of suitable linkages (such as interheavy chain disulfide bridges) between the two sets of fusion polypeptide. Vector constructs containing such dimerization domains can be used to achieve divalent display of antibody variable domains, for example the diversified fusion proteins described herein, on phage. Preferably, the intrinsic affinity of each monomeric antibody fragment (fusion polypeptide) is not significantly altered by fusion to the dimerization domain. Preferably, dimerization results in divalent phage display which provides increased avidity of phage binding, with significant decrease in off-rate, which can be determined by methods known in the art and as described herein. Dimerization domain-containing vectors of the invention may or may not also include an amber stop codon after the dimerization domain. Illustrative embodiments of vectors are shown in FIG. 34.

Dimerization can be varied to achieve different display characteristics. Dimerization domains can comprise a sequence comprising a cysteine residue, a hinge region from a full-length antibody, a dimerization sequence such as leucine zipper sequence or GCN4 zipper sequence or mixtures thereof. Dimerization sequences are known in the art, and include, for example, the GCN4 zipper sequence (GRMKQLEDKVEELLSKNYHLENE-VARLKKLVGERG) (SEQ ID NO: 3). The dimerization domain is preferably located at the C-terminal end of the heavy chain variable or constant domain sequence and/or between the heavy chain variable or constant domain sequence and any viral coat protein component sequence. An amber stop codon may also be present at or after the C-terminal end of the dimerization domain. In one embodiment, wherein an amber stop codon is present, the dimerization domain encodes at least one cysteine and a dimerizing sequence such as leucine zipper. In another embodiment, wherein no amber stop codon is present, then the dimerization domain comprises a single cysteine residue.

The polypeptides of the invention can also be fused to other types of polypeptides in order to provide for display of the variant polypeptides or to provide for purification, screening or sorting, and detection of the polypeptide. For embodiment involving phage display, the polypeptides of the invention are fused to all or a portion of a viral coat protein. Examples of viral coat protein include protein PIII, major coat protein, pVIII, Soc, Hoc, gpD, pVI and variants thereof. In addition, the variant polypeptides generated according to the methods of the invention can optionally be fused to a polypeptide marker or tag such as FLAG, polyhistidine, gD, c-myc, B-galactosidase and the like.

Methods of Generating Libraries of Randomized Variable Domains

Methods of substituting an amino acid of choice into a template nucleic acid are well established in the art, some of which are described herein. For example, libraries can be created by targeting solvent accessible and/or highly diverse positions in at least one CDR region for amino acid substitution with variant amino acids using the Kunkel method. See, for e.g., Kunkel et al., Methods Enzymol. (1987), 154:367-382. Generation of randomized sequences is also described below in the Examples.

The sequence of oligonucleotides includes one or more of the designed codon sets for different lengths of CDRH3 or for the solvent accessible and highly diverse positions in a CDR. A codon set is a set of different nucleotide triplet sequences used to encode desired variant amino acids. Codon sets can be represented using symbols to designate particular nucleotides or equimolar mixtures of nucleotides as shown in below according to the IUB code. Typically, a codon set is represented by three capital letters eg. NNK, NNS, DVK and the like.

IUB CODES
G Guanine
A Adenine
T Thymine
C Cytosine
R (A or G)
Y (C or T)
M (A or C)
K (G or T)
S (C or G)
W (A or T)
H (A or C or T)
B (C or G or T)
(A or C or G)
D (A or G or T)
N (A or C or G or T)

For example, in the codon set DVK, D can be nucleotides A or G or T; V can be A or G or C; and K can be G or T. This codon set can present 18 different codons and can encode amino acids Ala, Trp, Tyr, Lys, Thr, Asn, Ser, Arg, Asp, Glu, Gly, and Cys.

Oligonucleotide or primer sets can be synthesized using standard methods. A set of oligonucleotides can be synthesized, for example, by solid phase synthesis, containing sequences that represent all possible combinations of nucleotide triplets provided by the codon set and that will encode the desired group of amino acids. Synthesis of oligonucleotides with selected nucleotide "degeneracy" at certain positions is well known in that art. Such sets of nucleotides having certain codon sets can be synthesized using commercial nucleic acid synthesizers (available from, for example, Applied Biosystems, Foster City, Calif.), or can be obtained commercially (for example, from Life Technologies, Rockville, Md.). Therefore, a set of oligonucleotides synthesized having a particular codon set will typically include a plurality of oligonucleotides with different sequences, the differences established by the codon set within the overall sequence. Oligonucleotides, as used according to the invention, have sequences that allow for hybridization to a variable domain nucleic acid template and also can include restriction enzyme sites for cloning purposes.

In one method, nucleic acid sequences encoding variant amino acids can be created by oligonucleotide-mediated mutagenesis of a nucleic acid sequence encoding a source or template polypeptide such as the antibody variable domain of 4D5. This technique is well known in the art as described by Zoller et al. Nucleic Acids Res. 10:6487-6504 (1987). Briefly, nucleic acid sequences encoding variant amino acids are created by hybridizing an oligonucleotide set encoding the desired codon sets to a DNA template, where the template is the single-stranded form of the plasmid containing a variable region nucleic acid template sequence. After hybridization, DNA polymerase is used to synthesize an entire second complementary strand of the template that will thus incorporate the oligonucleotide primer, and will contain the codon sets as provided by the oligonucleotide set. Nucleic acids encoding other source or template molecules are known or can be readily determined.

Generally, oligonucleotides of at least 25 nucleotides in length are used. An optimal oligonucleotide will have 12 to 15 nucleotides that are completely complementary to the template on either side of the nucleotide(s) coding for the mutation(s). This ensures that the oligonucleotide will hybridize properly to the single-stranded DNA template molecule. The oligonucleotides are readily synthesized using techniques known in the art such as that described by Crea et al., *Proc. Nat'l. Acad. Sci. USA*, 75:5765 (1978).

The DNA template is generated by those vectors that are either derived from bacteriophage M13 vectors (the commercially available M13 mp18 and M13 mp19 vectors are suitable), or those vectors that contain a single-stranded phage origin of replication as described by Viera et al., *Meth. Enzymol.*, 153:3 (1987). Thus, the DNA that is to be mutated can be inserted into one of these vectors in order to generate single-stranded template. Production of the single-stranded template is described in sections 4.21-4.41 of Sambrook et al., above.

To alter the native DNA sequence, the oligonucleotide is hybridized to the single stranded template under suitable hybridization conditions. A DNA polymerizing enzyme, usually T7 DNA polymerase or the Klenow fragment of DNA polymerase I, is then added to synthesize the complementary strand of the template using the oligonucleotide as a primer for synthesis. A heteroduplex molecule is thus formed such that one strand of DNA encodes the mutated form of gene 1, and the other strand (the original template) encodes the native, unaltered sequence of gene 1. This heteroduplex molecule is then transformed into a suitable host cell, usually a prokaryote such as *E. coli* JM101. After growing the cells, they are plated onto agarose plates and screened using the oligonucleotide primer radiolabelled with a 32-Phosphate to identify the bacterial colonies that contain the mutated DNA.

The method described immediately above may be modified such that a homoduplex molecule is created wherein both strands of the plasmid contain the mutation(s). The modifications are as follows: The single stranded oligonucleotide is annealed to the single-stranded template as described above. A mixture of three deoxyribonucleotides, deoxyriboadenosine (dATP), deoxyriboguanosine (dGTP), and deoxyribothymidine (dTT), is combined with a modified thiodeoxyribocytosine called dCTP-(aS) (which can be obtained from Amersham). This mixture is added to the template-oligonucleotide complex. Upon addition of DNA polymerase to this mixture, a strand of DNA identical to the template except for the mutated bases is generated. In addition, this new strand of DNA will contain dCTP-(aS) instead of dCTP, which serves to protect it from restriction endonuclease digestion. After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell.

As indicated previously the sequence of the oligonucleotide set is of sufficient length to hybridize to the template nucleic acid and may also, but does not necessarily, contain restriction sites. The DNA template can be generated by those vectors that are either derived from bacteriophage M13 vectors or vectors that contain a single-stranded phage origin of replication as described by Viera et al. ((1987) Meth. Enzymol., 153:3). Thus, the DNA that is to be mutated must be inserted into one of these vectors in order to generate single-stranded template. Production of the single-stranded template is described in sections 4.21-4.41 of Sambrook et al., supra.

According to another method, a library can be generated by providing upstream and downstream oligonucleotide sets, each set having a plurality of oligonucleotides with different sequences, the different sequences established by the codon sets provided within the sequence of the oligonucleotides. The upstream and downstream oligonucleotide sets, along with a variable domain template nucleic acid sequence, can be used in a polymerase chain reaction to generate a "library" of PCR products. The PCR products can be referred to as "nucleic acid cassettes", as they can be fused with other related or unrelated nucleic acid sequences, for example, viral coat protein components and dimerization domains, using established molecular biology techniques.

The sequence of the PCR primers includes one or more of the designed codon sets for the solvent accessible and highly diverse positions in a CDR region. As described above, a codon set is a set of different nucleotide triplet sequences used to encode desired variant amino acids.

Oligonucleotide sets can be used in a polymerase chain reaction using a variable region nucleic acid template sequence as the template to create nucleic acid cassettes. The variable region nucleic acid template sequence can be any portion of the light or heavy immunoglobulin chains containing the target nucleic acid sequences (ie., nucleic acid sequences encoding amino acids targeted for substitution). The variable region nucleic acid template sequence is a portion of a double stranded DNA molecule having a first nucleic acid strand and complementary second nucleic acid strand. The variable region nucleic acid template sequence contains at least a portion of a variable domain and has at least one CDR. In some cases, the variable region nucleic acid template sequence contains more than one CDR. An upstream portion and a downstream portion of the variable region nucleic acid template sequence can be targeted for hybridization with members of an upstream oligonucleotide set and a downstream oligonucleotide set.

A first oligonucleotide of the upstream primer set can hybridize to the first nucleic acid strand and a second oligonucleotide of the downstream primer set can hybridize to the second nucleic acid strand. The oligonucleotide primers can include one or more codon sets and be designed to hybridize to a portion of the variable region nucleic acid template sequence. Use of these oligonucleotides can introduce two or more codon sets into the PCR product (ie., the nucleic acid cassette) following PCR. The oligonucleotide primer that hybridizes to regions of the nucleic acid sequence encoding the antibody variable domain includes portions that encode CDR residues that are targeted for amino acid substitution.

The upstream and downstream oligonucleotide sets can also be synthesized to include restriction sites within the oligonucleotide sequence. These restriction sites can facilitate the insertion of the nucleic acid cassettes [ie., PCR reaction products] into an expression vector having additional antibody sequences. Preferably, the restriction sites are designed to facilitate the cloning of the nucleic acid cassettes without introducing extraneous nucleic acid sequences or removing original CDR or framework nucleic acid sequences.

Nucleic acid cassettes can be cloned into any suitable vector for expression of a portion or the entire light or heavy chain sequence containing the targeted amino acid substitutions generated. According to methods detailed in the invention, the nucleic acid cassette is cloned into a vector allowing production of a portion or the entire light or heavy chain sequence fused to all or a portion of a viral coat protein (ie., creating a fusion protein) and displayed on the surface of a particle or cell. While several types of vectors are available and may be used to practice this invention, phagemid vectors are the preferred vectors for use herein, as they may be constructed with relative ease, and can be readily amplified. Phagemid vectors generally contain a variety of components including promoters, signal sequences, phenotypic selection genes, origin of replication sites, and other necessary components as are known to those of ordinary skill in the art.

In another embodiment, wherein a particular variant amino acid combination is to be expressed, the nucleic acid cassette contains a sequence that is able to encode all or a portion of the heavy or light chain variable domain, and is able to encode the variant amino acid combinations. For production of antibodies containing these variant amino acids or combinations of variant amino acids, as in a library, the nucleic acid cassettes can be inserted into an expression vector containing additional antibody sequence, for example all or portions of the variable or constant domains of the light and heavy chain variable regions. These additional antibody sequences can also be fused to other nucleic acids sequences, such as sequences which encode viral coat protein components and therefore allow production of a fusion protein.

Vectors

One aspect of the invention includes a replicable expression vector comprising a nucleic acid sequence encoding a gene fusion, wherein the gene fusion encodes a fusion protein comprising an antibody variable domain, or an antibody variable domain and a constant domain, fused to all or a portion of a viral coat protein. Also included is a library of diverse replicable expression vectors comprising a plurality of gene fusions encoding a plurality of different fusion proteins including a plurality of the antibody variable domains generated with diverse sequences as described above. The vectors can include a variety of components and are preferably constructed to allow for movement of antibody variable domain between different vectors and/or to provide for display of the fusion proteins in different formats.

Examples of vectors include phage vectors. The phage vector has a phage origin of replication allowing phage replication and phage particle formation. The phage is preferably a filamentous bacteriophage, such as an M13, f1, fd, Pf3 phage or a derivative thereof, or a lambdoid phage, such as lambda, 21, phi80, phi81, 82, 424, 434, etc., or a derivative thereof.

Examples of viral coat proteins include infectivity protein PIII, major coat protein PVIII, p3, Soc (T4), Hoc (T4), gpD (of bacteriophage lambda), minor bacteriophage coat protein 6 (pVI) (filamentous phage; J Immunol Methods. Dec. 10, 1999; 231(1-2):39-51), variants of the M13 bacteriophage major coat protein (P8) (Protein Sci April 2000; 9(4):647-54). The fusion protein can be displayed on the surface of a phage and suitable phage systems include M13KO7 helper phage, M13R408, M13-VCS, and Phi X 174, pJuFo phage system (J Virol. August 2001; 75(15):7107-13.v), hyperphage (Nat Biotechnol. January 2001; 19(1):75-8). The preferred helper phage is M13KO7, and the preferred coat protein is the M13 Phage gene III coat protein. The preferred host is $E.\ coli$, and protease deficient strains of $E.\ coli$. Vectors, such as the fth1 vector (Nucleic Acids Res. May 15, 2001; 29(10):E50-0) can be useful for the expression of the fusion protein.

The expression vector also can have a secretory signal sequence fused to the DNA encoding each subunit of the antibody or fragment thereof This sequence is typically located immediately 5' to the gene encoding the fusion protein, and will thus be transcribed at the amino terminus of the fusion protein. However, in certain cases, the signal sequence has been demonstrated to be located at positions other than 5' to the gene encoding the protein to be secreted. This sequence targets the protein to which it is attached across the inner membrane of the bacterial cell. The DNA encoding the signal sequence may be obtained as a restriction endonuclease fragment from any gene encoding a protein that has a signal sequence. Suitable prokaryotic signal sequences may be obtained from genes encoding, for example, LamB or OmpF (Wong et al., Gene, 68:1931 (1983), MalE, PhoA and other genes. A preferred prokaryotic signal sequence for practicing this invention is the $E.\ coli$ heat-stable enterotoxin II (STII) signal sequence as described by Chang et al., Gene 55:189 (1987), and malE.

The vector also typically includes a promoter to drive expression of the fusion protein. Promoters most commonly used in prokaryotic vectors include the lac Z promoter system, the alkaline phosphatase pho A promoter (Ap), the bacteriophage $\lambda_{PL}$ promoter (a temperature sensitive promoter), the tac promoter (a hybrid trp-lac promoter that is regulated by the lac repressor), the tryptophan promoter, and the bacteriophage T7 promoter. For general descriptions of promoters, see section 17 of Sambrook et al. supra. While these are the most commonly used promoters, other suitable microbial promoters may be used as well.

The vector can also include other nucleic acid sequences, for example, sequences encoding gD tags, c-Myc epitopes, poly-histidine tags, fluorescence proteins (eg., GFP), or beta-galactosidase protein which can be useful for detection or purification of the fusion protein expressed on the surface of the phage or cell. Nucleic acid sequences encoding, for example, a gD tag, also provide for positive or negative selection of cells or virus expressing the fusion protein. In some embodiments, the gD tag is preferably fused to an antibody variable domain which is not fused to the viral coat protein component. Nucleic acid sequences encoding, for example, a polyhistidine tag, are useful for identifying fusion proteins including antibody variable domains that bind to a specific antigen using immunohistochemistry. Tags useful for detection of antigen binding can be fused to either an antibody variable domain not fused to a viral coat protein component or an antibody variable domain fused to a viral coat protein component.

Another useful component of the vectors used to practice this invention is phenotypic selection genes. Typical phenotypic selection genes are those encoding proteins that confer antibiotic resistance upon the host cell. By way of illustration, the ampicillin resistance gene (ampr), and the tetracycline resistance gene (tetr) are readily employed for this purpose.

The vector can also include nucleic acid sequences containing unique restriction sites and suppressible stop codons. The unique restriction sites are useful for moving antibody variable domains between different vectors and expression systems, especially useful for production of full-length antibodies or antigen binding fragments in cell cultures. The suppressible stop codons are useful to control the level of expression of the fusion protein and to facilitate purification of soluble antibody fragments. For example, an amber stop codon can be read as Gln in a supE host to enable phage display, while in a non-supE host it is read as a stop codon to produce soluble antibody fragments without fusion to phage coat proteins. These synthetic sequences can be fused to one or more antibody variable domains in the vector.

It is preferable to use vector systems that allow the nucleic acid encoding an antibody sequence of interest, for example a CDR having variant amino acids, to be easily removed from the vector system and placed into another vector system. For example, appropriate restriction sites can be engineered in a vector system to facilitate the removal of the nucleic acid sequence encoding an antibody or antibody variable domain having variant amino acids. The restriction sequences are usually chosen to be unique in the vectors to facilitate efficient excision and ligation into new vectors. Antibodies or antibody variable domains can then be expressed from vectors without extraneous fusion sequences, such as viral coat proteins or other sequence tags.

Between nucleic acid encoding antibody variable or constant domain (gene 1) and the viral coat protein component (gene 2), DNA encoding a termination or stop codon may be inserted, such termination codons including UAG (amber), UAA (ocher) and UGA (opel). (*Microbiology*, Davis et al., Harper & Row, New York, 1980, pp. 237, 245-47 and 374). The termination or stop codon expressed in a wild type host cell results in the synthesis of the gene 1 protein product without the gene 2 protein attached. However, growth in a suppressor host cell results in the synthesis of detectable quantities of fused protein. Such suppressor host cells are well known and described, such as *E. coli* suppressor strain (Bullock et al., *BioTechniques* 5:376-379 (1987)). Any acceptable method may be used to place such a termination codon into the mRNA encoding the fusion polypeptide.

The suppressible codon may be inserted between the first gene encoding a antibody variable or constant domain, and a second gene encoding at least a portion of a phage coat protein. Alternatively, the suppressible termination codon may be inserted adjacent to the fusion site by replacing the last amino acid triplet in the antibody variable domain or the first amino acid in the phage coat protein. The suppressible termination codon may be located at or after the C-terminal end of a dimerization domain. When the plasmid containing the suppressible codon is grown in a suppressor host cell, it results in the detectable production of a fusion polypeptide containing the polypeptide and the coat protein. When the plasmid is grown in a non-suppressor host cell, the antibody variable domain is synthesized substantially without fusion to the phage coat protein due to termination at the inserted suppressible triplet UAG, UAA, or UGA. In the non-suppressor cell the antibody variable domain is synthesized and secreted from the host cell due to the absence of the fused phage coat protein which otherwise anchored it to the host membrane.

In some embodiments, the CDR being diversified (randomized) may have a stop codon engineered in the template sequence (referred to herein as a "stop template"). This feature provides for detection and selection of successfully diversified sequences based on successful repair of the stop codon(s) in the template sequence due to incorporation of the oligonucleotide(s) comprising the sequence(s) for the variant amino acids of interest. This feature is further illustrated in the Examples below.

The light and/or heavy chain antibody variable or constant domains can also be fused to an additional peptide sequence, the additional peptide sequence providing for the interaction of one or more fusion polypeptides on the surface of the viral particle or cell. These peptide sequences are herein referred to as "dimerization domains". Dimerization domains may comprise at least one or more of a dimerization sequence, or at least one sequence comprising a cysteine residue or both. Suitable dimerization sequences include those of proteins having amphipathic alpha helices in which hydrophobic residues are regularly spaced and allow the formation of a dimer by interaction of the hydrophobic residues of each protein; such proteins and portions of proteins include, for example, leucine zipper regions. Dimerization domains can also comprise one or more cysteine residues (e.g. as provided by inclusion of an antibody hinge sequence within the dimerization domain). The cysteine residues can provide for dimerization by formation of one or more disulfide bonds. In one embodiment, wherein a stop codon is present after the dimerization domain, the dimerization domain comprises at least one cysteine residue. The dimerization domains are preferably located between the antibody variable or constant domain and the viral coat protein component.

In some cases the vector encodes a single antibody-phage polypeptide in a single chain form containing, for example, both the heavy and light chain variable regions fused to a coat protein. In these cases the vector is considered to be "monocistronic", expressing one transcript under the control of a certain promoter. Illustrative examples of such vectors are shown in FIGS. 34C and D. In FIG. 34C, a vector is shown as utilizing the alkaline phosphatase (AP) or Tac promoter to drive expression of a monocistronic sequence encoding VL and VH domains, with a linker peptide between the VL and VH domains. This cistronic sequence is connected at the 5' end to an *E. coli* malE or heat-stable enterotoxin II (STII) signal sequence and at its 3' end to all or a portion of a viral coat protein (shown in the FIG. 34 as the pIII protein). The fusion polypeptide encoded by this vector is referred to herein as "ScFv-pIII". In some embodiments, illustrated in FIG. 34D, the vector may further comprise a sequence encoding a dimerization domain (such as a leucine zipper) at its 3' end, between the second variable domain sequence (VH in FIG. 34D) and the viral coat protein sequence. Fusion polypeptides comprising the dimerization domain are capable of dimerizing to form a complex of two scFv polypeptides (referred to herein as "(ScFv)2-pIII").

In other cases, the variable regions of the heavy and light chains can be expressed as separate polypeptides, the vector thus being "bicistronic", allowing the expression of separate transcripts. Examples of bicistronic vectors are schematically shown in FIGS. 34A and 34B. In these vectors, a suitable promoter, such as the Ptac or PhoA promoter, can be used to drive expression of a bicistronic message. A first cistron, encoding, for example, a light chain variable and constant domain, is connected at the 5' end to a *E. coli* malE or heat-stable enterotoxin II (STII) signal sequence and at the 3' end to a nucleic acid sequence encoding a gD tag. A second cistron, encoding, for example, a heavy chain variable domain and constant domain CH1, is connected at its 5' end to a *E. coli* malE or heat-stable enterotoxin II (STII) signal sequence and at the 3' end to all or a portion of a viral coat protein.

A vector which provides a bicistronic message and for display of F(ab')$_2$-pIII is shown in FIG. 34B. In this vector, a suitable promoter, such as Ptac or PhoA (AP) promoter drives expression of first cistron encoding a light chain variable and constant domain operably linked at 5' end to a *E. coli* malE or heat stable enteroxtoxin II (STII) signal sequence and at the 3' end to a nucleic acid sequence encoding a gD tag. The second cistron encodes, for example, a heavy chain variable and constant domain operatively linked at 5' end to a *E. coli* malE or heat stable enterotoxin II (STII) signal sequence and at 3' end has a dimerization domain comprising IgG hinge sequence and a leucine zipper sequence followed by at least a portion of viral coat protein.

Display of Fusion Polypeptides

Fusion polypeptides of an antibody variable domain can be displayed on the surface of a cell, virus, or phagemid particle in a variety of formats. These formats include single chain Fv fragment (scFv), F(ab) fragment and multivalent forms of these fragments. The multivalent forms preferably are a dimer of ScFv, Fab, or F(ab'), herein referred to as (ScFv)$_2$, F(ab)$_2$ and F(ab')$_2$, respectively. The multivalent forms of display are preferred in part because they have more than one antigen binding site which generally results in the identification of lower affinity clones and also allows for more efficient sorting of rare clones during the selection process.

Methods for displaying fusion polypeptides comprising antibody fragments, on the surface of bacteriophage, are well known in the art, for example as described in patent publication number WO 92/01047 and herein. Other patent publications WO 92/20791; WO 93/06213; WO 93/11236 and WO 93/19172, describe related methods and are all herein incorporated by reference. Other publications have shown the identification of antibodies with artificially rearranged V gene repertoires against a variety of antigens displayed on the surface of phage (for example, H. R. Hoogenboom & G. Winter J. Mol. Biol. 227 381-388 1992; and as disclosed in WO 93/06213 and WO 93/11236).

When a vector is constructed for display in a scFv format, it includes nucleic acid sequences encoding an antibody variable light chain domain and an antibody variable heavy chain variable domain. Typically, the nucleic acid sequence encoding an antibody variable heavy chain domain is fused to a viral coat protein component. One or both of the antibody variable domains can have variant amino acids in at least one CDR region. The nucleic acid sequence encoding the antibody variable light chain is connected to the antibody variable heavy chain domain by a nucleic acid sequence encoding a peptide linker. The peptide linker typically contains about 5 to 15 amino acids. Optionally, other sequences encoding, for example, tags useful for purification or detection can be fused at the 3' end of either the nucleic acid sequence encoding the antibody variable light chain or antibody variable heavy chain domain or both.

When a vector is constructed for F(ab) display, it includes nucleic acid sequences encoding antibody variable domains and antibody constant domains. A nucleic acid encoding a variable light chain domain is fused to a nucleic acid sequence encoding a light chain constant domain. A nucleic acid sequence encoding an antibody heavy chain variable domain is fused to a nucleic acid sequence encoding a heavy chain constant CH1 domain. Typically, the nucleic acid sequence encoding the heavy chain variable and constant domains are fused to a nucleic acid sequence encoding all or part of a viral coat protein. One or both of the antibody variable light or heavy chain domains can have variant amino acids in at least one CDR. The heavy chain variable and constant domains are preferably expressed as a fusion with at least a portion of a viral coat protein and the light chain variable and constant domains are expressed separately from the heavy chain viral coat fusion protein. The heavy and light chains associate with one another, which may be by covalent or non-covalent bonds. Optionally, other sequences encoding, for example, polypeptide tags useful for purification or detection, can be fused at the 3' end of either the nucleic acid sequence encoding the antibody light chain constant domain or antibody heavy chain constant domain or both.

Preferably a bivalent moiety, for example, a F(ab)$_2$ dimer or F(ab')$_2$ dimer, is used for displaying antibody fragments with the variant amino acid substitutions on the surface of a particle. It has been found that F(ab')$_2$ dimers have the same affinity as F(ab) dimers in a solution phase antigen binding assay but the off rate for F(ab')$_2$ are reduced because of a higher avidity. Therefore the bivalent format (for example, F(ab')$_2$) is a particularly useful format since it can allow for the identification of lower affinity clones and also allows more efficient sorting of rare clones during the selection process.

Introduction of Vectors into Host Cells

Vectors constructed as described in accordance with the invention are introduced into a host cell for amplification and/or expression. Vectors can be introduced into host cells using standard transformation methods including electroporation, calcium phosphate precipitation and the like. If the vector is an infectious particle such as a virus, the vector itself provides for entry into the host cell. Transfection of host cells containing a replicable expression vector which encodes the gene fusion and production of phage particles according to standard procedures provides phage particles in which the fusion protein is displayed on the surface of the phage particle.

Replicable expression vectors are introduced into host cells using a variety of methods. In one embodiment, vectors can be introduced into cells using electroporation as described in WO/00106717. Cells are grown in culture in standard culture broth, optionally for about 6-48 hours (or to $OD_{600}$=0.6-0.8) at about 37° C., and then the broth is centrifuged and the supernatant removed (e.g. decanted). Initial purification is preferably by resuspending the cell pellet in a buffer solution (e.g. 1.0 mM HEPES pH 7.4) followed by recentriguation and removal of supernatant. The resulting cell pellet is resuspended in dilute glycerol (e.g. 5-20% v/v) and again recentrifuged to form a cell pellet and the supernatant removed. The final cell concentration is obtained by resuspending the cell pellet in water or dilute glycerol to the desired concentration.

A particularly preferred recipient cell is the electroporation competent *E. coli* strain of the present invention, which is *E. coli* strain SS320 (Sidhu et al., *Methods Enzymol.* (2000), 328:333-363). Strain SS320 was prepared by mating MC1061 cells with XL1-BLUE cells under conditions sufficient to transfer the fertility episome (F' plasmid) or XL1-BLUE into the MC1061 cells. Strain SS320 has been deposited with the American Type Culture Collection (ATCC), 10801 University Boulevard, Manassas, Va. USA, on Jun. 18, 1998 and assigned Deposit Accession No. 98795. Any F' episome which enables phage replication in the strain may be used in the invention. Suitable episomes are available from strains deposited with ATCC or are commercially available (CJ236, CSH18, DHF', JM101, JM103, JM105, JM107, JM109, JM110), KS1000, XL1-BLUE, 71-18 and others).

The use of higher DNA concentrations during electroporation (about 10×) increases the transformation efficiency and increases the amount of DNA transformed into the host cells. The Use of High Cell Concentrations Also Increases the efficiency (about 10×). The larger amount of transferred DNA produces larger libraries having greater diversity and representing a greater number of unique members of a combinatorial library. Transformed cells are generally selected by growth on antibiotic containing medium.

Selection (Sorting) and Screening for Binders to Targets of Choice

Use of phage display for identifying target antigen binders, with its various permutations and variations in methodology, are well established in the art. One approach involves constructing a family of variant replicable vectors containing a transcription regulatory element operably linked to a gene fusion encoding a fusion polypeptide, transforming suitable host cells, culturing the transformed cells to form phage particles which display the fusion polypeptide on the surface of the phage particle, followed by a process that entails selection or sorting by contacting the recombinant phage particles with a target antigen so that at least a portion of the population of particles bind to the target with the objective to increase and enrich the subsets of the particles which bind from particles relative to particles that do not bind in the process of selection. The selected pool can be amplified by infecting host cells, such as fresh XL1-Blue cells, for another round of sorting on the same target with different or same stringency. The resulting pool of variants are then screened against the target antigens to identify novel high affinity binding proteins. These novel high affinity binding proteins can be useful as therapeutic agents as antagonists or agonists, and/or as diagnostic and research reagents.

Fusion polypeptides such as antibody variable domains comprising the variant amino acids can be expressed on the surface of a phage, phagemid particle or a cell and then selected and/or screened for the ability of members of the group of fusion polypeptides to bind a target antigen which is typically an antigen of interest. The processes of selection for binders to target can also be include sorting on a generic protein having affinity for antibody variable domains such as protein L or a tag specific antibody which binds to antibody or antibody fragments displayed on phage, which can be used to enrich for library members that display correctly folded antibody fragments (fusion polypeptides).

Target proteins, such as receptors, may be isolated from natural sources or prepared by recombinant methods by procedures known in the art. Target antigens can include a number of molecules of therapeutic interest.

Two main strategies of selection (sorting) for affinity can be used as depicted schematically in FIG. 45. The first strategy (left of Figure) is solid-support method or plate sorting or immobilized target sorting. The second strategy is a solution-binding method (right).

For the solid support method, the target protein may be attached to a suitable solid or semi solid matrix which are known in the art such as agarose beads, acrylamide beads, glass beads, cellulose, various acrylic copolymers, hydroxyalkyl methacrylate gels, polyacrylic and polymethacrylic copolymers, nylon, neutral and ionic carriers, and the like. Attachment of the target protein to the matrix may be accomplished by methods described in Methods in Enzymology, 44 (1976), or by other means known in the art.

After attachment of the target antigen to the matrix, the immobilized target is contacted with the library expressing the fusion polypeptides under conditions suitable for binding of at least a subset of the phage particle population with the immobilized target antigen. Normally, the conditions, including pH, ionic strength, temperature and the like will mimic physiological conditions. Bound particles ("binders") to the immobilized target are separated from those particles that do not bind to the target by washing. Wash conditions can be adjusted to result in removal of all but the high affinity binders. Binders may be dissociated from the immobilized target by a variety of methods. These methods include competitive dissociation using the wild-type ligand (e.g. excess target antigen), altering pH and/or ionic strength, and methods known in the art. Selection of binders typically involves elution from an affinity matrix with a suitable elution material such as acid like 0.1M HCl or ligand. Elution with increasing concentrations of ligand could elute displayed binding molecules of increasing affinity.

The binders can be isolated and then re-amplified in suitable host cells by infecting the cells with the viral particles that are binders (and helper phage if necessary, e.g. when viral particle is a phagemid particle) and the host cells are cultured under conditions suitable for amplification of the particles that display the desired fusion polypeptide. The phage particles are then collected and the selection process is repeated one or more times until binders of the target antigen are enriched in a way any number of rounds of selection or sorting can be utilized. One of the selection or sorting procedures can involve isolating binders that bind to a generic affinity protein such as protein L or an antibody to a polypeptide tag present in a displayed polypeptide such as antibody to the gD protein or polyhistidine tag.

One aspect of the invention involves a novel selection method which is termed "solution-binding method" as schematized in FIG. 45 (right panel). The invention allows solution phase sorting with much improved efficiency over the conventional solution sorting method. The solution binding method has been used for finding original binders from a random library or finding improved binders from a library that was designated to improve affinity of a particular binding clone or group of clones. The method comprises contacting a plurality of polypeptides, such as those displayed on phage or phagemid particles (library), with a target antigen labelled or fused with a tag molecule. The tag could be biotin or other moieties for which specific binders are available. The stringency of the solution phase can be varied by using decreasing concentrations of labelled target antigen in the first solution binding phase. To further increase the stringency, the first solution binding phase can be followed by a second solution phase having high concentration of unlabelled target antigen after the initial binding with the labelled target in the first solution phase. Usually, 100 to 1000 fold of unlabelled target over labelled target is used in the second phase (if included). The length of time of incubation of the first solution phase can vary from a few minutes to one to two hours or longer to reach equilibrium. Using a shorter time for binding in this first phase may bias or select for binders that have fast on-rate. The length of time and temperature of incubation in second phase can be varied to increase the stringency. This provides for a selection bias for binders that have slow rate of coining off the target (off-rate). After contacting the plurality of polypeptides (displayed on the phage/phagemid particles) with a target antigen, the phage or phagemid particles that are bound to labelled targets are separated from phage that do not bind. The particle-target mixture from solution phase of binding is isolated by contacting it with the labelled target moiety and allowing for its binding to, a molecule that binds the labelled target moiety for a short period of time (eg. 2-5 minutes). The initial concentration of the labelled target antigen can range from about 0.1 nM to about 1000 nM. The bound particles are eluted and can be propagated for next round of sorting. Multiple rounds of sorting are preferred using a lower concentration of labelled target antigen with each round of sorting.

For example, an initial sort or selection using about 100 to 250 nM labelled target antigen should be sufficient to capture a wide range of affinities, although this factor can be determined empirically and/or to suit the desire of the practitioner. In the second round of selection, about 25 to 100 nM of labelled target antigen may be used. In the third round of selection, about 0.1 to 25 nM of labeled target antigen may be used. For example, to improve the affinity of a 100 nM binder, it may be desirable to start with 20 nM and then progress to 5 and 1 nM labelled target, then, followed by even lower concentrations such as about 0.1 nM labelled target antigen.

The conventional solution sorting involves use of beads like strepavidin coated beads, which is very cumbersome to use and often results in very low efficiency of phage binders recovery. The conventional solution sorting with beads takes much longer than 2-5 minutes and is less feasible to adapt to high throughput automation than the invention described above.

As described herein, combinations of solid support and solution sorting methods can be advantageously used to isolate binders having desired characteristics. After selection/sorting on target antigen for a few rounds, screening of individual clones from the selected pool generally is performed to identify specific binders with the desired properties/characteristics. Preferably, the process of screening is carried out by automated systems to allow for high-throughput screening of library candidates.

Two major screening methods are described below. However, other methods known in the art may also be used in the methods of the invention. The first screening method comprises a phage ELISA assay with immobilized target antigen, which provides for identification of a specific binding clone from a non-binding clone. Specificity can be determined by simultaneous assay of the clone on target coated well and BSA or other non-target protein coated wells. This assay is automatable for high throughput screening.

One embodiment provides a method of selecting for an antibody variable domain that binds to a specific target antigen from a library of antibody variable domain by generating a library of replicable expression vectors comprising a plurality of polypeptides; contacting the library with a target antigen and at least one nontarget antigen under conditions suitable for binding; separating the polypeptide binders in the library from the nonbinders; identifying the binders that bind to the target antigen and do not bind to the nontarget antigen; eluting the binders from the target antigen; and amplifying the replicable expression vectors comprising the polypeptide binder that bind to a specific antigen.

The second screening assay is an invention embodied in this application which is a affinity screening assay that provides for screening for clones that have high affinity from clones that have low affinity in a high throughput manner. In the assay, each clone is assayed with and without first incubating with target antigen of certain concentration for a period of time (for e.g 30-60 minutes) before application to target coated wells briefly (e.g. 5-15 minutes). Then bound phage is measured by usual phage ELISA method, eg. using anti-M13 HRP conjugates. The ratio of binding signal of the two wells, one well having been preincubated with target and the other well not preincubated with target antigen is an indication of affinity. The selection of the concentration of target for first incubation depends on the affinity range of interest. For example, if binders with affinity higher than 10 nM are desired, 100 nM of target in the first incubation is often used. See FIG. 47 and example 9 for detailed description of one embodiment of the method. Once binders are found from a particular round of sorting (selection), these clones can be screened with affinity screening assay to identify binders with higher affinity.

Combinations of any of the sorting/selection methods described above may be combined with the screening methods. For example, in one embodiment, polypeptide binders are first selected for binding to immobilized target antigen. Polypeptide binders that bind to the immobilized target antigen can then be amplified and screened for binding to the target antigen and for lack of binding to nontarget antigens. Polypeptide binders that bind specifically to the target antigen are amplified. These polypeptide binders can then selected for higher affinity by contact with a concentration of a labelled target antigen to form a complex, wherein the concentration ranges of labelled target antigen from about 0.1 nM to about 1000 nM, the complexes are isolated by contact with an agent that binds to the label on the target antigen. The polypeptide binders are then eluted from the labeled target antigen and optionally, the rounds of selection are repeated, each time a lower concentration of labelled target antigen is used. The high affinity polypeptide binders isolated using this selection method can then be screened for high affinity using for example, the solution phase ELISA assay as described in Example 8 or the spot competition ELISA assay as described in Example 9.

These methods can provide for finding clones with high affinity without having to perform long and complex competition affinity assays on a large number of clones. The intensive aspect of doing complex assays of many clones often is a significant obstacle to finding best clones from a selection. This method is especially useful in affinity improvement efforts where multiple binders with similar affinity can be recovered from the selection process. Different clones may have very different efficiency of expression/display on phage or phagemid particles. Those clones more highly expressed have better chances being recovered. That is, the selection can be biased by the display or expression level of the variants. The solution-binding sorting method of the invention can improve the selection process for finding binders with high affinity. This method is an affinity screening assay that provides a significant advantage in screening for the best binders quickly and easily.

After binders are identified by binding to the target antigen, the nucleic acid can be extracted. Extracted DNA can then be used directly to transform *E. coli* host cells or alternatively, the encoding sequences can be amplified, for example using PCR with suitable primers, and sequenced by typical sequencing method. Variable domain DNA of the binders can be restriction enzyme digested and then inserted into a vector for protein expression.

In one embodiment, the invention provides isolation of novel antibody and antibody fragments that bind to mVEGF (murine Vascular Endothelial Growth Factor). Preferably, the antibody variable domains bind mVEGF with an $IC_{50}$ of less than 10 µM and more preferably less than 1 µM. In one embodiment, mVEGF-binding antibodies include members of the library created by substituting amino acid in residues in CDR-L3 and residues 95-100a of the CDRH3 region of the variable region of the heavy chain with DVK codon sets or a combination of DVK and NNK codon sets. It has been discovered that some members of the library, as created above, have a particularly high affinity for mVEGF.

In particular, antibodies including the heavy chain CDR3 sequences SRNAWAF (SEQ ID NO: 5; amino acid position 93-100c), SRNLSENSYAM4 (SEQ ID NO: 6; amino acid position 93-100c), SRAGWAGWYAM (SEQ ID NO: 7; amino acid position 93-100c), SRAAKAGWYAM (SEQ ID NO: 8; amino acid position 93-100c), and SRSDGRDSAYAM (SEQ ID NO: 9; amino acid position 93-100c) display high affinity binding to mVEGF. Novel antibody variable domains that bind to mVEGF, generated by substituting amino acids at positions in other CDRs, such as L1, L2, L3, H1 and H2 can also be generated according to the method described herein.

In some cases, novel CDRH1/H2/H3 binders for example, sequences can be combined with other sequences generated by introducing variant amino acids via codon sets into the other light chains CDRs, for example through a 2-step process. An example of a 2-step process comprises first determining binders (generally lower affinity binders) within one or more libraries generated by randomizing one or more CDRs, wherein the CDRs randomized are each library are different or, where the same CDR is randomized, it is randomized to generate different sequences. Binders from a heavy chain library can then be randomized with CDR diversity in a light chain CDRs by kunkle mutagenesis or by cloning (cut-and-paste, (eg. by ligating different CDR sequences together)) the new light chain library into the existing heavy chain binders that has only a fixed light chain. The pool can then be further sorted against target to identify binders possessing increased affinity. For example, binders (for example, low affinity binders) obtained from sorting an L3/H3, an H1/H2/H3 or an L3/H1/H2/H3 library may be fused with library of an L1/L2/H1/H2 or an L1/L2/L3 diversity to replace its original fixed L1/L2/H1/H2 or an L1/L2/L3, wherein the new libraries are then further sorted against a target of interest to obtain another set of binders (for example, high affinity binders). Novel antibody sequences can be identified that display higher binding affinity to either the IGF1 or mVEGF antigens.

In some embodiments, libraries comprising polypeptides of the invention are subjected to a plurality of sorting rounds, wherein each sorting round comprises contacting the binders obtained from the previous round with a target antigen distinct from the target antigen(s) of the previous round(s). Preferably, but not necessarily, the target antigens are homologous in sequence, for example members of a family of related but distinct polypeptides, such as, but not limited to, cytokines (for example, alpha interferon subtypes).

Generation of Antibody Variable Domain Libraries

Antibody libraries can be generated by mutating the solvent accessible and/or highly diverse positions in at least one CDR of an antibody variable domain. Some or all of the CDRs can be mutated using the methods of the invention. In some embodiments, it may be preferable to generate diverse antibody libraries by mutating positions in CDRH1, CDRH2 and CDRH3 to form a single library or by mutating positions in CDRL3 and CDRH3 to form a single library or by mutating positions in CDRL3 and CDRH1, CDRH2 and CDRH3 to form a single library.

A library of antibody variable domains can be generated, for example, having mutations in the solvent accessible and/or highly diverse positions of CDRH1, CDRH2 and CDRH3. Another library can be generated having mutations in CDRL1, CDRL2 and CDRL3. These libraries can also be used in conjunction with each other to generate binders of desired affinities. For example, after one or more rounds of selection of heavy chain libraries for binding to a target antigen, a light chain library can be replaced into the population of heavy chain binders for further rounds of selection to increase the affinity of the binders.

In one embodiment, a library is created by substitution of original amino acids with variant amino acids in the CDRH3 region of the variable region of the heavy chain sequence. According to the invention, this library can contain a plurality of antibody sequences, wherein the sequence diversity is primarily in the CDRH3 region of the heavy chain sequence.

In one aspect, the library is created in the context of the humanized antibody 4D5 sequence, or the sequence of the framework amino acids of the humanized antibody 4D5 sequence. Preferably, the library is created by substitution of at least residues 95-100 a of the heavy chain with amino acids encoded by the DVK codon set, wherein the DVK codon set is used to encode a set of variant amino acids for every one of these positions. An example of an oligonucleotide set that is useful for creating these substitutions comprises the sequence $(DVK)_7$; an example of an oligonucleotide set having this sequence is oligonucleotide (F63) (SEQ ID NO: 10). In some embodiments, a library is created by substitution of residues 95-100a with amino acids encoded by both DVK and NNK codon sets. An example of an oligonucleotide set that is useful for creating these substitutions comprises the sequence $(DVK)_6$ (NNK); an example of an oligonucleotide set having this sequence is oligonucleotide (F65) (SEQ ID NO: 11). In another embodiment, a library is created by substitution of at least residues 95-100a with amino acids encoded by both DVK and NNK codon sets. An example of an oligonucleotide set that is useful for creating these substitutions comprises the sequence $(DVK)_5$ (NNK); an example of an oligonucleotide set having this sequence is oligonucleotide (F64) (SEQ ID NO: 12). Another example of an oligonucleotide set that is useful for creating these substitutions comprises the sequence $(NNK)_6$; an example of an oligonucleotide set having this sequence is oligonucleotide (F66) (SEQ ID NO: 13). Other examples of suitable oligonucleotide sequences are listed in FIG. 4 and FIG. 43 and can be determined by one skilled in the art according to the criteria described herein.

In another embodiment, different CDRH3 designs are utilized to isolate high affinity binders and to isolate binders for a variety of epitopes. The range of lengths of CDRH3 generated in this library is 11 to 13 amino acids, although lengths different from this can also be generated. H3 diversity can be expanded by using NNK, DVK and NVK codon sets, as well as more limited diversity at N and/or C-terminal. Diversity can also be generated in CDRH1 and CDRH2.

In one embodiment of a library, diversity in H1 and H2 is generated utilizing the following oligonucleotides:

The oligonucleotides used for H1: F151 (GCA GCT TCT GGC TTC ACC ATT AVT RRT WMY KMT ATA CAC TGG GTG CGT CAG; SEQ ID NO: 14), F152 (GCA GCT TCT GGC TTC ACC ATT AVT RRT WMY KGG ATA CAC TGG GTG CGT CAG; SEQ ID NO: 15), F175 (GCA GCT TCT GGC TTC ACC ATT AVT RVM WMY KMT ATA CAC TGG GTG CGT CAG; SEQ ID NO: 16) and F176 (GCA GCT TCT GGC TTC ACC ATT AVT RVM WMY KGG ATA CAC TGG GTG CGT CAG; SEQ ID NO: 17) were pooled, and for H2, oligonucleotides F153 (AAG GGC CTG GAA TGG GTT GST DGG ATT WMT CCT DMT RRC GGC DMT ACT DAC TAT GCC GAT AGC GTC AAG GGC; SEQ ID NO: 18), F154 (AAG GGC CTG GAA TGG GTT GST DHT ATT WMT CCT DMT RRC GGC DMT ACT DAC TAT GCC GAT AGC GTC AAG GGC; SEQ ID NO:19), F173 (AAG GGC CTG GAA TGG GTT GST DGG ATT DMT CCT NMT RRC GGC DMT ACT DAC TAT GCC GAT AGC GTC AAG GGC; SEQ ID NO: 20) and F174 (AAG GGC CTG GAA TGG GTT GST DHT ATT DMT CCT NMT RRC GGC DMT ACT DAC TAT GCC GAT AGC GTC AAG GGC; SEQ ID NO: 21) were pooled.

For diversity in CDRH3, multiple libraries can be constructed separately with different lengths of H3 and then combined to select for binders to target antigens. Optionally, in one library, DVK codon sets are utilized in the context of oligonucleotides F163a, F164a, F1646, F165 and F166 (see FIG. 4), which are pooled (i.e., the oligonucleotides are used as a single pool). A second library may use the same oligonucleotides as the first library and oligonucleotide F125 (CGR TTC ACT ATA AGC CGT GAC ACA TCC AAA AAC; SEQ ID NO: 22). A third library may use oligonucleotides F165a and F1656. A fourth library can be constructed using a pool of NVT oligonucleotides with tryptophan doped in the sequences: F103, F134, F135, F155, F156, F157, F160, F160g and F167 pooled together. A fifth library can be constructed using codon sets NNS in oligonucleotides F66a and F66b.

The multiple libraries can be pooled and sorted using solid support selection and solution sorting methods as described previously and shown in FIG. 44 and FIG. 45. Multiple sorting strategies may be employed. For example, one variation involves sorting on target bound to a solid, followed by sorting for a tag that may be present on the fusion polypeptide (eg. anti-gD tag) and followed by another sort on target bound to solid. Alternatively, the libraries can be sorted first on target bound to a solid surface, the eluted binders are then sorted using solution phase binding with decreasing concentrations of target antigen. Utilizing combinations of different sorting methods provides for minimization of selection of only highly expressed sequences and provides for selection of a number of different high affinity clones.

High affinity binders for target antigens can be isolated from the libraries. Limiting diversity in the H1/H2 region decreases degeneracy about $10^4$ to $10^5$ fold and allowing more H3 diversity provides for more high affinity binders. Utilizing libraries with different types of diversity in CDRH3 (eg. utilizing DVK or NVT) provides for isolation of binders that may bind to different epitopes of a target antigen.

Of the binders isolated from the pooled libraries as described above, it has been discovered that affinity may be further improved by providing limited diversity in the light chain. Light chain diversity is generated in this embodiment as follows in CDRL1: amino acid position 28 is encoded by RDT; amino acid position 29 is encoded by RKT; amino acid position 30 is encoded by RVW; amino acid position 31 is encoded by ANW; amino acid position 32 is encoded by THT; optionally, amino acid position 33 is encoded by CTG; in CDRL2: amino acid position 50 is encoded by KBG; amino acid position 53 is encoded by AVC; and optionally, amino acid position 55 is encoded by GMA; in CDRL3: amino acid position 91 is encoded by TMT or SRT or both; amino acid position 92 is encoded by DMC; amino acid position 93 is encoded by RVT; amino acid position 94 is encoded by NHT; and amino acid position 96 is encoded by TWT or YKG or both.

In another embodiment, a library or libraries with diversity in CDRH1, CDRH2 and CDRH3 regions is generated. For diversity in CDRH1 and CDRH2, the following oligonucleotides are used: F151 (5'-GCA GCT TCT GGC TTC ACC ATT AVT RRT WMY KMT ATA CAC TGG GTG CGT CAG-3'; (SEQ ID NO: 14) and F152 (5'-GCA GCT TCT GGC TTC ACC ATT AVT RRT WMY KGG ATA CAC TGG GTG CGT CAG-3'; SEQ ID NO: 15) were pooled, and for H2, oligonucleotides 173 (5'-AAG GGC CTG GAA TGG GTT GST DGG ATT DMT CCT NMT RRC GGT DMT ACT DAC TAT GCC GAT AGC GTC AAG GGC-3'; SEQ ID NO: 20) and F174 (5'-AAG GGC CTG GAA TGG GTT GST DHT ATT DMT CCT NMT RRC GGC DMT ACT DAC TAT GCC GAT AGC GTC AAG GGC-3'; SEQ ID NO: 21) were pooled.

In this embodiment, diversity in CDRH3 is generated using a variety of lengths of H3 regions and using primarily codon sets XYZ and NNK or NNS. The oligonucleotides used include F66b, F66d, F66f, F66a$_1$, F66b$_1$, F66g, F66h, F66i, F66j, F171c, F171d, F171e, F171, F185, F186, F187, F190, F190a, F190b, F190c, F190d, and F190e. (See FIG. 4C.) Libraries can be formed using individual oligonucleotides and pooled or oligonucleotides can be pooled to form a subset of libraries. The libraries of this embodiment can be sorted against target bound to solid. Clones isolated from multiple sorts can be screened for specificity and affinity using ELISA assays. For specificity, the clones can be screened against the desired target antigens as well as other nontarget antigens. Those binders to the desired target antigen can then be screened for affinity in solution binding competition ELISA assay as described in Example 8 or spot competition assay described in Example 9. High affinity binders for target antigens can be isolated from the library utilizing XYZ codon sets prepared as described above. These binders can be readily produced as antibodies or antigen binding fragments in high yield in cell culture.

In some embodiments, it may be desirable to generate libraries with a greater diversity in lengths of CDRH3 region. For example, it may be desirable to generate libraries with CDRH3 regions ranging from about 7 to 19 amino acids. Illustrative oligonucleotides useful for this purpose are shown in FIG. 43.

High affinity binders isolated from the libraries of these embodiments are readily produced in bacterial and eukaryotic cell culture in high yield. The vectors can be designed to readily remove sequences such as gD tags, viral coat protein component sequence, and/or to add in constant region sequences to provide for production of full length antibodies or antigen binding fragments in high yield.

A library with mutations in CDRH3 can be combined with a library containing variant versions of other CDRs, for example CDRL1, CDRL2, CDRL3, CDRH1 and/or CDRH2. Thus, for example, in one embodiment, a CDRH3 library is combined with a CDRL3 library created in the context of the humanized 4D5 antibody sequence with variant amino acids at positions 28, 29, 30,31, and/or 32 using codon sets as described in FIG. 3. Examples of oligonucleotides useful in creating these substitutions include those that incorporate these codon sets. In another embodiment, a library with mutations to the CDRH3 can be combined with a library comprising variant CDRH1 and/or CDRH2 heavy chain variable domains. In one embodiment, the CDRH1 library is created with the humanized antibody 4D5 sequence with variant amino acids at positions 28, 30,31, 32 and 33 using codon sets as described in FIG. 3. Examples of oligonucleotide sets useful in creating these substitutions include those that incorporate these codon sets. A CDRH2 library may be created with the sequence of humanized antibody 4D5 with variant amino acids at positions 50, 52, 53, 54, 56 and 58 using the codon sets described in FIG. 3. Examples of oligonucleotide sets useful in creating these substitutions include those that incorporate these codon sets.

Any combination of codon sets and CDRs can be diversified according to the amino acid position selection criteria described herein. Examples of suitable codons in various combinations of CDRs are illustrated in FIGS. 5-13. FIGS.

5-7 also include illustrative calculations of designed diversity values of libraries generated according to the choice of codon sets used in the indicated CDRs and amino acid positions.

Having generally described the invention, the same will be more readily understood by reference to the following examples, which are provided by way of illustration and are not intended as limiting.

EXAMPLE 1

Vectors encoding fusion polypeptides comprising variant CDRs were constructed as follows.

Antibody Phage Display Vectors Based on pS1607

A vector for antibody phage display was constructed by modifying vector pS1607 (Sidhu et al., J. Mol. Biol. (2000), 296:487-495). Vector pS1607, which has pTac promoter sequence and malE secretion signal sequence, contained a sequence of human growth hormone fused to the C-terminal domain of the gene-3 minor coat protein (p3). The sequence encoding hGH was removed, and the resulting vector sequence served as the vector backbone for construction of vectors of the present invention that contain DNA fragments encoding the anti-her2 humanized antibody 4D5 light chain and heavy chain variable domain sequences in the form of:

(i) single chain Fv (scFv) (SEQ ID NO: 23; FIG. 14);
(ii) single chain Fv with zipper domain (scFvzip) (SEQ ID NO: 24; FIG. 15);
(iii) Fab fragment (Fab) (SEQ ID NO: 25; FIG. 16); or
(iv) Fab fragment with zipper domain (Fabzip) (SEQ ID NO: 26; FIG. 17).

The humanized antibody 4D5 is an antibody which has mostly human consensus sequence framework regions in the heavy and light chains, and CDR regions from a mouse monoclonal antibody specific for Her-2. The method of making the anti-Her-2 antibody and the identity of the variable domain sequences are provided in U.S. Pat. Nos. 5,821,337 and 6,054,297. The resulting vectors (schematically illustrated in FIGS. 34A-D) comprise the humanized antibody 4D5 variable domains under the control of the IPTG-inducible Ptac promoter (sequences as shown in FIGS. 14-17) or the alkaline phosphatase phoA promoter (as described in U.S. Pat. No. 5,750,373).

Construction of Fab-Zip Construct and Characterization of its Function in Phase Display Construction of an example of a vector is described in greater illustrative detail below for Fab-zip. Inclusion of the zipper region facilitates the formation and display of dimers of ScFv and F(ab) to form scFv$_2$ and F(ab')$_2$, respectively.

Fab-zip vectors were constructed as described below and shown in FIG. 34B.

Methods and Materials

Construction of Anti-Her2 F(ab')$_1$ vector: A phagemid construct comprising a sequence encoding an anti-Her2 polypeptide under the control of the Ptac promoter was generated using vector pS1607 as the backbone, as described above. malE secretion signal sequence was first fused to the N-terminal sequence of light chain (LC) to direct the LC synthesis to the periplasm of bacteria cell. A gD tag was added at the C-terminus of LC. Following the stop codon of LC, another ribosome binding site and STII signal sequence were fused to the N-terminus of heavy chain (HC) sequence and continued with the C-terminal domain of the pIII, a minor coat protein of M13 phage.

To generate F(ab')$_2$ displayed on phage, the dimerizable leucine zipper GCN4 sequence was utilized. Cassette mutagenesis was performed to insert in between HC and pIII first the hinge sequence that came from full length IgG1 antibody (TCPPCPAPELLG (SEQ ID NO: 27)) followed by GCN4 sequences (GRMKQLEDKVEELLSKNYHLENE-VARLKKLVGERG (SEQ ID NO: 3)). The GCN4 leucine zipper was expected to bring two sets of LC/HC-pIII fusion polypeptides together in the E. coli periplasm, which would allow the formation of disulfide bonds in the hinge region to secure the dimer formation before and after getting out of the E. coli periplasm.

Two versions of the vector schematically illustrated in FIG. 34B were made. One had an Amber stop codon (TAG) after the GCN4 zipper sequence and one did not. These two constructs would theoretically produce one or both of the divalently displaying phage as depicted in FIG. 18. The Amber-less construct would make only the form (C) that would have two copies out of the five copies of pIII on phage as fusion polypeptide which would be stabilized with both the hinge disulfide and GCN4 zipper. The construct with Amber after the GCN4 should be able to produce either form (B) or (C) of the phage depending on the efficiency of suppression of the Amber stop codon in XL-1 bacterial strain.

The formation of F(ab')$_2$ on phage: To demonstrate the formation of F(ab')$_2$, or the divalent display of F(ab') on the phage, the expected function of divalent display was measured. With the avidity effect of divalent display, the phage binding to ligand-modified solid phase should demonstrate significantly decreased off-rate, the rate at which it detaches off the solid phase, if the density of the ligand on the solid support is high enough to allow divalent binding. For divalent interaction to detach off the plate, both interactions have to be broken simultaneously for the phage to come off, which predictably would occur with much less frequency.

To produce displaying phage, E. Coli strain XL-1 Blue (Stratagene, San Diego, Calif.) infected first with F(ab) or zipped F(ab')$_2$ phage and then VCS helper phage (Strategene, San Diego, Calif.) were grown in 2YT media at 37° C. for 20 h and phage was harvested as described (Sidhu et al., Methods Enzymol. (2000), 328:333-363). Briefly, phage was purified by first precipitating them from the overnight culture media with polyethylene glycol, and resuspended in PBS. Phage were quantitated by spectrophotometer with its reading at 268 nm (1 OD=1.13×10$^{13}$/ml). Phage ELISA (Sidhu et al., supra) was first performed by titrating the phage in phage ELISA binding buffer (PBS with 0.5% BSA and 0.05% Tween 20) and its binding to ligand (Her-2 extracellular domain, Her-2ECD) coated on 96-well plate was quantified by HRP conjugated anti-M13 antibody followed by adding the peroxidase substrate, H202 and TMB (Kirkgaad) which can be read at wavelength 450 nm. The plate was coated with Her-2ECD at 2 µg/ml in PBS for 2 h at room temperature or 4° C. overnight, which is sufficient to allow divalent binding. We blocked the plate with 0.5% BSA and then 0.2% Tween20 for 1 hour before adding phage dilutions to the wells.

For the off-rate plate binding experiments or solution binding competition ELISA, a phage concentration was used of either F(ab) or zipped F(ab')$_2$ which gave about 90% of maximum binding to the coated plate. To show that the F(ab')$_2$ phage still maintain the same binding affinity where avidity plays less of a role, competition ELISA was performed by incubating the F(ab) or zipped F(ab')$_2$ phage with increasing concentrations of Her-2ECD ((0.1 to 500 nM) in solution for 5 hours at 37° C. The unbound phage was captured briefly (15 min.) with plates coated with HER-2ECD and measured with HRP-anti-M13 conjugate. The IC50, the concentration of Her-2ECD that inhibits 50% of the F(ab)-phage, represents the affinity (see FIG. 19).

For the off-rate experiment, F(ab) or zipped F(ab')$_2$ phage was allowed to bind to Her-2ECD coated wells first, which were then washed to get rid of excess phage. Serial dilutions of Her-2ECD (0.1 nM to 500 nM) were added to the well and incubated for 5 hours at 37° C., during which time the phage was allowed to detach off the plate and the rebinding was inhibited by the Her-2ECD in the solution. Phage that still remained on the plate was then quantified with HRP-antiM13 conjugate. The relative proportion of remaining phage was calculated by dividing the OD at the particular Her-2ECD concentration with OD in the absence of Her-2ECD and shown as % in the FIG. 20.

Figure 21:
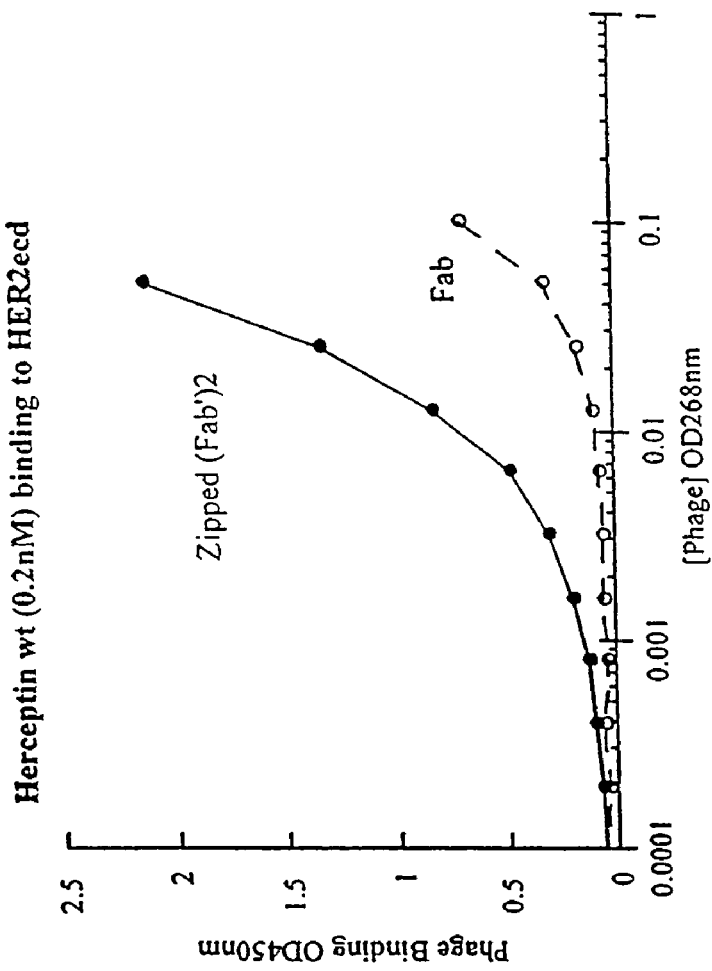
FIG. 21 shows the differences in the amount of phage F(ab) phage (-○-) or zipped F(ab')$_2$ (-o-) that is required to give detectable binding on a ligand coated support by standard phage ELISA. Differing concentrations of phage were diluted and the binding signal on Her-2ECD coated plates was detected with HRPanti-M13 measured at an O.D. of 450 nm.
Figure 22:
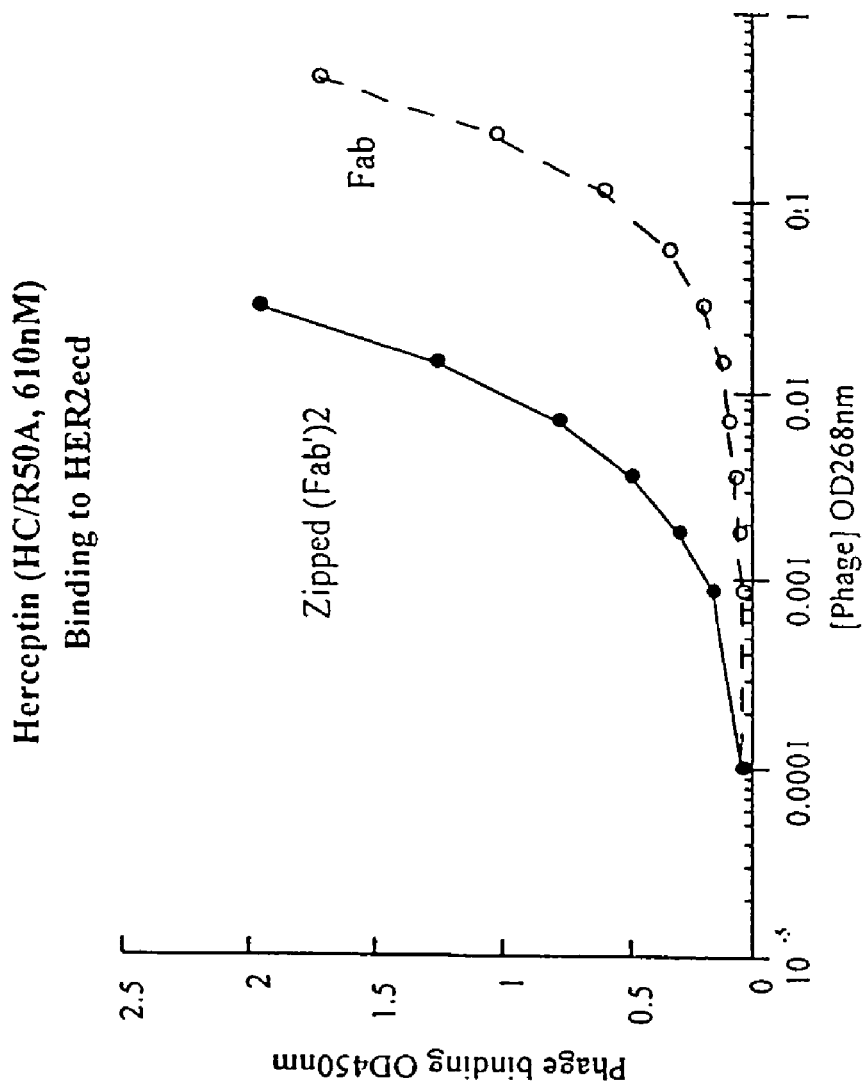
FIG. 22 shows the ability to detect a low affinity binder using divalent display. A humanized 4D5 mutant was prepared with arginine 50 changed to alanine (R50A) in both F(ab) phage (-○-) or zipped F(ab')$_2$ (-o-) format. The phage was diluted and the binding on Her-2ECD coated plates was detected with HRP anti-M13.

Another way to demonstrate the divalency of F(ab')$_2$ phage was to show a difference in the amount of phage that is required to give detectable binding on the ligand coated solid support by standard phage ELISA method as compared to its non-divalent counterpart. We also examined the detectability of low affinity binder. We generated a humanized antibody 4D5 mutant by Kunkel site-directed mutagenesis (Kunkle et al., 1985) in its heavy chain with Arginine 50 changed to Alanine (R50A), in both F(ab) and zipped F(ab')$_2$ format. Standard phage dilution versus its binding signal on Her-2ECD coated plate phage ELISA was performed (FIG. 21 and FIG. 22). The display level of the mutant was equivalent for these two formats judged from its binding to antibody to gD tag.

Results

Figure 20:
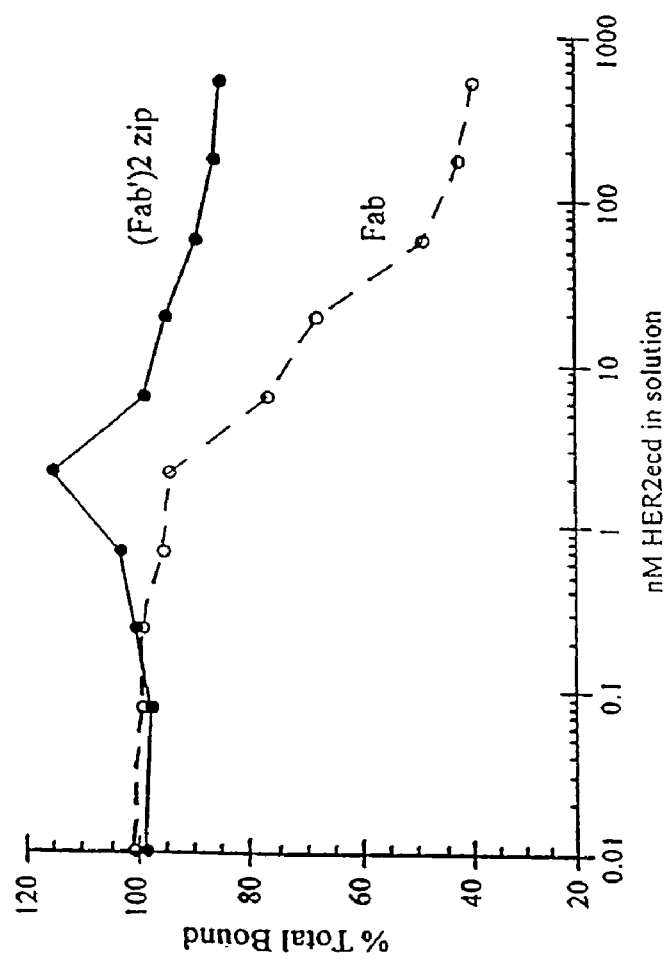
FIG. 20 shows the differences in off rate between Fab (-○-) or zipped F(ab')$_2$ (-o-) phage. Serial dilutions of Her-2ECD (0.01 nm to 1000 nM) were added to Fab or zipped F(ab')$_2$ phage bound to Her-2ECD coated wells. The phage remaining bound to the plate was quantified using HRP-anti-M13 conjugate. The relative proportion of remaining phage bound as a percentage was calculated by dividing OD at a particular Her-2ECD concentration with OD in absence of Her-2ECD.

Binding properties: The zipped F(ab')$_2$ displaying phage has essentially indistinguishable affinity (1 nM) in solution as F(ab) phage (FIG. 19). This means that the insertion of hinge and GCN4 zipper to the C-terminus of HC did not perturb its binding capability. However, the avidity effect of the divalent zipped F(ab')$_2$ is clearly demonstrated by the significantly different behavior from the monovalent F(ab) phage in the plate binding experiments (FIGS. 20 and 21). In FIG. 20, zipped F(ab')$_2$ phage of either construct with or without amber stop codon after the leucine zipper has a much slower rate of detachment from the ligand coated plate than F(ab) phage. In FIG. 21, we saw a consistent 40-50 fold difference in the concentration of phage concentration to achieve the same binding signal. The binding of a low affinity R50A (650 nM) binder can be detected and captured at 40-50 fold lower concentration of phage with divalent F(ab')$_2$ display (FIG. 22). This difference is commonly seen comparing monovalent and divalent interaction, e.g. F(ab) vs. M(ab).

Phage Display Vectors Based on Vector pS0643

Construction of Anti-Her2 Fab and F(ab')$_2$ phagemid: The phagemid vector, pS0643 (also known as phGHam-g3, e.g., U.S. Pat. No. 5,688,666), contains pBR322 and fl origins of replication, an ampicillin resistant gene, an *E. coli* alkaline phosphatase (phoA) promoter (Bass et al., (1990) *Proteins* 8:309-314), and a sequence encoding a stII secretion signal sequence fused to residues 1-191 of human growth hormone (hGH) and a sequence encoding the C-terminal residues 267-421 of protein III of M13 phage (hereinafter, cP3). The pS0643 phagemid also contains an XbaI site and an amber stop codon following residue 191 of hGH. The stII secretion signal sequence can export a protein to the periplasm of a bacteria cell (e.g., a light chain region (LC) of an antibody). The sequence encoding the human growth hormone (hGH) was removed from the pS0643 vector and replaced with a NsiI/XbaI nucleic acid fragment encoding a humanized anti-Her2 Fab fragment ("h4D5" sequence) ligated in frame with the stII secretion signal (humAb4D5-8, see Carter et al., (1992) PNAS 89:4285-4289, Table 1 and FIG. 1 therein or U.S. Pat. No. 5,821,337, for sequence).

The h4D5 antibody is a humanized antibody that specifically recognizes a cancer-associated antigen known as Her-2 (erbB2) developed as described previously. The h4d5 was obtained by polymerase chain reaction using the humAb4D5 version 8 ("hunAb4D5-8") sequence and primers engineered to give rise to a 5' NsiI site and a 3' XbaI site in the PCR product (Carter et al., (1992) PNAS 89:4285-4289). The PCR product was cleaved with NsiI and XbaI and ligated into the pS0643 phagemid vector.

The pS0643 plasmid containing humanized 4D5 (version 8) was still further modified. The LC was changed at residues 30, 66 and 91 by site-directed mutagenesis. Specifically, residue 30 was changed from asparagine to serine, residue 66 was changed from arginine to glycine, and residue 91 was changed from histidine to serine. These changes were made to increase the expression or the display of Fab on phage to improve the performance of the library and to convert the framework (66) back to the human consensus framework. Finally, the amber stop codon and XbaI site was removed from C-terminal end of the heavy chain.

A herpes simplex virus type 1 glycoprotein D epitope tag (gD tag) was added in frame to the C-terminus of the LC using site-directed mutagenesis. Following the stop codon downstream of the LC, a ribosome binding site and nucleic acid molecule encoding a stII signal sequence were ligated to the N-terminus of the HC sequence. Consequently, the HC sequence is in frame with the C-terminal domain of the p3 (cP3), a minor coat protein of M13 phage. Thus, a Fab displayed on phage can be produced from one construct. This Fab phagemid vector is referred to as pV0350-2b. The sequence of this vector is shown in FIG. 37 and has SEQ ID NO: 28.

To generate F(ab')$_2$ displayed on phage, the PV0350-2b vector was further modified by inserting a dimerizable leucine zipper GCN4 sequence (GRMKQLEDKVEELL-SKNYHLENEVARLKKLVGERG) (SEQ ID NO: 3) between the HC and cP3 sequences by cassette mutagenesis. The GCN4 leucine zipper brings two sets of LC/HC-cP3 fusion polypeptides together in the *E. coli* periplasm and presents the dimer on the surface of phage. This F(ab')$_2$ phagemid vector is referred to as pV0350-4. The sequence of this vector is shown in FIG. 38 and has SEQ ID NO: 29.

Vectors based on either ps1607 or ps0643 have been designed including restriction sites that allow for removal of the viral P3 sequences, leucine zipper and gD tag. The variable region domains from heavy and light chain can then be combined with constant region sequences to allow for expression of the variable region domain as Fab fragments or full-length antibodies. Sources of constant region sequences are known to those of skill in the art.

EXAMPLE 2

Modifications to Dimerization Domains

A series of mutations were made in the dimerizing domain, which for example, include the hinge region plus GCN4 leucine zipper for constructs such as Fab-zip as described in Example 1. The mutations were made to the dimerization domain to determine if both a disulfide bond as well as the zipper region were important to the display of F(ab')$_2$ or ScFV$_2$.

Figure 39:
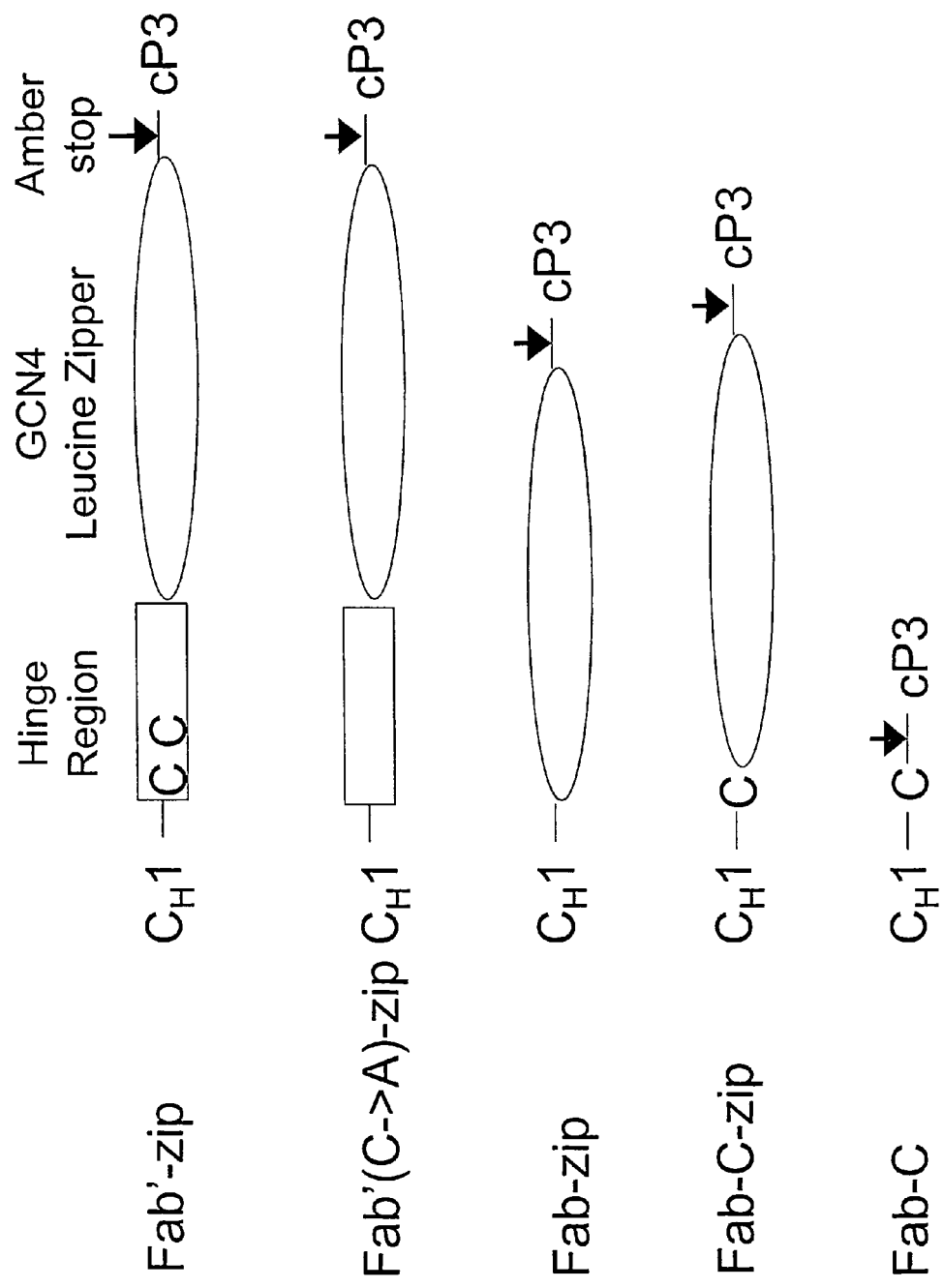
FIG. 39 shows a schematic illustration of constructs with different dimerization domains: Fab'-zip with hinge region and leucine zipper, cysteine-free hinge plus zipper (Fab' (C→A)-zip), zipper alone (Fab-zip), one cysteine plus zipper (Fab-C-zip) or just one cysteine (Fab-C) by itself between Fab and cP3.
Figure 40:
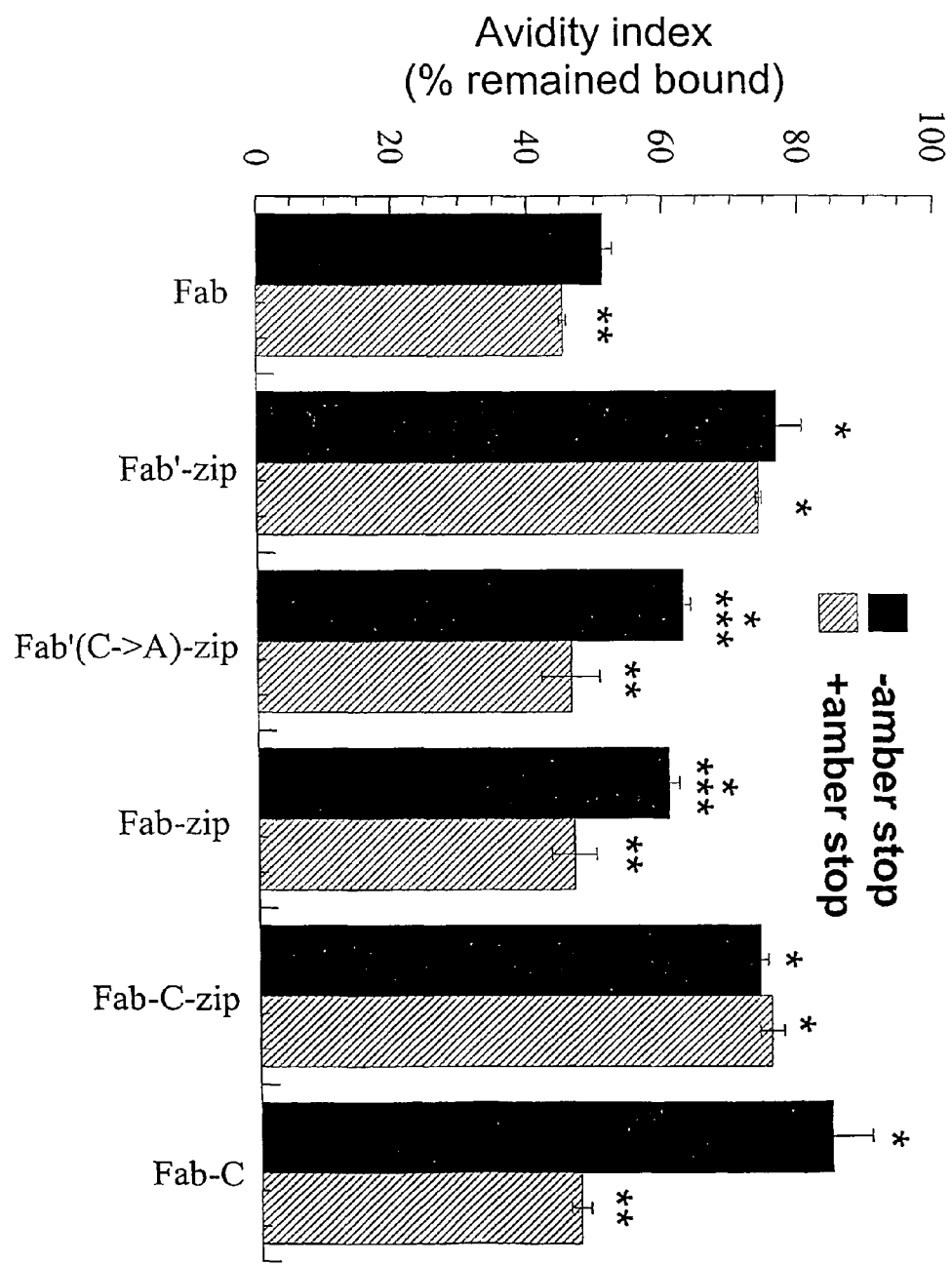
FIG. 40 shows the avidity index of variants with variations in dimerization domains in the presence of amber stop codons (cross hatch) or in the absence of an amber stop codon (solid bar) after the dimerization domain. Assays were performed as in FIG. 20 in triplicate and the avidity index is the percentage of phage remained bound after 500 nM ErbB2-ECD incubation relative to phage bound in a sample incubated without ErbB2-ECD. The significance of the differences were analysed with t-test. One asterisk (*) represents significant difference compared to Fab phage of equal amber stop status (p-values <0.001, except that Fab'(C→A)-zip and Fab-zip (-amber) have p value as 0.001-0.003). Two asterisks () represent significant difference comparing between with and without the amber stop codon (p<0.01). Three asterisks (*) indicate significant difference comparing amber-less constructs of Fab'(C→A)-zip and Fab-zip against Fab'-zip phage (p=0.003-0.007).

A series of mutations (FIG. 39) was made in the dimerization domain, i.e. hinge region plus GCN4 leucine zipper, and their effects on avidity were examined (FIG. 40). The phagemid vector phGHam.g3 with alkaline phosphatase (phoA) promoter was used as described previously since it is less toxic to bacterial cells and increases the phage yield compared to a vector with Ptac promoter (C. V. Lee, unpublished observation). The solution binding of all constructs was first examined to make certain the change in the construct did not disrupt the folding and function of the Fab. IC50s for all variants were between 0.05-0.07 nM measured at room temperature, which agreed well with Kd of h4D5 (0.1 nM).

The mutations were designed to examine the function of hinge region and leucine zipper in Fab'-zip phage in its bivalency. Constructs include a construct that has 1) that has the hinge region and the leucine zipper, Fab'-zip; 2) both cysteines in hinge region mutated to alanine (Fab'(C→A)-zip), 3) has the whole hinge region deleted (Fab-zip), 4) the hinge deleted leaving the first cysteine (Fab-C-zip), or 5) has both hinge and zipper deleted leaving a single cysteine (Fab-C). All of these constructs were made with or without amber stop codon before cP3 (C-terminal region of viralcoat protein p3) since the presence or absence of stop codons allows for the examination of the dependence of avidity on the interchain covalent bond between two Fabs. Avidity assay was performed as described in Example 1. Avidity index represents a measurement of functional avidity of individual construct and is defined as the percent phage bound to the immobilized antigen after the chase of 500 nM erbB2. High avidity is a functional consequence of displaying two copies of Fab per phage.

Without an amber stop codon, all constructs present Fab with significantly higher avidity than Fab-phage (FIG. 40). These results indicate that the probability of incorporating two copies of cP3 fusion on phage coat increases when the following are present: hinge plus zipper (Fab'-zip), cysteine-free hinge plus zipper (Fab'(C→A)-zip), zipper alone (Fab-zip), one cysteine plus zipper (Fab-C-zip) or just one cysteine (Fab-C) by itself between Fab and cP3. When both Fab' or Fab fusions are covalently linked to cP3 (no amber stop codon), bivalent display does not require the additional covalent links provided by the hinge region disulfides. However, the presence of an interchain covalent bond does appear to improve the frequency of incorporating two copies of fusion per phage since constructs that lack a cysteine residue such as, Fab' (C→A)-zip and Fab-zip (without amber stop), exhibited reduced avidity compared to Fab'-zip or other constructs that have disulfide bond in the linker, despite the fact that they do have significantly higher avidity than Fab-phage (no amber).

With the presence of an amber stop codon before cP3, most proteins were expressed into periplasm and associated with cP3 fusion protein via leucine zipper and/or disulfide bond since the read through of amber stop codon in the amber-suppressor strain XL-1 blue occur only at ~10% frequency. It is expected that a dimer should be linked to phage by single copy of cP3 as depicted in FIG. 18 and the bivalency be formed by forming an interchain covalent bond because the concentration of phage exuded into bacterial growth media is in the sub-nanomolar range, and thus, the binding energy of the leucine zipper interaction would not be sufficient to maintain the dimer during overnight growth at 37° C. Indeed, it was observed that those constructs that do not have disulfide bond in the hinge (Fab'(C→A)-zip) or with hinge deleted (Fab-zip) lose the bivalent dependent avidity in the presence of an amber stop codon. The constructs that contain disulfide bonds between Fab and cP3 maintained a high avidity of bivalency in the presence of an amber stop codon.

The exception is Fab-C. It was surprising that Fab-C, with just one cysteine between Fab and cP3, exhibited such high avidity, if not higher, as compared to the original Fab'-zip phage with full hinge and leucine zipper. These results suggest that Fab-C as cP3 fusion has good probability to associate with another cP3 fusion and get incorporated in the phage coat as dimers. However, the presence of amber stop between cysteine and cP3 in Fab-C construct reduced the avidity to the level of Fab-phage since most proteins were expressed as free Fab-C and the chance of free Fab-C in the periplasmic space forming dimer with a Fab-C-cP3 fusion appears to be very low.

The minimum element for bivalent display is either leucine zipper alone (Fab-zip) or one disulfide bond (Fab-C). When Fab-C is compared to Fab-zip, the results show that the disulfide bond is more effective in some circumstances to improve avidity than leucine zipper alone.

Western Blot Analysis

Western blotting was used to examine whether these constructs were displayed as covalently-linked dimers. We analyzed phage constructs Fab, Fab'-zip, Fab'(C→A)-zip, Fab-zip, Fab-C-zip, or Fab-C with or without amber stop codon. Phage samples (3×10$^{11}$) were denatured, subjected to SDS-PAGE and transferred to PVDF filters, which were then probed with either antibody that recognized the gD-tag, which was fused to the C-terminus of the light chain (FIGS. 41A and C), or antibody to phage coat protein P3 (Mobi-Tech) (FIGS. 41B and D).

Under reducing conditions (+DTT), the disulfide bond linking the light chain to the heavy chain fusion was reduced, and anti-gD blot (FIG. 41C) showed a single band with an apparent molecular weight (MW) of ~25 kDa, which was in good agreement with the calculated MW of a light chain plus gD-tag (26 kDa). When blotted with anti-P3, full length P3 (MW 48 kDa) supplied by helper phage and heavy chain-cP3 (MW 43-45 kDa depending on constructs) fusion in the reduced condition was expected. The results in FIG. 41D showed a main band at 60 kDa representing P3 and lower band with 50-52 kDa representing the fusion, based on the comparison with K07 alone (data not shown); both are greater than the calculated MW of the two main species expected. However, P3 is known to exhibit an anomalously high apparent MW under SDS-PAGE conditions {Gray, 1981 et al. 1981 J. Mol. Biol. 146:621-627; Crissman, 1984, Virology 132: 445-455}. Further, the relative position of the 50-52 kDa bands seems to correlate with the MW of the expected heavy chain-cP3 fusion of each construct with various insertions. It is interesting to note that the same 50-52 kDa band in the non-reduced gel blotted with anti-P3 was observed (FIG. 41B), which suggests that there are some heavy chain-cP3 fusion proteins that were not covalently linked with its light chain. Non-covalent linked light chain (25 kDa) was also observed in the non-reduced gel blotted with anti-gD antibody. (See FIG. 41A) In the reduced gel, the intensities of the 50-52 kDa bands from anti-P3 blot and the light chain bands from anti-gD blot indicate the level of display as Fab fusion for individual construct.

In general, adding amber stop codon reduced the display for all constructs as expected since the read-through of the amber stop codon is infrequent in amber suppressor strain. The insertion of the full dimerization domain (hinge and zipper) as in Fab'-zip reduces the display, and the culprit seems to reside in the two disulfide bonds in the hinge region since replacing the cysteine as in the Fab'(C→A)-zip or deleting the whole hinge (Fab-zip) increased most of the display to that of Fab-phage. Having just one cysteine in the dimerization domain appears to be well tolerated and displays well as in Fab-C-zip or Fab-C construct. The results show that reducing the number of disulfide bonds to one or zero increased expression of the fusion proteins.

Under non-reducing conditions (-DTT), interchain disulfide bonds were preserved and different patterns of bands for each of the constructs were observed (FIGS. 41A and B). As is often the case in western blots of phage preparations (Gray, 1981 supra; Crissman, 1984, supra), multiple bands can be observed resulting from proteolysis. However, comparing the highest MW major band in each lane should indicate the different products of the constructs as the intact cP3 fusion. Fab-phage produced a band with an apparent MW of 95 kDa, which was detected with both anti-gD and anti-P3 antibodies and agrees well with the calculated MW of 75 kDa of Fab-cP3 fusion. Again, the P3 fusion protein seems to have an effect on the mobility on SDS-PAGE system. In contrast, the Fab'-zip phage (-amber stop) contained a pair of bands with apparent MWs of ~180 and ~200 kDa which is in close agreement with the calculated MW of a dimeric Fab'-zip-cP3 fusion (155 kDa). It is interesting to note that the equivalent construct with amber stop codon produced only the 180 kDa band, which could represent the expected dimer fused to single cP3 as a monovalently displayed dimer complex depicted in FIG. 18. In any case, the covalently linked dimer is formed regardless of the presence of amber stop codon, which is expected since the leucine zipper promotes the dimer formation independent of any covalent link with phage coat in the periplasmic space and, functionally, avidity was observed with this set of constructs. Some lower MW bands were also seen which might be from proteolysis or alternatively disulfide bonded forms. There is a major band at 98 kDa which migrated slightly higher than Fab-cP3 but comigrated with the major band of Fab'(C→A)-zip construct, and would be the monomeric Fab'-zip-cP3 fusion which as expected is stained by anti-gD and anti-P3. So the expression of Fab'-zip fusion is reduced relative to Fab and there is significant portion of fusion protein that did not form disulfide bond.

With constructs Fab'(C→A)-zip and Fab-zip, a major band that migrated slight higher than Fab-cP3 at 98 kDa or 97 kDa individually was observed. These bands are the expected product for constructs with or without amber stop because there is no possibility of covalent disulfides between the two Fab moieties. The presence of dimeric Fab on Fab'(C→A)-zip and Fab-zip phage can not be observed in SDS-PAGE gel because of the lack of disulfide bond. Yet, the functional avidity suggests that the proportion of phage containing two copies of fusion is higher than Fab phage due to the presence of leucine zipper.

Constructs Fab-C-zip and Fab-C contain one interchain disulfide bond, and produce more covalently linked dimers as represented by the 180-200 MW band than Fab'-zip, which have two disulfide bond in the hinge linker. The increase of the covalent-linked dimers correlates with the overall increase of expression of the fusion including the monomer as shown in the 97 and 95 kDa band. It is interesting to note that the proportion of dimer is higher in Fab-C-zip than Fab-C, which suggests that leucine zipper, although not required, does improve the association of the fusion and the efficiency of forming interchain disulfide bond. Yet the net expression of Fab-C-cP3 fusion is slightly higher than Fab-C-zip construct.

Thus, western blotting suggests the presence of bivalent moieties displayed on Fab'-zip, Fab-C-zip, and Fab-C phage, mirroring what is observed functionally in avidity assays. For constructs, for which the dimer can not be observed on SDS-PAGE, like Fab'(C→A)-zip and Fab-zip, the avidity assay is relied upon to demonstrate its bivalency. The avidity assay shows the consequences of presenting two copies of Fab per phage particle since all constructs have same solution binding affinity and the avidity is not influenced by the display level. Net expression of Fab'-zip can be significantly improved by minimizing the dimerization domain. Potentially, the different extent of dimer display and avidity of these various constructs may provide useful tools for applications that may call for different extent of display and avidity.

EXAMPLE 3

Libraries of antibody variable domains were generated to isolate and screen for isolation of high affinity binders to particular target antigens. Diversity of antibody variable domains is preferably generated in CDR regions of the heavy and/or light chain variable domains. Generation of diversity in CDR regions of heavy chains is described below. Utilization of a single template molecule as the backbone for generation of the diversity in CDR regions is preferred because the single template can be modified to improve display and folding and may accommodate H3 regions of various sizes.

Library Design

H1, H2

Libraries of antibody variable domains were designed to maximize diversity in the heavy chain CDR regions while minimizing structural perturbations in the antibody variable domains. Structural perturbations in antibody variable domains are generally associated with improperly folded antibody domains resulting in low yield and unstable products, for example when produced in bacterial cells. Low yields decrease the number of binders detected in screening. Improperly folded and unstable antibody structures also can result in low yields and low affinity when antibodies are produced as Fab fragments or full-length antibodies in cell cultures. Production of properly folded antibodies in high yield in cell culture is desirable especially in the case of antibodies useful therapeutically.

Diversity in the CDR regions was generated by identifying solvent accessible and highly diverse positions in each CDR for CDRs H1 and H2 of the template molecule, and designing an oligonucleotide comprising at least one tailored (i.e., non-random) codon set encoding variant amino acids for the amino acid position corresponding to the position of at least one solvent accessible residue at a highly diverse position in at least one CDR region. A tailored codon set is a degenerate nucleic acid sequence that preferably encodes the most commonly occurring amino acids at the corresponding positions of the solvent accessible residues in known, natural antibodies.

Solvent accessible residues in the CDRs were identified in the antibody variable domain template molecule by analyzing the crystal structure of the template molecule. Humanized antibody 4D5 is efficiently produced and properly folded when produced in a variety of host cells, including bacterial cell culture. The crystal structure for the humanized antibody 4D5 variable region is known and publicly available at www/rcsb/org (accession code IFVC).

The solvent accessible positions in the CDRs of the light chain and CDRH1 and CDRH2 of the heavy chain were identified using the Insight II program (Accelrys, San Diego, Calif.).

CDR residues were also analyzed to determine which positions in the CDRs were highly diverse. Highly diverse positions in the CDR regions for the heavy chains were identified by examining the sequences of known, naturally occurring antibodies in the Kabat database. The Kabat database is available at immuno/bme/nwu/edu. In the Kabat database, there were about 1540 sequences of the human light chain and 3600 sequences for the human heavy chain. The CDR sites were aligned and numbered as described by Kabat (see immuno/bme/nwu/edu). Highly diverse amino acid positions were identified by lining up and ranking the amino acid usage, from most frequently used to less frequently used for each CDR residue. For example, H1-30 (i.e., residue 30 of the heavy chain CDR1) was found to be S (serine) in 2451 out of 3617 antibody sequences in the Kabat database, and it is the amino acid found most frequently at this position. Next on the list of frequency is threonine (occurring in 655 sequences), followed by asparagine (154 sequences), arginine (70 sequences), glycine (67 sequences), with the remaining 128 sequences being one of the remaining amino acids. Illustrative diverse sites, with corresponding diversity list of amino acids, are shown in FIG. 2 (for the heavy chain).

Amino acid residues found in a particular position that collectively constitute the most frequently occurring amino acids among the known, natural antibody sequences are selected as the basis for library design. The most frequently occurring amino acids were deemed to be those that are most commonly found in the top 90% of the list of diverse amino acids at that position (this group of amino acids is referred to herein as "target group of amino acids"). However, as described herein, the percent cutoff for a target group of amino acids can be varied, as described above, according to the circumstances and purpose of the diversity library that is to be achieved.

For humanized antibody 4D5, the positions identified as solvent accessible and highly diverse were:

| Heavy Chain | |
|---|---|
| CDR1 | 28, 30, 31, 32 |
| CDR2 | 50, 52, 53, 54, 56, 58 |

Examples of amino acids that occur at high frequency in natural diversity (i.e., among known, natural antibody sequences) (referred to as "target group" or "natural diversity" in FIG. 3), and the designed diversity of amino acids by DNA codons ("Diversity<DNA codon>") for each of these positions is shown in FIG. 3.

Codon sets encoding a specific group of amino acids were designed to include at least a certain percentage of the amino acids in the known, natural sequences (designated as "% covering" in FIG. 3). Of the amino acids encoded by a codon set, at least about 40% of the amino acids are target amino acids identified for a particular solvent accessible and highly diverse position (designated as "% good" in FIG. 3; amino acids encoded by a codon set that are target amino acids are shown in bold in column 3 of FIG. 3), more preferably any one of 40 to 100%, more preferably 70%. However, as described herein, the % good value can be varied according to circumstance and objectives. The codon sets were selected such that they preferably encoded the amino acids with the highest occurrences at a particular position. The number of non-target amino acids coded by a codon set for a particular position was minimized. Effectiveness of codon set selection/design was evaluated in part based on the "% good" value. A high percentage meant very low non-target amino acids; a high value of "% good" was deemed more important than having more target amino acids among the amino acids coded by a particular codon set. Redundancy was included in calculating the "% good" value. For evaluation purposes, the "% covering" value was also calculated. This value represents the percentage of natural diversity covered by the "good" or target amino acids encoded by a particular codon set. For example, for H-30, when codon set RMV is used, the "good" amino acids are STNRDG, which is 73% (% good) of the amino acids encoded by the codon set. STNRDG are amino acids that cover 3489 out of 3617 known, natural antibody sequences at this amino acid position. 3489/3617 equals 96%, which is the "% covering" value. Thus, in one design using RVM at H-30, 73% of the library covers 96% of the natural diversity in CDRH1 at position 30.

The codon sets were also designed to exclude, when possible, cysteine and stop codons. The presence of cysteine residues tends to cause folding problems and stop codons can decrease the effective library size. In the design of the codon sets, it was also deemed desirable to minimize the number of nontarget amino acids.

The codon sets designed for each solvent accessible and highly diverse residue of humanized antibody 4D5 are shown in FIG. 3. At any particular residue, one or more codon sets could be used depending on the target amino acids that were identified. For example, combining two H1 oligonucleotides, one having residue H1-33 as KMT, the other having H1-33 as KGG, results in 100% of the codons used for H1-33 covering 86% (50%+30%) of the natural diversity at the H1-33 position. Other examples of instances where two codon sets can be beneficially used include using codons DGG and DHT at H2-50.

The various codon sets could be used to generate diverse libraries with diversity in one or more CDR regions, including CDRH1 and CDRH2. For example, FIGS. 5-13 and FIG. 24 show various illustrative versions of codon set designs that can be used to generate diversity. FIGS. 3A and 3B provide a summary of the amino acid coverage of these designs. In general, it is preferable, but not necessary, that the designs narrow the diversity to cover more of the natural diversity and exclude as much as possible the "non-target" amino acids.

Library Design

H3

In comparison to other CDRs, heavy chain CDR3 (H3) regions exhibit the greatest diversity in sequences and lengths, although the sequence diversity is not completely random (i.e., some amino acids were found to occur more often than other in particular amino acid positions). Because of this diversity in sequences and sequence lengths, it is difficult to design a strategy that provides for diversity in H3 region. Using a single antibody template molecule allows for a strategy that includes different lengths of H3 because the template can be selected and designed to accommodate H3 regions of varying lengths in the initial design of the library. The template is selected to accommodate different lengths of H3 region while maintaining good structural characteristics of folding and stability. The diversity in the H3 region is preferably tailored to mimic natural diversity, although different libraries generated with different codon sets can also be used to develop antibodies that bind to a variety of different epitopes in the target antigen or to provide for isolation of more binders having unique H3 sequences.

Figure 23:
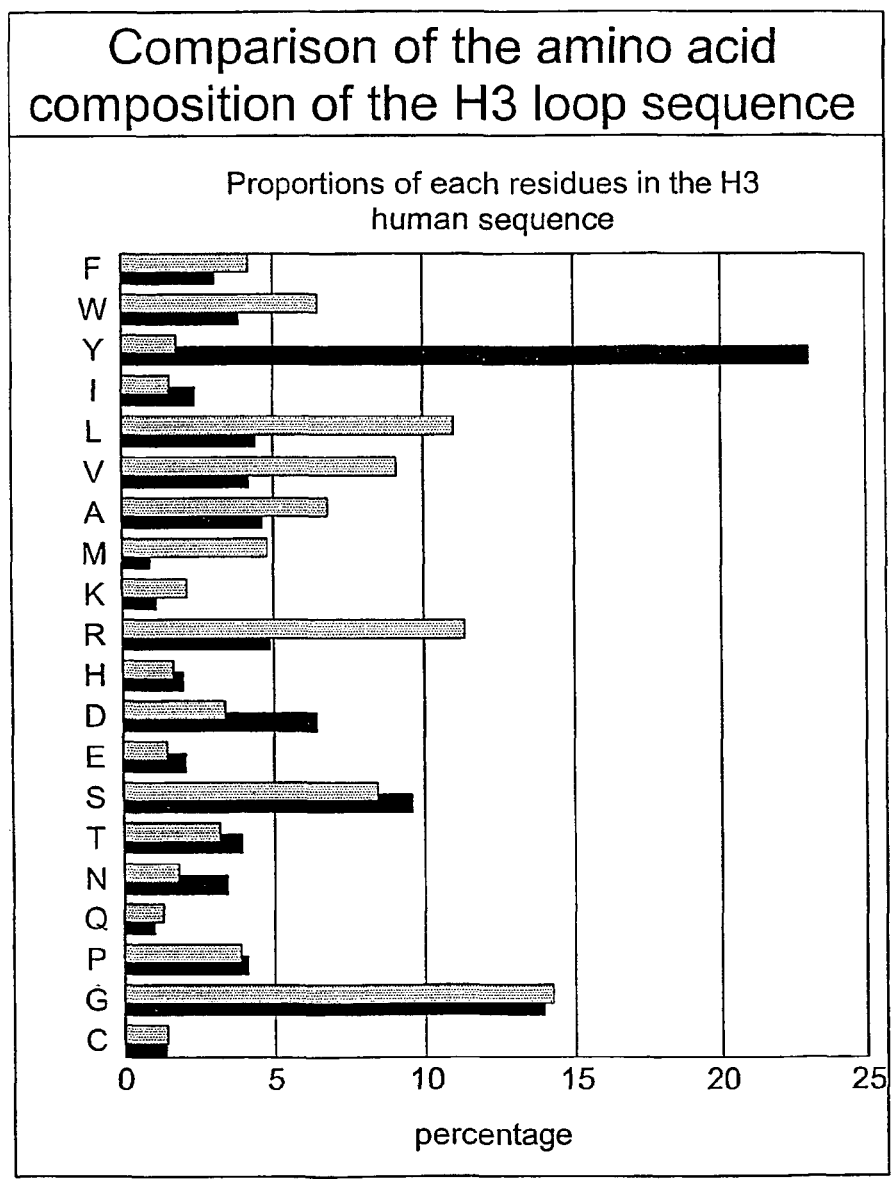
FIG. 23 shows the comparison of the frequency of amino acid types in CDRH3 regions in naturally occurring antibodies (solid bar) and in antibody variable domains with diversity generated with NNK codon sets (stippled bar). Amino acids are grouped as follows: phenylalanine (F), trytophan (W) and tyrosine (Y) are aromatic amino acids; isoleucine (I), leucine (L), valine (V), alanine (A), and methionine (M) are aliphatic, lysine (K), arginine (R), and histidine (H) are basic; aspartic acid (D) and glutamic acid (E) are acidic; serine (S), threonine (T), asparagine (N), and glutamine (Q) are polar; and proline (P), glycine (G), and cysteine (C) are conformational.

In a preliminary analysis to assess the amino acid preferences for each position in H3, a library with diverse H3 was generated using an NNK codon set for residues 95-100a of the humanized antibody 4D5 H3 region. The NNK codon set encodes all 20 amino acids and stop codons. This library was generated in a Fab phage display format and 400 clones that displayed functionally on phage were identified and sequenced. The amino acid sequence found in H3 regions in the NNK library were compared to those found in the Kabat database. A comparison of those amino acids is shown in FIG. 23. When the amino acid sequences in the NNK library and Kabat database were analyzed, it was determined there was good agreement in most amino acid usage between the library sequences and the sequences of Kabat. Interestingly, there appeared to be more aliphatic/hydrophobic amino acids in the NNK library than in the known, naturally occurring sequences. See FIG. 23.

Diversity in H3 was also determined using codon sets DVK and XYZ. The amino acid frequency for each amino acid in the H3 region randomized with DVK or XYZ was identified and compared to the amino acid frequency of naturally occurring antibodies in the Kabat database as described above. The results are shown in FIG. 42. The results show that both the DVK aid XYZ library had amino acid usage that was generally in good agreement with that of naturally occurring antibodies. The DVK library did show decreases in usage of tyrosine, leucine, valine and isoleucine. The XYZ library also showed less frequent usage of tyrosine.

Codon sets are identified by 3 capitol letters in italics (eg. DVT, NNK, NVT). These letters refer to generic codon formulas as follows: R is 50% A/50% G; M is 50% A/50% C; K is 50% G/50% T; S is 50% G/50% C; W is 50% A/50% T; H is 33% A/33% T/33% C; B is 33% G/33% T/33% C; V is 33% G/33% A/33% C; D is 33% G/33% A/33% T; N is any nucleic acid; X ix 38% G, 19% A, 26% T, and 17% C; Y is 31% G, 34% A, 17% T, and 18% C; and Z is 24% G/76% C.

Codon sets that resulted in similar amino acid usage in H3 as compared to natural diversity were then used to design libraries containing diversified H3. These codon sets include NNK, NNS, NVT, DVK and XYZ. In some embodiments, codon sets encoding all 20 amino acids at a position, such as NNK or NNS were utilized as shown in FIG. 4.

One of the codon sets was DVK. DVK encodes ACDEGKNRSTYW and a stop codon. Amino acids that do not occur frequently in known, natural antibody sequences were excluded, for example, LPHQFIMV. Oligonucleotides encoding H3 regions of varying lengths utilizing DVK codons are shown in FIG. 4. In one embodiment, a pool of oligonucleotides including F59, F63, F64, F65, F66, and F78 were utilized to form a library of molecules with diversity in H3.

Another codon set used was NVT. NVT encodes ACDNGHPRSTY and excludes W (tryptophan) and a stop codon. Tryptophan is favored in phage display and tends to dominate. Stop codons can decrease library diversity. In some instances, the NVT design was doped with W by walking W across the residues. Oligonucleotides encoding H3 regions of oligonucleotides including F134, F136, FF137, F138, F142, F155, F156, F157, F158, F160 and F160g were utilized to form a library of molecules with diversity in H3.

In another embodiment, a codon set XYZ was used as shown in the oligonucleotides represented in FIG. 4 and FIG. 43. The codon set XYZ encodes all 20 amino acids.

In terms of which residues to diversify in H3, it was determined that the C-terminus of H3 can be less diversified. In some embodiments, the H3 C terminal was held constant. The C-terminus of H3 had mainly two types of sequences in the Kabat database, the sequences being either:

$Y_{100a}AMD_{101}(Y/V)_{102}$ (sometimes $Y_{100a}$ can vary slightly)

or $F_{100a}D_{101}(Y/V)_{102}$.

In humanized antibody 4D5, the C-terminus of H3 is YAMDY. The libraries were designed to keep this part mostly constant, except $Y_{100a}$ was varied. $Y_{100a}$ was varied using a variety of codon sets such as DVK, DSG, KSG, NVT and XYZ. Alternatively, single amino acid substitutions at this residue can be made with substitution of Y with glycine, serine, alanine, tryptophan, valine or aspartic acid.

Libraries were generated using oligonucleotides that encode different sequence lengths in the H3 region. H3 lengths in naturally occurring antibodies range from about 2 amino acids to about 24 amino acids. A series of oligonucleotides was prepared encoding H3 regions of varying lengths from about 7 amino acids to about 19 amino acids as shown in FIG. 43. These oligonucleotides also provided for limited variation at the C-terminal end. Less diversity is found at the C-terminal end but the oligonucleotides provide for variation at the C-terminal end of YAMD (Y/V) or FD (Y/V). Variations at the 100a and/or 100b position were also included. The H3 residues that were varied were varied using codon sets NNK, NNS, XYZ or mixtures thereof. Other examples including varying lengths of H3 regions are shown in FIG. 4. In FIG. 4, the HC region varies from about 11 to 13 residues some embodiments have the more constant C-terminal of YAMDY. Some variation is provided at the residue position 100a(Y). The CDRH3 amino acid positions are varied using codon sets such as DVK, NVT, NNK, XYZ and NNS or mixtures thereof.

In one embodiment, multiple libraries were prepared with diversity in the H3 in both sequence and length using each of the oligonucleotides shown in FIG. 43. These libraries provide diversity in the sequence and length of the H3 region. Diversity was also generated in the H1/H2 regions as described previously. The libraries were pooled and then sorted against target antigen murine or human VEGF. The high affinity and specific binders were isolated and sequenced. Isolating and sequencing the binders allows identification of the optimal length of the H3 for binders to murine or human VEGF was about 11 to 13 amino acids. (Data not shown)

In some designs, framework residue 93 was changed to alanine to reflect the natural consensus (humanized antibody 4D5 has the mouse residue serine). Framework residue 94 (right before the first H3 residue) was designed to be arginine, or arginine and lysine (using codon ARA) to reflect the natural sequence consensus. In addition, in some embodiments, 3 amino acids at the N-terminus of the heavy chain were removed right after the secretion signal.

EXAMPLE 4

Library Design

L1, L2, L3

Libraries of antibody variable domains were designed to maximize diversity in the CDR regions of light chains while minimizing structural perturbations in the antibody variable domains. Structural perturbations in antibody variable domains are generally associated with improperly folded antibody domains resulting in low yield, for example when produced in bacterial cells. Low yields decrease the number of binders detected in screening. Diversity in the CDR regions was generated by identifying solvent accessible and highly diverse positions in each CDR for CDRs L1, L2 and L3, and designing an oligonucleotide comprising at least one tailored (i.e., non-random) codon set encoding variant amino acids for the amino acid position corresponding to the position of at least one solvent accessible residue at a highly diverse position in at least one CDR region. A tailored codon set is a degenerate nucleic acid sequence that preferably encodes the most commonly occurring amino acids at the corresponding positions of the solvent accessible residues in known, natural antibodies.

Solvent accessible residues in the CDRs were identified in the antibody variable domain template molecule by analyzing the crystal structure of the template molecule. Humanized antibody 4D5 is efficiently produced and properly folded when produced in a variety of host cells, including bacterial cell culture. The crystal structure for the humanized antibody 4D5 variable region is known and publicly available at www/rcsb/org (accession code IFVC).

The solvent accessible positions in the CDRs of the light chain and CDR1 and CDR2 of the heavy chain were identified using the Insight II program (Accelrys, San Diego, Calif.).

CDR residues were also analyzed to determine which positions in the CDRs were highly diverse. Highly diverse positions in the CDR regions for the heavy and light chains were identified by examining the sequences of known, naturally occurring antibodies in the Kabat database. The Kabat database is available at immuno/bme/nwu/edu. In the Kabat database, there were about 1540 sequences of the human light chain and 3600 sequences for the human heavy chain. The CDR sites were aligned and numbered as described by Kabat (see immuno/bme/nwu/edu). Highly diverse amino acid positions were identified by lining up and ranking the amino acid usage, from most frequently used to less frequently used for each CDR residue. For example, L3-91 (i.e., residue 91 of the light chain CDR3) was found to be Y (tyrosine) in 849 out of 1582 antibody sequences in the Kabat database, and it is the amino acid found most frequently at this position. Next on the list of frequency serine (occurring in 196 sequences), followed by arginine (169 sequences), alanine (118 sequences), glycine (61 sequences), histidine (41 sequences), with the remaining 35 sequences being one of the remaining amino acids. Illustrative diverse sites, with corresponding diversity list of amino acids, are shown in FIG. 1 (for the light chain). The highly diverse positions, as well as the most frequent amino acids at those positions, may change over time as more sequences are incorporated into the database.

Amino acid residues found in a particular position that collectively constitute the most frequently occurring amino acids among the known, natural antibody sequences are selected as the basis for library design. The most frequently occurring amino acids were deemed to be those that most commonly found in the top 90% of the list of diverse amino acids (this group of amino acids is referred to herein as "target group of amino acids"). However, as described herein, the percent cutoff for a target group of amino acids can be varied, as described above, according to the circumstances and purpose of the diversity library that is to be achieved.

For humanized antibody 4D5, the positions identified as solvent accessible and highly diverse were:

| Light Chain | |
|---|---|
| CDR1 | 28, 29, 30, 31, 32 |
| CDR2 | 50, 53 |
| CDR3 | 91, 92, 93, 94, 96 |

Examples of amino acids that occur at high frequency in natural diversity (i.e., among known, natural antibody sequences) (referred to as "target group" or "natural diversity" in FIG. 3), and the designed diversity of amino acids by DNA codons ("Diversity<DNA codon>") for each of these positions is shown in FIG. 3.

Codon sets encoding a specific group of amino acids (Diversity) were designed to include at least a certain percentage of the amino acids in the known, natural sequences (designated as "% covering" in FIG. 3). Of the amino acids encoded by a codon set, at least about 40% of the amino acids, more preferably 70%, are target amino acids identified for a particular solvent accessible and highly diverse position (designated as "% good" in FIG. 3; amino acids encoded by a codon set that are target amino acids are shown in bold in column 3 of FIG. 3). However, as described herein, the % good value can be varied according to circumstance and objectives. The codon sets were selected such that they preferably encoded the amino acids with the highest occurrences at a particular position. The number of non-target amino acids coded by a codon set for a particular position was minimized. Effectiveness of codon set selection/design was evaluated in part based on the "% good" value. A high percentage meant very low non-target amino acids; a high value of "% good" was deemed more important than having more target amino acids among the amino acids coded by a particular codon set. Redundancy was included in calculating the "% good" value. For evaluation purposes, the "% covering" value was also calculated. This value represents the percentage of natural diversity covered by the "good" amino acids (of the amino acids encoded by a particular codon set). For example, for L3-91, when codon set KMT is used, the "good" amino acids are YSA, which is 75% of the YSAD amino acids encoded by the codon set. YSA are amino acids that cover 1190 out of 1580 known, natural antibody sequences at this amino acid position. 1190/1580 equals 75%, which is the "% covering" value. Thus, in one design using KMT at L3-91, 75% of the library covers 75% of the natural diversity in CDRL3 at position 91.

The codon sets were also designed to exclude, when possible, cysteine and stop codons. The presence of cysteine residues tends to cause folding problems and stop codons can decrease the effective library size. In the design of the codon sets, it was also deemed desirable to minimize the number of nontarget amino acids.

The codon sets designed for each solvent accessible and highly diverse residue of humanized antibody 4D5 are shown in FIG. 3. At any particular residue, one or more codon sets could be used depending on the target amino acids that were identified. Codon sets YKG and TWT can each be used to generate diversity at L3-96.

The various codon sets could be used to generate diverse libraries with diversity in one or more CDR regions, including CDRL1, CDRL2 and CDRL3. For example, FIGS. 5-13 and FIG. 24 show various illustrative versions of codon set designs that can be used to generate diversity. FIGS. 3A and 3B provide a summary of the amino acid coverage of these designs. In general, it is preferable, but not necessary, that the designs narrow the diversity to cover more of the natural diversity and exclude as much as possible the "non-target" amino acids.

EXAMPLE 5

Construction, Sorting and Analysis of scFv Libraries

Libraries with diversified CDRs were generated using vectors comprising 4D5 variable domains in the scFv or scFv-zip formats in vector pS1607 as described in Example 1. In total, five libraries were generated and the library characteristics were as follows:

| Library name | Format | CDR Diversity |
|---|---|---|
| ScFv-1 | zipper | H1, H2, H3 |
| ScFv-2 | Zipper | H1, H2, H3, L3 |
| ScFv-3 | Zipper | H3, L3 |
| ScFv-4 | No zipper | H1, H2, H3 |
| ScFv-5 | No zipper | H1, H2, H3, L3 |

Libraries were constructed using the method of Kunkel (Kunkel et al., *Methods Enzymol.* (1987), 154, 367-382) with previously described methods (Sidhu et al., *Methods Enzymol.* (2000), 328, 333-363). For each library a "stop template" version of a scFv or scFv-zip display vector was used; in each case, a stop template with TAA stop codons within each of the CDRs to be randomized was used. Mutagenic oligonucleotides with degenerate codons at the positions to be diversified were used to simultaneously introduce CDR diversity and repair the stop codons. For example, for the construction of library scFv-1, three oligonucleotides were simultaneously used to introduce diversity into CDR-H1, CDR-H2, and CDR-H3. Successful incorporation of all the mutagenic oligonucleotides resulted in the introduction of the designed diversity at each position and simultaneously repaired the stop codons, thus generating an open reading frame that encoded either a scFv or scFv-zip fused to the C-terminal domain of the gene-3 minor coat protein. Residues in each CDR were chosen for diversification based on their solvent accessibility and their level of diversity in the Kabat data base of natural antibodies (as described in Examples 2 and 3). For CDRs H1 and H2, the residues chosen for diversification and the diversity introduced at each position are shown in FIG. 24. For CDR-H3, diversity was introduced using an equimolar mixture of four mutagenic oligonucleotides (F59, F63, F64 and F65 in FIG. 4).

The mutagenesis reactions were electroporated into *E. coli* SS320 (Sidhu et al., *Methods Enzymol.* (2000), 328, 333-363), and the transformed cells were grown overnight in the presence of M13-VCS helper phage to produce phage particles that encapsulated the phagemid DNA and displayed scFv or scFv-zip fragments on their surfaces. Each library contained greater than $2 \times 10^{10}$ unique members.

1. Selection of Specific Antibodies from the Naïve Libraries.

Phage from each library described above were cycled through rounds of binding selection to enrich for clones binding to targets of interest. Three target proteins were analyzed: Her2, IGF-1, and mVEGF. The binding selections were conducted using previously described methods (Sidhu et al., supra).

NUNC 96-well Maxisorp immunoplates were coated overnight at 4° C. with capture target (5 ug/mL) and blocked for 2 h with bovine serum albumin (BSA) (Sigma). After overnight growth at 37° C., phage were concentrated by precipitation with PEG/NaCl and resuspended in PBS, 0.5% BSA, 0.1% Tween 20 (Sigma), as described previously (Sidhu et al., supra). Phage solutions ($10^{13}$ phage/mL) were added to the coated immunoplates. Following a 2 h incubation to allow for phage binding, the plates were washed 10 times with PBS, 0.05% Tween20. Bound phage were eluted with 0.1 M HCl for 10 min and the eluant was neutralized with 1.0 M Tris base. Eluted phage were amplified in *E. coli* XL1-blue and used for further rounds of selection.

The libraries were subjected to two rounds of selection against each target protein (Her-2, IGF-1 or mVEGF), followed by a round of selection (round 2a) against an anti-gD epitope antibody to enrich for clones displaying scFv or scFv-zip (there is a gD epitope in the linker between the light chain and heavy chain regions of the scFv). Following the anti-gD enrichment, each library was selected for a third round against the target protein.

Individual clones from each round of selection were grown in a 96-well format in 500 uL of 2YT broth supplemented with carbenicillin and M13-VCS, and the culture supernatants were used directly in phage ELISAs (Sidhu et al., supra) to detect phage-displayed scFvs that bound to plates coated with target protein. The results for each library against each target protein after three rounds of sorting are shown in FIG. 25, and it can be seen that each library produced binders against each target protein.

The three scFv-zip libraries (scFv-1, scFv-2 and scFv-3) were subjected to more detailed analysis. Phage clones from round 3 of selections against IGF-1 or mVEGF were analyzed for specific binding to target by doing phage ELISAs against both IGF-1 and mVEGF. Clones that bound only to the target against which they were selected were classified as specific while those that bound both targets were classified as non-specific. The results are shown in FIG. 26 which indicates the percentage of clones from each selection that bound targets (Total) and the percentage of clones that bound only the target against which they were selected (specific). All three libraries produced specific binding clones against target, although library scFv-3 produced considerably fewer specific binders than did libraries scFv-1 and scFv-2.

For library scFv-1, clones were also screened from round 2 of selection. From the IGF-1 selection, 140 out of 960 screened clones (15%) were positive. From the mVEGF selection, 24 out of 1152 screened clones (2%) were positive.

For one scFv library (library scFv-4), several hundred clones from round 3 of the IGF-1 or mVEGF binding selections were screened for specific binders. In this case, the IGF-1 selection yielded 35% specific binders while the mVEGF selection yielded 40% specific binders.

FIG. 29 shows the sequences and affinities of some positive binders from scfv and ScFv-zip libraries.

2. Sequencing of Antigen Specific Binders

Representatives of the specific binding clones characterized above were sequenced using standard methods. The results are shown in FIG. 27.

From the IGF-1-specific binders, a total of 255 clones were sequenced and 192 of these were unique sequences. From the mVEGF-specific binders, 202 clones were sequenced and 86 of these were unique sequences. These results confirmed that the methods of the invention for generating CDR diversity and selecting for antigen specific binders resulted in a multiplicity of antigen specific antibody variable domains with different sequences.

The complete sequences from about 450 binding clones were analyzed for amino acid diversity at the heavy chain residues that were diversified in the library designs. The results indicated that all the designed substitutions occurred with a good distribution of amino acid type (data not shown).

Figure 28:
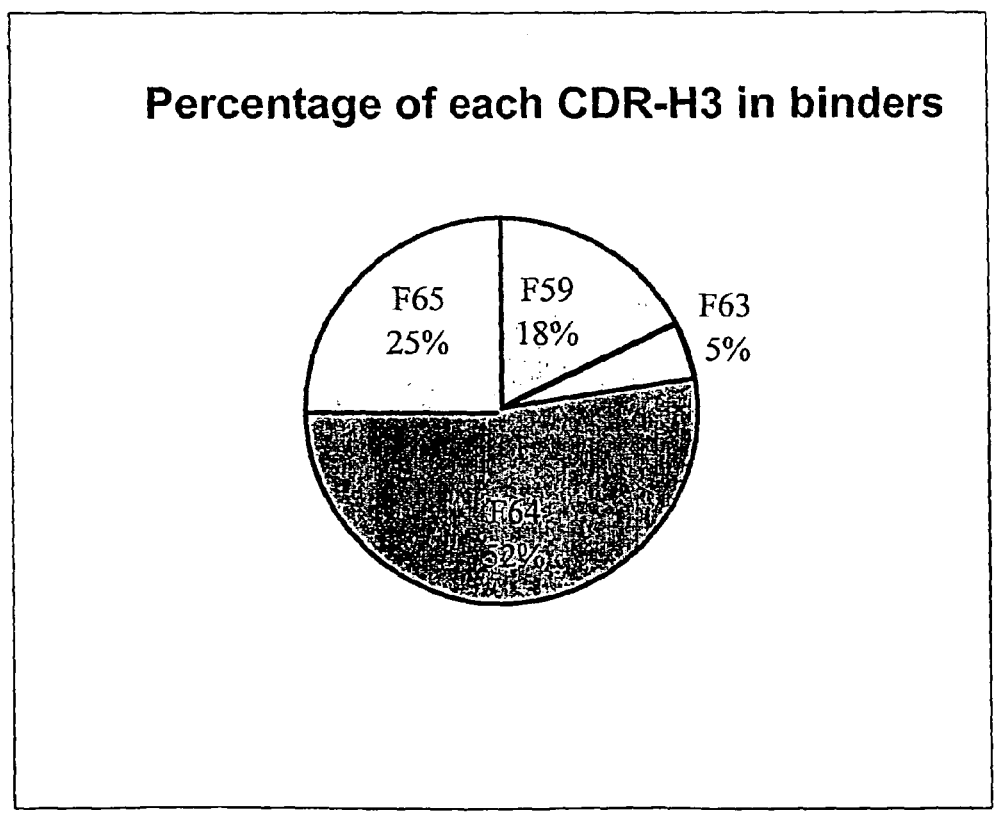
FIG. 28 shows an example of CDRH3 codon/amino acid usage distribution in one set of binders. "X" denotes codon set usage as shown for each oligonucleotides in FIG. 4. The percentage of the CDR-H3 design of each oligonucleotides in the sequences of binders isolated from the library are shown.

Analysis of the sequences of the CDR-H3 region indicated that all four different designs included in the naïve libraries (F59, F63, F64 and F65 in FIG. 4) were also present in the selected binding clones, as shown in FIG. 28. However, the four CDR designs were not equally common among the selected binders, indicating that some CDR designs may be better suited for generating positive binding clones against particular targets. In particular, the design F64 was the most prevalent (52%) while the design F63 was the rarest (5%) (FIG. 28).

EXAMPLE 6

F(ab')₂ Libraries with L3/H3 Diversity

Libraries with diversity in CDRL3 and H3 were generated using the template Fab-zip 4D5 vector pS1607 as described in Example 1. For CDRL3, oligonucleotide F61 (F61: GCA ACT TAT TAC TGT CAG CAA NRT NRT RVM NNK CCT TDK ACG TTC GGA CAG GGT ACC; the underlined nucleotides encoding amino acid residues/positions that were diversified; SEQ ID NO: 30). For CDRH3, oligonucleotides used were designated F59, F63, F64, F65, F66, and F78. (See FIG. 4). A pair of L3 and H3 oligonucleotides were used per Kunkle mutagenesis reaction, and libraries were made and amplified in *E. coli* as described in Example 4. In total, six libraries with different H3 diversity (generated with six different oligonucleotides as described above) were made and combined after amplification for sorting on targets. Sorting was done as in Example 4, except that this library underwent two tracks of sorting: with or without presorting on anti-gD before target sorts. The library was either directly sorted on targets (i.e., with no presort) or first on anti-gD as a presorted library before sorting on targets. After one presort, the library was sorted on targets two times and then on anti-gD once before sorting on targets another time. Library without presorting went through targets twice and then was enriched on anti-gD once and then another time on targets.

The hit rate was significantly better with presorted library sorted against mVEGF or IGF-1. For HER2ECD as targets, both presorting or no presorting worked well. The hit rate after two target sorts and one anti-gD sort was about 1-4%. A final sort on target after anti-gD sort resulted in a >90% hit rate. Hit rate was calculated as specific binders found per 100 clones screened. Specific binding clones were defined as in Example 5.

Positive clones were sequenced for their H3 sequences and IC50 (affinity) analyzed as previously described (Sidhu et al, supra). FIG. 29 shows the results of analysis of each clone. Clones were obtained with variable sequences and affinity in the range of sub-micromolar and micro-molar. Most binders came from libraries with DVK design in H3. In column 2 of FIG. 29, underlined residues represent residues that were fixed in the source library of the clones. Most binding clones came from the library that fixed the $Y_{100a}$ position.

Figure 30:
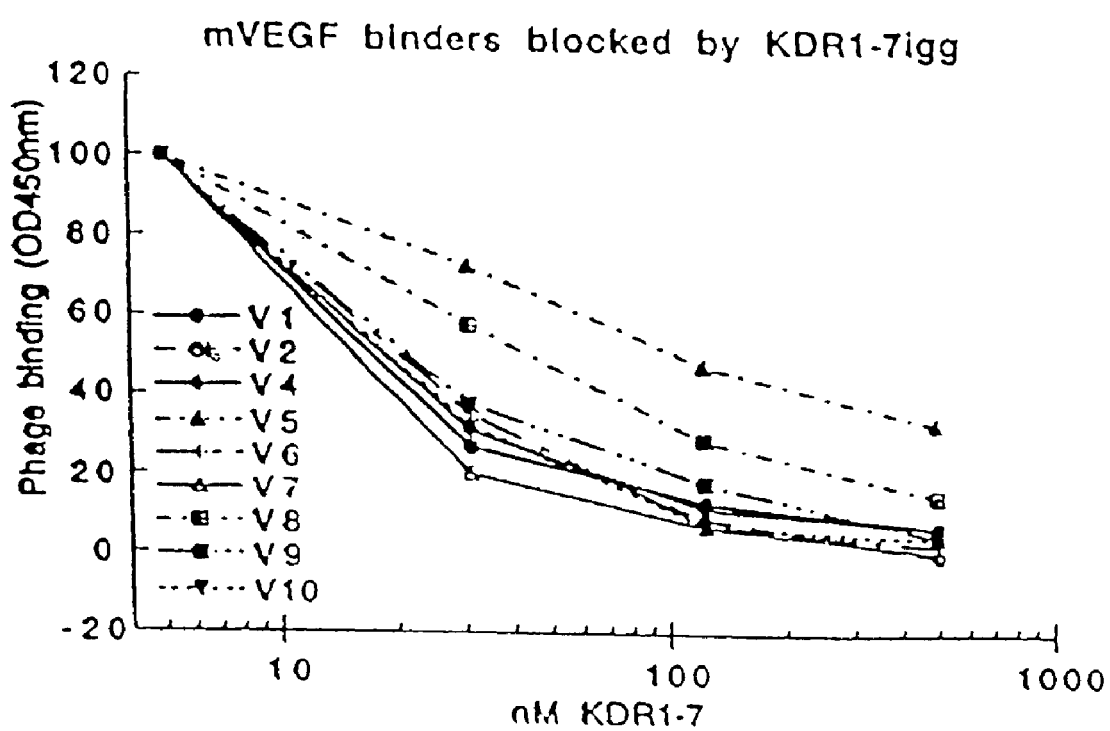
FIG. 30 shows the identity of the epitope bound by some of the clones. Murine VEGF was coated on plate and phage clones competitively inhibited in the present of KDR-7igg were identified. Clones V1 (-○-), V2(-◯-), V4 (-◇-), V5 (-△-), V6 (-+-), V7 (-▲-), V8 (- -), V9 (-□-), V10 (-▽-) were tested.
Figure 31:
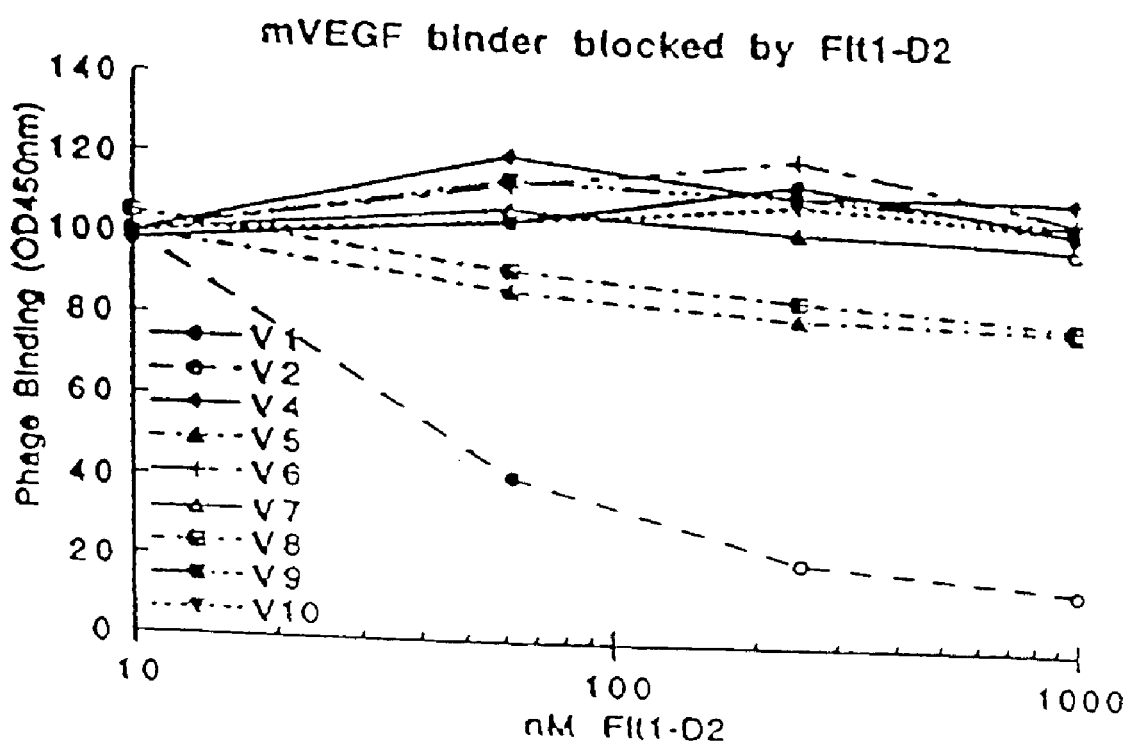
FIG. 31 shows the identity of the epitope bound by some of the clones. Murine VEGF was coated on a plate and phage clones competitively inhibited in the present of F1t1-D2 were identified. Clones V1 (-○-), V2(-◯-), V4 (-◇-), V5 (-△-), V6 (-+-), V7 (-▲-), V8 (- -), V9 (-□-), V10 (-▽-) were tested.

The binding epitope of some of the clones was also analyzed by competitive binding ELISA. Target (murine VEGF) was coated on 96-well NUNC-maxisorb plate. Phage clones binding to the target in the presence of blocking reagent which bound to a particular epitope on mVEGF was measured. Two mVEGF receptor fragments were used, Flt-D2 (Wiesmann et al., Cell (1997), 91:695-704) or KDR1-7-igg (Fuh et al., J. Biol. Chem. (1998), 273:11197-11204). The results showed that all analyzed binders bound to a similar epitope as KDR1-7-igg since they competed with each other (FIG. 30). Flt-D2 (Domain 2 of Flt-1), which has a smaller epitope on mVEGF, only blocked one clone but not the others (FIG. 31).

To demonstrate that the binding phage clones did present Fab polypeptide sequences that could become Fab antibody fragments, we generated Fab protein from some of the clones. Phage constructs from binding clones were transformed into E. Coli strain 27C7 that does not have amber stop suppressors, and the bacteria were grown to produce Fab protein. FIG. 32 summarizes the characterization of these clones. Fab protein was successfully generated from clones V2, V5 and V8.

EXAMPLE 7

Fab and F(ab')$_2$ Libraries with H1/H2/H3 Diversity

Libraries were generated as described above. Template construct was pV0116b for Fab or pV0116g for F(ab')$_2$. These vectors encode light chain variable domains that change the 4D5 residues at position 30 and 66 to reflect human consensus sequence (N30S; R66S), both of which had phoA promoter and stII signal sequences for both light chain and heavy chain. To make Fab H1/H2/H3 libraries, each mutagenesis reaction used oligonucleotides that coded for H1, H2 and H3 diversity. To ensure the incorporation of all three CDRs in the randomization scheme, a stop codon (TAA) was incorporated in each CDR that was intended to be diversified. Only clones that incorporated all three CDR oligonucleotides would have positive display since the stop codons would have been replaced. Oligonucleotides of different diversity were first combined to use as a source to diversify each CDR.

For this experiment, two H1 oligonucleotides, F151 (GCA GCT TCT GGC TTC ACC ATT AVT RRT WMY KMT ATA CAC TGG GTG CGT CAG; SEQ ID NO: 16) and F152 (GCA GCT TCT GGC TTC ACC ATT AVT RRT WMY KGG ATA CAC TGG GTG CGT CAG; SEQ ID NO: 14) (See also FIG. 13) were pooled, and for H2, oligonucleotides F153 (AAG GGC CTG GAA TGG GTT GST DGG ATT WMT CCT DMT RRC GGT DMT ACT DAC TAT GCC GAT AGC GTC AAG GGC; SEQ ID NO: 18) and F154 (AAG GGC CTG GAA TGG GTT GST DHT ATT WMT CCT DMT RRC GGT DMT ACT DAC TAT GCC GAT AGC GTC AAG GGC; SEQ ID NO: 19) (See also FIG. 13) were pooled.

For H3, a DVK pool of oligonucleotides (F165, F166) and NVT pool (F134, F136, F137, F138, F142, F155, F156, F157, F158, F160, F160g) were used. FIG. 4 shows H3 positions that were subjected to diversification. Two Fab libraries were generated: one with DVK H3 pool and one with NVT H3 pool. The two libraries were amplified in E. Coli before being combined for sorting on the targets.

Mutagenized DNA was used to transform E. Coli strain SS320 by electroporation and size of the libraries were in the range of 109. Transformed bacterial cells were grown up overnight in the presence of helper phage KO7 to produce displaying phage that could still infect other bacterial cells as described in Example 4.

Sorting on Mouse Vascular Endothelial Cell Growth Factor (mVEGF) and Human IgG1-Fc (hFc)

DVK and NVT libraries were pooled for sorting on the targets. Sorting was performed as with other libraries as described above. The combined library was sorted first on target once, next sorted with anti-gD antibody which could get rid of the non-displaying clones, and next with two sorts on targets (S3, S4). About 96 clones from S3, S4 were screened. Positive clones were clones that had above background binding to the targets (binders) and not to other non-relevant proteins (i.e., specific binders). For mVEGF as target, S4 provided the highest hit rate for positive specific binders. For human Fc, S3 and S4 provided high rate of specific binders.

| | mVEGF | | hFc | |
|---|---|---|---|---|
| Library | Total binders | Specific binders | Total binders | Specific binders |
| Fab S3 | 36% | 1-2% | 88% | 83% |
| Fab S4 | 91% | 72% | 99% | 90% |
| F(ab')$_2$ S3 | 42% | 3-5% | ND | ND |
| F(ab')$_2$ S4 | 73% | 72% | ND | ND |

ND: Not determined

The DNA sequences of the binders and the binding affinity of the unique binders were analyzed. Examples of sequences and binding affinity of binders are shown in FIG. 33. For specific hFc binders, many distinct Fab clones, some of which binding at 40 nM, 2 uM and >5 uM individually were obtained. From the F(ab')$_2$ library, clones with affinities at 41, 47 and 110 nM were obtained. Additional sequences of VEGF binders are shown in FIG. 35.

EXAMPLE 8

Solution Binding Competition ELISA

To determine a binding affinity for selected anti-Her2 F(ab) and F(ab')2 phage, competition ELISAs were performed as described below. The solution binding competition assay had been previously shown to correlate with Fab protein affinity Kd as shown in FIG. 46. The solution binding assay was used as an efficient method for identifying the affinity of clones for a target antigen from the library.

First, the phage were propagated and purified. Ten uls of XL-1 bacteria infected with one of the clones for 30 minutes at 37° C. was plated on a carbenicillin plate. A colony was picked and grown in 2 mls (2YT and 50 ug/ml carbenicillin) at 37° C. for 3-4 hours. Helper phage, KO7 or VCS (VCS is a variant of K07) was added to the culture at a final concentration of $10^{10}$ pfu/ml for another 1 hour at 37° C. Twenty mls of media (2YT/CRAP 50:50 with 50 ug/mil carbenicillin was added to the culture for growth overnight at 37° C. The phage was purified as described previously.

Second, the concentration of purified phage that would be optimal for use in the following competition ELISA assay was determined (i.e., approximately 90% of maximal binding capacity on the coated plate). 96-well Nunc Maxisorp plates were coated with Her-2 extracellular domain (2 ug/ml in PBS) at 4° C. overnight or at room temperature for 2 hours. The wells were blocked by adding 65 ul 1% BSA for 30 minutes followed by 40 ul 1% Tween20 for another 30 minutes. Next, the wells were washed with PBS-0.05% Tween20.5 times. Various dilutions of F(ab) or F(ab')$_2$ phage down to 0.1 O.D./ml in ELISA buffer (PBS-0.1% BSA and 0.05% Tween20) were added to the wells for 15 minutes at room temperature. The wells were then washed with PBS-0.05% Tween20 at least three times. 75 ul of HRP-conjugated anti-M13 antibody (Amersham, 1/5000 dilution with ELISA buffer) per well was added and incubated at room temperature for 30 minutes. The wells were washed again with PBS-0.05% Tween20 at least five times. Next, 100 ul/well of a 1:1 ratio of 3,3',5,5'-tetramethylbenzidine (TMB) Peroxidase substrate and Peroxidase Solution B ($H_2O_2$) ((Kirkegaard-Perry Laboratories (Gaithersburg, Md.)) was added to the well and incubated for 5 minutes at room temperature. The reaction was stopped by adding 100 ul 1M Phosphoric Acid ($H_3PO_4$) ((Kirkegaard-Perry Laboratories (Gaithersburg, Md.)) to each well. The optical density of the color in each well was determined using a standard ELISA plate reader at 450 nm. The dilutions of phage were plotted against the O.D. readings.

Third, a competition ELISA was performed. 96-well Nunc Maxisorp plates were coated with human Her-2 ECD (2 ug/ml in PBS) at 4° C. overnight or at room temperature for 2 hours. The wells were blocked by adding 65 ul 1% BSA for 30 minutes followed by 40 ul 1% Tween20 for another 30 minutes. The wells were washed with PBS-0.05% Tween20 5 times. Based on the binding assay above, 50 ul of the dilution of phage that resulted in about 90% of maximum binding to the coated plate was incubated with 50 ul of various concentrations of human Her-2ECD (0.1 to 500 nM) in ELISA buffer solution for 1 hour at room temperature in a well. The unbound phage was assayed by transferring 75 ul of the well mixture to second 96-well plate pre-coated with human Her-2ECD and incubating at room temperature for 15 minutes. The wells of the second plate were washed with PBS-0.5% Tween20 at least three times. 75 ul of HRP-conjugated anti-M13 antibody (1/5000 dilution with ELISA buffer) per well was added and incubated at room temperature for 30 minutes. The wells were washed again with PBS-0.05% Tween20 at least five times. Next, 100 ul/well of a 1:1 ratio of 3,3',5,5'-tetramethylbenzidine (TMB) Peroxidase substrate and Peroxidase Solution B (H202) ((Kirkegaard-Perry Laboratories (Gaithersburg, Md.)) was added to the well and incubated for 5 minutes at room temperature. The reaction was stopped by adding 100 ul 1M Phosphoric Acid ($H_3PO_4$) ((Kirkegaard-Perry Laboratories (Gaithersburg, Md.)) to each well. The optical density of the color in each well was determined using a standard ELISA plate reader at 450 nm. The concentrations of competitor were plotted against the O.D. readings. The IC50, the concentration of Her-2 ECD that inhibits 50% of the F(ab)-phage or F(ab')$_2$-phage, represents the affinity. See also FIG. 19.

EXAMPLE 9

A combination of different sorting and screening methods can be used for any of the libraries generated as described herein. Assays utilizing target bound to a solid and solution phase assays may be utilized as described below.
Selection for Affinity A combination of sorting methods and high throughput affinity screening assays has been shown effective to select binders with high affinity from a library of either monovalent (Fab) or multivalent F(ab'2) polypeptides. (FIG. 45) Different sorting methods can be used to combine with the screening assay as means to find the high affinity clones. Described below is a method of solution sorting method and a high throughput affinity screening assay.

For the first round of sorting, the usual plate-based selection/sorting is preferred because it is more efficient in capturing binding clones. (See also FIG. 44.) Add 100 ul/well library of phage 1-3 OD (270 nM) in PBS/BSA buffer on target coated Maxisorb wells at room temperature for 1 hour. Wash plate with PBS/0.05% tween20 about five times. Elute with 0.1N HCl for 20 min. at room temperature. Titer and propagate from 4 wells. The washing of the plates is low stringency in order to capture the most binders with a wide range of affinities.

For solution sorting, biotinylated target antigen can be used. (See also FIG. 45.) To biotinylate the target protein, target protein should preferably be in amine-free buffer (for e.g., no Tris, no Glycine or any other primary amine containing buffer or free amino acids), preferably at pH higher than 7.0 and protein is preferably >0.5 mg/ml concentration (eg. PBS). Buffer exchange can be done with NAP-5 (Amersham Pharmacia Biotech) column if needed. Stock NHS-Biotin reagent (Pierce Biotechnology) in PBS (100×) is preferably prepared fresh before use. Add in about 3:1 molar ratio to target protein and incubate at room temperature for 30 min. to 1 hour. Add Tris pH7.5 or ethylamine to 100 nM to quench the unreacted NHS for 30 min. Buffer exchange with NAP-5 can be used to remove the free biotin reagent. This is not necessary in most cases since there is very low amount of remaining biotin and the concentration of protein can be calculated from dilution after biotinylation. Biotinylated protein should be tested, if possible, for the ability to bind to natural binding partner, e.g. receptor and/or antibody, to make sure biotinylation did not disrupt the function.

Coat plates with 2-5 ug/mil neutravidin (Pierce Biotechnology) in PBS 100 ul/well 4° C. or room temperature for 2 hours. Block the plate with Superblock (Pierce) in PBS for 30 min., then, add Tween20 to 0.2% and block for another 30 min.

Incubate 0.5-1 OD phage with appropriate concentration of biotinylated target protein in 120-150 ul buffer containing Superblock 0.5% and 0.1% tween20 for 0.5-1 hour. Dilute 5-10× with binding buffer and apply 100 ul/well to neutravidin coated wells to allow capture of biotinylated target bound with phage for 5 min at room temperature with gentle shak ing. Wash plate with PBS/tween20 multiple times, for e.g. eight times. For determination of background binding, phage not incubated with biotinylated target antigen is also captured on neutravidin-coated plate. Another possible control is based on biotinylated target antigen mixed with phage captured in a well not coated with neutravidin. Bound phage are eluted with 0.1N HCl for 20 min, neutralized and titered and propagated to next round.

The concentration of biotinylated reagent to use depends on situation. In one instance, using 100-250 nM target concentration is equivalent to plate sorting in terms of stringency. For example, to improve affinity of a 100 nM binder, it is good to start with 20 nM as first solution sort and progress to 5 and 1 nM at the second sort. Multiple concentrations should be included. The concentration that provides for enrichment should be used with the screening assay. For the third sort, adding excess of unbiotinylated target as competitive sorting (described below) may be called for. When low concentration (e.g. <2 nM) of biotinylated target is used, 5× instead of 10× dilution before capture is preferred. Input phage may decrease to 0.1 OD in later round of sorting which will further increase the selection pressure.

Competitive sorting can be done to increase the pressure of selection. After the 30 min.-1 hour incubation of phage and biotinylated targets (described above), before dilution for capturing, 1000 fold excess of unbiotinylated target may be added and incubated for different length of time at different temperature. Longer time and higher temperatures (e.g., 37° C. vs room temperature) increase the pressure of selection. For example, to improve affinity from a 1 nM anti-VEGF binder: In the first round of solution sorting, using 1 nM biotinylated target to select. Before dilution for capturing, adding 1 uM unbiotinylated target at room temperature for 15 min. to compete off high off-rate binders. In the following rounds of solution sorting, using 0.1 nM biotinylated target to select tighter binders, and before dilution for capturing, adding 100 nM unbiotinylated target at 37° C. for 30 min. or, more stringently, 2 hours to select for the low off-rate binders.

High Throughput Affinity Screening Assay:

A schematic of this assay is shown in FIG. 47. Colonies (freshly grown) were picked and grown in 96 well plate (150 ul/well) or rack (300 ul/tube) overnight at 37° C. in 2YT/CRAP (1:1) with 50 ug/ml carbenicillin and 1 n/ml K07. After growth, the colonies were spun down to obtain the phage supernatant.

The phage supernatant was diluted 1:6-10 if grown from plate or 1:3-5 if grown from rack in ELISA binding buffer (PBS, 0.5% BSA, 0.05% Tween20) with or without target antigen in 150 ul total volume and incubated for 1 hour at room temperature. Final concentration of target in this binding experiment depends on expected/desired the affinity. For screening for sub-nM affinity binders, 10-25 nM were used. To screen for 1-100 nM binders, a 100-150 nM target concentration is preferred.

Plates were coated with 5 ug/ml of target antigen overnight or 2 hours at room temperature and blocked as described above. About 70-100 ul of phage was transferred with or without target antigen to the coated plate, transferring sample (with or without target antigen) into side by side wells simultaneously. The plates were shaken gently for 10-15 minutes to allow the capture of unbound phage to plate. The plates were washed quickly six times with washing buffer. HRP-conjugated anti-M13 antibody in binding buffer (1:5000) was added to the plates and incubated for 30 min., the plates were washed 6 times, and the substrate $TMB/H_2O_2$ was added for 5-10 min. and absorbance was measured at 450 nM.

The % inhibition of binding was calculated by calculating the ratio of OD of samples plus target over samples minus target. The lower the %, the higher the potential affinity of the clones. The graph shows the data from screening about 40 clones. The results show that a great variety of affinities ranging from high affinity (low ratio) to low affinity (high ratio) were present in the 40 clones.

All publications (including patents and patent applications) cited herein are hereby incorporated in their entirety by reference.

---

We claim:

1. A library comprising a plurality of distinct polypeptides each comprising a heavy chain variable domain and a light chain variable domain, wherein each heavy chain variable domain comprises a variant CDRH3 region that comprises an amino acid sequence:

$(X_1)_n$-$X_2$-$X_3$-$X_4$-$X_5$-$X_6$ wherein $X_1$ is any naturally occurring amino acid encoded by a codon set of NNK, NNS, DVK, NVT, XYZ or is tryptophan or glycine or mixtures thereof, and n=4 to 14;

$X_2$ is any naturally occurring amino acid encoded by a codon set of KSG, DVK, DSG, NVT, KSG, NNS, XYZ, NNK or is tyrosine, phenylalanine, serine, alanine, glycine, leucine, or tryptophan;

$X_3$ is missing when $X_2$ is phenylalanine or leucine, or if present, is alanine, valine, aspartic acid or glycine;

$X_4$ is missing when $X_2$ is phenylalanine or leucine, or if present, is methionine;

$X_5$ is aspartic acid, alanine, valine, or glycine; and $X_6$ is tyrosine or valine; and a variant CDRH1 and a variant CDRH2, wherein each of the variant CDRH1 and the variant CDRH2 has a variant amino acid at all solvent accessible and highly diverse amino acid positions, wherein CDRH1 comprises a variant amino acid at amino acid positions 28, 30, 31, 32 and 33; and CDRH2 comprises a variant amino acid at amino acid positions 50, 52, 53, 54, 56 and 58, the amino acid position numbering corresponding to the Kabat numbering system; and wherein each variant amino acid is encoded by a nonrandom codon set, and wherein at least 70% of the amino acids encoded by the nonrandom codon set are target amino acids for each of those positions in known antibody variable domains and 30% or less of the amino acids encoded by the nonrandom codon set are nontarget amino acids.

2. The library of claim 1, wherein in the variant CDRH3, $X_1$ corresponds to amino acid 95 and n=6, $X_2$ corresponds to amino acid 100a, $X_3$ corresponds to amino acid 100b, and $X_6$ corresponds to amino acid 102 in CDRH3 of antibody 4D5.

3. The library of claim 2, wherein $X_3$ is alanine, $X_4$ is methionine, $X_5$ is aspartic acid and $X_6$ is tyrosine.

4. The library of claim 1, wherein $X_2$ is phenylalanine or leucine, $X_3$ and $X_4$ are missing, $X_5$ is aspartic acid and $X_6$ is tyrosine.

5. The library according to claim 1, wherein 1) in CDRH1,
  a) the variant amino acid at position 28 is encoded by codon set WCC, the combination of codon sets AVT and WCC, or is threonine;
  b) the variant amino acid at position 30 is encoded by codon set RVM or AVT;
  c) the variant amino acid at position 31 is encoded by codon set RVM, RVT, or RRT;
  d) the variant amino acid at position 32 is encoded by codon set WMY; and
  e) the variant amino acid at position 33 is encoded by codon set KVK, RNT, DMT, KMT, or KGG, or the combination of codon sets KMT and KGG; and wherein 2) in CDRH2,
  a) the variant amino acid at position 50 is encoded by codon set KDK, or DBG, or the combination of codon sets DGG and DHT;
  b) the variant amino acid at position 52 is encoded by codon set DMT, or the combination of codon sets DHT and DMT;
  c) the variant amino acid at position 53 is encoded by codon set NMT or DMT;
  d) the variant amino acid at position 54 is encoded by codon set RRC, the combination of codon sets RRC and DMK, the combination of codon sets RRC and DMT, or the combination of codon sets RRC, DMK, and DMT;
  e) the variant amino acid at position 56 is encoded by codon set DMK or DMT; and
  f) the variant amino acid at position 58 is encoded by codon set DMT or DAC.

6. The library according to claim 5, wherein in the variant CDRH3, $X_1$ corresponds to amino acid position 95 and n=6, $X_2$ corresponds to amino acid position 100a, $X_3$ corresponds to amino acid position 100b, and $X_6$ corresponds to amino acid position 102 in CDRH3 of antibody 4D5.

7. The library of claim 1, wherein the light chain variable domain comprises a CDRL1, CDRL2, and CDRL3, wherein at least one CDRL1, CDRL2 or CDRL3 comprises a variant amino acid in at least one solvent accessible and highly diverse amino acid position, wherein the variant amino acid is encoded by a non-random codon set, and wherein at least 70% of the amino acids encoded by the nonrandom codon set are target amino acids for that position in known antibody variable domains.

8. The library of claim 7, wherein
CDRL1 comprises a variant amino acid in one or more amino acid positions 28, 29, 30, 31 and 32;
CDRL2 comprises a variant amino acid in one or more amino acid positions 50 and 53; and
CDRL3 comprises a variant amino acid in one or more amino acid positions 91, 92, 93, 94 and 96.

9. The library of claim 7, wherein each solvent accessible and highly diverse amino acid position in each of CDRL1, CDRL2, and CDRL3 has a variant amino acid, wherein
1) in CDRL1,
a) the variant amino acid at position 28 is encoded by codon set RDT;
b) the variant amino acid at position 29 is encoded by codon set RKT or RTT;
c) the variant amino acid at position 30 is encoded by codon set RVW;
d) the variant amino acid at position 31 is encoded by codon set RVW or ANW; and
e) the variant amino acid at position 32 is encoded by codon set THT, or the combination of codon sets DHT and THT;
2) in CDRL2,
a) the variant amino acid at position 50 is encoded by codon set KBG; and
b) the variant amino acid at position 53 is encoded by codon set AVC;
3) in CDRL3,
a) the variant amino acid at position 91 is encoded by codon set KMT or TMT, or a combination of TMT and SRT;
b) the variant amino acid at position 92 is encoded by codon set DMC, or the combination of codon sets DHT and DMC;
c) the variant amino acid at position 93 is encoded by codon RVT;
d) the variant amino acid at position 94 is encoded by codon set NHT or WHT; and
e) the variant amino acid at position 96 is encoded by codon set HTT, TDK, the combination of codon sets YKG and TWT, the combination of YHT and at least one of HTT, YKG, and TWT, or the combination HWT and at least one of HTT, YKG, and TWT.

10. The library according to claim 9, wherein in the variant CDRH3 $X_1$ corresponds to amino acid position 95 and n=$X_2$ corresponds to amino acid position 100a; $X_3$ corresponds to amino acid position 100b; and $X_6$ corresponds to amino acid position 102 in CDRH3 of antibody 4D5.

11. The library according to claim 1, wherein each polypeptide further comprises a dimerization domain linked to C-terminal region of the heavy chain variable domain.

12. The library according to claim 11, wherein the dimerization domain comprises a leucine zipper domain or a sequence comprising at least one cysteine residue.

13. The library according to claim 12, wherein the dimerization domain comprises a hinge region from an antibody or a leucine zipper.

14. The library according to claim 11, wherein the dimerization domain is a single cysteine.

15. The library of claim 1, wherein in each polypeptide the heavy chain variable domain is fused to at least a portion of a viral coat protein.

16. The library of claim 15, wherein the viral coat protein is selected from the group consisting of protein pIII, major coat protein pVIII, Soc, Hoc, gpD, and pv1.

17. The library of claim 15, further comprising a dimerization domain between the heavy chain variable domain and the viral coat protein.

18. The library of claim 15, wherein each polypeptide further comprises a peptide tag fused to the light chain variable domain.

19. The library of claim 18, wherein the peptide tag is selected from the group consisting of gD, c-myc, poly-his, fluorescence protein, and B-galactosidase.

20. The library of claim 1, wherein in each polypeptide the heavy chain variable domain comprises FR1, FR2, FR3 or FR4 from a single antibody template.

21. The library of claim 20, wherein each of the FR1, FR2, FR3, and FR4 is from antibody 4D5 (SEQ ID NO: 2).

22. The library of claim 21, wherein heavy chain FR residues at one, two, three or all amino acid positions 49, 93, 94 or 97 of the heavy chain of antibody 4D5 have been altered.

23. The library of claim 22, wherein heavy chain FR at position 49 is alanine or glycine, at position 93 is alanine or serine, and position 94 is arginine or lysine or threonin.

24. A library comprising a plurality of fusion polypeptides, wherein each fusion polypeptide comprises a heavy chain variable domain fused to at least a portion of a viral coat protein and a light chain variable domain, wherein each heavy chain variable domain comprises:
a variant CDRH3 region that comprises an amino acid sequence:
$(X_1)_n$-$X_2$-$X_3$-$X_4$-$X_5$-$X_6$
wherein $X_1$ is any naturally occurring amino acid encoded by a codon set of NNK, NNS, DVK, NVT XYZ or is tryptophan or glycine or mixtures thereof, and n=4 to 14;
$X_2$ is any naturally occurring amino acid encoded by a codon set of KSG, DVK, DSG, NVT, KSG, NNS, XYZ, NNK or is tyrosine, phenylalanine, serine, alanine, glycine, leucine, or tryptophan;
$X_3$ is missing when $X_2$ is phenylalanine or leucine, or if present, is alanine, valine, aspartic acid or glycine;
$X_4$ is missing when $X_2$ is phenylalanine or leucine, or if present, is methionine;
$X_5$ is aspartic acid, alanine, valine, or glycine; and
$X_6$ is tyrosine or valine; and
a variant CDRH1 and a variant CDRH2, wherein each of the variant CDRH1 and the variant CDRH2 has a variant amino acid at all solvent accessible and highly diverse amino acid positions, wherein CDRH1 comprises a variant amino acid at amino acid positions 28, 30, 31, 32 and 33; and CDRH2 comprises a variant amino acid at amino acid positions 50, 52, 53, 54, 56 and 58, the amino acid position numbering corresponding to the Kabat numbering system; and
wherein each variant amino acid is encoded by a nonrandom codon set, and wherein at least 70% of the amino acids encoded by the nonrandom codon set are target amino acids for that position in known antibody variable domains and 30% or less of the amino acids encoded by the nonrandom codon set are nontarget amino acids.

25. The library of claim 2, wherein position 95 can have a variant amino acid encoded by codon set DVK, NVT, NNS, XYZ, NNK or is tryptophan; position 96 can be encoded by DVK, NVT, NNS, XYZ, or is glycine or tryptophan; position 97 can be encoded by DVK, NVT, NNS, XYZ, or is tryptophan; position 98 can be encoded by DVK, NVT, NNS, XYZ, or is tryptophan; position 99 can be encoded by DVK, NVT, NNS, or XYZ; position 100 can be encoded by DVK, NVT, NNS, XYZ, or is tryptophan; position 100a can be encoded by DVK, DSG, KSG, NVT, NNS, XYZ, or can be tyrosine, glycine, serine, alanine, tryptophan, phenylalanine, or leucine; position 100b is alanine, glycine, valine, or aspartic acid; Position 100c is methionine; position 101 is aspartic acid, alanine, valine, or glycine; and position 102 is tyrosine, or valine.

26. The library of claim 1, wherein each polypeptide comprises a variant CDRH3 that comprises the C terminal amino acid sequence AMDY or FDY.

27. The library of claim 1, wherein $X_1$ of the variant CDRH3 is 6 to 8 amino acids.

28. The library of claim 1, wherein the amino acids in each position of $X_1$ are encoded by a codon set of NNS, NNK or XYZ.

29. The library of claim 1, wherein the variant amino acid at position 28 is selected from the group consisting of threonine, serine, and asparagine.

30. The library of claim 29, wherein the variant amino acid at position 30 is selected from the group consisting of serine, threonine, asparagine, arginine, aspartic acid, glycine, alanine, and glutamic acid.

31. The library of claim 30, wherein the variant amino acid at position 31 is selected from the group consisting of serine, asparagine, aspartic acid, glycine, threonine, alanine, arginine, and glutamic acid.

32. The library of claim 31, wherein the variant amino acid at amino acid position 32 is selected from the group consisting of tyrosine, serine, asparagine and threonine.

33. The library of claim 32, wherein the variant amino acid at position 33 is selected from the group consisting of alanine, tyrosine, tryptophan, glycine, serine, aspartic acid, cysteine, glutamine acid, threonine, asparagine, valine and isoleucine.

34. The library of claim 1, wherein the variant amino acid at position 50 is selected from the group consisting of tyrosine, tryptophan, valine, glycine, glutamic acid, leucine, cysteine, aspartic acid, phenylalanine, arginine, alanine, serine, methionine, threonine, isoleucine and asparagine.

35. The library of claim 34, wherein the variant amino acid at position 52 is selected from the group consisting of serine, tyrosine, asparagine, isoleucine, aspartic acid, threonine, alanine, phenylalanine and valine.

36. The library of claim 35, wherein the variant amino acid at position 53 is selected from the group consisting of serine, aspartic acid, tyrosine, histidine, asparagine, threonine, alanine and proline.

37. The library of claim 36, wherein the variant amino acid at position 54 is selected from the group consisting of serine, aspartic acid, lysine, threonine, alanine, glutamine acid, tyrosine, glycine and asparagine.

38. The library of claim 37, wherein the variant amino acid at position 56 is selected from the group consisting of serine, threonine, asparagine, aspartic acid, tyrosine, glutamic acid and alanine.

39. The library of claim 38, wherein the variant amino acid at position 58 is selected from the group consisting of tyrosine, asparagine, aspartic acid, serine, threonine and alanine.

40. A method of selecting a polypeptide that binds to a target antigen from the library of claim 1 comprising:
　a) contacting the library of claim 1 with the target antigen to form binding complexes;
　b) separating the binding complexes from nonbinding polypeptides, and eluting a population of polypeptides from the binding complexes;
　c) incubating the population of eluted polypeptides in a solution with decreasing amounts of the target antigen in a concentration from about 0.1 nM to 1000 nM; and
　d) selecting the polypeptide from the population of eluted polypeptides that can bind to the lowest concentration of the target antigen and that has an affinity of about 0.1 nM to 200 nM.

41. The method according to claim 40, wherein the target antigen is VEGF, IGF-1, or Her-2.

42. The method according to claim 40, wherein the concentration of target antigen in step c) is about 100 to 250 nM.

43. The method according to claim 40, wherein the concentration of target antigen in step c) is about 25 to 100 nM.

44. A method of selecting a polypeptide that binds to a target antigen from the library of claim 1 comprising:
　a) contacting the library of claim 1 with an immobilized target antigen under conditions suitable to form binding complexes; and
　b) separating nonbinding polypeptides from the binding complexes and eluting polypeptides from the binding complexes to obtain a first subpopulation enriched for polypeptides that bind to the target antigen.

45. The method of claim 44, further comprising:
　c) incubating the first subpopulation of polypeptides with a concentration of labelled target antigen in the range of 0.1 nM to 1000 nM under conditions suitable for binding to form a second set of binding complexes;
　d) contacting the second set of binding complexes with an immobilized agent that binds to the label on the target antigen;
　e) detecting the second set of binding complexes and eluting the polypeptides from the second set of binding complexes to form a second subpopulation of polypeptides; and
　f) optionally, repeating steps a)-e) at least twice, each repetition using the second subpopulation of polypeptides obtained from the previous round of selection and using a lower concentration of labelled target antigen than the previous round.

46. The method according to claim 45, wherein step e) further comprises adding an excess of unlabelled target antigen to the second set of binding complexes and incubating for a period of time sufficient to elute low affinity polypeptides from the second set of binding complexes.

47. A method for selecting polypeptides from the library of claim 1 comprising:
　a) contacting the library of claim 1 with a labelled target antigen in a concentration range of 0.1 nM to 1000 nM, under conditions suitable for binding to form a complexes of a polypeptide and the labelled target antigen;
　b) isolating the complexes and separating the polypeptides from the complexes to obtain a subpopulation enriched for the polypeptides that bind to the target antigen; and
　c) optionally, repeating steps a-b at least twice, each time using the subpopulation of polypeptides obtained from the previous round of selection and using a lower concentration of target antigen than the previous round.

48. The method of claim 47, wherein step a) further comprises adding an excess of unlabelled target antigen to the complexes of the polypeptide and the labeled target antigen.

49. The method of claim 47, wherein the steps a-b are repeated twice and the concentration of target antigen in step a) in the first round of selection is about 100 nM to 250 nM, and in the second round of selection is about 25 nM to 100 nM, and in the third round of selection is about 0.1 nM to 25 nM.

* * * * *

UNITED STATES PATENT AND TRADEMARK OFFICE
CERTIFICATE OF CORRECTION

PATENT NO. : 7,985,840 B2
APPLICATION NO. : 10/939309
DATED : July 26, 2011
INVENTOR(S) : Fuh et al.

It is certified that error appears in the above-identified patent and that said Letters Patent is hereby corrected as shown below:

Col. 11, line 20: "comprises a valiant" should read --comprises a variant--

Col. 33, line 47: "a promoter or enhancer" should read --a promotor or enhancer--

Col. 33, line 63: "efficiently soiled for those" should read --efficiently sorted for--

Col. 34, line 2: "either gene m or gene" should read --either gene III or gene--

Col. 55, line 8: "The Use of High Cell Concentrations Also Increases the" should read --The use of high cell concentrations also increases the--

Col. 56, line 61: "slow rate of coining off the" should read --slow rate of coming off the--

Col. 59, line 5: "93-100c), SRNLSENSYAM4" should read --93-100c), SRNLSENSYAM--

Col. 60, line 15: "residues 95-100 a of the heavy" should read --residues 95-100a of the heavy--

Col. 63, line 56: "Anti-Her2 F(ab')$_1$ vector:" should read --Anti-Her2 F(ab')$_2$ vector:--

Col. 66, line 9: "version 8 ("hunAb4D5-8")" should read --version 8 ("humAb4D5-8")--

Col. 73, line 15: "DVK aid XYZ library" should read --DVK and XYZ library--

Col. 73, line 33: "GKNRS_TYW and a stop" should read --GKNRSTYW and a stop--

Col. 81, line 65: "Solution B (H202)" should read --Solution B ($H_2O_2$)--

Col. 84, line 9: "The phage supernatant" should read --The phage supernatent--

Signed and Sealed this
Twenty-seventh Day of March, 2012

David J. Kappos
*Director of the United States Patent and Trademark Office*

CERTIFICATE OF CORRECTION (continued)
U.S. Pat. No. 7,985,840 B2

Col. 191, line 33, claim 1: "$(X_1)$-$X_2$-$X_3$-$X_4$-$X_5$-$X_6$" should read --$(X_1)_n$-$X_2$-$X_3$-$X_4$-$X_5$-$X_6$--

Col. 193, line 48, claim 10: "95 and n=$X_2$" should read --95 and n=6; $X_2$--

Col. 194, line 20, claim 23: "lysine or threonin." should read --lysine or threonine.--

Col. 196, line 44, claim 47: "to form a" should read --to form--

SEQUENCE LISTING

```
<160> NUMBER OF SEQ ID NOS: 175

<210> SEQ ID NO 1
<211> LENGTH: 109
<212> TYPE: PRT
<213> ORGANISM: Artificial Sequence
<220> FEATURE:
<223> OTHER INFORMATION: 4D5 Light chain variable domain

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Glu Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr
            100                 105

<210> SEQ ID NO 2
<211> LENGTH: 120
<212> TYPE: PRT
<213> ORGANISM: Artificial Sequence
<220> FEATURE:
<223> OTHER INFORMATION: 4D5 Heavy chain variable domain

<400> SEQUENCE: 2

Glu Val Gln Leu Val Glu Ser Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Val Trp Gly Gln
            100                 105                 110

Gly Thr Leu Val Thr Val Ser Ser
        115                 120

<210> SEQ ID NO 3
<211> LENGTH: 35
<212> TYPE: PRT
<213> ORGANISM: Artificial Sequence
<220> FEATURE:
<223> OTHER INFORMATION: GNC4 Leucine zipper

<400> SEQUENCE: 3

Gly Arg Met Lys Gln Leu Glu Asp Lys Val Glu Glu Leu Leu Ser Lys
1               5                   10                  15

Asn Tyr His Leu Glu Asn Glu Val Ala Arg Leu Lys Lys Leu Val Gly
            20                  25                  30

Glu Arg Gly
        35

<210> SEQ ID NO 4
<211> LENGTH: 5
<212> TYPE: PRT
<213> ORGANISM: Artificial Sequence
<220> FEATURE:
<223> OTHER INFORMATION: C-terminal of CDRH3

<400> SEQUENCE: 4

Tyr Ala Met Asp Tyr
1               5

<210> SEQ ID NO 5
<211> LENGTH: 7
<212> TYPE: PRT
<213> ORGANISM: Artificial Sequence
<220> FEATURE:
<223> OTHER INFORMATION: Heavy chain CDR3
```

```
<400> SEQUENCE: 5

Ser Arg Asn Ala Trp Ala Phe
1               5

<210> SEQ ID NO 6
<211> LENGTH: 11
<212> TYPE: PRT
<213> ORGANISM: Artificial Sequence
<220> FEATURE:
<223> OTHER INFORMATION: Heavy chain CDR3

<400> SEQUENCE: 6

Ser Arg Asn Leu Ser Glu Asn Ser Tyr Ala Met
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Heavy chain CDR3

<400> SEQUENCE: 7

Ser Arg Ala Gly Trp Ala Gly Trp Tyr Ala Met
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Heavy chain CDR3

<400> SEQUENCE: 8

Ser Arg Ala Ala Lys Ala Gly Trp Tyr Ala Met
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Heavy chain CDR3

<400> SEQUENCE: 9

Ser Arg Ser Asp Gly Arg Asp Ser Ala Tyr Ala Met
1               5                   10

<210> SEQ ID NO 10
<211> LENGTH: 13
<212> TYPE: PRT
<213> ORGANISM: Artificial Sequence
<220> FEATURE:
<223> OTHER INFORMATION: Randomized CDRH3
<220> FEATURE:
<221> NAME/KEY: MISC_FEATURE
<222> LOCATION: (3)..(9)
<223> OTHER INFORMATION: Xaa is Ala, Cys, Asp, Glu, Gly, Lys, Asn, Arg,
      Ser, Tyr, Trp or Thr

<400> SEQUENCE: 10

Ser Arg Xaa Xaa Xaa Xaa Xaa Xaa Xaa Ala Met Asp Tyr
1               5                   10

<210> SEQ ID NO 11
<211> LENGTH: 14
<212> TYPE: PRT
```

```
<213> ORGANISM: Artificial Sequence
<220> FEATURE:
<223> OTHER INFORMATION: Randomized CDRH3
<220> FEATURE:
<221> NAME/KEY: MISC_FEATURE
<222> LOCATION: (3)..(8)
<223> OTHER INFORMATION: Xaa is Ala, Cys, Asp, Glu, Gly, Lys, Asn, Arg,
      Ser, Tyr, Trp or Thr
<220> FEATURE:
<221> NAME/KEY: MISC_FEATURE
<222> LOCATION: (9)..(9)
<223> OTHER INFORMATION: Xaa is any naturally occurring amino acid

<400> SEQUENCE: 11

Ser Arg Xaa Xaa Xaa Xaa Xaa Xaa Xaa Tyr Ala Met Asp Tyr
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Randomized CDRH3
<220> FEATURE:
<221> NAME/KEY: MISC_FEATURE
<222> LOCATION: (3)..(7)
<223> OTHER INFORMATION: Xaa is Ala, Cys, Asp, Glu, Gly, Lys, Asn, Arg,
      Ser, Tyr, Trp or Thr
<220> FEATURE:
<221> NAME/KEY: MISC_FEATURE
<222> LOCATION: (8)..(8)
<223> OTHER INFORMATION: Xaa is any naturally occurring amino acid

<400> SEQUENCE: 12

Ser Arg Xaa Xaa Xaa Xaa Xaa Xaa Tyr Ala Met Asp Tyr
1               5                   10

<210> SEQ ID NO 13
<211> LENGTH: 13
<212> TYPE: PRT
<213> ORGANISM: Artificial Sequence
<220> FEATURE:
<223> OTHER INFORMATION: Randomized CDRH3
<220> FEATURE:
<221> NAME/KEY: MISC_FEATURE
<222> LOCATION: (3)..(8)
<223> OTHER INFORMATION: Xaa is any naturally occurring amino acid

<400> SEQUENCE: 13

Ser Arg Xaa Xaa Xaa Xaa Xaa Xaa Tyr Ala Met Asp Tyr
1               5                   10

<210> SEQ ID NO 14
<211> LENGTH: 51
<212> TYPE: DNA
<213> ORGANISM: Artificial Sequence
<220> FEATURE:
<223> OTHER INFORMATION: Oligonucleotide encoding randomized CDRH3
<220> FEATURE:
<221> NAME/KEY: misc_feature
<222> LOCATION: (23)..(23)
<223> OTHER INFORMATION: n=a, c or g
<220> FEATURE:
<221> NAME/KEY: misc_feature
<222> LOCATION: (25)..(26)
<223> OTHER INFORMATION: n=a or g
<220> FEATURE:
<221> NAME/KEY: misc_feature
<222> LOCATION: (28)..(28)
<223> OTHER INFORMATION: n=a or t
<220> FEATURE:
<221> NAME/KEY: misc_feature
<222> LOCATION: (29)..(29)
<223> OTHER INFORMATION: n=a or c
```

-continued

```
<220> FEATURE:
<221> NAME/KEY: misc_feature
<222> LOCATION: (30)..(30)
<223> OTHER INFORMATION: n=c or t
<220> FEATURE:
<221> NAME/KEY: misc_feature
<222> LOCATION: (31)..(31)
<223> OTHER INFORMATION: n=g or t
<220> FEATURE:
<221> NAME/KEY: misc_feature
<222> LOCATION: (32)..(32)
<223> OTHER INFORMATION: n=a or c

<400> SEQUENCE: 14
gcagcttctg gcttcaccat tantnntnnn nntatacact gggtgcgtca g         51

<210> SEQ ID NO 15
<211> LENGTH: 51
<212> TYPE: DNA
<213> ORGANISM: Artificial Sequence
<220> FEATURE:
<223> OTHER INFORMATION: Oligonucleotide encoding randomized CDRH3
<220> FEATURE:
<221> NAME/KEY: misc_feature
<222> LOCATION: (23)..(23)
<223> OTHER INFORMATION: n=a, c or g
<220> FEATURE:
<221> NAME/KEY: misc_feature
<222> LOCATION: (25)..(26)
<223> OTHER INFORMATION: n=a or g
<220> FEATURE:
<221> NAME/KEY: misc_feature
<222> LOCATION: (28)..(28)
<223> OTHER INFORMATION: n=a or t
<220> FEATURE:
<221> NAME/KEY: misc_feature
<222> LOCATION: (29)..(29)
<223> OTHER INFORMATION: n=a or c
<220> FEATURE:
<221> NAME/KEY: misc_feature
<222> LOCATION: (30)..(30)
<223> OTHER INFORMATION: n=c or t
<220> FEATURE:
<221> NAME/KEY: misc_feature
<222> LOCATION: (31)..(31)
<223> OTHER INFORMATION: n=g or t

<400> SEQUENCE: 15
gcagcttctg gcttcaccat tantnntnnn nggatacact gggtgcgtca g         51

<210> SEQ ID NO 16
<211> LENGTH: 51
<212> TYPE: DNA
<213> ORGANISM: Artificial Sequence
<220> FEATURE:
<223> OTHER INFORMATION: Oligonucleotide encoding randomized CDRH3
<220> FEATURE:
<221> NAME/KEY: misc_feature
<222> LOCATION: (23)..(23)
<223> OTHER INFORMATION: n=a, c or g
<220> FEATURE:
<221> NAME/KEY: misc_feature
<222> LOCATION: (25)..(25)
<223> OTHER INFORMATION: n=a or g
<220> FEATURE:
<221> NAME/KEY: misc_feature
<222> LOCATION: (26)..(26)
<223> OTHER INFORMATION: n=a, c or g
<220> FEATURE:
<221> NAME/KEY: misc_feature
<222> LOCATION: (27)..(27)
<223> OTHER INFORMATION: n=a or c
<220> FEATURE:
<221> NAME/KEY: misc_feature
<222> LOCATION: (28)..(28)
<223> OTHER INFORMATION: n=a or t
```

```
<220> FEATURE:
<221> NAME/KEY: misc_feature
<222> LOCATION: (29)..(29)
<223> OTHER INFORMATION: n=a or c
<220> FEATURE:
<221> NAME/KEY: misc_feature
<222> LOCATION: (30)..(30)
<223> OTHER INFORMATION: n=c or t
<220> FEATURE:
<221> NAME/KEY: misc_feature
<222> LOCATION: (31)..(31)
<223> OTHER INFORMATION: n=g or t
<220> FEATURE:
<221> NAME/KEY: misc_feature
<222> LOCATION: (32)..(32)
<223> OTHER INFORMATION: n=a or c

<400> SEQUENCE: 16
gcagcttctg gcttcaccat tantnnnnnn nntatacact gggtgcgtca g            51

<210> SEQ ID NO 17
<211> LENGTH: 51
<212> TYPE: DNA
<213> ORGANISM: Artificial Sequence
<220> FEATURE:
<223> OTHER INFORMATION: Oligonucleotide encoding randomized CDRH3
<220> FEATURE:
<221> NAME/KEY: misc_feature
<222> LOCATION: (23)..(23)
<223> OTHER INFORMATION: n=a, c or g
<220> FEATURE:
<221> NAME/KEY: misc_feature
<222> LOCATION: (25)..(25)
<223> OTHER INFORMATION: n=a or g
<220> FEATURE:
<221> NAME/KEY: misc_feature
<222> LOCATION: (26)..(26)
<223> OTHER INFORMATION: n=a, c or g
<220> FEATURE:
<221> NAME/KEY: misc_feature
<222> LOCATION: (27)..(27)
<223> OTHER INFORMATION: n=a or c
<220> FEATURE:
<221> NAME/KEY: misc_feature
<222> LOCATION: (28)..(28)
<223> OTHER INFORMATION: n=a or t
<220> FEATURE:
<221> NAME/KEY: misc_feature
<222> LOCATION: (29)..(29)
<223> OTHER INFORMATION: n=a or c
<220> FEATURE:
<221> NAME/KEY: misc_feature
<222> LOCATION: (30)..(30)
<223> OTHER INFORMATION: n=c or t
<220> FEATURE:
<221> NAME/KEY: misc_feature
<222> LOCATION: (31)..(31)
<223> OTHER INFORMATION: n=g or t

<400> SEQUENCE: 17
gcagcttctg gcttcaccat tantnnnnnn nggatacact gggtgcgtca g            51

<210> SEQ ID NO 18
<211> LENGTH: 72
<212> TYPE: DNA
<213> ORGANISM: Artificial Sequence
<220> FEATURE:
<223> OTHER INFORMATION: Oligonucleotide encoding randomized CDRH3
<220> FEATURE:
<221> NAME/KEY: misc_feature
<222> LOCATION: (20)..(20)
<223> OTHER INFORMATION: n=c or g
<220> FEATURE:
<221> NAME/KEY: misc_feature
<222> LOCATION: (22)..(22)
<223> OTHER INFORMATION: n=a, g or t
```

```
<220> FEATURE:
<221> NAME/KEY: misc_feature
<222> LOCATION: (28)..(28)
<223> OTHER INFORMATION: n=a or t
<220> FEATURE:
<221> NAME/KEY: misc_feature
<222> LOCATION: (29)..(29)
<223> OTHER INFORMATION: n=a or c
<220> FEATURE:
<221> NAME/KEY: misc_feature
<222> LOCATION: (34)..(34)
<223> OTHER INFORMATION: n=a, g or t
<220> FEATURE:
<221> NAME/KEY: misc_feature
<222> LOCATION: (35)..(35)
<223> OTHER INFORMATION: n=a or c
<220> FEATURE:
<221> NAME/KEY: misc_feature
<222> LOCATION: (37)..(38)
<223> OTHER INFORMATION: n=a or g
<220> FEATURE:
<221> NAME/KEY: misc_feature
<222> LOCATION: (43)..(43)
<223> OTHER INFORMATION: n=a, g or t
<220> FEATURE:
<221> NAME/KEY: misc_feature
<222> LOCATION: (44)..(44)
<223> OTHER INFORMATION: n=a or c
<220> FEATURE:
<221> NAME/KEY: misc_feature
<222> LOCATION: (49)..(49)
<223> OTHER INFORMATION: n=a, g or t

<400> SEQUENCE: 18
aagggcctgg aatgggttgn tnggattnnt cctnntnncg gcnntactna ctatgccgat    60
agcgtcaagg gc                                                        72

<210> SEQ ID NO 19
<211> LENGTH: 72
<212> TYPE: DNA
<213> ORGANISM: Artificial Sequence
<220> FEATURE:
<223> OTHER INFORMATION: Oligonucleotide encoding randomized CDRH3
<220> FEATURE:
<221> NAME/KEY: misc_feature
<222> LOCATION: (20)..(20)
<223> OTHER INFORMATION: n=c or g
<220> FEATURE:
<221> NAME/KEY: misc_feature
<222> LOCATION: (22)..(22)
<223> OTHER INFORMATION: n=a, g or t
<220> FEATURE:
<221> NAME/KEY: misc_feature
<222> LOCATION: (23)..(23)
<223> OTHER INFORMATION: n=a, c or t
<220> FEATURE:
<221> NAME/KEY: misc_feature
<222> LOCATION: (28)..(28)
<223> OTHER INFORMATION: n=a or t
<220> FEATURE:
<221> NAME/KEY: misc_feature
<222> LOCATION: (29)..(29)
<223> OTHER INFORMATION: n=a or c
<220> FEATURE:
<221> NAME/KEY: misc_feature
<222> LOCATION: (34)..(34)
<223> OTHER INFORMATION: n=a, g or t
<220> FEATURE:
<221> NAME/KEY: misc_feature
<222> LOCATION: (35)..(35)
<223> OTHER INFORMATION: n=a or c
<220> FEATURE:
<221> NAME/KEY: misc_feature
<222> LOCATION: (37)..(38)
<223> OTHER INFORMATION: n=a or g
<220> FEATURE:
<221> NAME/KEY: misc_feature
```

<222> LOCATION: (43)..(43)
<223> OTHER INFORMATION: n=a, g or t
<220> FEATURE:
<221> NAME/KEY: misc_feature
<222> LOCATION: (44)..(44)
<223> OTHER INFORMATION: n=a or c
<220> FEATURE:
<221> NAME/KEY: misc_feature
<222> LOCATION: (49)..(49)
<223> OTHER INFORMATION: n=a, g or t

<400> SEQUENCE: 19
aagggcctgg aatgggttgn tnntattnnt cctnntnncg gcnntactna ctatgccgat    60
agcgtcaagg gc                                                        72

<210> SEQ ID NO 20
<211> LENGTH: 72
<212> TYPE: DNA
<213> ORGANISM: Artificial Sequence
<220> FEATURE:
<223> OTHER INFORMATION: Oligonucleotide encoding randomized CDRH3
<220> FEATURE:
<221> NAME/KEY: misc_feature
<222> LOCATION: (20)..(20)
<223> OTHER INFORMATION: n=c or g
<220> FEATURE:
<221> NAME/KEY: misc_feature
<222> LOCATION: (22)..(22)
<223> OTHER INFORMATION: n=a, g or t
<220> FEATURE:
<221> NAME/KEY: misc_feature
<222> LOCATION: (28)..(28)
<223> OTHER INFORMATION: n=a, g or t
<220> FEATURE:
<221> NAME/KEY: misc_feature
<222> LOCATION: (29)..(29)
<223> OTHER INFORMATION: n=a or c
<220> FEATURE:
<221> NAME/KEY: misc_feature
<222> LOCATION: (34)..(34)
<223> OTHER INFORMATION: n=a, c, g or t
<220> FEATURE:
<221> NAME/KEY: misc_feature
<222> LOCATION: (35)..(35)
<223> OTHER INFORMATION: n=a or c
<220> FEATURE:
<221> NAME/KEY: misc_feature
<222> LOCATION: (37)..(38)
<223> OTHER INFORMATION: n=a or g
<220> FEATURE:
<221> NAME/KEY: misc_feature
<222> LOCATION: (43)..(43)
<223> OTHER INFORMATION: n=a, g or t
<220> FEATURE:
<221> NAME/KEY: misc_feature
<222> LOCATION: (44)..(44)
<223> OTHER INFORMATION: n=a or c
<220> FEATURE:
<221> NAME/KEY: misc_feature
<222> LOCATION: (49)..(49)
<223> OTHER INFORMATION: n=a, g or t

<400> SEQUENCE: 20
agggccctgg aatgggttgn tnggattnnt cctnntnncg gcnntactna ctatgccgat    60
agcgtcaagg gc                                                        72

<210> SEQ ID NO 21
<211> LENGTH: 72
<212> TYPE: DNA
<213> ORGANISM: Artificial Sequence
<220> FEATURE:
<223> OTHER INFORMATION: Oligonucleotide encoding randomized CDRH3
<220> FEATURE:
<221> NAME/KEY: misc_feature

```
<222> LOCATION: (20)..(20)
<223> OTHER INFORMATION: n=c or g
<220> FEATURE:
<221> NAME/KEY: misc_feature
<222> LOCATION: (22)..(22)
<223> OTHER INFORMATION: n=a, g or t
<220> FEATURE:
<221> NAME/KEY: misc_feature
<222> LOCATION: (23)..(23)
<223> OTHER INFORMATION: n=a, c or t
<220> FEATURE:
<221> NAME/KEY: misc_feature
<222> LOCATION: (28)..(28)
<223> OTHER INFORMATION: n=a, g or t
<220> FEATURE:
<221> NAME/KEY: misc_feature
<222> LOCATION: (29)..(29)
<223> OTHER INFORMATION: n=a or c
<220> FEATURE:
<221> NAME/KEY: misc_feature
<222> LOCATION: (34)..(34)
<223> OTHER INFORMATION: n=a, c, g or t
<220> FEATURE:
<221> NAME/KEY: misc_feature
<222> LOCATION: (35)..(35)
<223> OTHER INFORMATION: n=a or c
<220> FEATURE:
<221> NAME/KEY: misc_feature
<222> LOCATION: (37)..(38)
<223> OTHER INFORMATION: n=a or g
<220> FEATURE:
<221> NAME/KEY: misc_feature
<222> LOCATION: (43)..(43)
<223> OTHER INFORMATION: n=a, g or t
<220> FEATURE:
<221> NAME/KEY: misc_feature
<222> LOCATION: (44)..(44)
<223> OTHER INFORMATION: n=a or c
<220> FEATURE:
<221> NAME/KEY: misc_feature
<222> LOCATION: (49)..(49)
<223> OTHER INFORMATION: n=a, g or t

<400> SEQUENCE: 21
aagggcctgg aatgggttgn tnntattnnt cctnntnncg gcnntactna ctatgccgat      60
agcgtcaagg gc                                                          72

<210> SEQ ID NO 22
<211> LENGTH: 33
<212> TYPE: DNA
<213> ORGANISM: Artificial Sequence
<220> FEATURE:
<223> OTHER INFORMATION: Oligonucleotide encoding randomized CDRH3
<220> FEATURE:
<221> NAME/KEY: misc_feature
<222> LOCATION: (3)..(3)
<223> OTHER INFORMATION: n=a or g

<400> SEQUENCE: 22
cgnttcacta taagccgtga cacatccaaa aac                                   33

<210> SEQ ID NO 23
<211> LENGTH: 1441
<212> TYPE: DNA
<213> ORGANISM: Artificial Sequence
<220> FEATURE:
<223> OTHER INFORMATION: Single chain Fv

<400> SEQUENCE: 23
gaaatgagct gttgacaatt aatcatcggc tcgtataatg tgtggaattg tgagcggata      60
acaatttcac acaggaaaca gccagtccgt ttaggtgttt tcacgagcac ttcaccaaca     120
aggaccatag attatgaaaa taaaaacagg tgcacgcatc ctcgcattat ccgcattaac     180
```

```
gacgatgatg ttttccgcct cggcttatgc atccgatatc cagatgaccc agtccccgag    240
ctccctgtcc gcctctgtgg gcgatagggt caccatcacc tgccgtgcca gtcaggatgt    300
gaatactgct gtagcctggt atcaacagaa accaggaaaa gctccgaagc ttctgattta    360
ctcggcatcc ttcctctact ctggagtccc ttctcgcttc tctggtagcc gttccgggac    420
ggatttcact ctgaccatca gcagtctgca gccggaagac ttcgcaactt attactgtca    480
gcaacattat actactcctc ccacgttcgg acagggtacc aaggtggaga tcaaatcgga    540
tatgccgatg gctgatccga accgtttccg cggtaagaac ctggttttc attctgagat    600 ctccgaggtt cagctggtgg agtctggcgg tggcctggtg cagccagggg gctcactccg    660
tttgtcctgt gcagcttctg gcttcaacat taaagacacc tatatacact gggtgcgtca    720
ggcccccggt aagggcctgg aatgggttgc aaggatttat cctacgaatg gttatactag    780
atatgccgat agcgtcaagg gccgtttcac tataagcgca gacacatcca aaaacagc     840 ctacctacaa atgaacagct aagagctga ggacactgcc gtctattatt gtagccgctg    900
gggaggggac ggcttctatg ctatggacta ctggggtcaa ggaacactag tcaccgtctc    960
cagcagtggc ggtggctctg gttccggtga ttttgattat gaaaagatgg caaacgctaa   1020 taaggggct atgaccgaaa atgccgatga aaacgcgcta cagtctgacg ctaaaggcaa   1080
acttgattct gtcgctactg attcggtgc tgctatcgat ggtttcattg gtgacgtttc   1140
cggccttgct aatggtaatg tgctactgg tgattttgct ggctctaatt cccaaatggc   1200
tcaagtcggt gacggtgata attcaccttt aatgaataat ttccgtcaat atttaccttc   1260
cctccctcaa tcggttgaat gtcgccttt tgtctttagc gctggtaaac catatgaatt   1320
ttctattgat tgtgacaaaa taaacttatt ccgtggtgtc tttgcgtttc ttttatatgt   1380
tgccaccttt atgtatgtat tttctacgtt tgctaacata ctgcgtaata aggagtctta   1440
a                                                                    1441
```

<210> SEQ ID NO 24
<211> LENGTH: 1588
<212> TYPE: DNA
<213> ORGANISM: Artificial Sequence
<220> FEATURE:
<223> OTHER INFORMATION: Single chain Fv with zipper domain

<400> SEQUENCE: 24

```
gaaatgagct gttgacaatt aatcatcggc tcgtataatg tgtggaattg tgagcggata    60
acaatttcac acaggaaaca gccagtccgt ttaggtgttt tcacgagcac ttcaccaaca   120
aggaccatag attatgaaaa taaaacagg tgcacgcatc ctcgcattat ccgcattaac   180
gacgatgatg ttttccgcct cggcttatgc atccgatatc cagatgaccc agtccccgag   240
ctccctgtcc gcctctgtgg gcgatagggt caccatcacc tgccgtgcca gtcaggatgt   300
gaatactgct gtagcctggt atcaacagaa accaggaaaa gctccgaagc ttctgattta   360
ctcggcatcc ttcctctact ctggagtccc ttctcgcttc tctggtagcc gttccgggac   420
ggatttcact ctgaccatca gcagtctgca gccggaagac ttcgcaactt attactgtca   480
gcaacattat actactcctc ccacgttcgg acagggtacc aaggtggaga tcaaatcgga   540
tatgccgatg gctgatccga accgtttccg cggtaagaac ctggttttc attctgagat   600 ctccgaggtt cagctggtgg agtctggcgg tggcctggtg cagccagggg gctcactccg   660
tttgtcctgt gcagcttctg gcttcaacat taaagacacc tatatacact gggtgcgtca   720
ggcccccggt aagggcctgg aatgggttgc aaggatttat cctacgaatg gttatactag   780
```

| | |
|---|---|
| atatgccgat agcgtcaagg gccgtttcac tataagcgca gacacatcca aaaacacagc | 840 |
| ctacctacaa atgaacagct taagagctga ggacactgcc gtctattatt gtagccgctg | 900 |
| gggaggggac ggcttctatg ctatggacta ctggggtcaa ggaacactag tcaccgtctc | 960 |
| cagcacatgc ccgccgtgcc cagcaccaga actgctgggc ggccgcatga acagctaga | 1020 |
| ggacaaggtc gaagagctac tctccaagaa ctaccaccta gagaatgaag tggcaagact | 1080 |
| caaaaaactt gtcggggagc gcggaaagct tagtggcggt ggctctggtt ccggtgattt | 1140 |
| tgattatgaa aagatggcaa acgctaataa gggggctatg accgaaaatg ccgatgaaaa | 1200 |
| cgcgctacag tctgacgcta aaggcaaact tgattctgtc gctactgatt acggtgctgc | 1260 |
| tatcgatggt ttcattggtg acgtttccgg ccttgctaat ggtaatggtg ctactggtga | 1320 |
| ttttgctggc tctaattccc aaatggctca agtcggtgac ggtgataatt cacctttaat | 1380 |
| gaataatttc cgtcaatatt taccttccct ccctcaatcg ttgaatgtc gcccttttgt | 1440 |
| ctttagcgct ggtaaaccat atgaattttc tattgattgt gacaaaataa acttattccg | 1500 |
| tggtgtcttt gcgtttcttt tatatgttgc cacctttatg tatgtatttt ctacgtttgc | 1560 |
| taacatactg cgtaataagg agtcttaa | 1588 |

<210> SEQ ID NO 25
<211> LENGTH: 2239
<212> TYPE: DNA
<213> ORGANISM: Artificial Sequence
<220> FEATURE:
<223> OTHER INFORMATION: Fab fragment

<400> SEQUENCE: 25

| | |
|---|---|
| gaaatgagct gttgacaatt aatcatcggc tcgtataatg tgtggaattg tgagcggata | 60 |
| acaatttcac acaggaaaca gccagtccgt ttaggtgttt tcacgagcac ttcaccaaca | 120 |
| aggaccatag attatgaaaa taaaacagg tgcacgcatc ctcgcattat ccgcattaac | 180 |
| gacgatgatg tttccgcct cggcttatgc atccgatatc cagatgaccc agtccccgag | 240 |
| ctccctgtcc gcctctgtgg gcgatagggt caccatcacc tgccgtgcca gtcaggatgt | 300 |
| gaatactgct gtagcctggt atcaacagaa accaggaaaa gctccgaagc ttctgattta | 360 |
| ctcggcatcc ttcctctact ctggagtccc ttctcgcttc tctggtagcc gttccgggac | 420 |
| ggatttcact ctgaccatca gcagtctgca gccggaagac ttcgcaactt attactgtca | 480 |
| gcaacattat actactcctc ccacgttcgg acagggtacc aaggtggaga tcaaacgaac | 540 |
| tgtggctgca ccatctgtct tcatcttccc gccatctgat gagcagttga aatctggaac | 600 |
| tgcctctgtt gtgtgcctgc tgaataactt ctatcccaga gaggccaaag tacagtggaa | 660 |
| ggtggataac gccctccaat cgggtaactc ccaggagagt gtcacagagc aggacagcaa | 720 |
| ggacagcacc tacagcctca gcagcaccct gacgctgagc aaagcagact acgagaaaca | 780 |
| caaagtctac gcctgcgaag tcacccatca gggcctgagc tcgcccgtca caaagagctt | 840 |
| caacagggga gagtgtggtg ccagctccgg tatggctgat ccgaaccgtt tccgcggtaa | 900 |
| ggacctggca taactcgagg ctgatcctct acgccggacg catcgtggcc ctagtacgca | 960 |
| agttcacgta aaagggtaa ctagaggttg aggtgatttt atgaaaaaga atatcgcatt | 1020 |
| tcttcttgca tctatgttcg ttttttctat tgctacaaac gcgtacgctg agatctccga | 1080 |
| ggttcagctg gtggagtctg gcggtggcct ggtgcagcca gggggctcac tccgtttgtc | 1140 |
| ctgtgcagct tctggcttca acattaaaga cacctatata cactgggtgc gtcaggcccc | 1200 |
| gggtaagggc ctggaatggg ttgcaaggat ttatcctacg aatggttata ctagatatgc | 1260 |

-continued

```
cgatagcgtc aagggccgtt tcactataag cgcagacaca tccaaaaaca cagcctacct      1320
acaaatgaac agcttaagag ctgaggacac tgccgtctat tattgtagcc gctggggagg      1380
ggacggcttc tatgctatgg actactgggg tcaaggaacc ctggtcaccg tctcctcggc      1440
ctccaccaag ggcccatcgg tcttccccct ggcaccctcc tccaagagca cctctggggg      1500
cacagcggcc ctgggctgcc tggtcaagga ctacttcccc gaaccggtga cggtgtcgtg      1560
gaactcaggc gccctgacca gcggcgtgca caccttcccg gctgtcctac agtcctcagg      1620
actctactcc ctcagcagcg tggtgaccgt gccctccagc agcttgggca cccagaccta      1680
catctgcaac gtgaatcaca agcccagcaa caccaaggtc gacaagaaag ttgagcccaa      1740
atcttgtgac aaaactcacc tcagtggcgg tggctctggt tccggtgatt ttgattatga      1800
aaagatggca aacgctaata aggggctat gaccgaaaat gccgatgaaa acgcgctaca       1860
gtctgacgct aaaggcaaac ttgattctgt cgctactgat tacggtgctg ctatcgatgg      1920
tttcattggt gacgtttccg gccttgctaa tggtaatggt gctactggtg attttgctgg      1980
ctctaattcc caaatggctc aagtcggtga cggtgataat tcacctttaa tgaataattt      2040
ccgtcaatat ttaccttccc tccctcaatc ggttgaatgt cgcccttttg tctttagcgc      2100
tggtaaacca tatgaatttt ctattgattg tgacaaaata aacttattcc gtggtgtctt      2160
tgcgtttctt ttatatgttg ccacctttat gtatgtattt tctacgtttg ctaacatact      2220
gcgtaataag gagtcttaa                                                  2239
```

<210> SEQ ID NO 26
<211> LENGTH: 2383
<212> TYPE: DNA
<213> ORGANISM: Artificial Sequence
<220> FEATURE:
<223> OTHER INFORMATION: Fab fragment with zipper domain

<400> SEQUENCE: 26

```
gaaatgagct gttgacaatt aatcatcggc tcgtataatg tgtggaattg tgagcggata      60
acaatttcac acaggaaaca gccagtccgt ttaggtgttt tcacgagcac ttcaccaaca      120
aggaccatag attatgaaaa taaaaacagg tgcacgcatc ctcgcattat ccgcattaac      180
gacgatgatg ttttccgcct cggcttatgc atccgatatc cagatgaccc agtccccgag      240
ctccctgtcc gcctctgtgg gcgatagggt caccatcacc tgccgtgcca gtcaggatgt      300
gaatactgct gtagcctggt atcaacagaa accaggaaaa gctccgaagc ttctgattta      360
ctcggcatcc ttcctctact ctggagtccc ttctcgcttc tctggtagcc gttccgggac      420
ggatttcact ctgaccatca gcagtctgca gccggaagac ttcgcaactt attactgtca      480
gcaacattat actactcctc ccacgttcgg acagggtacc aaggtggaga tcaaacgaac      540
tgtggctgca ccatctgtct tcatcttccc gccatctgat gagcagttga aatctggaac      600
tgcctctgtt gtgtgcctgc tgaataactt ctatcccaga gaggccaaag tacagtggaa      660
ggtggataac gccctccaat cgggtaactc ccaggagagt gtcacagagc aggacagcaa      720
ggacagcacc tacagcctca gcagcaccct gacgctgagc aaagcagact acgagaaaca      780
caaagtctac gcctgcgaag tcacccatca gggcctgagc tcgcccgtca caaagagctt      840
caacagggga gagtgtggtg ccagctcgg tatggctgat ccgaaccgtt ccgcggtaa       900 ggacctggca taactcgagg ctgatcctct acgccggacg catcgtggcc ctagtacgca      960
agttcacgta aaaagggtaa ctagaggttg aggtgatttt atgaaaaaga atatcgcatt      1020
tcttcttgca tctatgttcg ttttttctat tgctacaaac gcgtacgctg agatctccga      1080
```

```
ggttcagctg gtggagtctg gcggtggcct ggtgcagcca gggggctcac tccgtttgtc    1140
ctgtgcagct tctggcttca acattaaaga cacctatata cactgggtgc gtcaggcccc    1200
gggtaagggc ctggaatggg ttgcaaggat ttatcctacg aatggttata ctagatatgc    1260
cgatagcgtc aagggccgtt tcactataag cgcagacaca tccaaaaaca gcctacct     1320 acaaatgaac agcttaagag ctgaggacac tgccgtctat tattgtagcc gctggggagg    1380
ggacggcttc tatgctatgg actactgggg tcaaggaacc ctggtcaccg tctcctcggc    1440
ctccaccaag ggcccatcgg tcttccccct ggcaccctcc tccaagagca cctctggggg    1500
cacagcggcc ctgggctgcc tggtcaagga ctacttcccc gaaccggtga cggtgtcgtg    1560
gaactcaggc gccctgacca gcggcgtgca ccttcccg gctgtcctac agtcctcagg     1620
actctactcc ctcagcagcg tggtgaccgt gccctccagc agcttgggca cccagaccta    1680
catctgcaac gtgaatcaca agcccagcaa caccaaggtc gacaagaaag ttgagcccaa    1740
atcttgtgac aaaactcaca catgcccgcc gtgcccagca ccagaactgc tgggcggccg    1800
catgaaacag ctagaggaca aggtcgaaga gctactctcc aagaactacc acctagagaa    1860
tgaagtggca agactcaaaa aacttgtcgg ggagcgcgga aagcttagtg gcggtggctc    1920
tggttccggt gattttgatt atgaaaagat ggcaaacgct aataaggggg ctatgaccga    1980
aaatgccgat gaaacgcgc tacagtctga cgctaaaggc aaacttgatt ctgtcgctac     2040
tgattacggt gctgctatcg atggtttcat tggtgacgtt ccggccttg ctaatggtaa     2100 tggtgctact ggtgattttg ctggctctaa ttcccaaatg gctcaagtcg gtgacgtga    2160 taattcacct ttaatgaata atttccgtca atatttacct tccctccctc aatcggttga    2220
atgtcgcccc tttgtcttta gcgctggtaa accatatgaa ttttctattg attgtgacaa    2280
aataaactta ttccgtggtg tctttgcgtt tcttttatat gttgccacct ttatgtatgt    2340
attttctacg tttgctaaca tactgcgtaa taaggagtct taa                      2383
```

```
<210> SEQ ID NO 27
<211> LENGTH: 12
<212> TYPE: PRT
<213> ORGANISM: Artificial Sequence
<220> FEATURE:
<223> OTHER INFORMATION: Hinge sequence from full length IgG1 antibody

<400> SEQUENCE: 27

Thr Cys Pro Pro Cys Pro Ala Pro Glu Leu Leu Gly
1               5                   10

<210> SEQ ID NO 28
<211> LENGTH: 7060
<212> TYPE: DNA
<213> ORGANISM: Artificial Sequence
<220> FEATURE:
<223> OTHER INFORMATION: Fab phagemid vector pV0350-2b

<400> SEQUENCE: 28
```

```
gaattcaact ctccatact ttggataagg aaatacagac atgaaaaatc tcattgctga     60
gttgttattt aagcttgccc aaaaagaaga agagtcgaat gaactgtgtg cgcaggtaga    120
agctttggag attatcgtca ctgcaatgct tcgcaatatg gcgcaaaatg accaacagcg    180
gttgattgat caggtagagg gggcgctgta cgaggtaaag cccgatgcca gcattcctga    240
cgacgatacg gagctgctgc gcgattacgt aaagaagtta ttgaagcatc ctcgtcagta    300
aaaagttaat cttttcaaca gctgtcataa agttgtcacg gccgagactt atagtcgctt    360
```

```
tgtttttatt ttttaatgta tttgtaacta gtacgcaagt tcacgtaaaa agggtatgta    420
gaggttgagg tgattttatg aaaaagaata tcgcatttct tcttgcatct atgttcgttt    480
tttctattgc tacaaatgcc tatgcagata tccagatgac ccagtcccg  agctccctgt    540
ccgcctctgt gggcgatagg gtcaccatca cctgccgtgc cagtcaggat gtgtccactg    600
ctgtagcctg gtatcaacag aaaccaggaa aagctccgaa gcttctgatt tactcggcat    660
ccttcctcta ctctggagtc ccttctcgct tctctggtag cggttccggg acggatttca    720
ctctgaccat cagcagtctg cagccggaag acttcgcaac ttattactgt cagcaatctt    780
atactactcc tcccacgttc ggacagggta ccaaggtgga gatcaaacga actgtggctg    840
caccatctgt cttcatcttc ccgccatctg atgagcagtt gaaatctgga actgcctctg    900
ttgtgtgcct gctgaataac ttctatccca gagaggccaa agtacagtgg aaggtggata    960
acgccctcca atcgggtaac tcccaggaga gtgtcacaga gcaggacagc aaggacagca   1020
cctacagcct cagcagcacc ctgacgctga gcaaagcaga ctacgagaaa cacaaagtct   1080
acgcctgcga agtcacccat cagggcctga gctcgcccgt cacaaagagc ttcaacaggg   1140
gagagtgtgg tgccagctcc ggtatggctg atccgaaccg tttccgcggt aaggacctgg   1200
cataactcga ggctgatcct ctacgccgga cgcatcgtgg ccctagtacg caagttcacg   1260
taaaaagggt aactagaggt tgaggtgatt ttatgaaaaa gaatatcgca tttcttcttg   1320
catctatgtt cgtttttcct attgctacaa acgcgtacgc tgaggttcag ctggtggagt   1380
ctggcggtgg cctggtgcag ccagggggct cactccgttt gtcctgtgca gcttctggct   1440
tcaacattaa agacacctat atacactggg tgcgtcaggc ccccgggtaag ggcctggaat   1500
gggttgcaag gatttatcct acgaatggtt atactagata tgccgatagc gtcaagggcc   1560
gtttcactat aagcgcagac acatccaaaa acacagccta cctacaaatg aacagcttaa   1620
gagctgagga cactgccgtc tattattgta gccgctgggg aggggacggc ttctatgcta   1680
tggactactg gggtcaagga acactagtca ccgtctcctc ggcctccacc aagggcccat   1740
cggtcttccc cctggcaccc tcctccaaga gcacctctgg gggcacagcg gccctgggct   1800
gcctggtcaa ggactacttc cccgaaccgg tgacggtgtc gtggaactca ggcgccctga   1860
ccagcggcgt gcacaccttc ccggctgtcc tacagtcctc aggactctac tccctcagca   1920
gcgtggtgac cgtgccctcc agcagcttgg gcacccagac ctacatctgc aacgtgaatc   1980
acaagcccag caacaccaag gtcgacaaga agttgagcc  caaatcttgt gacaaaactc   2040
acctcagtgg cggtggctct ggttccggtg attttgatta tgaaaagatg gcaaacgcta   2100
ataaggggc  tatgaccgaa aatgccgatg aaaacgcgct acagtctgac gctaaaggca   2160
aacttgattc tgtcgctact gattacggtg ctgctatcga tggtttcatt ggtgacgttt   2220
ccggccttgc taatggtaat ggtgctactg gtgattttgc tggctctaat tcccaaatgg   2280
ctcaagtcgg tgacggtgat aattcacctt aatgaataa  tttccgtcaa tatttacctt   2340
ccctccctca atcggttgaa tgtcgccctt ttgtctttag cgctggtaaa ccatatgaat   2400
tttctattga ttgtgacaaa ataaacttat tccgtggtgt ctttgcgttt cttttatatg   2460
ttgccacctt tatgtatgta ttttctacgt ttgctaacat actgcgtaat aaggagtctt   2520
aatcatgcca gttctttggg ctagcgccgc cctataccttg tctgcctcc  cgcgttgcg   2580
tcgcggtgca tggagccggg ccacctcgac ctgaatggaa gccggcggca cctcgctaac   2640
ggattcacca ctccaagaat tggagccaat caattcttgc ggagaactgt gaatgcgcaa   2700
accaacccct tggcagaacat atccatcgcg tccgccatct ccagcagccg cacgcggcgc   2760
```

```
atctcgggca gcgttgggtc ctggccacgg gtgcgcatga tcgtgctcct gtcgttgagg    2820
acccggctag gctggcgggg ttgccttact ggttagcaga atgaatcacc gatacgcgag    2880
cgaacgtgaa gcgactgctg ctgcaaaacg tctgcgacct gagcaacaac atgaatggtc    2940
ttcggtttcc gtgtttcgta aagtctggaa acgcggaagt cagcgccctg caccattatg    3000
ttccggatct gcatcgcagg atgctgctgg ctaccctgtg gaacacctac atctgtatta    3060
acgaagcgct ggcattgacc ctgagtgatt tttctctggt cccgccgcat ccataccgcc    3120
agttgtttac cctcacaacg ttccagtaac cgggcatgtt catcatcagt aacccgtatc    3180
gtgagcatcc tctctcgttt catcggtatc attaccccca tgaacagaaa ttcccccctta   3240 cacggaggca tcaagtgacc aaacaggaaa aaaccgccct taacatggcc cgctttatca    3300
gaagccagac attaacgctt ctggagaaac tcaacgagct ggacgcggat gaacaggcag    3360
acatctgtga atcgcttcac gaccacgctg atgagcttta ccgcaggatc cggaaattgt    3420
aaacgttaat attttgttaa aattcgcgtt aaatttttgt taaatcagct catttttaa     3480 ccaataggcc gaaatcggca aaatccctta taatcaaaa gaatagaccg ataagggtt      3540 gagtgttgtt ccagtttgga acaagagtcc actattaaag aacgtggact ccaacgtcaa    3600
agggcgaaaa accgtctatc agggctatgg cccactacgt gaaccatcac cctaatcaag    3660
ttttttgggg tcgaggtgcc gtaaagcact aaatcggaac cctaaaggga gcccccgatt    3720
tagagcttga cggggaaagc cggcgaacgt ggcgagaaag gaagggaaga aagcgaaagg    3780
agcgggcgct agggcgctgg caagtgtagc ggtcacgctg cgcgtaacca ccacacccgc    3840
cgcgcttaat gcgccgctac agggcgcgtc cggatcctgc ctcgcgcgtt cggtgatga    3900 cggtgaaaac ctctgacaca tgcagctccc ggagacggtc acagcttgtc tgtaagcgga    3960
tgccgggagc agacaagccc gtcagggcgc gtcagcgggt gttggcgggt gtcggggcgc    4020
agccatgacc cagtcacgta gcgatagcgg agtgtatact ggcttaacta tgcggcatca    4080
gagcagattg tactgagagt gcaccatatg cggtgtgaaa taccgcacag atgcgtaagg    4140
agaaaatacc gcatcaggcg ctcttccgct tcctcgctca ctgactcgct gcgctcggtc    4200
gttcggctgc ggcgagcggt atcagctcac tcaaaggcgg taatacggtt atccacagaa    4260
tcaggggata acgcaggaaa gaacatgtga gcaaaaggcc agcaaaaggc caggaaccgt    4320
aaaaaggccg cgttgctggc gtttttccat aggctccgcc cccctgacga gcatcacaaa    4380
aatcgacgct caagtcagag gtggcgaaac ccgacaggac tataaagata ccaggcgttt    4440
ccccctggaa gctccctcgt gcgctctcct gttccgaccc tgccgcttac cggatacctg    4500
tccgcctttc tcccttcggg aagcgtggcg ctttctcata gctcacgctg taggtatctc    4560
agttcggtgt aggtcgttcg ctccaagctg ggctgtgtgc acgaaccccc cgttcagccc    4620
gaccgctgcg ccttatccgg taactatcgt cttgagtcca acccggtaag acacgactta    4680
tcgccactgg cagcagccac tggtaacagg attagcagag cgaggtatgt aggcggtgct    4740
acagagttct tgaagtggtg gcctaactac ggctacacta aaggacagt atttggtatc     4800 tgcgctctgc tgaagccagt taccttcgga aaaagagttg gtagctcttg atccggcaaa    4860
caaaccaccg ctggtagcgg tggtttttt gtttgcaagc agcagattac gcgcagaaaa     4920
aaaggatctc aagaagatcc tttgatcttt tctacgggt ctgacgctca gtggaacgaa     4980
aactcacgtt aagggatttt ggtcatgaga ttatcaaaaa ggatcttcac ctagatcctt    5040
ttaaattaaa aatgaagttt taatcaatc taaagtatat atgagtaaac ttggtctgac     5100
agttaccaat gcttaatcag tgaggcacct atctcagcga tctgtctatt tcgttcatcc    5160
```

-continued

```
atagttgcct gactccccgt cgtgtagata actacgatac gggagggctt accatctggc    5220
cccagtgctg caatgatacc gcgagaccca cgctcaccgg ctccagattt atcagcaata    5280
aaccagccag ccggaagggc cgagcgcaga agtggtcctg caactttatc cgcctccatc    5340
cagtctatta attgttgccg ggaagctaga gtaagtagtt cgccagttaa tagttttgcgc   5400 aacgttgttg ccattgctgc aggcatcgtg gtgtcacgct cgtcgtttgg tatggcttca    5460
ttcagctccg gttcccaacg atcaaggcga gttacatgat cccccatgtt gtgcaaaaaa    5520
gcggttagct ccttcggtcc tccgatcgtt gtcagaagta agttggccgc agtgttatca    5580
ctcatggtta tggcagcact gcataattct cttactgtca tgccatccgt aagatgcttt    5640
tctgtgactg gtgagtactc aaccaagtca ttctgagaat agtgtatgcg gcgaccgagt    5700
tgctcttgcc cggcgtcaac acgggataat accgcgccac atagcagaac tttaaaagtg    5760
ctcatcattg gaaaacgttc ttcggggcga aaactctcaa ggatcttacc gctgttgaga    5820
tccagttcga tgtaacccac tcgtgcaccc aactgatctt cagcatcttt tactttcacc    5880
agcgtttctg ggtgagcaaa aacaggaagg caaaatgccg caaaaaaggg aataagggcg    5940
acacggaaat gttgaatact catactcttc ctttttcaat attattgaag catttatcag    6000
ggttattgtc tcatgagcgg atacatattt gaatgtattt agaaaaataa acaaataggg    6060
gttccgcgca catttccccg aaaagtgcca cctgacgtct aagaaaccat tattatcatg    6120
acattaacct ataaaaatag gcgtatcacg aggccctttc gtcttcaata caggtagacc    6180
tttcgtagag atgtacagtg aaatcccga aattatacac atgactgaag aagggagct    6240 cgtcattccc tgccgggtta cgtcacctaa catcactgtt actttaaaaa agtttccact    6300
tgacactttg atccctgatg gaaaacgcat aatctgggac agtagaaagg gcttcatcat    6360
atcaaatgca acgtacaaag aaatagggct tctgacctgt gaagcaacag tcaatgggca    6420
tttgtataag acaaactatc tcacacatcg acaaaccaat acaatacagg tagacctttc    6480
gtagagatgt acagtgaaat ccccgaaatt atacacatga ctgaaggaag ggagctcgtc    6540
attccctgcc gggttacgtc acctaacatc actgttactt taaaaaagtt ccacttgac    6600 actttgatcc ctgatggaaa acgcataatc tgggacagta gaaagggctt catcatatca    6660
aatgcaacgt acaaagaaat agggcttctg acctgtgaag caacagtcaa tgggcatttg    6720
tataagacaa actatctcac acatcgacaa accaatacaa tctacaggta gacctttcgt    6780
agagatgtac agtgaaatcc ccgaaattat acacatgact gaaggaaggg agctcgtcat    6840
tccctgccgg gttacgtcac ctaacatcac tgttacttta aaaagtttc cacttgacac    6900 tttgatccct gatggaaaac gcataatctg ggacagtaga aagggcttca tcatatcaaa    6960
tgcaacgtac aaagaaatag gcttctgac ctgtgaagca acagtcaatg gcatttgta    7020 taagacaaac tatctcacac atcgacaaac caatacaatc                          7060
```

<210> SEQ ID NO 29
<211> LENGTH: 7171
<212> TYPE: DNA
<213> ORGANISM: Artificial Sequence
<220> FEATURE:
<223> OTHER INFORMATION: F(ab)'2 phagemid vector pV0350-4

<400> SEQUENCE: 29

```
gaattcaact tctccatact ttggataagg aaatacagac atgaaaaatc tcattgctga      60
gttgttattt aagcttgccc aaaaagaaga agagtcgaat gaactgtgtg cgcaggtaga    120
agctttggag attatcgtca ctgcaatgct tcgcaatatg gcgcaaaatg accaacagcg    180
```

-continued

```
gttgattgat caggtagagg gggcgctgta cgaggtaaag cccgatgcca gcattcctga    240
cgacgatacg gagctgctgc gcgattacgt aaagaagtta ttgaagcatc ctcgtcagta    300
aaaagttaat cttttcaaca gctgtcataa agttgtcacg gccgagactt atagtcgctt    360
tgtttttatt tttaatgta tttgtaacta gtacgcaagt tcacgtaaaa agggtatgta     420
gaggttgagg tgattttatg aaaaagaata tcgcatttct tcttgcatct atgttcgttt    480
tttctattgc tacaaatgcc tatgcatccg atatccagat gacccagtcc ccgagctccc    540
tgtccgcctc tgtgggcgat agggtcacca tcacctgccg tgccagtcag gatgtgtcca    600
ctgctgtagc ctggtatcaa cagaaaccag gaaaagctcc gaagcttctg atttactcgg    660
catccttcct ctactctgga gtcccttctc gcttctctgg tagcggttcc gggacggatt    720
tcactctgac catcagcagt ctgcagccgg aagacttcgc aacttattac tgtcagcaat    780
cttatactac tcctcccacg ttcggacagg gtaccaaggt ggagatcaaa cgaactgtgg    840
ctgcaccatc tgtcttcatc ttcccgccat ctgatgagca gttgaaatct ggaactgcct    900
ctgttgtgtg cctgctgaat aacttctatc ccagagaggc caaagtacag tggaaggtgg    960
ataacgccct ccaatcgggt aactcccagg agagtgtcac agagcaggac agcaaggaca   1020
gcacctacag cctcagcagc accctgacgc tgagcaaagc agactacgag aaacacaaag   1080
tctacgcctg cgaagtcacc catcagggcc tgagctcgcc cgtcacaaag agcttcaaca   1140
ggggagagtg tggtgccagc tccggtatgg ctgatccgaa ccgtttccgc ggtaaggacc   1200
tggcataact cgaggctgat cctctacgcc ggacgcatcg tggccctagt acgcaagttc   1260
acgtaaaaag ggtaactaga ggttgaggtg attttatgaa aaagaatatc gcatttcttc   1320
ttgcatctat gttcgttttt tctattgcta caaacgcgta cgctgaggtt cagctggtgg   1380
agtctggcgg tggcctggtg cagccagggg gctcactccg tttgtcctgt gcagcttctg   1440
gcttcaacat taaagacacc tatatacact gggtgcgtca ggcccgggt aagggcctgg    1500 aatgggttgc aaggatttat cctacgaatg gttatactag atatgccgat agcgtcaagg   1560
gccgtttcac tataagcgca gacacatcca aaaacacagc ctacctacaa atgaacagct   1620
taagagctga ggacactgcc gtctattatt gtagccgctg ggggagggac ggcttctatg   1680
ctatggacta ctggggtcaa ggaacactag tcaccgtctc ctcggcctcc accaagggcc   1740
catcggtctt ccccctggca ccctcctcca agagcacctc tggggcaca gcggccctgg    1800 gctgcctggt caaggactac ttccccgaac cggtgacggt gtcgtggaac tcaggcgccc   1860
tgaccagcgg cgtgcacacc ttcccggctg tcctacagtc ctcaggactc tactccctca   1920
gcagcgtggt gaccgtgccc tccagcagct gggcaccca gacctacatc tgcaacgtga    1980
atcacaagcc cagcaacacc aaggtcgaca gaaagttga gcccaaatct tgtgacaaaa    2040
ctcacggccg catgaaacag ctagaggaca aggtcgaaga gctactctcc aagaactacc   2100
acctagagaa tgaagtggca agactcaaaa aacttgtcgg ggagcgcgga agcttagtg    2160 gcggtggctc tggttccggt gattttgatt atgaaaagat ggcaaacgct aataagggg    2220 ctatgaccga aaatgccgat gaaaacgcgc tacagtctga cgctaaaggc aaacttgatt   2280
ctgtcgctac tgattacggt gctgctatcg atggtttcat tggtgacgtt tccggccttg   2340
ctaatggtaa tggtgctact ggtgattttg ctggctctaa ttcccaaatg gctcaagtcg   2400
gtgacggtga taattcacct ttaatgaata atttccgtca atatttacct tccctccctc   2460
aatcggttga atgtcgccct tttgtcttta gcgctggtaa accatatgaa ttttctattg   2520
attgtgacaa aataaactta ttccgtggtg tctttgcgtt tcttttatat gttgccacct   2580
```

```
ttatgtatgt attttctacg tttgctaaca tactgcgtaa taaggagtct taatcatgcc     2640
agttcttttg gctagcgccg ccctatacct tgtctgcctc cccgcgttgc gtcgcggtgc     2700
atggagccgg gccacctcga cctgaatgga agccggcggc acctcgctaa cggattcacc     2760
actccaagaa ttggagccaa tcaattcttg cggagaactg tgaatgcgca aaccaaccct     2820
tggcagaaca tatccatcgc gtccgccatc tccagcagcc gcacgcggcg catctcgggc     2880
agcgttgggt cctggccacg ggtgcgcatg atcgtgctcc tgtcgttgag gacccggcta     2940
ggctggcggg gttgccttac tggttagcag aatgaatcac cgatacgcga gcgaacgtga     3000
agcgactgct gctgcaaaac gtctgcgacc tgagcaacaa catgaatggt cttcggtttc     3060
cgtgtttcgt aaagtctgga aacgcggaag tcagcgccct gcaccattat gttccggatc     3120
tgcatcgcag gatgctgctg gctaccctgt ggaacaccta catctgtatt aacgaagcgc     3180
tggcattgac cctgagtgat ttttctctgg tcccgccgca tccataccgc cagttgttta     3240
ccctcacaac gttccagtaa ccgggcatgt tcatcatcag taacccgtat cgtgagcatc     3300
ctctctcgtt tcatcggtat cattaccccc atgaacagaa attcccccta acacggaggc     3360
atcaagtgac caaacaggaa aaaccgccc ttaacatggc ccgctttatc agaagccaga     3420
cattaacgct tctggagaaa ctcaacgagc tggacgcgga tgaacaggca gacatctgtg     3480
aatcgcttca cgaccacgct gatgagcttt accgcaggat ccggaaattg taaacgttaa     3540
tattttgtta aaattcgcgt taaattttg ttaaatcagc tcattttta accaataggc     3600 cgaaatcggc aaaatccctt ataaatcaaa agaatagacc gagataggt tgagtgttgt     3660 tccagtttgg aacaagagtc cactattaaa gaacgtggac tccaacgtca aagggcgaaa     3720
aaccgtctat cagggctatg gcccactacg tgaaccatca ccctaatcaa gttttttggg     3780
gtcgaggtgc cgtaaagcac taaatcggaa ccctaaaggg agccccgat ttagagcttg     3840 acggggaaag ccggcgaacg tggcgagaaa ggaagggaag aaagcgaaag gagcgggcgc     3900
tagggcgctg gcaagtgtag cggtcacgct gcgcgtaacc accacacccg ccgcgcttaa     3960
tgcgccgcta cagggcgcgt ccggatcctg cctcgcgcgt ttcggtgatg acggtgaaaa     4020
cctctgacac atgcagctcc cggagacggt cacagcttgt ctgtaagcgg atgccggag     4080 cagacaagcc cgtcagggcg cgtcagcggg tgttggcggg tgtcggggcg cagccatgac     4140
ccagtcacgt agcgatagcg gagtgtatac tggcttaact atgcggcatc agagcagatt     4200
gtactgagag tgcaccatat gcggtgtgaa ataccgcaca gatgcgtaag gagaaaatac     4260
cgcatcaggc gctcttccgc ttcctcgctc actgactcgc tgcgctcggt cgttcggctg     4320
cggcgagcgg tatcagctca ctcaaaggcg gtaatacggt tatccacaga atcaggggat     4380
aacgcaggaa agaacatgtg agcaaaaggc cagcaaaagg ccaggaaccg taaaaaggcc     4440
gcgttgctgg cgttttttcca taggctccgc cccctgacg agcatcacaa aaatcgacgc     4500
tcaagtcaga ggtggcgaaa cccgacagga ctataaagat accaggcgtt ccccctgga     4560 agctccctcg tgcgctctcc tgttccgacc ctgccgctta ccggatacct gtccgccttt     4620
ctcccttcgg gaagcgtggc gctttctcat agctcacgct gtaggtatct cagttcggtg     4680
taggtcgttc gctccaagct gggctgtgtg cacgaacccc ccgttcagcc cgaccgctgc     4740
gccttatccg gtaactatcg tcttgagtcc aacccggtaa gacacgactt atcgccactg     4800
gcagcagcca ctggtaacag gattagcaga gcgaggtatg taggcggtgc tacagagttc     4860
ttgaagtggt ggcctaacta cggctacact agaaggacag tatttggtat ctgcgctctg     4920
ctgaagccag ttaccttcgg aaaaagagtt ggtagctctt gatccggcaa acaaaccacc     4980
```

```
gctggtagcg gtggttttt tgtttgcaag cagcagatta cgcgcagaaa aaaggatct    5040 caagaagatc ctttgatctt ttctacgggg tctgacgctc agtggaacga aaactcacgt    5100
taagggattt tggtcatgag attatcaaaa aggatcttca cctagatcct tttaaattaa    5160
aaatgaagtt ttaaatcaat ctaaagtata tatgagtaaa cttggtctga cagttaccaa    5220
tgcttaatca gtgaggcacc tatctcagcg atctgtctat ttcgttcatc catagttgcc    5280
tgactccccg tcgtgtagat aactacgata cgggagggct taccatctgg ccccagtgct    5340
gcaatgatac cgcgagaccc acgctcaccg gctccagatt tatcagcaat aaaccagcca    5400 gccgaaggg ccgagcgcag aagtggtcct gcaactttat ccgcctccat ccagtctatt    5460
aattgttgcc gggaagctag agtaagtagt tcgccagtta atagtttgcg caacgttgtt    5520
gccattgctg caggcatcgt ggtgtcacgc tcgtcgtttg gtatggcttc attcagctcc    5580
ggttcccaac gatcaaggcg agttacatga tcccccatgt tgtgcaaaaa agcggttagc    5640
tccttcggtc ctccgatcgt tgtcagaagt aagttggccg cagtgttatc actcatggtt    5700
atggcagcac tgcataattc tcttactgtc atgccatccg taagatgctt ttctgtgact    5760
ggtgagtact caaccaagtc attctgagaa tagtgtatgc ggcgaccgag ttgctcttgc    5820
ccggcgtcaa cacgggataa taccgcgcca catagcagaa ctttaaaagt gctcatcatt    5880
ggaaaacgtt cttcggggcg aaaactctca aggatcttac cgctgttgag atccagttcg    5940
atgtaaccca ctcgtgcacc caactgatct tcagcatctt ttactttcac cagcgtttct    6000
gggtgagcaa aaacaggaag gcaaaatgcc gcaaaaaagg gaataagggc gacacggaaa    6060
tgttgaatac tcatactctt cctttttcaa tattattgaa gcatttatca gggttattgt    6120
ctcatgagcg gatacatatt tgaatgtatt tagaaaaata aacaaatagg ggttccgcgc    6180
acatttcccc gaaaagtgcc acctgacgtc taagaaacca ttattatcat gacattaacc    6240
tataaaaata ggcgtatcac gaggcccttt cgtcttcaat acaggtagac ctttcgtaga    6300
gatgtacagt gaaatccccg aaattataca catgactgaa ggaagggagc tcgtcattcc    6360
ctgccgggtt acgtcaccta acatcactgt tactttaaaa aagtttccac ttgacacttt    6420
gatccctgat ggaaaacgca taatctggga cagtagaaag gcttcatca tatcaaatgc    6480 aacgtacaaa gaaatagggc ttctgacctg tgaagcaaca gtcaatgggc atttgtataa    6540
gacaaactat ctcacacatc gacaaaccaa tacaatacag gtagaccttt cgtagagatg    6600
tacagtgaaa tccccgaaat tatacacatg actgaaggaa gggagctcgt cattccctgc    6660
cgggttacgt cacctaacat cactgttact ttaaaaaagt ttccacttga cactttgatc    6720
cctgatggaa aacgcataat ctgggacagt agaaagggct tcatcatatc aaatgcaacg    6780
tacaaagaaa tagggcttct gacctgtgaa gcaacagtca tgggcatttt gtataagaca    6840
aactatctca cacatcgaca aaccaataca atctacaggt agacctttcg tagagatgta    6900
cagtgaaatc cccgaaatta tacacatgac tgaaggaagg gagctcgtca ttccctgccg    6960
ggttacgtca cctaacatca ctgttacttt aaaaaagttt ccacttgaca ctttgatccc    7020
tgatggaaaa cgcataatct gggacagtag aaagggcttc atcatatcaa atgcaacgta    7080
caaagaaata gggcttctga cctgtgaagc aacagtcaat gggcatttgt ataagacaaa    7140
ctatctcaca catcgacaaa ccaatacaat c                                   7171
```

<210> SEQ ID NO 30
<211> LENGTH: 57
<212> TYPE: DNA
<213> ORGANISM: Artificial Sequence
<220> FEATURE:

```
<223> OTHER INFORMATION: CDR Oligonucleotide
<220> FEATURE:
<221> NAME/KEY: misc_feature
<222> LOCATION: (22)..(22)
<223> OTHER INFORMATION: n=a, c, t or g
<220> FEATURE:
<221> NAME/KEY: misc_feature
<222> LOCATION: (23)..(23)
<223> OTHER INFORMATION: n=a or g
<220> FEATURE:
<221> NAME/KEY: misc_feature
<222> LOCATION: (25)..(25)
<223> OTHER INFORMATION: n=a, c, t or g
<220> FEATURE:
<221> NAME/KEY: misc_feature
<222> LOCATION: (26)..(26)
<223> OTHER INFORMATION: n=a or g
<220> FEATURE:
<221> NAME/KEY: misc_feature
<222> LOCATION: (28)..(28)
<223> OTHER INFORMATION: n=a or g
<220> FEATURE:
<221> NAME/KEY: misc_feature
<222> LOCATION: (29)..(29)
<223> OTHER INFORMATION: n=a, c or g
<220> FEATURE:
<221> NAME/KEY: misc_feature
<222> LOCATION: (30)..(30)
<223> OTHER INFORMATION: n=a or c
<220> FEATURE:
<221> NAME/KEY: misc_feature
<222> LOCATION: (31)..(32)
<223> OTHER INFORMATION: n=a, c, g or t
<220> FEATURE:
<221> NAME/KEY: misc_feature
<222> LOCATION: (33)..(33)
<223> OTHER INFORMATION: n=g or t
<220> FEATURE:
<221> NAME/KEY: misc_feature
<222> LOCATION: (38)..(38)
<223> OTHER INFORMATION: n=a, g or t
<220> FEATURE:
<221> NAME/KEY: misc_feature
<222> LOCATION: (39)..(39)
<223> OTHER INFORMATION: n=g or t

<400> SEQUENCE: 30
gcaacttatt actgtcagca anntnntnnn nnnccttnna cgttcggaca gggtacc      57

<210> SEQ ID NO 31
<211> LENGTH: 13
<212> TYPE: PRT
<213> ORGANISM: Artificial Sequence
<220> FEATURE:
<223> OTHER INFORMATION: CDRH3

<400> SEQUENCE: 31

Ser Arg Trp Gly Gly Asp Gly Phe Tyr Ala Met Asp Tyr
1               5                   10

<210> SEQ ID NO 32
<211> LENGTH: 10
<212> TYPE: PRT
<213> ORGANISM: Artificial Sequence
<220> FEATURE:
<223> OTHER INFORMATION: Randomized CDRH3
<220> FEATURE:
<221> NAME/KEY: MISC_FEATURE
<222> LOCATION: (3)..(7)
<223> OTHER INFORMATION: Xaa is Ala, Cys, Asp, Glu, Gly, Lys, Asn, Arg,
      Ser, Tyr, Trp or Thr

<400> SEQUENCE: 32

Ser Arg Xaa Xaa Xaa Xaa Xaa Phe Asp Tyr
1               5                   10
```

```
<210> SEQ ID NO 33
<211> LENGTH: 13
<212> TYPE: PRT
<213> ORGANISM: Artificial Sequence
<220> FEATURE:
<223> OTHER INFORMATION: Randomized CDRH3
<220> FEATURE:
<221> NAME/KEY: MISC_FEATURE
<222> LOCATION: (2)..(2)
<223> OTHER INFORMATION: Xaa is Arg or Lys
<220> FEATURE:
<221> NAME/KEY: MISC_FEATURE
<222> LOCATION: (3)..(7)
<223> OTHER INFORMATION: Xaa is Ala, Cys, Asp, Glu, Gly, Lys, Asn, Arg,
      Ser, Tyr, Trp or Thr
<220> FEATURE:
<221> NAME/KEY: MISC_FEATURE
<222> LOCATION: (8)..(8)
<223> OTHER INFORMATION: Xaa is any naturally occurring amino acid

<400> SEQUENCE: 33

Ala Xaa Xaa Xaa Xaa Xaa Xaa Xaa Tyr Ala Met Asp Tyr
1               5                   10

<210> SEQ ID NO 34
<211> LENGTH: 13
<212> TYPE: PRT
<213> ORGANISM: Artificial Sequence
<220> FEATURE:
<223> OTHER INFORMATION: Randomized CDRH3
<220> FEATURE:
<221> NAME/KEY: MISC_FEATURE
<222> LOCATION: (2)..(2)
<223> OTHER INFORMATION: Xaa is Arg or Lys
<220> FEATURE:
<221> NAME/KEY: MISC_FEATURE
<222> LOCATION: (4)..(4)
<223> OTHER INFORMATION: Xaa is Ala, Cys, Asp, Gly, His, Asn, Pro, Arg,
      Ser, Thr or Tyr
<220> FEATURE:
<221> NAME/KEY: MISC_FEATURE
<222> LOCATION: (5)..(8)
<223> OTHER INFORMATION: Xaa is Lys, Asn, Thr, Arg, Ser, Glu, Asp, Ala,
      Gly, Tyr, Trp or Cys
<220> FEATURE:
<221> NAME/KEY: MISC_FEATURE
<222> LOCATION: (9)..(9)
<223> OTHER INFORMATION: Xaa is Ala, Gly, Arg, Ser, Thr or Trp

<400> SEQUENCE: 34

Ala Xaa Trp Xaa Xaa Xaa Xaa Xaa Xaa Ala Met Asp Tyr
1               5                   10

<210> SEQ ID NO 35
<211> LENGTH: 13
<212> TYPE: PRT
<213> ORGANISM: Artificial Sequence
<220> FEATURE:
<223> OTHER INFORMATION: Randomized CDRH3
<220> FEATURE:
<221> NAME/KEY: MISC_FEATURE
<222> LOCATION: (2)..(2)
<223> OTHER INFORMATION: Xaa is Arg, Lys or Thr
<220> FEATURE:
<221> NAME/KEY: MISC_FEATURE
<222> LOCATION: (3)..(8)
<223> OTHER INFORMATION: Xaa is Ala, Cys, Asp, Gly, His, Asn, Pro, Arg,
      Ser, Thr or Tyr

<400> SEQUENCE: 35

Ala Xaa Xaa Xaa Xaa Xaa Xaa Xaa Tyr Ala Met Asp Tyr
1               5                   10
```

<210> SEQ ID NO 36
<211> LENGTH: 14
<212> TYPE: PRT
<213> ORGANISM: Artificial Sequence
<220> FEATURE:
<223> OTHER INFORMATION: Randomized CDRH3
<220> FEATURE:
<221> NAME/KEY: MISC_FEATURE
<222> LOCATION: (2)..(2)
<223> OTHER INFORMATION: Xaa is Arg, Lys or Thr
<220> FEATURE:
<221> NAME/KEY: MISC_FEATURE
<222> LOCATION: (4)..(9)
<223> OTHER INFORMATION: Xaa is Ala, Cys, Asp, Gly, His, Asn, Pro, Arg,
      Ser, Thr or Tyr

<400> SEQUENCE: 36

Ala Xaa Trp Xaa Xaa Xaa Xaa Xaa Xaa Tyr Ala Met Asp Tyr
1               5                   10

<210> SEQ ID NO 37
<211> LENGTH: 14
<212> TYPE: PRT
<213> ORGANISM: Artificial Sequence
<220> FEATURE:
<223> OTHER INFORMATION: Randomized CDRH3
<220> FEATURE:
<221> NAME/KEY: MISC_FEATURE
<222> LOCATION: (2)..(2)
<223> OTHER INFORMATION: Xaa is Arg, Lys or Thr
<220> FEATURE:
<221> NAME/KEY: MISC_FEATURE
<222> LOCATION: (3)..(3)
<223> OTHER INFORMATION: Xaa is Ala, Cys, Asp, Gly, His, Asn, Pro, Arg,
      Ser, Thr or Tyr
<220> FEATURE:
<221> NAME/KEY: MISC_FEATURE
<222> LOCATION: (5)..(9)
<223> OTHER INFORMATION: Xaa is Ala, Cys, Asp, Gly, His, Asn, Pro, Arg,
      Ser, Thr or Tyr

<400> SEQUENCE: 37

Ala Xaa Xaa Trp Xaa Xaa Xaa Xaa Xaa Tyr Ala Met Asp Tyr
1               5                   10

<210> SEQ ID NO 38
<211> LENGTH: 14
<212> TYPE: PRT
<213> ORGANISM: Artificial Sequence
<220> FEATURE:
<223> OTHER INFORMATION: Randomized CDRH3
<220> FEATURE:
<221> NAME/KEY: MISC_FEATURE
<222> LOCATION: (2)..(2)
<223> OTHER INFORMATION: Xaa is Arg, Lys or Thr
<220> FEATURE:
<221> NAME/KEY: MISC_FEATURE
<222> LOCATION: (3)..(4)
<223> OTHER INFORMATION: Xaa is Ala, Cys, Asp, Gly, His, Asn, Pro, Arg,
      Ser, Thr or Tyr
<220> FEATURE:
<221> NAME/KEY: MISC_FEATURE
<222> LOCATION: (6)..(9)
<223> OTHER INFORMATION: Xaa is Ala, Cys, Asp, Gly, His, Asn, Pro, Arg,
      Ser, Thr or Tyr

<400> SEQUENCE: 38

Ala Xaa Xaa Xaa Trp Xaa Xaa Xaa Xaa Tyr Ala Met Asp Tyr
1               5                   10

<210> SEQ ID NO 39
<211> LENGTH: 14
<212> TYPE: PRT

-continued

```
<213> ORGANISM: Artificial Sequence
<220> FEATURE:
<223> OTHER INFORMATION: Randomized CDRH3
<220> FEATURE:
<221> NAME/KEY: MISC_FEATURE
<222> LOCATION: (2)..(2)
<223> OTHER INFORMATION: Xaa is Arg, Lys or Thr
<220> FEATURE:
<221> NAME/KEY: MISC_FEATURE
<222> LOCATION: (3)..(8)
<223> OTHER INFORMATION: Xaa is Ala, Cys, Asp, Gly, His, Pro, Arg, Ser,
      Thr, Tyr or Asn

<400> SEQUENCE: 39

Ala Xaa Xaa Xaa Xaa Xaa Xaa Xaa Trp Tyr Ala Met Asp Tyr
1               5                   10

<210> SEQ ID NO 40
<211> LENGTH: 13
<212> TYPE: PRT
<213> ORGANISM: Artificial Sequence
<220> FEATURE:
<223> OTHER INFORMATION: Randomized CDRH3
<220> FEATURE:
<221> NAME/KEY: MISC_FEATURE
<222> LOCATION: (2)..(2)
<223> OTHER INFORMATION: Xaa is Arg or Lys
<220> FEATURE:
<221> NAME/KEY: MISC_FEATURE
<222> LOCATION: (4)..(9)
<223> OTHER INFORMATION: Xaa is Ala, Cys, Asp, Gly, His, Asn, Pro, Arg,
      Ser, Thr or Tyr
<220> FEATURE:
<221> NAME/KEY: MISC_FEATURE
<222> LOCATION: (10)..(10)
<223> OTHER INFORMATION: Xaa is Gly, Ser, Ala or Trp

<400> SEQUENCE: 40

Ala Xaa Trp Xaa Xaa Xaa Xaa Xaa Xaa Xaa Ala Met Tyr
1               5                   10

<210> SEQ ID NO 41
<211> LENGTH: 14
<212> TYPE: PRT
<213> ORGANISM: Artificial Sequence
<220> FEATURE:
<223> OTHER INFORMATION: Randomized CDRH3
<220> FEATURE:
<221> NAME/KEY: MISC_FEATURE
<222> LOCATION: (2)..(2)
<223> OTHER INFORMATION: Xaa is Arg or Lys
<220> FEATURE:
<221> NAME/KEY: MISC_FEATURE
<222> LOCATION: (3)..(3)
<223> OTHER INFORMATION: Xaa is Ala, Cys, Asp, Gly, His, Asn, Pro, Arg,
      Ser, Thr or Tyr
<220> FEATURE:
<221> NAME/KEY: MISC_FEATURE
<222> LOCATION: (5)..(9)
<223> OTHER INFORMATION: Xaa is Ala, Cys, Asp, Gly, His, Asn, Pro, Arg,
      Ser, Thr or Tyr
<220> FEATURE:
<221> NAME/KEY: MISC_FEATURE
<222> LOCATION: (10)..(10)
<223> OTHER INFORMATION: Xaa is Gly, Ser, Ala or Trp

<400> SEQUENCE: 41

Ala Xaa Xaa Trp Xaa Xaa Xaa Xaa Xaa Xaa Ala Met Asp Tyr
1               5                   10

<210> SEQ ID NO 42
<211> LENGTH: 14
<212> TYPE: PRT
<213> ORGANISM: Artificial Sequence
```

```
<220> FEATURE:
<223> OTHER INFORMATION: Randomized CDRH3
<220> FEATURE:
<221> NAME/KEY: MISC_FEATURE
<222> LOCATION: (2)..(2)
<223> OTHER INFORMATION: Xaa is Arg or Lys
<220> FEATURE:
<221> NAME/KEY: MISC_FEATURE
<222> LOCATION: (3)..(4)
<223> OTHER INFORMATION: Xaa is Ala, Cys, Asp, Gly, His, Asn, Pro, Arg,
      Ser, Thr or Tyr
<220> FEATURE:
<221> NAME/KEY: MISC_FEATURE
<222> LOCATION: (6)..(9)
<223> OTHER INFORMATION: Xaa is Ala, Cys, Asp, Gly, His, Asn, Pro, Arg,
      Ser, Thr or Tyr
<220> FEATURE:
<221> NAME/KEY: MISC_FEATURE
<222> LOCATION: (10)..(10)
<223> OTHER INFORMATION: Xaa is Gly, Ser, Ala or Trp

<400> SEQUENCE: 42

Ala Xaa Xaa Xaa Trp Xaa Xaa Xaa Xaa Xaa Ala Met Asp Tyr
1               5                   10

<210> SEQ ID NO 43
<211> LENGTH: 14
<212> TYPE: PRT
<213> ORGANISM: Artificial Sequence
<220> FEATURE:
<223> OTHER INFORMATION: Randomized CDRH3
<220> FEATURE:
<221> NAME/KEY: MISC_FEATURE
<222> LOCATION: (2)..(2)
<223> OTHER INFORMATION: Xaa is Arg or Lys
<220> FEATURE:
<221> NAME/KEY: MISC_FEATURE
<222> LOCATION: (3)..(5)
<223> OTHER INFORMATION: Xaa is Ala, Cys, Asp, Gly, His, Asn, Pro, Arg,
      Ser, Thr or Tyr
<220> FEATURE:
<221> NAME/KEY: MISC_FEATURE
<222> LOCATION: (7)..(9)
<223> OTHER INFORMATION: Xaa is Ala, Cys, Asp, Gly, His, Asn, Pro, Arg,
      Ser, Thr or Tyr
<220> FEATURE:
<221> NAME/KEY: MISC_FEATURE
<222> LOCATION: (10)..(10)
<223> OTHER INFORMATION: Xaa is Gly, Ser, Ala or Trp

<400> SEQUENCE: 43

Ala Xaa Xaa Xaa Xaa Trp Xaa Xaa Xaa Xaa Ala Met Asp Tyr
1               5                   10

<210> SEQ ID NO 44
<211> LENGTH: 14
<212> TYPE: PRT
<213> ORGANISM: Artificial Sequence
<220> FEATURE:
<223> OTHER INFORMATION: Randomized CDRH3
<220> FEATURE:
<221> NAME/KEY: MISC_FEATURE
<222> LOCATION: (2)..(2)
<223> OTHER INFORMATION: Xaa is Arg or Lys
<220> FEATURE:
<221> NAME/KEY: MISC_FEATURE
<222> LOCATION: (3)..(7)
<223> OTHER INFORMATION: Xaa is Ala, Cys, Asp, Gly, His, Asn, Pro, Arg,
      Ser, Thr or Tyr
<220> FEATURE:
<221> NAME/KEY: MISC_FEATURE
<222> LOCATION: (9)..(9)
<223> OTHER INFORMATION: Xaa is Ala, Cys, Asp, Gly, His, Asn, Pro, Arg,
      Ser, Thr or Tyr
<220> FEATURE:
<221> NAME/KEY: MISC_FEATURE
```

```
<222> LOCATION: (10)..(10)
<223> OTHER INFORMATION: Xaa is Gly, Ser, Ala or Trp

<400> SEQUENCE: 44

Ala Xaa Xaa Xaa Xaa Xaa Xaa Trp Xaa Xaa Ala Met Asp Tyr
1               5                   10

<210> SEQ ID NO 45
<211> LENGTH: 14
<212> TYPE: PRT
<213> ORGANISM: Artificial Sequence
<220> FEATURE:
<223> OTHER INFORMATION: Randomized CDRH3
<220> FEATURE:
<221> NAME/KEY: MISC_FEATURE
<222> LOCATION: (2)..(2)
<223> OTHER INFORMATION: Xaa is Arg or Lys
<220> FEATURE:
<221> NAME/KEY: MISC_FEATURE
<222> LOCATION: (3)..(8)
<223> OTHER INFORMATION: Xaa is Ala, Cys, Asp, Gly, His, Asn, Pro, Arg,
      Ser, Thr or Tyr
<220> FEATURE:
<221> NAME/KEY: MISC_FEATURE
<222> LOCATION: (10)..(10)
<223> OTHER INFORMATION: Xaa is Gly, Ser, Ala or Trp

<400> SEQUENCE: 45

Ala Xaa Xaa Xaa Xaa Xaa Xaa Xaa Trp Xaa Ala Met Asp Tyr
1               5                   10

<210> SEQ ID NO 46
<211> LENGTH: 13
<212> TYPE: PRT
<213> ORGANISM: Artificial Sequence
<220> FEATURE:
<223> OTHER INFORMATION: Randomized CDRH3
<220> FEATURE:
<221> NAME/KEY: MISC_FEATURE
<222> LOCATION: (2)..(2)
<223> OTHER INFORMATION: Xaa is Arg or Lys
<220> FEATURE:
<221> NAME/KEY: MISC_FEATURE
<222> LOCATION: (3)..(8)
<223> OTHER INFORMATION: Xaa is Ala, Cys, Asp, Glu, Gly, Lys, Asn, Arg,
      Ser, Tyr, Trp or Thr
<220> FEATURE:
<221> NAME/KEY: MISC_FEATURE
<222> LOCATION: (9)..(9)
<223> OTHER INFORMATION: Xaa is Trp, Ser, Ala or Gly

<400> SEQUENCE: 46

Ala Xaa Xaa Xaa Xaa Xaa Xaa Xaa Xaa Ala Met Asp Tyr
1               5                   10

<210> SEQ ID NO 47
<211> LENGTH: 14
<212> TYPE: PRT
<213> ORGANISM: Artificial Sequence
<220> FEATURE:
<223> OTHER INFORMATION: Randomized CDRH3
<220> FEATURE:
<221> NAME/KEY: MISC_FEATURE
<222> LOCATION: (3)..(9)
<223> OTHER INFORMATION: Xaa is Ala, Cys, Asp, Glu, Gly, Lys, Asn, Arg,
      Ser, Tyr, Trp or Thr

<400> SEQUENCE: 47

Ala Arg Xaa Xaa Xaa Xaa Xaa Xaa Xaa Tyr Ala Met Asp Tyr
1               5                   10

<210> SEQ ID NO 48
```

```
<211> LENGTH: 14
<212> TYPE: PRT
<213> ORGANISM: Artificial Sequence
<220> FEATURE:
<223> OTHER INFORMATION: Randomized CDRH3
<220> FEATURE:
<221> NAME/KEY: MISC_FEATURE
<222> LOCATION: (3)..(9)
<223> OTHER INFORMATION: Xaa is Ala, Cys, Asp, Glu, Gly, Lys, Asn, Arg,
      Ser, Tyr, Trp or Thr
<220> FEATURE:
<221> NAME/KEY: MISC_FEATURE
<222> LOCATION: (10)..(10)
<223> OTHER INFORMATION: Xaa is Ala, Gly, Arg, Ser, Thr or Trp

<400> SEQUENCE: 48

Ala Arg Xaa Xaa Xaa Xaa Xaa Xaa Xaa Xaa Ala Met Asp Tyr
1               5                   10

<210> SEQ ID NO 49
<211> LENGTH: 15
<212> TYPE: PRT
<213> ORGANISM: Artificial Sequence
<220> FEATURE:
<223> OTHER INFORMATION: Randomized CDRH3
<220> FEATURE:
<221> NAME/KEY: MISC_FEATURE
<222> LOCATION: (3)..(10)
<223> OTHER INFORMATION: Xaa is Ala, Cys, Asp, Glu, Gly, Lys, Asn, Arg,
      Ser, Tyr, Trp or Thr

<400> SEQUENCE: 49

Ala Arg Xaa Xaa Xaa Xaa Xaa Xaa Xaa Xaa Tyr Ala Met Asp Tyr
1               5                   10                  15

<210> SEQ ID NO 50
<211> LENGTH: 15
<212> TYPE: PRT
<213> ORGANISM: Artificial Sequence
<220> FEATURE:
<223> OTHER INFORMATION: Randomized CDRH3
<220> FEATURE:
<221> NAME/KEY: MISC_FEATURE
<222> LOCATION: (3)..(10)
<223> OTHER INFORMATION: Xaa is Ala, Cys, Asp, Glu, Gly, Lys, Asn, Arg,
      Ser, Tyr, Trp or Thr
<220> FEATURE:
<221> NAME/KEY: MISC_FEATURE
<222> LOCATION: (11)..(11)
<223> OTHER INFORMATION: Xaa is Ala, Gly, Arg, Ser, Thr or Trp

<400> SEQUENCE: 50

Ala Arg Xaa Xaa Xaa Xaa Xaa Xaa Xaa Xaa Xaa Ala Met Asp Tyr
1               5                   10                  15

<210> SEQ ID NO 51
<211> LENGTH: 13
<212> TYPE: PRT
<213> ORGANISM: Artificial Sequence
<220> FEATURE:
<223> OTHER INFORMATION: Randomized CDRH3
<220> FEATURE:
<221> NAME/KEY: MISC_FEATURE
<222> LOCATION: (2)..(2)
<223> OTHER INFORMATION: Xaa is Arg or Lys
<220> FEATURE:
<221> NAME/KEY: MISC_FEATURE
<222> LOCATION: (4)..(9)
<223> OTHER INFORMATION: Xaa is Ala, Cys, Asp, Gly, His, Asn, Pro, Arg,
      Ser, Thr or Tyr
<220> FEATURE:
<221> NAME/KEY: MISC_FEATURE
<222> LOCATION: (10)..(10)
<223> OTHER INFORMATION: Xaa is Gly, Ser, Ala or Trp
```

```
<400> SEQUENCE: 51

Ala Xaa Trp Xaa Xaa Xaa Xaa Xaa Xaa Xaa Ala Met Tyr
1               5                   10

<210> SEQ ID NO 52
<211> LENGTH: 13
<212> TYPE: PRT
<213> ORGANISM: Artificial Sequence
<220> FEATURE:
<223> OTHER INFORMATION: Randomized CDRH3
<220> FEATURE:
<221> NAME/KEY: MISC_FEATURE
<222> LOCATION: (2)..(2)
<223> OTHER INFORMATION: Xaa is Arg or Lys
<220> FEATURE:
<221> NAME/KEY: MISC_FEATURE
<222> LOCATION: (4)..(8)
<223> OTHER INFORMATION: Xaa is Ala, Cys, Asp, Gly, His, Asn, Pro, Arg,
      Ser, Thr or Tyr
<220> FEATURE:
<221> NAME/KEY: MISC_FEATURE
<222> LOCATION: (9)..(9)
<223> OTHER INFORMATION: Xaa is Ala, Gly, Arg, Ser, Thr or Trp

<400> SEQUENCE: 52

Ala Xaa Trp Xaa Xaa Xaa Xaa Xaa Xaa Ala Met Asp Tyr
1               5                   10

<210> SEQ ID NO 53
<211> LENGTH: 13
<212> TYPE: PRT
<213> ORGANISM: Artificial Sequence
<220> FEATURE:
<223> OTHER INFORMATION: Randomized CDRH3
<220> FEATURE:
<221> NAME/KEY: MISC_FEATURE
<222> LOCATION: (2)..(2)
<223> OTHER INFORMATION: Xaa is Arg, Lys or Thr
<220> FEATURE:
<221> NAME/KEY: MISC_FEATURE
<222> LOCATION: (4)..(9)
<223> OTHER INFORMATION: Xaa is Ala, Cys, Asp, Gly, His, Asn, Pro, Arg,
      Ser, Thr or Tyr

<400> SEQUENCE: 53

Ala Xaa Trp Xaa Xaa Xaa Xaa Xaa Xaa Ala Met Asp Tyr
1               5                   10

<210> SEQ ID NO 54
<211> LENGTH: 15
<212> TYPE: PRT
<213> ORGANISM: Artificial Sequence
<220> FEATURE:
<223> OTHER INFORMATION: Randomized CDRH3
<220> FEATURE:
<221> NAME/KEY: MISC_FEATURE
<222> LOCATION: (3)..(10)
<223> OTHER INFORMATION: Xaa is Ala, Cys, Asp, Gly, His, Asn, Pro, Arg,
      Ser, Thr or Tyr

<400> SEQUENCE: 54

Ser Arg Xaa Xaa Xaa Xaa Xaa Xaa Xaa Xaa Tyr Ala Met Asp Tyr
1               5                   10                  15

<210> SEQ ID NO 55
<211> LENGTH: 13
<212> TYPE: PRT
<213> ORGANISM: Artificial Sequence
<220> FEATURE:
<223> OTHER INFORMATION: Randomized CDRH3
<220> FEATURE:
```

```
<221> NAME/KEY: MISC_FEATURE
<222> LOCATION: (3)..(8)
<223> OTHER INFORMATION: Xaa is any naturally occurring amino acid

<400> SEQUENCE: 55

Ala Arg Xaa Xaa Xaa Xaa Xaa Xaa Tyr Ala Met Asp Tyr
1               5                   10

<210> SEQ ID NO 56
<211> LENGTH: 13
<212> TYPE: PRT
<213> ORGANISM: Artificial Sequence
<220> FEATURE:
<223> OTHER INFORMATION: Randomized CDRH3
<220> FEATURE:
<221> NAME/KEY: MISC_FEATURE
<222> LOCATION: (3)..(8)
<223> OTHER INFORMATION: Xaa is any naturally occurring amino acid
<220> FEATURE:
<221> NAME/KEY: MISC_FEATURE
<222> LOCATION: (9)..(9)
<223> OTHER INFORMATION: Xaa is Ala, Gly, Arg, Ser, Thr or Trp

<400> SEQUENCE: 56

Ala Arg Xaa Xaa Xaa Xaa Xaa Xaa Xaa Ala Met Asp Tyr
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Randomized CDRH3
<220> FEATURE:
<221> NAME/KEY: MISC_FEATURE
<222> LOCATION: (3)..(7)
<223> OTHER INFORMATION: Xaa is any naturally occurring amino acid
<220> FEATURE:
<221> NAME/KEY: MISC_FEATURE
<222> LOCATION: (9)..(9)
<223> OTHER INFORMATION: Xaa is Ala, Gly or Val

<400> SEQUENCE: 57

Ala Arg Xaa Xaa Xaa Xaa Xaa Tyr Xaa Met Asp Tyr
1               5                   10

<210> SEQ ID NO 58
<211> LENGTH: 12
<212> TYPE: PRT
<213> ORGANISM: Artificial Sequence
<220> FEATURE:
<223> OTHER INFORMATION: Randomized CDRH3
<220> FEATURE:
<221> NAME/KEY: MISC_FEATURE
<222> LOCATION: (3)..(7)
<223> OTHER INFORMATION: Xaa is any naturally occurring amino acid
<220> FEATURE:
<221> NAME/KEY: MISC_FEATURE
<222> LOCATION: (8)..(8)
<223> OTHER INFORMATION: Xaa is Trp, Ser, Ala or Gly
<220> FEATURE:
<221> NAME/KEY: MISC_FEATURE
<222> LOCATION: (9)..(9)
<223> OTHER INFORMATION: Xaa is Ala, Gly or Val

<400> SEQUENCE: 58

Ala Arg Xaa Xaa Xaa Xaa Xaa Xaa Xaa Met Asp Tyr
1               5                   10

<210> SEQ ID NO 59
<211> LENGTH: 11
<212> TYPE: PRT
```

```
<213> ORGANISM: Artificial Sequence
<220> FEATURE:
<223> OTHER INFORMATION: Randomized CDRH3
<220> FEATURE:
<221> NAME/KEY: MISC_FEATURE
<222> LOCATION: (3)..(6)
<223> OTHER INFORMATION: Xaa is any naturally occurring amino acid
<220> FEATURE:
<221> NAME/KEY: MISC_FEATURE
<222> LOCATION: (8)..(8)
<223> OTHER INFORMATION: Xaa is Ala, Gly or Val

<400> SEQUENCE: 59

Ala Arg Xaa Xaa Xaa Xaa Tyr Xaa Met Asp Tyr
1               5                   10

<210> SEQ ID NO 60
<211> LENGTH: 11
<212> TYPE: PRT
<213> ORGANISM: Artificial Sequence
<220> FEATURE:
<223> OTHER INFORMATION: Randomized CDRH3
<220> FEATURE:
<221> NAME/KEY: MISC_FEATURE
<222> LOCATION: (3)..(6)
<223> OTHER INFORMATION: Xaa is any naturally occurring amino acid
<220> FEATURE:
<221> NAME/KEY: MISC_FEATURE
<222> LOCATION: (7)..(7)
<223> OTHER INFORMATION: Xaa is Trp, Ser, Ala or Gly
<220> FEATURE:
<221> NAME/KEY: MISC_FEATURE
<222> LOCATION: (8)..(8)
<223> OTHER INFORMATION: Xaa is Ala, Gly or Val

<400> SEQUENCE: 60

Ala Arg Xaa Xaa Xaa Xaa Xaa Xaa Met Asp Tyr
1               5                   10

<210> SEQ ID NO 61
<211> LENGTH: 13
<212> TYPE: PRT
<213> ORGANISM: Artificial Sequence
<220> FEATURE:
<223> OTHER INFORMATION: Randomized CDRH3
<220> FEATURE:
<221> NAME/KEY: MISC_FEATURE
<222> LOCATION: (3)..(8)
<223> OTHER INFORMATION: Xaa is any naturally occurring amino acid
<220> FEATURE:
<221> NAME/KEY: MISC_FEATURE
<222> LOCATION: (10)..(10)
<223> OTHER INFORMATION: Xaa is Ala, Gly or Val

<400> SEQUENCE: 61

Ala Arg Xaa Xaa Xaa Xaa Xaa Xaa Tyr Xaa Met Asp Tyr
1               5                   10

<210> SEQ ID NO 62
<211> LENGTH: 13
<212> TYPE: PRT
<213> ORGANISM: Artificial Sequence
<220> FEATURE:
<223> OTHER INFORMATION: Randomized CDRH3
<220> FEATURE:
<221> NAME/KEY: MISC_FEATURE
<222> LOCATION: (3)..(8)
<223> OTHER INFORMATION: Xaa is any naturally occurring amino acid
<220> FEATURE:
<221> NAME/KEY: MISC_FEATURE
<222> LOCATION: (9)..(9)
<223> OTHER INFORMATION: Xaa is Trp, Ser, Ala or Gly
<220> FEATURE:
<221> NAME/KEY: MISC_FEATURE
```

```
<222> LOCATION: (10)..(10)
<223> OTHER INFORMATION: Xaa is Ala, Gly or Val

<400> SEQUENCE: 62

Ala Arg Xaa Xaa Xaa Xaa Xaa Xaa Xaa Xaa Met Asp Tyr
1               5                   10

<210> SEQ ID NO 63
<211> LENGTH: 14
<212> TYPE: PRT
<213> ORGANISM: Artificial Sequence
<220> FEATURE:
<223> OTHER INFORMATION: Randomized CDRH3
<220> FEATURE:
<221> NAME/KEY: MISC_FEATURE
<222> LOCATION: (3)..(9)
<223> OTHER INFORMATION: Xaa is any naturally occurring amino acid
<220> FEATURE:
<221> NAME/KEY: MISC_FEATURE
<222> LOCATION: (10)..(10)
<223> OTHER INFORMATION: Xaa is Trp, Ser, Ala or Gly
<220> FEATURE:
<221> NAME/KEY: MISC_FEATURE
<222> LOCATION: (11)..(11)
<223> OTHER INFORMATION: Xaa is Ala, Gly or Val

<400> SEQUENCE: 63

Ala Arg Xaa Xaa Xaa Xaa Xaa Xaa Xaa Xaa Xaa Met Asp Tyr
1               5                   10

<210> SEQ ID NO 64
<211> LENGTH: 14
<212> TYPE: PRT
<213> ORGANISM: Artificial Sequence
<220> FEATURE:
<223> OTHER INFORMATION: Randomized CDRH3
<220> FEATURE:
<221> NAME/KEY: MISC_FEATURE
<222> LOCATION: (3)..(9)
<223> OTHER INFORMATION: Xaa is any naturally occurring amino acid
<220> FEATURE:
<221> NAME/KEY: MISC_FEATURE
<222> LOCATION: (11)..(11)
<223> OTHER INFORMATION: Xaa is Ala, Gly or Val

<400> SEQUENCE: 64

Ala Arg Xaa Xaa Xaa Xaa Xaa Xaa Xaa Tyr Xaa Met Asp Tyr
1               5                   10

<210> SEQ ID NO 65
<211> LENGTH: 15
<212> TYPE: PRT
<213> ORGANISM: Artificial Sequence
<220> FEATURE:
<223> OTHER INFORMATION: Randomized CDRH3
<220> FEATURE:
<221> NAME/KEY: MISC_FEATURE
<222> LOCATION: (3)..(10)
<223> OTHER INFORMATION: Xaa is any naturally occurring amino acid
<220> FEATURE:
<221> NAME/KEY: MISC_FEATURE
<222> LOCATION: (12)..(12)
<223> OTHER INFORMATION: Xaa is Ala, Gly or Val

<400> SEQUENCE: 65

Ala Arg Xaa Xaa Xaa Xaa Xaa Xaa Xaa Xaa Tyr Xaa Met Asp Tyr
1               5                   10                  15

<210> SEQ ID NO 66
<211> LENGTH: 15
<212> TYPE: PRT
<213> ORGANISM: Artificial Sequence
```

```
<220> FEATURE:
<223> OTHER INFORMATION: Randomized CDRH3
<220> FEATURE:
<221> NAME/KEY: MISC_FEATURE
<222> LOCATION: (3)..(10)
<223> OTHER INFORMATION: Xaa is any naturally occurring amino acid
<220> FEATURE:
<221> NAME/KEY: MISC_FEATURE
<222> LOCATION: (11)..(11)
<223> OTHER INFORMATION: Xaa is Trp, Ser, Ala or Gly
<220> FEATURE:
<221> NAME/KEY: MISC_FEATURE
<222> LOCATION: (12)..(12)
<223> OTHER INFORMATION: Xaa is Ala, Gly or Val

<400> SEQUENCE: 66

Ala Arg Xaa Xaa Xaa Xaa Xaa Xaa Xaa Xaa Xaa Xaa Met Asp Tyr
1               5                   10                  15

<210> SEQ ID NO 67
<211> LENGTH: 10
<212> TYPE: PRT
<213> ORGANISM: Artificial Sequence
<220> FEATURE:
<223> OTHER INFORMATION: Randomized CDRH3
<220> FEATURE:
<221> NAME/KEY: MISC_FEATURE
<222> LOCATION: (2)..(2)
<223> OTHER INFORMATION: Xaa is Arg or Lys
<220> FEATURE:
<221> NAME/KEY: MISC_FEATURE
<222> LOCATION: (3)..(7)
<223> OTHER INFORMATION: Xaa is any naturally occurring amino acid

<400> SEQUENCE: 67

Ala Xaa Xaa Xaa Xaa Xaa Xaa Phe Asp Tyr
1               5                   10

<210> SEQ ID NO 68
<211> LENGTH: 11
<212> TYPE: PRT
<213> ORGANISM: Artificial Sequence
<220> FEATURE:
<223> OTHER INFORMATION: Randomized CDRH3
<220> FEATURE:
<221> NAME/KEY: MISC_FEATURE
<222> LOCATION: (2)..(2)
<223> OTHER INFORMATION: Xaa is Arg or Lys
<220> FEATURE:
<221> NAME/KEY: MISC_FEATURE
<222> LOCATION: (3)..(8)
<223> OTHER INFORMATION: Xaa is any naturally occurring amino acid

<400> SEQUENCE: 68

Ala Xaa Xaa Xaa Xaa Xaa Xaa Xaa Phe Asp Tyr
1               5                   10

<210> SEQ ID NO 69
<211> LENGTH: 12
<212> TYPE: PRT
<213> ORGANISM: Artificial Sequence
<220> FEATURE:
<223> OTHER INFORMATION: Embodiment of oligonucleotide for randomized
      CDRH3
<220> FEATURE:
<221> NAME/KEY: MISC_FEATURE
<222> LOCATION: (2)..(2)
<223> OTHER INFORMATION: Xaa is Arg or Lys
<220> FEATURE:
<221> NAME/KEY: MISC_FEATURE
<222> LOCATION: (3)..(9)
<223> OTHER INFORMATION: Xaa is any naturally occurring amino acid

<400> SEQUENCE: 69
```

Ala Xaa Xaa Xaa Xaa Xaa Xaa Xaa Phe Asp Tyr
1               5                   10

<210> SEQ ID NO 70
<211> LENGTH: 9
<212> TYPE: PRT
<213> ORGANISM: Artificial Sequence
<220> FEATURE:
<223> OTHER INFORMATION: Randomized CDRH3
<220> FEATURE:
<221> NAME/KEY: MISC_FEATURE
<222> LOCATION: (2)..(2)
<223> OTHER INFORMATION: Xaa is Arg or Lys
<220> FEATURE:
<221> NAME/KEY: MISC_FEATURE
<222> LOCATION: (3)..(6)
<223> OTHER INFORMATION: Xaa is any naturally occurring amino acid

<400> SEQUENCE: 70

Ala Xaa Xaa Xaa Xaa Xaa Phe Asp Tyr
1               5

<210> SEQ ID NO 71
<211> LENGTH: 12
<212> TYPE: PRT
<213> ORGANISM: Artificial Sequence
<220> FEATURE:
<223> OTHER INFORMATION: Randomized CDRH3
<220> FEATURE:
<221> NAME/KEY: MISC_FEATURE
<222> LOCATION: (2)..(2)
<223> OTHER INFORMATION: Xaa is Arg or Lys
<220> FEATURE:
<221> NAME/KEY: MISC_FEATURE
<222> LOCATION: (3)..(9)
<223> OTHER INFORMATION: Xaa is any naturally occurring amino acid

<400> SEQUENCE: 71

Ala Xaa Xaa Xaa Xaa Xaa Xaa Xaa Xaa Phe Asp Tyr
1               5                   10

<210> SEQ ID NO 72
<211> LENGTH: 13
<212> TYPE: PRT
<213> ORGANISM: Artificial Sequence
<220> FEATURE:
<223> OTHER INFORMATION: Randomized CDRH3
<220> FEATURE:
<221> NAME/KEY: MISC_FEATURE
<222> LOCATION: (2)..(2)
<223> OTHER INFORMATION: Xaa is Arg or Lys
<220> FEATURE:
<221> NAME/KEY: MISC_FEATURE
<222> LOCATION: (3)..(10)
<223> OTHER INFORMATION: Xaa is any naturally occurring amino acid

<400> SEQUENCE: 72

Ala Xaa Xaa Xaa Xaa Xaa Xaa Xaa Xaa Xaa Phe Asp Tyr
1               5                   10

<210> SEQ ID NO 73
<211> LENGTH: 16
<212> TYPE: PRT
<213> ORGANISM: Artificial Sequence
<220> FEATURE:
<223> OTHER INFORMATION: Randomized CDRH3
<220> FEATURE:
<221> NAME/KEY: MISC_FEATURE
<222> LOCATION: (2)..(2)
<223> OTHER INFORMATION: Xaa is Arg or Lys
<220> FEATURE:
<221> NAME/KEY: MISC_FEATURE

```
<222> LOCATION: (3)..(11)
<223> OTHER INFORMATION: Xaa is any naturally occurring amino acid

<400> SEQUENCE: 73

Ala Xaa Xaa Xaa Xaa Xaa Xaa Xaa Xaa Xaa Xaa Tyr Ala Met Asp Tyr
1               5                   10                  15

<210> SEQ ID NO 74
<211> LENGTH: 15
<212> TYPE: PRT
<213> ORGANISM: Artificial Sequence
<220> FEATURE:
<223> OTHER INFORMATION: Embodiment of oligonucleotide for randomized
      CDRH3
<220> FEATURE:
<221> NAME/KEY: MISC_FEATURE
<222> LOCATION: (2)..(2)
<223> OTHER INFORMATION: Xaa is Arg or Lys
<220> FEATURE:
<221> NAME/KEY: MISC_FEATURE
<222> LOCATION: (3)..(10)
<223> OTHER INFORMATION: Xaa is any naturally occurring amino acid
<220> FEATURE:
<221> NAME/KEY: MISC_FEATURE
<222> LOCATION: (12)..(12)
<223> OTHER INFORMATION: Xaa is Ala, Val or Gly

<400> SEQUENCE: 74

Ala Xaa Xaa Xaa Xaa Xaa Xaa Xaa Xaa Xaa Tyr Xaa Met Asp Tyr
1               5                   10                  15

<210> SEQ ID NO 75
<211> LENGTH: 17
<212> TYPE: PRT
<213> ORGANISM: Artificial Sequence
<220> FEATURE:
<223> OTHER INFORMATION: Randomized CDRH3
<220> FEATURE:
<221> NAME/KEY: MISC_FEATURE
<222> LOCATION: (2)..(2)
<223> OTHER INFORMATION: Xaa is Arg or Lys
<220> FEATURE:
<221> NAME/KEY: MISC_FEATURE
<222> LOCATION: (3)..(12)
<223> OTHER INFORMATION: Xaa is any naturally occurring amino acid
<220> FEATURE:
<221> NAME/KEY: MISC_FEATURE
<222> LOCATION: (14)..(14)
<223> OTHER INFORMATION: Xaa is Ala, Val or Gly

<400> SEQUENCE: 75

Ala Xaa Xaa Xaa Xaa Xaa Xaa Xaa Xaa Xaa Xaa Xaa Tyr Xaa Met Asp
1               5                   10                  15

Tyr

<210> SEQ ID NO 76
<211> LENGTH: 7
<212> TYPE: PRT
<213> ORGANISM: Artificial Sequence
<220> FEATURE:
<223> OTHER INFORMATION: 4D5 Heavy chain CDR

<400> SEQUENCE: 76

Trp Gly Gly Asp Gly Phe Tyr
1               5

<210> SEQ ID NO 77
<211> LENGTH: 11
<212> TYPE: PRT
<213> ORGANISM: Artificial Sequence
<220> FEATURE:
```

<223> OTHER INFORMATION: CDRH3

<400> SEQUENCE: 77

Ser Arg Trp Lys Tyr Ala Thr Arg Tyr Ala Met
1               5                   10

<210> SEQ ID NO 78
<211> LENGTH: 11
<212> TYPE: PRT
<213> ORGANISM: Artificial Sequence
<220> FEATURE:
<223> OTHER INFORMATION: CDRH3

<400> SEQUENCE: 78

Ser Arg Ser Arg Gly Trp Trp Thr Ala Ala Met
1               5                   10

<210> SEQ ID NO 79
<211> LENGTH: 11
<212> TYPE: PRT
<213> ORGANISM: Artificial Sequence
<220> FEATURE:
<223> OTHER INFORMATION: CDRH3

<400> SEQUENCE: 79

Ser Arg Ala Ser Arg Asp Trp Tyr Gly Ala Met
1               5                   10

<210> SEQ ID NO 80
<211> LENGTH: 5
<212> TYPE: PRT
<213> ORGANISM: Artificial Sequence
<220> FEATURE:
<223> OTHER INFORMATION: CDRH1

<400> SEQUENCE: 80

Thr Thr Ser Asn Gly
1               5

<210> SEQ ID NO 81
<211> LENGTH: 8
<212> TYPE: PRT
<213> ORGANISM: Artificial Sequence
<220> FEATURE:
<223> OTHER INFORMATION: CDRH2

<400> SEQUENCE: 81

Ala Tyr Ser Ser Asn Tyr Tyr Arg
1               5

<210> SEQ ID NO 82
<211> LENGTH: 9
<212> TYPE: PRT
<213> ORGANISM: Artificial Sequence
<220> FEATURE:
<223> OTHER INFORMATION: CDRH3

<400> SEQUENCE: 82

Ala Arg Trp Ser Arg Ala Ser Phe Tyr
1               5

<210> SEQ ID NO 83
<211> LENGTH: 5
<212> TYPE: PRT
<213> ORGANISM: Artificial Sequence
<220> FEATURE:
<223> OTHER INFORMATION: CDRH1

```
<400> SEQUENCE: 83

Thr Thr Gly Thr Asp
1               5

<210> SEQ ID NO 84
<211> LENGTH: 8
<212> TYPE: PRT
<213> ORGANISM: Artificial Sequence
<220> FEATURE:
<223> OTHER INFORMATION: CDRH2

<400> SEQUENCE: 84

Ala Ile Thr Tyr Asp Ser Tyr Arg
1               5

<210> SEQ ID NO 85
<211> LENGTH: 9
<212> TYPE: PRT
<213> ORGANISM: Artificial Sequence
<220> FEATURE:
<223> OTHER INFORMATION: CDRH3

<400> SEQUENCE: 85

Ala Lys Ala Gly Asp Arg Glu Gly Tyr
1               5

<210> SEQ ID NO 86
<211> LENGTH: 5
<212> TYPE: PRT
<213> ORGANISM: Artificial Sequence
<220> FEATURE:
<223> OTHER INFORMATION: CDRH1

<400> SEQUENCE: 86

Thr Thr Asp Ser Gly
1               5

<210> SEQ ID NO 87
<211> LENGTH: 8
<212> TYPE: PRT
<213> ORGANISM: Artificial Sequence
<220> FEATURE:
<223> OTHER INFORMATION: CDRH2

<400> SEQUENCE: 87

Gly Arg Ser Tyr Ser Ser Asn Arg
1               5

<210> SEQ ID NO 88
<211> LENGTH: 9
<212> TYPE: PRT
<213> ORGANISM: Artificial Sequence
<220> FEATURE:
<223> OTHER INFORMATION: CDRH3

<400> SEQUENCE: 88

Ala Lys Trp Pro Trp Tyr Asn Ala Trp
1               5

<210> SEQ ID NO 89
<211> LENGTH: 5
<212> TYPE: PRT
<213> ORGANISM: Artificial Sequence
<220> FEATURE:
<223> OTHER INFORMATION: CDRH1

<400> SEQUENCE: 89
```

```
Thr Asn Asn Tyr Trp
1               5

<210> SEQ ID NO 90
<211> LENGTH: 7
<212> TYPE: PRT
<213> ORGANISM: Artificial Sequence
<220> FEATURE:
<223> OTHER INFORMATION: CDRH2

<400> SEQUENCE: 90

Gly Tyr Ser Tyr Gly Thr Arg
1               5

<210> SEQ ID NO 91
<211> LENGTH: 9
<212> TYPE: PRT
<213> ORGANISM: Artificial Sequence
<220> FEATURE:
<223> OTHER INFORMATION: CDRH3
<220> FEATURE:
<221> NAME/KEY: MISC_FEATURE
<222> LOCATION: (4)..(4)
<223> OTHER INFORMATION: Xaa is unknown

<400> SEQUENCE: 91

Ala Lys Ala Xaa Lys Gly Ser Leu Tyr
1               5

<210> SEQ ID NO 92
<211> LENGTH: 5
<212> TYPE: PRT
<213> ORGANISM: Artificial Sequence
<220> FEATURE:
<223> OTHER INFORMATION: CDRH1

<400> SEQUENCE: 92

Thr Thr Gly Asn Ala
1               5

<210> SEQ ID NO 93
<211> LENGTH: 5
<212> TYPE: PRT
<213> ORGANISM: Artificial Sequence
<220> FEATURE:
<223> OTHER INFORMATION: CDRH1

<400> SEQUENCE: 93

Thr Asn Asp Tyr Tyr
1               5

<210> SEQ ID NO 94
<211> LENGTH: 5
<212> TYPE: PRT
<213> ORGANISM: Artificial Sequence
<220> FEATURE:
<223> OTHER INFORMATION: CDRH1

<400> SEQUENCE: 94

Thr Ser Asn Thr Gly
1               5

<210> SEQ ID NO 95
<211> LENGTH: 5
<212> TYPE: PRT
<213> ORGANISM: Artificial Sequence
<220> FEATURE:
<223> OTHER INFORMATION: CDRH1
```

```
<400> SEQUENCE: 95

Thr Thr Ser Tyr Gly
1               5

<210> SEQ ID NO 96
<211> LENGTH: 7
<212> TYPE: PRT
<213> ORGANISM: Artificial Sequence
<220> FEATURE:
<223> OTHER INFORMATION: CDRH2

<400> SEQUENCE: 96

Ala Ser Ser Tyr Ser Tyr Arg
1               5

<210> SEQ ID NO 97
<211> LENGTH: 9
<212> TYPE: PRT
<213> ORGANISM: Artificial Sequence
<220> FEATURE:
<223> OTHER INFORMATION: CDRH3
<220> FEATURE:
<221> NAME/KEY: MISC_FEATURE
<222> LOCATION: (4)..(4)
<223> OTHER INFORMATION: Xaa is unknown
<220> FEATURE:
<221> NAME/KEY: MISC_FEATURE
<222> LOCATION: (9)..(9)
<223> OTHER INFORMATION: Xaa is unknown

<400> SEQUENCE: 97

Ala Lys Tyr Xaa Ala Arg Glu Gly Xaa
1               5

<210> SEQ ID NO 98
<211> LENGTH: 5
<212> TYPE: PRT
<213> ORGANISM: Artificial Sequence
<220> FEATURE:
<223> OTHER INFORMATION: CDRH1

<400> SEQUENCE: 98

Thr Asn Asn Asn Ser
1               5

<210> SEQ ID NO 99
<211> LENGTH: 7
<212> TYPE: PRT
<213> ORGANISM: Artificial Sequence
<220> FEATURE:
<223> OTHER INFORMATION: CDRH2

<400> SEQUENCE: 99

Gly Tyr Asn Ser Gly Ser Arg
1               5

<210> SEQ ID NO 100
<211> LENGTH: 9
<212> TYPE: PRT
<213> ORGANISM: Artificial Sequence
<220> FEATURE:
<223> OTHER INFORMATION: CDRH3

<400> SEQUENCE: 100

Ala Lys Trp Arg Thr Ser Trp Lys Tyr
1               5

<210> SEQ ID NO 101
```

```
<211> LENGTH: 5
<212> TYPE: PRT
<213> ORGANISM: Artificial Sequence
<220> FEATURE:
<223> OTHER INFORMATION: CDRH1

<400> SEQUENCE: 101

Thr Ser Ser Ser Ala
1               5

<210> SEQ ID NO 102
<211> LENGTH: 7
<212> TYPE: PRT
<213> ORGANISM: Artificial Sequence
<220> FEATURE:
<223> OTHER INFORMATION: CDRH2

<400> SEQUENCE: 102

Ala Trp Ser Asn Gly Ser Arg
1               5

<210> SEQ ID NO 103
<211> LENGTH: 9
<212> TYPE: PRT
<213> ORGANISM: Artificial Sequence
<220> FEATURE:
<223> OTHER INFORMATION: CDRH3
<220> FEATURE:
<221> NAME/KEY: MISC_FEATURE
<222> LOCATION: (2)..(2)
<223> OTHER INFORMATION: Xaa is unknown

<400> SEQUENCE: 103

Ala Xaa Thr Ala Gly Gly Ala Lys Tyr
1               5

<210> SEQ ID NO 104
<211> LENGTH: 5
<212> TYPE: PRT
<213> ORGANISM: Artificial Sequence
<220> FEATURE:
<223> OTHER INFORMATION: CDRH1

<400> SEQUENCE: 104

Thr Thr Asn Thr Trp
1               5

<210> SEQ ID NO 105
<211> LENGTH: 7
<212> TYPE: PRT
<213> ORGANISM: Artificial Sequence
<220> FEATURE:
<223> OTHER INFORMATION: CDRH2

<400> SEQUENCE: 105

Gly Asp Tyr Asp Gly Tyr Arg
1               5

<210> SEQ ID NO 106
<211> LENGTH: 9
<212> TYPE: PRT
<213> ORGANISM: Artificial Sequence
<220> FEATURE:
<223> OTHER INFORMATION: CDRH3
<220> FEATURE:
<221> NAME/KEY: MISC_FEATURE
<222> LOCATION: (2)..(2)
<223> OTHER INFORMATION: Xaa is unknown

<400> SEQUENCE: 106
```

```
Ala Xaa Trp Arg Trp Trp Gly Arg Tyr
1               5
```

<210> SEQ ID NO 107
<211> LENGTH: 5
<212> TYPE: PRT
<213> ORGANISM: Artificial Sequence
<220> FEATURE:
<223> OTHER INFORMATION: CDRH1

<400> SEQUENCE: 107

```
Thr Asn Gly Asn Tyr
1               5
```

<210> SEQ ID NO 108
<211> LENGTH: 7
<212> TYPE: PRT
<213> ORGANISM: Artificial Sequence
<220> FEATURE:
<223> OTHER INFORMATION: CDRH2

<400> SEQUENCE: 108

```
Gly Trp Ser Asn Gly Tyr Arg
1               5
```

<210> SEQ ID NO 109
<211> LENGTH: 9
<212> TYPE: PRT
<213> ORGANISM: Artificial Sequence
<220> FEATURE:
<223> OTHER INFORMATION: CDRH3

<400> SEQUENCE: 109

```
Ala Arg Tyr Ser Gly Gly Arg Arg Tyr
1               5
```

<210> SEQ ID NO 110
<211> LENGTH: 5
<212> TYPE: PRT
<213> ORGANISM: Artificial Sequence
<220> FEATURE:
<223> OTHER INFORMATION: CDRH1

<400> SEQUENCE: 110

```
Thr Ser Asn Asn Ala
1               5
```

<210> SEQ ID NO 111
<211> LENGTH: 7
<212> TYPE: PRT
<213> ORGANISM: Artificial Sequence
<220> FEATURE:
<223> OTHER INFORMATION: CDRH2

<400> SEQUENCE: 111

```
Gly Arg Ser Tyr Asn Tyr Arg
1               5
```

<210> SEQ ID NO 112
<211> LENGTH: 9
<212> TYPE: PRT
<213> ORGANISM: Artificial Sequence
<220> FEATURE:
<223> OTHER INFORMATION: CDRH3
<220> FEATURE:
<221> NAME/KEY: MISC_FEATURE
<222> LOCATION: (2)..(2)
<223> OTHER INFORMATION: Xaa is unknown

```
<220> FEATURE:
<221> NAME/KEY: MISC_FEATURE
<222> LOCATION: (4)..(4)
<223> OTHER INFORMATION: Xaa is unknown

<400> SEQUENCE: 112

Ala Xaa Gly Xaa Thr Ser Gly Gly Tyr
1               5

<210> SEQ ID NO 113
<211> LENGTH: 5
<212> TYPE: PRT
<213> ORGANISM: Artificial Sequence
<220> FEATURE:
<223> OTHER INFORMATION: CDRH1

<400> SEQUENCE: 113

Thr Thr Ser Asn Asp
1               5

<210> SEQ ID NO 114
<211> LENGTH: 7
<212> TYPE: PRT
<213> ORGANISM: Artificial Sequence
<220> FEATURE:
<223> OTHER INFORMATION: CDRH2

<400> SEQUENCE: 114

Ala Trp Ser Tyr Asn Tyr Arg
1               5

<210> SEQ ID NO 115
<211> LENGTH: 9
<212> TYPE: PRT
<213> ORGANISM: Artificial Sequence
<220> FEATURE:
<223> OTHER INFORMATION: CDRH3

<400> SEQUENCE: 115

Ala Arg Arg Ser Arg Trp Ser Arg Ala
1               5

<210> SEQ ID NO 116
<211> LENGTH: 5
<212> TYPE: PRT
<213> ORGANISM: Artificial Sequence
<220> FEATURE:
<223> OTHER INFORMATION: CDRH1

<400> SEQUENCE: 116

Thr Gly Asn Ser Trp
1               5

<210> SEQ ID NO 117
<211> LENGTH: 6
<212> TYPE: PRT
<213> ORGANISM: Artificial Sequence
<220> FEATURE:
<223> OTHER INFORMATION: CDRH2

<400> SEQUENCE: 117

Val Ala Thr Tyr Tyr Asn
1               5

<210> SEQ ID NO 118
<211> LENGTH: 7
<212> TYPE: PRT
<213> ORGANISM: Artificial Sequence
```

```
<220> FEATURE:
<223> OTHER INFORMATION: CDRH3

<400> SEQUENCE: 118

Trp Gly Ala Lys Gly Thr Trp
1               5

<210> SEQ ID NO 119
<211> LENGTH: 5
<212> TYPE: PRT
<213> ORGANISM: Artificial Sequence
<220> FEATURE:
<223> OTHER INFORMATION: CDRH1

<400> SEQUENCE: 119

Asn Ala Asp Ser Ala
1               5

<210> SEQ ID NO 120
<211> LENGTH: 6
<212> TYPE: PRT
<213> ORGANISM: Artificial Sequence
<220> FEATURE:
<223> OTHER INFORMATION: CDRH2

<400> SEQUENCE: 120

Tyr Ala Tyr Asp Tyr Tyr
1               5

<210> SEQ ID NO 121
<211> LENGTH: 7
<212> TYPE: PRT
<213> ORGANISM: Artificial Sequence
<220> FEATURE:
<223> OTHER INFORMATION: CDRH3

<400> SEQUENCE: 121

Trp Gly Trp Thr Thr Asn Gly
1               5

<210> SEQ ID NO 122
<211> LENGTH: 5
<212> TYPE: PRT
<213> ORGANISM: Artificial Sequence
<220> FEATURE:
<223> OTHER INFORMATION: CDRH1

<400> SEQUENCE: 122

Asn Asp Asn Thr Ala
1               5

<210> SEQ ID NO 123
<211> LENGTH: 6
<212> TYPE: PRT
<213> ORGANISM: Artificial Sequence
<220> FEATURE:
<223> OTHER INFORMATION: CDRH2

<400> SEQUENCE: 123

Val Ser His Asp Thr Tyr
1               5

<210> SEQ ID NO 124
<211> LENGTH: 7
<212> TYPE: PRT
<213> ORGANISM: Artificial Sequence
<220> FEATURE:
<223> OTHER INFORMATION: CDRH3
```

```
<400> SEQUENCE: 124

Trp Gly Trp Glu Thr Asp Gly
1               5

<210> SEQ ID NO 125
<211> LENGTH: 6
<212> TYPE: PRT
<213> ORGANISM: Artificial Sequence
<220> FEATURE:
<223> OTHER INFORMATION: CDRH2

<400> SEQUENCE: 125

Leu Asp Ser Ser Tyr Asp
1               5

<210> SEQ ID NO 126
<211> LENGTH: 7
<212> TYPE: PRT
<213> ORGANISM: Artificial Sequence
<220> FEATURE:
<223> OTHER INFORMATION: CDRH3

<400> SEQUENCE: 126

Ser Arg Ala Gly Tyr Thr Tyr
1               5

<210> SEQ ID NO 127
<211> LENGTH: 5
<212> TYPE: PRT
<213> ORGANISM: Artificial Sequence
<220> FEATURE:
<223> OTHER INFORMATION: CDRH1

<400> SEQUENCE: 127

Asn Gly Lys Ser Ser
1               5

<210> SEQ ID NO 128
<211> LENGTH: 6
<212> TYPE: PRT
<213> ORGANISM: Artificial Sequence
<220> FEATURE:
<223> OTHER INFORMATION: CDRH2

<400> SEQUENCE: 128

Trp Ser Tyr Glu Ala Ala
1               5

<210> SEQ ID NO 129
<211> LENGTH: 7
<212> TYPE: PRT
<213> ORGANISM: Artificial Sequence
<220> FEATURE:
<223> OTHER INFORMATION: CDRH3

<400> SEQUENCE: 129

Thr Ser Trp Ser Lys Pro Tyr
1               5

<210> SEQ ID NO 130
<211> LENGTH: 5
<212> TYPE: PRT
<213> ORGANISM: Artificial Sequence
<220> FEATURE:
<223> OTHER INFORMATION: CDRH1

<400> SEQUENCE: 130
```

Asn Thr Ala Tyr Gly
1               5

<210> SEQ ID NO 131
<211> LENGTH: 6
<212> TYPE: PRT
<213> ORGANISM: Artificial Sequence
<220> FEATURE:
<223> OTHER INFORMATION: CDRH2

<400> SEQUENCE: 131

Val Thr Tyr Asp Asp Thr
1               5

<210> SEQ ID NO 132
<211> LENGTH: 7
<212> TYPE: PRT
<213> ORGANISM: Artificial Sequence
<220> FEATURE:
<223> OTHER INFORMATION: CDRH3

<400> SEQUENCE: 132

Trp Gly Trp Glu Ala Asn Trp
1               5

<210> SEQ ID NO 133
<211> LENGTH: 5
<212> TYPE: PRT
<213> ORGANISM: Artificial Sequence
<220> FEATURE:
<223> OTHER INFORMATION: CDRH1

<400> SEQUENCE: 133

Thr Gly Gly Ser Trp
1               5

<210> SEQ ID NO 134
<211> LENGTH: 6
<212> TYPE: PRT
<213> ORGANISM: Artificial Sequence
<220> FEATURE:
<223> OTHER INFORMATION: CDRH2

<400> SEQUENCE: 134

Val Tyr Thr Tyr Tyr Asp
1               5

<210> SEQ ID NO 135
<211> LENGTH: 7
<212> TYPE: PRT
<213> ORGANISM: Artificial Sequence
<220> FEATURE:
<223> OTHER INFORMATION: CDRH3

<400> SEQUENCE: 135

Trp Gly Ala Gly Gly Thr Trp
1               5

<210> SEQ ID NO 136
<211> LENGTH: 6
<212> TYPE: PRT
<213> ORGANISM: Artificial Sequence
<220> FEATURE:
<223> OTHER INFORMATION: CDRH2

<400> SEQUENCE: 136

Val Ser Asp Tyr Tyr Asp

```
1               5

<210> SEQ ID NO 137
<211> LENGTH: 7
<212> TYPE: PRT
<213> ORGANISM: Artificial Sequence
<220> FEATURE:
<223> OTHER INFORMATION: CDRH3

<400> SEQUENCE: 137

Trp Gly Ser Gly Tyr Thr Trp
1               5

<210> SEQ ID NO 138
<211> LENGTH: 5
<212> TYPE: PRT
<213> ORGANISM: Artificial Sequence
<220> FEATURE:
<223> OTHER INFORMATION: CDRH1

<400> SEQUENCE: 138

Ser Ala Gly Tyr Asp
1               5

<210> SEQ ID NO 139
<211> LENGTH: 6
<212> TYPE: PRT
<213> ORGANISM: Artificial Sequence
<220> FEATURE:
<223> OTHER INFORMATION: CDRH2

<400> SEQUENCE: 139

Leu Ala Tyr Ala Tyr Asn
1               5

<210> SEQ ID NO 140
<211> LENGTH: 7
<212> TYPE: PRT
<213> ORGANISM: Artificial Sequence
<220> FEATURE:
<223> OTHER INFORMATION: CDRH3

<400> SEQUENCE: 140

Ala Ala Ala Trp Ala Ser Tyr
1               5

<210> SEQ ID NO 141
<211> LENGTH: 5
<212> TYPE: PRT
<213> ORGANISM: Artificial Sequence
<220> FEATURE:
<223> OTHER INFORMATION: CDRH1

<400> SEQUENCE: 141

Thr Thr Glu Ser Gly
1               5

<210> SEQ ID NO 142
<211> LENGTH: 6
<212> TYPE: PRT
<213> ORGANISM: Artificial Sequence
<220> FEATURE:
<223> OTHER INFORMATION: CDRH2

<400> SEQUENCE: 142

Val Tyr His Asp Lys Tyr
1               5
```

```
<210> SEQ ID NO 143
<211> LENGTH: 7
<212> TYPE: PRT
<213> ORGANISM: Artificial Sequence
<220> FEATURE:
<223> OTHER INFORMATION: CDRH3

<400> SEQUENCE: 143

Trp Trp Tyr Ser Trp Asn Trp
1               5

<210> SEQ ID NO 144
<211> LENGTH: 11
<212> TYPE: PRT
<213> ORGANISM: Artificial Sequence
<220> FEATURE:
<223> OTHER INFORMATION: Randomized CDRH3
<220> FEATURE:
<221> NAME/KEY: MISC_FEATURE
<222> LOCATION: (2)..(2)
<223> OTHER INFORMATION: Xaa is Arg or Lys
<220> FEATURE:
<221> NAME/KEY: MISC_FEATURE
<222> LOCATION: (3)..(6)
<223> OTHER INFORMATION: Xaa is any naturally occurring amino acid

<400> SEQUENCE: 144

Ala Xaa Xaa Xaa Xaa Xaa Tyr Ala Met Asp Tyr
1               5                   10

<210> SEQ ID NO 145
<211> LENGTH: 11
<212> TYPE: PRT
<213> ORGANISM: Artificial Sequence
<220> FEATURE:
<223> OTHER INFORMATION: Randomized CDRH3
<220> FEATURE:
<221> NAME/KEY: MISC_FEATURE
<222> LOCATION: (2)..(2)
<223> OTHER INFORMATION: Xaa is Arg or Lys
<220> FEATURE:
<221> NAME/KEY: MISC_FEATURE
<222> LOCATION: (3)..(6)
<223> OTHER INFORMATION: Xaa is any naturally occurring amino acid
<220> FEATURE:
<221> NAME/KEY: MISC_FEATURE
<222> LOCATION: (7)..(7)
<223> OTHER INFORMATION: Xaa is Trp, Ser, Ala or Gly

<400> SEQUENCE: 145

Ala Xaa Xaa Xaa Xaa Xaa Xaa Ala Met Asp Tyr
1               5                   10

<210> SEQ ID NO 146
<211> LENGTH: 13
<212> TYPE: PRT
<213> ORGANISM: Artificial Sequence
<220> FEATURE:
<223> OTHER INFORMATION: Randomized CDRH3
<220> FEATURE:
<221> NAME/KEY: MISC_FEATURE
<222> LOCATION: (2)..(2)
<223> OTHER INFORMATION: Xaa is Arg, His, Ser or Asn
<220> FEATURE:
<221> NAME/KEY: MISC_FEATURE
<222> LOCATION: (3)..(8)
<223> OTHER INFORMATION: Xaa is any naturally occurring amino acid
<220> FEATURE:
<221> NAME/KEY: MISC_FEATURE
<222> LOCATION: (9)..(9)
<223> OTHER INFORMATION: Xaa is Trp, Ser, Ala or Gly
<220> FEATURE:
<221> NAME/KEY: MISC_FEATURE
```

```
<222> LOCATION: (10)..(10)
<223> OTHER INFORMATION: Xaa is Ala, Val, Gly or Asp

<400> SEQUENCE: 146

Ala Xaa Xaa Xaa Xaa Xaa Xaa Xaa Xaa Xaa Met Asp Tyr
1               5                   10

<210> SEQ ID NO 147
<211> LENGTH: 13
<212> TYPE: PRT
<213> ORGANISM: Artificial Sequence
<220> FEATURE:
<223> OTHER INFORMATION: Randomized CDRH3
<220> FEATURE:
<221> NAME/KEY: MISC_FEATURE
<222> LOCATION: (2)..(2)
<223> OTHER INFORMATION: Xaa is Arg, His, Ser or Asn
<220> FEATURE:
<221> NAME/KEY: MISC_FEATURE
<222> LOCATION: (3)..(8)
<223> OTHER INFORMATION: Xaa is any naturally occurring amino acid
<220> FEATURE:
<221> NAME/KEY: MISC_FEATURE
<222> LOCATION: (10)..(10)
<223> OTHER INFORMATION: Xaa is Ala, Val, Gly or Asp

<400> SEQUENCE: 147

Ala Xaa Xaa Xaa Xaa Xaa Xaa Xaa Tyr Xaa Met Asp Tyr
1               5                   10

<210> SEQ ID NO 148
<211> LENGTH: 14
<212> TYPE: PRT
<213> ORGANISM: Artificial Sequence
<220> FEATURE:
<223> OTHER INFORMATION: Randomized CDRH3
<220> FEATURE:
<221> NAME/KEY: MISC_FEATURE
<222> LOCATION: (3)..(11)
<223> OTHER INFORMATION: Xaa is any naturally occurring amino acid
<220> FEATURE:
<221> NAME/KEY: MISC_FEATURE
<222> LOCATION: (12)..(12)
<223> OTHER INFORMATION: Xaa is Phe or Leu

<400> SEQUENCE: 148

Ala Arg Xaa Xaa Xaa Xaa Xaa Xaa Xaa Xaa Xaa Xaa Asp Tyr
1               5                   10

<210> SEQ ID NO 149
<211> LENGTH: 14
<212> TYPE: PRT
<213> ORGANISM: Artificial Sequence
<220> FEATURE:
<223> OTHER INFORMATION: Randomized CDRH3
<220> FEATURE:
<221> NAME/KEY: MISC_FEATURE
<222> LOCATION: (2)..(2)
<223> OTHER INFORMATION: Xaa is Arg or Lys
<220> FEATURE:
<221> NAME/KEY: MISC_FEATURE
<222> LOCATION: (3)..(9)
<223> OTHER INFORMATION: Xaa is any naturally occurring amino acid
<220> FEATURE:
<221> NAME/KEY: MISC_FEATURE
<222> LOCATION: (10)..(10)
<223> OTHER INFORMATION: Xaa is Trp, Ser, Ala or Gly

<400> SEQUENCE: 149

Ala Xaa Xaa Xaa Xaa Xaa Xaa Xaa Xaa Xaa Ala Met Asp Tyr
1               5                   10
```

```
<210> SEQ ID NO 150
<211> LENGTH: 14
<212> TYPE: PRT
<213> ORGANISM: Artificial Sequence
<220> FEATURE:
<223> OTHER INFORMATION: Randomized CDRH3
<220> FEATURE:
<221> NAME/KEY: MISC_FEATURE
<222> LOCATION: (2)..(2)
<223> OTHER INFORMATION: Xaa is Arg, His, Ser or Asn
<220> FEATURE:
<221> NAME/KEY: MISC_FEATURE
<222> LOCATION: (3)..(9)
<223> OTHER INFORMATION: Xaa is any naturally occurring amino acid
<220> FEATURE:
<221> NAME/KEY: MISC_FEATURE
<222> LOCATION: (10)..(10)
<223> OTHER INFORMATION: Xaa is Trp, Ser, Ala or Gly
<220> FEATURE:
<221> NAME/KEY: MISC_FEATURE
<222> LOCATION: (11)..(11)
<223> OTHER INFORMATION: Xaa is Ala, Val, Gly or Asp

<400> SEQUENCE: 150

Ala Xaa Xaa Xaa Xaa Xaa Xaa Xaa Xaa Xaa Xaa Met Asp Tyr
1               5                   10

<210> SEQ ID NO 151
<211> LENGTH: 14
<212> TYPE: PRT
<213> ORGANISM: Artificial Sequence
<220> FEATURE:
<223> OTHER INFORMATION: Randomized CDRH3
<220> FEATURE:
<221> NAME/KEY: MISC_FEATURE
<222> LOCATION: (2)..(2)
<223> OTHER INFORMATION: Xaa is Arg, His, Ser or Asn
<220> FEATURE:
<221> NAME/KEY: MISC_FEATURE
<222> LOCATION: (3)..(9)
<223> OTHER INFORMATION: Xaa is any naturally occurring amino acid
<220> FEATURE:
<221> NAME/KEY: MISC_FEATURE
<222> LOCATION: (11)..(11)
<223> OTHER INFORMATION: Xaa is Ala, Val, Gly or Asp

<400> SEQUENCE: 151

Ala Xaa Xaa Xaa Xaa Xaa Xaa Xaa Xaa Tyr Xaa Met Asp Tyr
1               5                   10

<210> SEQ ID NO 152
<211> LENGTH: 15
<212> TYPE: PRT
<213> ORGANISM: Artificial Sequence
<220> FEATURE:
<223> OTHER INFORMATION: Randomized CDRH3
<220> FEATURE:
<221> NAME/KEY: MISC_FEATURE
<222> LOCATION: (3)..(12)
<223> OTHER INFORMATION: Xaa is any naturally occurring amino acid
<220> FEATURE:
<221> NAME/KEY: MISC_FEATURE
<222> LOCATION: (13)..(13)
<223> OTHER INFORMATION: Xaa is Phe or Leu

<400> SEQUENCE: 152

Ala Arg Xaa Xaa Xaa Xaa Xaa Xaa Xaa Xaa Xaa Xaa Xaa Asp Tyr
1               5                   10                  15

<210> SEQ ID NO 153
<211> LENGTH: 15
<212> TYPE: PRT
<213> ORGANISM: Artificial Sequence
<220> FEATURE:
```

```
<223> OTHER INFORMATION: Randomized CDRH3
<220> FEATURE:
<221> NAME/KEY: MISC_FEATURE
<222> LOCATION: (2)..(2)
<223> OTHER INFORMATION: Xaa is Arg or Lys
<220> FEATURE:
<221> NAME/KEY: MISC_FEATURE
<222> LOCATION: (3)..(10)
<223> OTHER INFORMATION: Xaa is any naturally occurring amino acid

<400> SEQUENCE: 153

Ala Xaa Xaa Xaa Xaa Xaa Xaa Xaa Xaa Xaa Tyr Ala Met Asp Tyr
 1               5                  10                  15

<210> SEQ ID NO 154
<211> LENGTH: 15
<212> TYPE: PRT
<213> ORGANISM: Artificial Sequence
<220> FEATURE:
<223> OTHER INFORMATION: Randomized CDRH3
<220> FEATURE:
<221> NAME/KEY: MISC_FEATURE
<222> LOCATION: (2)..(2)
<223> OTHER INFORMATION: Xaa is Arg or Lys
<220> FEATURE:
<221> NAME/KEY: MISC_FEATURE
<222> LOCATION: (3)..(10)
<223> OTHER INFORMATION: Xaa is any naturally occurring amino acid
<220> FEATURE:
<221> NAME/KEY: MISC_FEATURE
<222> LOCATION: (11)..(11)
<223> OTHER INFORMATION: Xaa is Trp, Ser, Ala or Gly

<400> SEQUENCE: 154

Ala Xaa Xaa Xaa Xaa Xaa Xaa Xaa Xaa Xaa Xaa Ala Met Asp Tyr
 1               5                  10                  15

<210> SEQ ID NO 155
<211> LENGTH: 18
<212> TYPE: PRT
<213> ORGANISM: Artificial Sequence
<220> FEATURE:
<223> OTHER INFORMATION: Randomized CDRH3
<220> FEATURE:
<221> NAME/KEY: MISC_FEATURE
<222> LOCATION: (3)..(13)
<223> OTHER INFORMATION: Xaa is any naturally occurring amino acid
<220> FEATURE:
<221> NAME/KEY: MISC_FEATURE
<222> LOCATION: (14)..(14)
<223> OTHER INFORMATION: Xaa is Trp, Ser, Ala or Gly
<220> FEATURE:
<221> NAME/KEY: MISC_FEATURE
<222> LOCATION: (15)..(15)
<223> OTHER INFORMATION: Xaa is Ala, Val or Gly

<400> SEQUENCE: 155

Ala Arg Xaa Xaa Xaa Xaa Xaa Xaa Xaa Xaa Xaa Xaa Xaa Xaa Xaa Met
 1               5                  10                  15

Asp Tyr

<210> SEQ ID NO 156
<211> LENGTH: 18
<212> TYPE: PRT
<213> ORGANISM: Artificial Sequence
<220> FEATURE:
<223> OTHER INFORMATION: Randomized CDRH3
<220> FEATURE:
<221> NAME/KEY: MISC_FEATURE
<222> LOCATION: (3)..(13)
<223> OTHER INFORMATION: Xaa is any naturally occurring amino acid
<220> FEATURE:
<221> NAME/KEY: MISC_FEATURE
```

```
<222> LOCATION: (15)..(15)
<223> OTHER INFORMATION: Xaa is Ala, Val or Gly

<400> SEQUENCE: 156

Ala Arg Xaa Xaa Xaa Xaa Xaa Xaa Xaa Xaa Xaa Xaa Xaa Tyr Xaa Met
1               5                   10                  15

Asp Tyr

<210> SEQ ID NO 157
<211> LENGTH: 19
<212> TYPE: PRT
<213> ORGANISM: Artificial Sequence
<220> FEATURE:
<223> OTHER INFORMATION: Randomized CDRH3
<220> FEATURE:
<221> NAME/KEY: MISC_FEATURE
<222> LOCATION: (3)..(14)
<223> OTHER INFORMATION: Xaa is any naturally occurring amino acid
<220> FEATURE:
<221> NAME/KEY: MISC_FEATURE
<222> LOCATION: (15)..(15)
<223> OTHER INFORMATION: Xaa is Trp, His, Ala or Gly
<220> FEATURE:
<221> NAME/KEY: MISC_FEATURE
<222> LOCATION: (16)..(16)
<223> OTHER INFORMATION: Xaa is Ala, Val or Gly

<400> SEQUENCE: 157

Ala Arg Xaa Xaa Xaa Xaa Xaa Xaa Xaa Xaa Xaa Xaa Xaa Xaa Xaa Xaa
1               5                   10                  15

Met Asp Tyr

<210> SEQ ID NO 158
<211> LENGTH: 19
<212> TYPE: PRT
<213> ORGANISM: Artificial Sequence
<220> FEATURE:
<223> OTHER INFORMATION: Randomized CDRH3
<220> FEATURE:
<221> NAME/KEY: MISC_FEATURE
<222> LOCATION: (3)..(14)
<223> OTHER INFORMATION: Xaa is any naturally occurring amino acid
<220> FEATURE:
<221> NAME/KEY: MISC_FEATURE
<222> LOCATION: (16)..(16)
<223> OTHER INFORMATION: Xaa is Ala, Val or Gly

<400> SEQUENCE: 158

Ala Arg Xaa Xaa Xaa Xaa Xaa Xaa Xaa Xaa Xaa Xaa Xaa Xaa Tyr Xaa
1               5                   10                  15

Met Asp Tyr

<210> SEQ ID NO 159
<211> LENGTH: 20
<212> TYPE: PRT
<213> ORGANISM: Artificial Sequence
<220> FEATURE:
<223> OTHER INFORMATION: Randomized CDRH3
<220> FEATURE:
<221> NAME/KEY: MISC_FEATURE
<222> LOCATION: (3)..(15)
<223> OTHER INFORMATION: Xaa is any naturally occurring amino acid
<220> FEATURE:
<221> NAME/KEY: MISC_FEATURE
<222> LOCATION: (16)..(16)
<223> OTHER INFORMATION: Xaa is Trp, Ser, Ala or Gly
<220> FEATURE:
<221> NAME/KEY: MISC_FEATURE
<222> LOCATION: (17)..(17)
<223> OTHER INFORMATION: Xaa is Ala, Val or Gly
```

```
<400> SEQUENCE: 159

Ala Arg Xaa Xaa Xaa Xaa Xaa Xaa Xaa Xaa Xaa Xaa Xaa Xaa Xaa
1               5                   10                  15

Xaa Met Asp Tyr
        20

<210> SEQ ID NO 160
<211> LENGTH: 20
<212> TYPE: PRT
<213> ORGANISM: Artificial Sequence
<220> FEATURE:
<223> OTHER INFORMATION: Randomized CDRH3
<220> FEATURE:
<221> NAME/KEY: MISC_FEATURE
<222> LOCATION: (3)..(15)
<223> OTHER INFORMATION: Xaa is any naturally occurring amino acid
<220> FEATURE:
<221> NAME/KEY: MISC_FEATURE
<222> LOCATION: (17)..(17)
<223> OTHER INFORMATION: Xaa is Ala, Val or Gly

<400> SEQUENCE: 160

Ala Arg Xaa Xaa Xaa Xaa Xaa Xaa Xaa Xaa Xaa Xaa Xaa Xaa Tyr
1               5                   10                  15

Xaa Met Asp Tyr
        20

<210> SEQ ID NO 161
<211> LENGTH: 21
<212> TYPE: PRT
<213> ORGANISM: Artificial Sequence
<220> FEATURE:
<223> OTHER INFORMATION: Randomized CDRH3
<220> FEATURE:
<221> NAME/KEY: MISC_FEATURE
<222> LOCATION: (3)..(16)
<223> OTHER INFORMATION: Xaa is any naturally occurring amino acid
<220> FEATURE:
<221> NAME/KEY: MISC_FEATURE
<222> LOCATION: (18)..(18)
<223> OTHER INFORMATION: Xaa is Ala, Val or Gly

<400> SEQUENCE: 161

Ala Arg Xaa Xaa Xaa Xaa Xaa Xaa Xaa Xaa Xaa Xaa Xaa Xaa Xaa
1               5                   10                  15

Tyr Xaa Met Asp Tyr
        20

<210> SEQ ID NO 162
<211> LENGTH: 13
<212> TYPE: PRT
<213> ORGANISM: Artificial Sequence
<220> FEATURE:
<223> OTHER INFORMATION: Embodiment of oligonucleotide for CDRH3
<220> FEATURE:
<221> NAME/KEY: MISC_FEATURE
<222> LOCATION: (5)..(9)
<223> OTHER INFORMATION: Xaa is Ala, Cys, Asp, Glu, Gly, Lys, Asn, Arg,
      Ser, Tyr, Trp or Thr

<400> SEQUENCE: 162

Ser Arg Trp Gly Xaa Xaa Xaa Xaa Xaa Ala Met Asp Tyr
1               5                   10

<210> SEQ ID NO 163
<211> LENGTH: 5
<212> TYPE: PRT
<213> ORGANISM: Artificial Sequence
<220> FEATURE:
```

```
<223> OTHER INFORMATION: C-Terminal of CDRH3
<220> FEATURE:
<221> NAME/KEY: MISC_FEATURE
<222> LOCATION: (5)..(5)
<223> OTHER INFORMATION: Xaa is Tyr or Val

<400> SEQUENCE: 163

Tyr Ala Met Asp Xaa
1               5

<210> SEQ ID NO 164
<211> LENGTH: 19
<212> TYPE: PRT
<213> ORGANISM: Artificial Sequence
<220> FEATURE:
<223> OTHER INFORMATION: CDRH3
<220> FEATURE:
<221> NAME/KEY: MISC_FEATURE
<222> LOCATION: (1)..(14)
<223> OTHER INFORMATION: Xaa is any naturally occurring amino acid and
      10 may be absent
<220> FEATURE:
<221> NAME/KEY: MISC_FEATURE
<222> LOCATION: (15)..(15)
<223> OTHER INFORMATION: Xaa is any naturally occurring amino acid

<400> SEQUENCE: 164

Xaa Xaa Xaa Xaa Xaa Xaa Xaa Xaa Xaa Xaa Xaa Xaa Xaa Xaa Xaa Ala
1               5                   10                  15

Met Asp Tyr

<210> SEQ ID NO 165
<211> LENGTH: 16
<212> TYPE: PRT
<213> ORGANISM: Artificial Sequence
<220> FEATURE:
<223> OTHER INFORMATION: Randomized CDRH3
<220> FEATURE:
<221> NAME/KEY: MISC_FEATURE
<222> LOCATION: (2)..(2)
<223> OTHER INFORMATION: Xaa is Arg or Lys
<220> FEATURE:
<221> NAME/KEY: MISC_FEATURE
<222> LOCATION: (3)..(11)
<223> OTHER INFORMATION: Xaa is any amino acid
<220> FEATURE:
<221> NAME/KEY: MISC_FEATURE
<222> LOCATION: (12)..(12)
<223> OTHER INFORMATION: Xaa is Trp, Ser, Ala or Gly
<220> FEATURE:
<221> NAME/KEY: MISC_FEATURE
<222> LOCATION: (13)..(13)
<223> OTHER INFORMATION: Xaa is Ala, Val or Gly

<400> SEQUENCE: 165

Ala Xaa Xaa Xaa Xaa Xaa Xaa Xaa Xaa Xaa Xaa Xaa Xaa Met Asp Tyr
1               5                   10                  15

<210> SEQ ID NO 166
<211> LENGTH: 16
<212> TYPE: PRT
<213> ORGANISM: Artificial Sequence
<220> FEATURE:
<223> OTHER INFORMATION: Randomized CDRH3
<220> FEATURE:
<221> NAME/KEY: MISC_FEATURE
<222> LOCATION: (2)..(2)
<223> OTHER INFORMATION: Xaa is Arg or Lys
<220> FEATURE:
<221> NAME/KEY: MISC_FEATURE
<222> LOCATION: (3)..(11)
<223> OTHER INFORMATION: Xaa is any amino acid
<220> FEATURE:
```

```
<221> NAME/KEY: MISC_FEATURE
<222> LOCATION: (12)..(12)
<223> OTHER INFORMATION: Xaa is Trp, Ser, Ala or Gly
<220> FEATURE:
<221> NAME/KEY: MISC_FEATURE
<222> LOCATION: (13)..(13)
<223> OTHER INFORMATION: Xaa is Ala, Val or Gly

<400> SEQUENCE: 166

Ala Xaa Xaa Xaa Xaa Xaa Xaa Xaa Xaa Xaa Xaa Xaa Xaa Met Asp Tyr
1               5                   10                  15

<210> SEQ ID NO 167
<211> LENGTH: 15
<212> TYPE: PRT
<213> ORGANISM: Artificial Sequence
<220> FEATURE:
<223> OTHER INFORMATION: Randomized CDRH3
<220> FEATURE:
<221> NAME/KEY: MISC_FEATURE
<222> LOCATION: (2)..(2)
<223> OTHER INFORMATION: Xaa is Arg or Lys
<220> FEATURE:
<221> NAME/KEY: MISC_FEATURE
<222> LOCATION: (3)..(10)
<223> OTHER INFORMATION: Xaa is any amino acid
<220> FEATURE:
<221> NAME/KEY: MISC_FEATURE
<222> LOCATION: (12)..(12)
<223> OTHER INFORMATION: Xaa is Ala, Val or Gly

<400> SEQUENCE: 167

Ala Xaa Xaa Xaa Xaa Xaa Xaa Xaa Xaa Xaa Tyr Xaa Met Asp Tyr
1               5                   10                  15

<210> SEQ ID NO 168
<211> LENGTH: 9
<212> TYPE: PRT
<213> ORGANISM: Artificial Sequence
<220> FEATURE:
<223> OTHER INFORMATION: Randomized CDRH3
<220> FEATURE:
<221> NAME/KEY: MISC_FEATURE
<222> LOCATION: (2)..(2)
<223> OTHER INFORMATION: Xaa is Arg or Lys
<220> FEATURE:
<221> NAME/KEY: MISC_FEATURE
<222> LOCATION: (3)..(6)
<223> OTHER INFORMATION: Xaa is any amino acid
<220> FEATURE:
<221> NAME/KEY: MISC_FEATURE
<222> LOCATION: (8)..(8)
<223> OTHER INFORMATION: Xaa is Asp or Ala

<400> SEQUENCE: 168

Ala Xaa Xaa Xaa Xaa Xaa Phe Xaa Tyr
1               5

<210> SEQ ID NO 169
<211> LENGTH: 9
<212> TYPE: PRT
<213> ORGANISM: Artificial Sequence
<220> FEATURE:
<223> OTHER INFORMATION: Randomized CDRH3
<220> FEATURE:
<221> NAME/KEY: MISC_FEATURE
<222> LOCATION: (2)..(2)
<223> OTHER INFORMATION: Xaa is Arg, His, Ser or Asn
<220> FEATURE:
<221> NAME/KEY: MISC_FEATURE
<222> LOCATION: (3)..(6)
<223> OTHER INFORMATION: Xaa is any amino acid
<220> FEATURE:
<221> NAME/KEY: MISC_FEATURE
```

<222> LOCATION: (7)..(7)
<223> OTHER INFORMATION: Xaa is Phe or Leu
<220> FEATURE:
<221> NAME/KEY: MISC_FEATURE
<222> LOCATION: (8)..(8)
<223> OTHER INFORMATION: Xaa is Gly, Val, Asp or Ala

<400> SEQUENCE: 169

Ala Xaa Xaa Xaa Xaa Xaa Xaa Xaa Tyr
1               5

<210> SEQ ID NO 170
<211> LENGTH: 10
<212> TYPE: PRT
<213> ORGANISM: Artificial Sequence
<220> FEATURE:
<223> OTHER INFORMATION: Randomized CDRH3
<220> FEATURE:
<221> NAME/KEY: MISC_FEATURE
<222> LOCATION: (2)..(2)
<223> OTHER INFORMATION: Xaa is Arg, His, Ser or Asn
<220> FEATURE:
<221> NAME/KEY: MISC_FEATURE
<222> LOCATION: (3)..(7)
<223> OTHER INFORMATION: Xaa is any amino acid
<220> FEATURE:
<221> NAME/KEY: MISC_FEATURE
<222> LOCATION: (8)..(8)
<223> OTHER INFORMATION: Xaa is Phe or Leu
<220> FEATURE:
<221> NAME/KEY: MISC_FEATURE
<222> LOCATION: (9)..(9)
<223> OTHER INFORMATION: Xaa is Gly, Val, Asp or Ala

<400> SEQUENCE: 170

Ala Xaa Xaa Xaa Xaa Xaa Xaa Xaa Xaa Tyr
1               5                   10

<210> SEQ ID NO 171
<211> LENGTH: 10
<212> TYPE: PRT
<213> ORGANISM: Artificial Sequence
<220> FEATURE:
<223> OTHER INFORMATION: Randomized CDRH3
<220> FEATURE:
<221> NAME/KEY: MISC_FEATURE
<222> LOCATION: (2)..(2)
<223> OTHER INFORMATION: Xaa is Arg, His, Ser or Asn
<220> FEATURE:
<221> NAME/KEY: MISC_FEATURE
<222> LOCATION: (3)..(7)
<223> OTHER INFORMATION: Xaa is any amino acid
<220> FEATURE:
<221> NAME/KEY: MISC_FEATURE
<222> LOCATION: (8)..(8)
<223> OTHER INFORMATION: Xaa is Phe or Leu
<220> FEATURE:
<221> NAME/KEY: MISC_FEATURE
<222> LOCATION: (9)..(9)
<223> OTHER INFORMATION: Xaa is Asp or Ala

<400> SEQUENCE: 171

Ala Xaa Xaa Xaa Xaa Xaa Xaa Xaa Xaa Tyr
1               5                   10

<210> SEQ ID NO 172
<211> LENGTH: 11
<212> TYPE: PRT
<213> ORGANISM: Artificial Sequence
<220> FEATURE:
<223> OTHER INFORMATION: Randomized CDRH3
<220> FEATURE:
<221> NAME/KEY: MISC_FEATURE
<222> LOCATION: (2)..(2)

```
<223> OTHER INFORMATION: Xaa is Arg or Lys
<220> FEATURE:
<221> NAME/KEY: MISC_FEATURE
<222> LOCATION: (3)..(8)
<223> OTHER INFORMATION: Xaa is any amino acid
<220> FEATURE:
<221> NAME/KEY: MISC_FEATURE
<222> LOCATION: (10)..(10)
<223> OTHER INFORMATION: Xaa is Asp or Ala

<400> SEQUENCE: 172

Ala Xaa Xaa Xaa Xaa Xaa Xaa Xaa Phe Xaa Tyr
1               5                   10

<210> SEQ ID NO 173
<211> LENGTH: 12
<212> TYPE: PRT
<213> ORGANISM: Artificial Sequence
<220> FEATURE:
<223> OTHER INFORMATION: Randomized CDRH3
<220> FEATURE:
<221> NAME/KEY: MISC_FEATURE
<222> LOCATION: (2)..(2)
<223> OTHER INFORMATION: Xaa is Arg or Lys
<220> FEATURE:
<221> NAME/KEY: MISC_FEATURE
<222> LOCATION: (3)..(9)
<223> OTHER INFORMATION: Xaa is any amino acid
<220> FEATURE:
<221> NAME/KEY: MISC_FEATURE
<222> LOCATION: (10)..(10)
<223> OTHER INFORMATION: Xaa is Phe or Leu
<220> FEATURE:
<221> NAME/KEY: MISC_FEATURE
<222> LOCATION: (11)..(11)
<223> OTHER INFORMATION: Xaa is Gly, Val, Asp or Ala

<400> SEQUENCE: 173

Ala Xaa Xaa Xaa Xaa Xaa Xaa Xaa Xaa Xaa Xaa Tyr
1               5                   10

<210> SEQ ID NO 174
<211> LENGTH: 6
<212> TYPE: PRT
<213> ORGANISM: Artificial Sequence
<220> FEATURE:
<223> OTHER INFORMATION: Randomized CDRH3
<220> FEATURE:
<221> NAME/KEY: MISC_FEATURE
<222> LOCATION: (1)..(1)
<223> OTHER INFORMATION: Xaa is any amino acid, n = 4 to 14
<220> FEATURE:
<221> NAME/KEY: MISC_FEATURE
<222> LOCATION: (2)..(2)
<223> OTHER INFORMATION: Xaa is any amino acid or is Tyr, Phe, Gly, Ser,
      Ala, Leu or Trp
<220> FEATURE:
<221> NAME/KEY: MISC_FEATURE
<222> LOCATION: (3)..(3)
<223> OTHER INFORMATION: Xaa is missing when Xaa (2)...(2) is Phe or Leu
      or is Ala, Val, Asp or Gly
<220> FEATURE:
<221> NAME/KEY: MISC_FEATURE
<222> LOCATION: (4)..(4)
<223> OTHER INFORMATION: Xaa is missing when Xaa (2)...(2) is Phe or Leu
      or is Met
<220> FEATURE:
<221> NAME/KEY: MISC_FEATURE
<222> LOCATION: (5)..(5)
<223> OTHER INFORMATION: Xaa is Asp, Ala, Val or Gly
<220> FEATURE:
<221> NAME/KEY: MISC_FEATURE
<222> LOCATION: (6)..(6)
<223> OTHER INFORMATION: Xaa is Tyr or Val

<400> SEQUENCE: 174
```

```
Xaa Xaa Xaa Xaa Xaa Xaa
1               5

<210> SEQ ID NO 175
<211> LENGTH: 9
<212> TYPE: PRT
<213> ORGANISM: Artificial Sequence
<220> FEATURE:
<223> OTHER INFORMATION: Randomized CDRH3
<220> FEATURE:
<221> NAME/KEY: MISC_FEATURE
<222> LOCATION: (1)..(4)
<223> OTHER INFORMATION: Xaa is any amino acid or is Tyr or Gly, n = 4
      to 14
<220> FEATURE:
<221> NAME/KEY: MISC_FEATURE
<222> LOCATION: (5)..(5)
<223> OTHER INFORMATION: Xaa is any amino acid or is Tyr, Gly, Phe, Ser,
      Ala, Leu or Trp

<400> SEQUENCE: 175

Xaa Xaa Xaa Xaa Xaa Ala Met Asp Tyr
1               5
```